US012758400B2

(12) United States Patent
Alva et al.

(10) Patent No.: US 12,758,400 B2
(45) Date of Patent: Oct. 13, 2026

(54) IMPLANT ENCODER

(71) Applicant: Orthosensor Inc., Dania, FL (US)

(72) Inventors: Carlos O. Alva, Boynton Beach, FL (US); Ezra S. Johnson, Reeds Spring, MT (US); Larry Hazbun, Davie, FL (US); Matthias Verstraete, Chaam (NL); Wael Hazin, Plantation, FL (US)

(73) Assignee: Howmedica Osteonics Corp., Mahwah, NJ (US)

( * ) Notice: Subject to any disclaimer, the term of this patent is extended or adjusted under 35 U.S.C. 154(b) by 897 days.

(21) Appl. No.: 18/108,954

(22) Filed: Feb. 13, 2023

(65) Prior Publication Data

US 2023/0255794 A1 Aug. 17, 2023

Related U.S. Application Data

(60) Provisional application No. 63/444,056, filed on Feb. 8, 2023, provisional application No. 63/444,045, filed (Continued)

(51) Int. Cl.

| | |
|---|---|
| ***A61F 2/46*** | (2006.01) |
| ***A61B 5/00*** | (2006.01) |
| ***A61B 5/06*** | (2006.01) |

(52) U.S. Cl.

CPC ............ *A61F 2/4657* (2013.01); *A61B 5/062* (2013.01); *A61B 5/4528* (2013.01); (Continued)

(58) Field of Classification Search

CPC ..... A61F 2/4657; A61B 5/062; A61B 5/4528; A61B 5/6878; A61B 5/6812

See application file for complete search history.

(56) References Cited

U.S. PATENT DOCUMENTS

| | | | |
|---|---|---|---|
| 6,245,109 | B1 | 6/2001 | Mendes et al. |
| 6,447,448 | B1 | 9/2002 | Ishikawa et al. |

(Continued)

FOREIGN PATENT DOCUMENTS

| | | |
|---|---|---|
| DE | 202015009423 U1 | 7/2017 |
| IT | UB2015006086 | 6/2017 |

(Continued)

OTHER PUBLICATIONS

Arami, A. et al., "Accurate Measurement of Concurrent Flexion-Extension and Internal-External Rotations in Smart Knee Prostheses," IEEE Transactions on Biomedical Engineering, Sep. 2013, 8 pgs.

(Continued)

*Primary Examiner* — Brian A Dukert

(74) *Attorney, Agent, or Firm* — Lerner David LLP

(57) ABSTRACT

Disclosed herein are joint implants and methods for tracking joint implant performance. A joint implant according to the present disclosure can include a first implant on a first bone and a second implant on a second bone of a joint. The first implant can include medial and lateral markers. The second implant can include a medial marker reader to identify the medial markers and a lateral marker reader to identify the lateral markers to provide positional data of the first implant with respect to the second implant. The second implant can include a medial load sensor to measure medial load data and a lateral load sensor to measure lateral load data. A processor coupled to the medial marker reader, the lateral marker reader, the medial load sensor, and the lateral load sensor can transmit the positional data, the medial and lateral load data to an external source.

15 Claims, 145 Drawing Sheets

Related U.S. Application Data on Feb. 8, 2023, provisional application No. 63/483,045, filed on Feb. 3, 2023, provisional application No. 63/443,146, filed on Feb. 3, 2023, provisional application No. 63/482,656, filed on Feb. 1, 2023, provisional application No. 63/482,659, filed on Feb. 1, 2023, provisional application No. 63/482,097, filed on Jan. 30, 2023, provisional application No. 63/482,109, filed on Jan. 30, 2023, provisional application No. 63/481,660, filed on Jan. 26, 2023, provisional application No. 63/481,053, filed on Jan. 23, 2023, provisional application No. 63/431,094, filed on Dec. 8, 2022, provisional application No. 63/423,932, filed on Nov. 9, 2022, provisional application No. 63/419,781, filed on Oct. 27, 2022, provisional application No. 63/419,522, filed on Oct. 26, 2022, provisional application No. 63/419,455, filed on Oct. 26, 2022, provisional application No. 63/359,384, filed on Jul. 8, 2022, provisional application No. 63/309,809, filed on Feb. 14, 2022.

(52) U.S. Cl.
CPC ............ *A61B 5/4851* (2013.01); *A61B 5/686* (2013.01); *A61B 5/6878* (2013.01); *A61B 2560/0209* (2013.01); *A61B 2560/029* (2013.01); *A61F 2002/4666* (2013.01)

(56) References Cited

U.S. PATENT DOCUMENTS 6,573,706 B2 6/2003 Mendes et al.
6,583,630 B2 6/2003 Mendes et al.
6,610,096 B2 8/2003 MacDonald
6,821,299 B2 11/2004 Kirking et al.
6,926,670 B2 8/2005 Rich et al.
6,968,743 B2 11/2005 Rich et al.
7,190,273 B2 3/2007 Liao et al.
7,195,645 B2 3/2007 Disilvestro et al.
7,218,232 B2 5/2007 DiSilvestro et al.
7,328,131 B2 2/2008 Donofrio et al.
7,347,874 B2 * 3/2008 Disilvestro ............ A61B 5/076 600/587
7,384,403 B2 6/2008 Sherman
7,470,288 B2 12/2008 Dietz et al.
7,704,282 B2 4/2010 Disilvestro et al.
7,766,862 B2 8/2010 Gerber et al.
7,776,686 B2 8/2010 Makabe et al.
7,900,518 B2 3/2011 Tai et al.
7,976,534 B2 7/2011 Gerber et al.
8,083,741 B2 12/2011 Morgan et al.
8,121,678 B2 2/2012 Linder et al.
8,241,296 B2 8/2012 Wasielewski
8,388,553 B2 3/2013 James et al.
8,419,801 B2 4/2013 DiSilvestro et al.
8,506,514 B2 8/2013 Pedersen et al.
8,509,888 B2 8/2013 Linder et al.
8,551,092 B2 10/2013 Morgan et al.
8,707,782 B2 4/2014 Stein et al.
8,744,580 B2 6/2014 Doron et al.
8,814,877 B2 8/2014 Wasielewski
8,911,448 B2 12/2014 Stein
8,956,418 B2 * 2/2015 Wasielewski .......... G16H 40/63 623/20.14
9,005,263 B2 4/2015 Boyden et al.
9,380,980 B2 7/2016 Revie et al.
9,439,797 B2 9/2016 Baym et al.
9,459,087 B2 10/2016 Dunbar et al.
9,532,730 B2 1/2017 Wasielewski
9,622,701 B2 4/2017 Stein et al.
9,687,670 B2 6/2017 Dacey, Jr. et al.
RE46,582 E 10/2017 Morgan et al.
9,839,374 B2 12/2017 Roche et al.
10,034,779 B2 7/2018 Chen et al.
10,080,509 B2 9/2018 Wasielewski
10,188,464 B2 1/2019 Britton et al.
10,219,696 B2 3/2019 Araci et al.
10,234,934 B2 3/2019 Connor
10,492,686 B2 12/2019 Hunter et al.
10,531,826 B2 1/2020 Wasielewski et al.
10,582,896 B2 3/2020 Revie et al.
10,660,760 B2 5/2020 Johannaber et al.
10,667,745 B2 6/2020 Anker et al.
10,792,162 B2 10/2020 Johannaber et al.
10,842,636 B2 11/2020 Johannaber et al.
10,898,106 B2 1/2021 Bodewes et al.
10,966,788 B2 4/2021 Britton et al.
11,027,140 B2 6/2021 Wang et al.
11,071,456 B2 7/2021 Hunter et al.
11,134,870 B2 10/2021 Lieb et al.
11,234,825 B2 2/2022 Johannaber et al.
11,234,852 B2 2/2022 Koo
11,389,111 B2 7/2022 Bae
2004/0158294 A1 8/2004 Thompson
2004/0243148 A1 12/2004 Wasielewski
2005/0010301 A1 1/2005 Disilvestro et al.
2006/0047283 A1 3/2006 Evans et al.
2006/0271199 A1 11/2006 Johnson
2007/0005141 A1 1/2007 Sherman
2007/0089518 A1 4/2007 Ericson et al.
2007/0239165 A1 10/2007 Amirouche
2008/0033527 A1 2/2008 Nunez et al.
2008/0065225 A1 3/2008 Wasielewski et al.
2008/0077016 A1 3/2008 Sparks et al.
2010/0171394 A1 7/2010 Glenn et al.
2010/0204551 A1 8/2010 Roche
2010/0204802 A1 8/2010 Wilson et al.
2010/0249576 A1 9/2010 Askarinya et al.
2014/0303739 A1 10/2014 Mentink et al.
2016/0015319 A1 1/2016 Billi et al.
2016/0029952 A1 2/2016 Hunter
2016/0089079 A1 3/2016 Stein
2016/0192878 A1 7/2016 Hunter
2016/0242646 A1 8/2016 Obma
2016/0302721 A1 10/2016 Wiedenhoefer et al.
2016/0338644 A1 11/2016 Connor
2017/0065436 A1 3/2017 Singh et al.
2017/0196508 A1 7/2017 Hunter
2017/0231559 A1 8/2017 Cuevas et al.
2017/0296118 A1 10/2017 Swanson et al.
2017/0319141 A1 11/2017 Revie et al.
2017/0340243 A1 11/2017 Jain et al.
2018/0116805 A1 5/2018 Johannaber et al.
2018/0160966 A1 6/2018 Inan et al.
2018/0235514 A1 8/2018 DiSilvestro et al.
2019/0167447 A1 6/2019 Angibaud
2019/0167988 A1 6/2019 Shahriari et al.
2019/0283247 A1 9/2019 Chang et al.
2019/0298998 A1 10/2019 Coleman et al.
2019/0336049 A1 11/2019 Shah et al.
2019/0350523 A1 11/2019 Bailey et al.
2020/0000400 A1 1/2020 McKinnon et al.
2020/0178898 A1 6/2020 Revie et al.
2020/0383796 A1 12/2020 Johannaber et al.
2021/0022874 A1 1/2021 Johannaber et al.
2021/0059554 A1 3/2021 Armbruster
2021/0141034 A1 5/2021 Sharma et al.
2021/0153947 A1 5/2021 Britton et al.
2021/0186454 A1 6/2021 Behzadi et al.
2021/0228160 A1 7/2021 Braganza et al.
2021/0290063 A1 9/2021 Roche
2021/0366610 A1 11/2021 Gross et al.
2021/0369471 A1 12/2021 Gross et al.
2021/0378841 A1 12/2021 Mokete
2021/0386292 A1 12/2021 Hunter et al.
2022/0000422 A1 1/2022 Gross et al.

(56) References Cited

U.S. PATENT DOCUMENTS

| | | | |
|---|---|---|---|
| 2022/0015672 | A1 | 1/2022 | Lieb et al. |
| 2022/0047162 | A1 | 2/2022 | Hunter et al. |

FOREIGN PATENT DOCUMENTS

| | | | |
|---|---|---|---|
| WO | 2017096138 | A1 | 6/2017 |
| WO | 2021154885 | A2 | 8/2021 |

OTHER PUBLICATIONS

Ibrahim A, Jain M, et al., "A Smart Knee Implant Using Triboelectric Energy Harvesters". Smart Mater Struct. Feb. 2019;28(2):025040. doi: 10.1088/1361-665X/aaf3f1. Epub Jan. 25, 2019. 39 pgs.

Bhatnagar, Vikrant & Owende, Philip, "Energy Harvesting for Assistive and Mobile Applications". Energy Science & Engineering. 3. 10.1002/ese3.63. (Feb. 2015). 21 pgs.

Schaufler, Anna, et al. "Sensor-based measurement for advanced monitoring and early detection of PE wear in total knee arthroplasties" Current Directions in Biomedical Engineering, vol. 7, No. 2, Oct. 2021, pp. 283-286. <https://doi.org/10.1515/cdbme-2021-2072>.

International Search Report and Written Opinion issued in Appln. No. PCT/US2023/013019 mailed May 24, 2023 (22 pages).

* cited by examiner

3300

9300

9400

9500

9600

IMPLANT ENCODER

CROSS-REFERENCE TO RELATED APPLICATION

This application claims the benefit of the filing date of U.S. Provisional Patent Application No. 63/309,809 filed Feb. 14, 2022, and claims the benefit of U.S. Provisional Patent Application No. 63/482,097 filed Jan. 30, 2023, and claims the benefit of U.S. Provisional Patent Application No. 63/359,384 filed Jul. 8, 2022, and claims the benefit of U.S. Provisional Patent Application No. 63/481,660 filed Jan. 26, 2023, and claims the benefit of U.S. Provisional Patent Application No. 63/419,455 filed Oct. 26, 2022, and claims the benefit of U.S. Provisional Patent Application No. 63/431,094 filed Dec. 8, 2022, and claims the benefit of U.S. Provisional Patent Application No. 63/419,781 filed Oct. 27, 2022, and claims the benefit of U.S. Provisional Patent Application No. 63/423,932 filed Nov. 9, 2022, and claims the benefit of U.S. Provisional Patent Application No. 63/419,522 filed Oct. 26, 2022, and claims the benefit of U.S. Provisional Patent Application No. 63/481,053 filed Jan. 23, 2023, and claims the benefit of U.S. Provisional Patent Application No. 63/482,659 filed Feb. 1, 2023, and claims the benefit of U.S. Provisional Patent Application No. 63/482,109 filed Jan. 30, 2023, and claims the benefit of U.S. Provisional Patent Application No. 63/483,045 filed Feb. 3, 2023, and claims the benefit of U.S. Provisional Patent Application No. 63/482,656 filed Feb. 1, 2023, and claims the benefit of U.S. Provisional Patent Application No. 63/443,146 filed Feb. 3, 2023; and claims the benefit of U.S. Provisional Patent Application No. 63/444,056 filed Feb. 8, 2023; and claims the benefit of U.S. Provisional Patent Application No. 63/444,045 filed Feb. 8, 2023, the disclosures of all of which are hereby incorporated herein by reference in their entirety.

FIELD OF INVENTION

The present disclosure relates to implants and methods for tracking implant performance, and particularly to joint implants and methods for tracking joint implant performance.

BACKGROUND OF THE INVENTION

Monitoring patient recovery after joint replacement surgery is critical for proper patient rehabilitation. A key component of monitoring a patient's recovery is evaluating the performance of the implant to detect implant dislocation, implant wear, implant malfunction, implant breakage, etc. For example, a tibial insert made of polyethylene ("PE") implanted in a total knee arthroscopy ("TKA") is susceptible to macroscopic premature failure due to excessive loading and mechanical loosening. Early identification of improper implant functioning and/or infection and inflammation at the implantation site can lead to corrective treatment solutions prior to implant failure. Data relating to postoperative range of motion and load balancing of the new TKA implants can be critical for managing recovery and identification of a proper replacement solution if necessary.

However, diagnostic techniques to evaluate implant performance are generally limited to patient feedback and imaging modalities such as X-ray fluoroscopy or magnetic resonance imaging ("MRI"). Patient feedback can be misleading in some instances. For example, gradual implant wear or dislocation, onset of infection, etc., may be imperceptible to a patient. Further, imaging modalities offer only limited insight into implant performance. For example, X-ray images will not reveal information related to the patient's range of motion or the amount of stress on the knee joint of a patient recovering from a TKA. Furthermore, the imaging modalities may provide only an instantaneous snapshot of the implant performance, and therefore fail to provide continuous real time information related to implant performance. Therefore, there exists a need for implants and related methods for tracking implant performance.

BRIEF SUMMARY OF THE INVENTION

Disclosed herein are joint implants and methods for tracking joint implant performance.

In accordance with an aspect of the present disclosure a joint implant is provided. A joint implant according to this aspect, may include a first implant coupled to a first bone of a joint and a second implant coupled to a second bone of the joint. The first implant may include at least one marker. The second implant may contact the first implant. The second implant may include at least one marker reader to detect a position of the marker to identify positional data of the first implant with respect to the second implant. The second implant may include at least one load sensor to measure load data between the first and second implants. A processor may be operatively coupled to the marker reader and the load sensor. The processor may simultaneously output the positional data and the load data to an external source.

Continuing in accordance with this aspect, the marker may be a magnet and the marker reader may be a magnetic sensor. The magnetic sensor may be a Hall sensor assembly including at least one Hall sensor. The magnet may be a magnetic track disposed along a surface of the first implant. The first implant may include a first magnetic track extending along a medial side of the first implant and a second magnetic track extending along a lateral side of the first implant.

Continuing in accordance with this aspect, the second implant may include a first Hall sensor assembly on a medial side of the second implant and a second Hall sensor assembly on a lateral side of the second implant. The first Hall sensor assembly may be configured to read a magnetic flux density of the first magnetic track and the second Hall sensor assembly configured to read a magnetic flux density of the second magnetic track.

Continuing in accordance with this aspect, a central portion of the first magnetic track may be narrower than an anterior end and a posterior end of the first magnetic track. The first magnetic track may include curved magnetic lines extending across the first magnetic track.

Continuing in accordance with this aspect, the magnetic sensor may be coupled to the load sensor by a connecting element. The connecting element may be a rod configured to transmit loads from the magnetic sensor to the load sensor. The load sensor may be a strain gauge.

Continuing in accordance with this aspect, the joint may be a knee joint. The first implant may be a femoral implant and the second implant may be a tibial implant. The tibial implant may include a tibial insert and a tibial stem. The marker reader and the processor may be disposed within the tibial insert.

Continuing in accordance with this aspect, the positional data may include any of a knee flexion angle, knee varus-valgus rotation, knee internal-external rotation, knee medial-lateral translation, superior-inferior translation, anterior-posterior translation, and time derivatives thereof. The load data may include any of a medial load magnitude, lateral load magnitude, medial load center and lateral load center. The tibial insert may include any of a pH sensor, a temperature sensor and a pressure sensor operatively coupled to the processor. The tibial insert may include a spectroscopy sensor. The tibial insert may be made of polyethylene.

Continuing in accordance with this aspect, the joint implant may include an antenna to transmit the positional data and the load data to an external source. The external source may be any of a tablet, computer, smart phone, and remote workstation.

In accordance with another aspect of the present disclosure, a joint implant is provided. A joint implant according to this aspect, may include a first implant coupled to a first bone of a joint and a second implant coupled to a second bone of the joint. The first implant may include a plurality of medial markers located on a medial side of the first implant, and a plurality of lateral markers located on a lateral side of the first implant. The second implant may contact the first implant. The second implant may include at least one medial marker reader to identify a position of the medial markers and at least one lateral marker reader to identify a position of the lateral markers. The position of the medial markers and the position of the lateral markers may provide positional data of the first implant with respect to the second implant. The second implant may include a medial load sensor to measure medial load data between the first and second implants on a medial side of the joint implant, a lateral load sensor to measure lateral load data between the first and second implants on a lateral side of the joint implant. A processor may be operatively coupled to the medial marker reader, the lateral marker reader, the medial load sensor, and the lateral load sensor. The processor may simultaneously output the positional data, the medial load data, and the lateral load data to an external source.

Continuing in accordance with this aspect, a number of medial markers may be different from a number of lateral markers. The medial markers and the lateral markers may include magnets located at discrete locations on the first implant. The medial marker reader and the lateral marker reader may include a Hall sensor assembly with at least one Hall sensor. The medial load sensor and the lateral load sensor may include piezo stacks.

Continuing in accordance with this aspect, the joint implant may include a battery disposed within the second implant. The joint implant may include a charging circuit disposed within the second implant to charge the battery using power generated by the piezo stacks during loading between the first and second implants.

Continuing in accordance with this aspect, the joint may be a knee joint. The first implant may be a femoral implant and the second implant may be a tibial implant. The tibial implant may include a tibial insert and a tibial stem. The marker reader and the processor may be disposed within the tibial insert. The positional data may include any of a knee flexion angle, knee varus-valgus rotation, knee internal-external rotation, knee medial-lateral translation, anterior-posterior translation, superior-inferior translation, and time derivatives thereof.

Continuing in accordance with this aspect, the medial load data may include a medial load magnitude and a medial load center. The tibial insert may include any of a pH sensor, a temperature sensor, accelerometer, gyroscope, inertial measure unit and a pressure sensor operatively coupled to the processor. The tibial insert may include a spectroscopy sensor.

In accordance with another aspect of the present disclosure, a joint implant system is provided. A joint implant system according to this aspect, may include a first implant coupled to a first bone of a joint, a second implant coupled to a second bone of the joint, and an external sleeve configured to be removably attached to the joint. The first implant may include at least one marker. The second implant may contact the first implant. The second implant may include at least one marker reader to detect a position of the marker to identify positional data of the first implant with respect to the second implant. The second implant may include at least one load sensor to measure load data between the first and second implants. A processor may be operatively coupled to the marker reader and the load sensor. The processor may be configured to simultaneously output the positional data and the load data to an external source.

Continuing in accordance with this aspect, the joint implant system may include a battery to power the marker reader and the processor. The battery may be disposed within the second implant and including a joint implant charging coil. The external sleeve may include an external charging coil to charge the battery. The battery may be configured to be charged by ultrasonic wireless charging or optical charging.

In another aspect of the present disclosure, a method for monitoring a joint implant performance is provided. A method according to this aspect, may include the steps of providing a first implant couplable to a first bone of a joint, providing a second implant couplable to a second bone of the joint, tracking magnetic flux density magnitudes over time using a magnetic sensor, and initiating a warning when a tracked magnetic flux density magnitude is different from a predetermined value. The first implant may include at least one magnetic marker. The second implant may be configured to contact the first implant. The second implant may include at least one magnetic sensor to detect the magnetic flux density of the magnetic marker. The magnetic flux density value may be proportional to a thickness of the second implant.

In accordance with another aspect of the present disclosure, a method for monitoring a joint implant performance is provided. A method according to this aspect, may include the steps of providing a first implant couplable to a first bone of a joint, providing a second implant couplable to a second bone of the joint, tracking a rate of change of a magnetic flux density over time using a magnetic sensor, and initiating a warning when a tracked rate of change of the magnetic flux density exceeds a predetermined value. The first implant may include at least one magnetic marker. The second implant may be configured to contact the first implant. The second implant may include at least one magnetic sensor to detect the magnetic flux density of the magnetic marker. The rate of change of the magnetic flux density may be proportional to a wear rate of the second implant.

In accordance with another aspect of the present disclosure, a method of monitoring implant performance is provided. A method according to this aspect, may include the steps of providing an implant with a first sensor to detect implant temperature, a second sensor to detect a fluid pressure, and a third sensor to detect implant alkalinity, tracking and outputting implant temperature, implant pressure and implant alkalinity over time to an external source using a processor disposed within the implant, and initiating a notification when any of the implant temperature, implant pressure and implant alkalinity, or any combination thereof, exceeds a predetermined value. The implant temperature, implant pressure and implant alkalinity may be related to any of an implant failure and an implant infection. The fluid pressure may be a synovial fluid pressure.

In accordance with an aspect of the present disclosure a method for monitoring a joint implant performance is provided. A method according to this aspect, may include the steps of coupling a first implant to a first bone of a joint, the first implant may include at least one magnetic marker, coupling a second implant to a second bone of the joint, the second implant may include at least one magnetic sensor to detect a position of the magnetic marker, performing a first joint stress test to measure a baseline joint stability value, the baseline joint stability value may be generated by the at least one magnetic sensor, performing a second joint stress test to measure a second joint stability value, the second joint stability value may be generated by the at least one magnetic sensor, and determining joint stability of the joint by comparing the baseline joint stability value to the second joint stability value.

Continuing in accordance with this aspect, the joint may be any of a knee joint, shoulder joint, and hip joint.

Continuing in accordance with this aspect, the joint may be a knee joint. The first implant may be a femoral implant and the second implant may be a tibial insert. The first bone may be a femur and the second bone may be a tibia. The first joint stress test and second joint stress test may be any of a varus-valgus stress test, anterior-posterior drawer stress test and flexion-extension stress test. The first joint stress test may be performed intra-operatively. The second joint stress test may be performed post-operatively on the implanted joint implant. The baseline joint stability value and the second joint stability value are tibiofemoral gaps between the femoral implant and the tibial insert measured by the at least one magnetic sensor. A difference between the baseline joint stability value and the second joint stability value below a predetermined threshold may indicate a stable joint. A difference between the baseline joint stability value and the second joint stability value exceeding the predetermined threshold may indicate an unstable joint.

In accordance with another aspect of the present disclosure, a method for monitoring a joint implant performance is provided. A method according to this aspect, may include the steps of coupling a first implant to a first bone of a joint, coupling a second implant to a second bone of the joint, the second implant may include a plurality of load sensors to detect a load and contact points between the first and second implants, performing a first joint stress test to measure a baseline joint stability value, the baseline joint stability value may be generated by the load sensors, performing a second joint stress test to measure a second joint stability value, the second joint stability value may be generated by the load sensors, and determining joint stability of the joint by comparing the baseline joint stability value to the second joint stability value.

Continuing in accordance with this aspect, the joint may be any of a knee joint, shoulder joint, and hip joint.

Continuing in accordance with this aspect, the joint may be a knee joint. The first implant may be a femoral implant and the second implant may be a tibial insert. The first bone may be a femur and the second bone may be a tibia.

Continuing in accordance with this aspect, the first joint stress test and second joint stress test may be any of an internal-external rotational torque test, anterior-posterior shear force test and flexion-extension stress test. The first joint stress test may be performed intra-operatively. The second joint stress test may be performed post-operatively on the implanted joint implant. The baseline joint stability value and the second joint stability value may be load contact points between a medial and lateral condyle of the femoral implant and the tibial insert measured by the load sensors.

Continuing in accordance with this aspect, a difference between the baseline joint stability value and the second joint stability value under a predetermined threshold may indicate a stable joint.

Continuing in accordance with this aspect, a difference between the baseline joint stability and the second joint stability exceeding the predetermined threshold may indicate an unstable joint.

In accordance with another aspect of the present disclosure, a method for monitoring a joint implant performance is provided. A method according to this aspect, may include the steps of coupling a first implant to a first bone of a joint, coupling a second implant to a second bone of the joint, the second implant may include a plurality of load sensors to detect a load and contact points between the first and second implants, establishing a baseline joint stability value, performing a post-operative joint stress test to measure a second joint stability value, the second joint stability value may be generated by the load sensors, and determining joint stability of the joint by comparing the baseline joint stability value to the second joint stability value.

Disclosed herein are joint implants with sensors and methods for manufacturing joint implants with sensors.

In accordance with an aspect of the present disclosure a knee implant is provided. A knee implant according to this aspect, may include a femoral implant configured to be coupled to a femur, a tibial implant configured to be coupled to a tibia, and a tibial insert disposed between the femoral implant and the tibial implant. The tibial insert may include a medial side with a medial central region defined around a medial center, a lateral side with a lateral central region defined around a lateral center, a central region disposed between the medial central region and the lateral central region, and at least one sensor and a battery disposed within the tibial insert. The medial central region and the lateral central region may be defined by solid volumes extending from a proximal surface to a distal surface of the tibial insert.

Continuing in accordance with this aspect, the medial central region and the lateral central region may extend from an anterior surface to a posterior surface of the tibial insert. The at least one sensor and the battery may be located away from the medial central region and the lateral central region. The at least one sensor and the battery may be disposed within the central region. The at least one sensor and the battery may be disposed around a periphery of the tibial insert. The at least one sensor and the battery may be disposed around a periphery of the tibial insert.

Continuing in accordance with this aspect, the at least one sensor may include a Hall sensors and the femoral implant may include a magnet. The Hall sensor may be configured to track a location of the magnet. The at least one sensor may include a plurality of sensors. The plurality of sensors may include at least one load sensor. The plurality of sensors may include a temperature sensor, a pressure sensor, and a pH sensor. The at least one battery may include a plurality of batteries.

Continuing in accordance with this aspect, the tibial insert may further include a printed circuit board assembly, a processor, a charging coil, and an antenna, all of which may be located away from the medial central region and the lateral central region.

In accordance with another aspect of the present disclosure a method for manufacturing an implant is provided. A method according to this aspect, may include the steps of determining expected loading levels on an implant during implant life, identifying high load regions on the implant, and placing at least one sensor and at least one battery within the implant. The high load regions may represent implant regions determined to experience greater loading force than non-high load regions on the implant. The at least one sensor and at least one battery may be placed away from the identified high load regions.

Continuing in accordance with this aspect, the step of determining loading levels may be performed by a computer simulation of an implant model. The computer simulation may include a finite element analysis. The implant may be a tibial insert tibial insert configured to be located between a femoral implant and a tibial implant.

Continuing in accordance with this aspect, the method may further include a step of configuring the high load regions as solid volumes.

Continuing in accordance with this aspect, the method may further include a step of placing the at least one sensor and the at least one battery in a cavity of the implant and hermetically sealing the cavity. The at least one sensor may include a Hall sensor. The at least one sensor may include a plurality of sensors. The plurality of sensors may include at least one load sensor. The plurality of sensors may include a temperature sensor, a pressure sensor, and a pH sensor. The at least one battery may include a plurality of batteries.

Disclosed herein are joint implants with sensors and methods for manufacturing joint implants with sensors.

In accordance with an aspect of the present disclosure a knee implant is provided. A knee implant according to this aspect, may include a femoral implant configured to be coupled to a femur, a tibial implant configured to be coupled to a tibia, and a tibial insert disposed between the femoral implant and the tibial implant. The tibial insert may include a medial side with a medial central region defined around a medial center, a lateral side with a lateral central region defined around a lateral center, a central region disposed between the medial central region and the lateral central region, and at least one sensor and a battery disposed within the tibial insert. The medial central region and the lateral central region may be defined by solid volumes extending from a proximal surface to a distal surface of the tibial insert.

Continuing in accordance with this aspect, the medial central region and the lateral central region may extend from an anterior surface to a posterior surface of the tibial insert. The at least one sensor and the battery may be located away from the medial central region and the lateral central region. The at least one sensor and the battery may be disposed within the central region. The at least one sensor and the battery may be disposed around a periphery of the tibial insert. The at least one sensor and the battery may be disposed around a periphery of the tibial insert.

Continuing in accordance with this aspect, the at least one sensor may include a Hall sensors and the femoral implant may include a magnet. The Hall sensor may be configured to track a location of the magnet. The at least one sensor may include a plurality of sensors. The plurality of sensors may include at least one load sensor. The plurality of sensors may include a temperature sensor, a pressure sensor, and a pH sensor. The at least one battery may include a plurality of batteries.

Continuing in accordance with this aspect, the tibial insert may further include a printed circuit board assembly, a processor, a charging coil, and an antenna, all of which may be located away from the medial central region and the lateral central region.

In accordance with another aspect of the present disclosure a method for manufacturing an implant is provided. A method according to this aspect, may include the steps of determining expected loading levels on an implant during implant life, identifying high load regions on the implant, and placing at least one sensor and at least one battery within the implant. The high load regions may represent implant regions determined to experience greater loading force than non-high load regions on the implant. The at least one sensor and at least one battery may be placed away from the identified high load regions.

Continuing in accordance with this aspect, the step of determining loading levels may be performed by a computer simulation of an implant model. The computer simulation may include a finite element analysis. The implant may be a tibial insert tibial insert configured to be located between a femoral implant and a tibial implant.

Continuing in accordance with this aspect, the method may further include a step of configuring the high load regions as solid volumes.

Continuing in accordance with this aspect, the method may further include a step of placing the at least one sensor and the at least one battery in a cavity of the implant and hermetically sealing the cavity. The at least one sensor may include a Hall sensor. The at least one sensor may include a plurality of sensors. The plurality of sensors may include at least one load sensor. The plurality of sensors may include a temperature sensor, a pressure sensor, and a pH sensor. The at least one battery may include a plurality of batteries.

Disclosed herein are implants with sensors and methods for powering implants with sensors.

In accordance with an aspect of the present disclosure, a joint implant is provided. A joint implant according to this aspect may include a first implant and a second implant in contact with or disposed adjacent the first implant. The first implant may be coupled to a first bone of a joint. The first implant may include an energy generator coupled to a transducer. The transducer may be disposed within the first implant. The second implant may include at least one sensor, a battery coupled and a receiver. The battery may be coupled to the least one sensor. The receiver may be coupled to the battery. The receiver may be disposed within the second implant adjacent the transducer. Energy from the energy generator may be transmitted from the transducer of the first implant to the receiver of the second implant.

Continuing in accordance with this aspect, energy from the energy generator may be acoustically transmitted from the transducer of the first implant to the receiver of the second implant. The transducer may be an ultrasonic transducer. The receiver may be an ultrasonic receiver. Energy from the energy generator may be ultrasonically transmitted from the ultrasonic transducer of the first implant to the ultrasonic receiver of the second implant.

Continuing in accordance with this aspect, the energy generator may include a plurality of magnets. The energy generator may generate energy by magnetic induction caused by motion between the plurality of magnets. The motion between the plurality of magnets may be caused by joint implant motion. The energy generator may include one or more biasing elements coupled to the magnets. The biasing elements may be springs.

Continuing in accordance with this aspect, the energy generator may include triboelectric material. The triboelectric material may include a first triboelectric layer with a first electron affinity and a second triboelectric layer with a second electron affinity. The first electron affinity may be different from the second electron affinity. The first triboelectric layer may be separated by a distance from the second triboelectric layer. A motion of the joint implant may cause the distance to vary to generate energy. The first triboelectric layer may slide along the second triboelectric layer during joint implant motion to generate energy.

Continuing in accordance with this aspect, a plurality of sensors may be coupled to the battery. The plurality of sensors may include any of a magnetic sensor, a load sensor, a pH sensor, a temperature sensor, and a pressure sensor coupled to the battery.

Continuing in accordance with this aspect, the battery may receive energy from the receiver.

Continuing in accordance with this aspect, the plurality of sensors, the battery and the receiver may be disposed within a housing of the second implant. The housing may be hermetically sealed. The housing may be metallic.

Continuing in accordance with this aspect, the first implant may define a first monolithic body and the second implant defines a second monolithic body.

Continuing in accordance with this aspect, the joint implant may be a knee implant. The first implant may be a tibial stem and the second implant may be a tibial insert. The tibial stem may be made of cobalt-chrome or titanium. The tibial insert may be made of a cross-linked polyethylene. The first bone may be a tibia.

Continuing in accordance with this aspect, the joint implant may be any of a shoulder, a hip, an ankle, and a wrist implant.

In accordance with another aspect of the present disclosure, an implant system is provided. An implant system according to this aspect, may include a first implant and a second implant disposed adjacent the first implant. The first implant may be coupled to a first bone. The first implant may include an energy generator coupled to a transducer. The transducer may be disposed within the first implant. The second implant may include at least one sensor, and a receiver. The receiver may be coupled to the at least one sensor. The receiver may be disposed within the second implant adjacent the transducer. Energy from the energy generator may be acoustically transmitted from the transducer of the first implant to the receiver of the second implant. The transducer may be an ultrasonic transducer. The receiver may be an ultrasonic receiver.

Continuing in accordance with this aspect, energy from the energy generator may be ultrasonically transmitted from the ultrasonic transducer of the first implant to the ultrasonic receiver of the second implant. The energy generator may include a plurality of magnets. The energy generator may generate energy by magnetic induction caused by motion between the plurality of magnets. The motion between the plurality of magnets may be caused by first and/or second implant motion. The energy generator may include one or more biasing elements coupled to the magnets. The biasing elements may be a spring.

Continuing in accordance with this aspect, the energy generator may include triboelectric material. The triboelectric material may include a first triboelectric layer with a first electron affinity and a second triboelectric layer with a second electron affinity. The first electron affinity may be different from the second electron affinity. The first triboelectric layer may be separated by a distance from the second triboelectric layer. A motion of the first and/or second implant may cause the distance to vary to generate energy. The first triboelectric layer may slide along the second triboelectric layer during first and/or second motion to generate energy.

Continuing in accordance with this aspect, the plurality of sensors may include any of a magnetic sensor, a load sensor, a pH sensor, a temperature sensor, an accelerometer, a gyroscope, an inertial measurement unit ("IMU") and a pressure sensor coupled to the battery. The plurality of sensors may receive energy from the receiver.

Continuing in accordance with this aspect, the plurality of sensors and the receiver may be disposed within a housing of the second implant. The housing may be hermetically sealed. The housing may be metallic.

Continuing in accordance with this aspect, the first implant may define a first monolithic body and the second implant may define a second monolithic body.

Continuing in accordance with this aspect, the implant system may be any of a knee implant, a shoulder implant, a hip implant, an ankle implant, and a wrist implant.

In accordance with another aspect of the present disclosure, a joint implant is provided. A joint implant according to this aspect may include a first implant and a second implant. The first implant may be coupled to a first bone of a joint. The first implant may include a battery coupled to a transducer. The transducer may be disposed within the first implant. The second implant may be in contact with the first implant. The second implant may include at least one sensor and a receiver. The receiver may be coupled to the at least one sensor. The receiver may be disposed within the second implant adjacent the transducer. Energy from the battery may be acoustically transmitted from the transducer of the first implant to the receiver of the second implant.

Continuing in accordance with this aspect, the battery may be rechargeable.

In accordance with another aspect of the present a disclosure, a method for powering a joint implant is provided. A method according to this aspect may include the steps of providing a first implant, coupling an energy generator of the first implant to a transducer, providing a second implant, coupling at least one sensor disposed within the second implant to a battery, coupling a receiver to the battery, and transmitting energy from the energy generator to the transducer of the first implant to the receiver of the second implant. The first implant may be configured to be placed on a first bone. The transducer may be disposed within the first implant. The second implant may be configured to be placed in contact with the first implant. The battery may be disposed within the second implant. The receiver may be disposed within the second implant adjacent the transducer.

Continuing in accordance with this aspect, the step of transmitting energy may include acoustically transmitting energy from the transducer of the first implant to the receiver of the second implant.

In accordance with another aspect of the present disclosure, a method for powering a joint implant is provided. A method according to this aspect may include the steps of providing a first implant configured to be placed on a first bone and providing a second implant configured to be placed adjacent the first implant. The first implant may include an energy generator coupled to a transducer. The transducer may be disposed within the first implant. The second implant may include at least one sensor coupled to a battery. The battery may be coupled to a receiver. The receiver may be disposed within the second implant adjacent the transducer such that the energy generator may transmit energy from the energy generator to the transducer of the first implant to the receiver of the second implant.

Disclosed herein are joint implants and methods for tracking joint implant performance.

In accordance with an aspect of the present disclosure, a joint implant is provided. A joint implant according to this aspect, may include a first implant coupled to a first bone of a joint; and a second implant coupled to a second bone of the joint. The second implant may include a first sensor configured to measure a first type of data, and a processor operatively coupled to the first sensor. The processor may output the first type of data to a network. One of the joint or the implant may be determined to be in a first state based on a comparison of the first type of data to a set of predetermined values. The predetermined values may be adapted to change with the addition of new data.

Continuing in accordance with this aspect, the joint may be a knee joint. The first implant may be a femoral implant and the second implant may be a tibial implant. The tibial implant may include any of a pH sensor, a temperature sensor, a Hall sensor, a pressure sensor, an optical sensor, and a blood sensor operatively coupled to the processor. The tibial implant may include a tibial insert and a tibial stem. The tibial insert may be made of polyethylene.

Continuing in accordance with this aspect, the processor may output the data to an external source connected to the network. The joint implant may further comprise a transmitter to transmit the first type of data to the external source.

Continuing in accordance with this aspect, the external source may be any of a tablet, computer, smart phone, and remote workstation. A battery may be disposed within the second implant. A charging circuit may be disposed within the second implant to charge the battery using power generated by piezo stacks.

Continuing in accordance with this aspect, the joint may be a hip joint. The first implant may be a hip insert and the second implant may be a femoral head.

Continuing in accordance with this aspect, the joint may be a shoulder joint. The first implant may be a glenoid sphere and the second implant may be a shoulder insert.

Continuing in accordance with this aspect, the joint implant may include at least one of a second sensor configured to measure a second type of data. The joint implant may include a plurality of the first sensor and a plurality of the second sensor. The processor may output the first and second types of data to the network.

Continuing in accordance with this aspect, the data received from other joint implants may include data measured by a sensor. The data received from the other joint implants may include determinations of a state of the respective joint or a state of the respective implant as determined by a user.

Continuing in accordance with this aspect, the addition of new data may include the first type of data output by the processor of the joint implant. The addition of new data may include the data received from the other joint implants. The addition of new data may include a determination of a state of one of the other joint implants based on a type of data output from the respective one of the joint implants as determined by a user.

Continuing in accordance with this aspect, the joint implant may be configured to initiate a warning when the joint implant is determined to be in the first state. The first state may be any one of inflamed, infected, or injured In accordance with an aspect of the present disclosure, a joint implant is provided. A joint implant according to this aspect, may include a first implant coupled to a first bone of a joint, and a second implant coupled to a second bone of the joint and contacting the first implant. The second implant may include a first sensor configured to measure a first type of data, a second sensor configured to measure a second type of data, and a processor operatively coupled to the at least one of the first and second sensors. The joint implant may be operatively coupled to a network of joint implants. The processor may output the first and second types of data to the network to determine a state of the joint implant based on data received in the network from other joint implants. The joint implant may be configured to initiate an alert when the joint implant is determined to be in a first state.

In accordance with an aspect of the present disclosure, a system for detecting the state of a joint implant is provided. A system according to this aspect, may include a joint implant. The joint implant may include a first implant coupled to a first bone of a joint, a second implant coupled to a second bone of the joint and contacting the first implant. The second implant may include at least one of a first sensor configured to measure a first type of data, and a processor operatively coupled to the at least one of the first sensor, and a device operatively coupled to the processor. The device may have a network adapted to receive data from the processor and at least a second source, process the data from the processor and the second source, and output a state of the joint based on the data from the processor and the data from the second source.

Continuing in accordance with this aspect, the joint implant may be a first joint implant. The second source may include a second joint implant including at least one of a first sensor configured to measure a first type of data.

Continuing in accordance with this aspect, the second source may include a determination of a state of a joint based on data provided by sensors of a joint implant as determined by a user. The device may define a predetermined range of values and determines that the joint is in a first state when the data is within the predetermined range. The device may initiate a warning when the first type of data is outside of the predetermined range of values. The joint may be determined to be any one of injured, infected, or inflamed when the data is outside of the predetermined range of values. The predetermined range may be adapted to change upon receipt of data from a joint implant or the determination of the state by the user.

Continuing in accordance with this aspect, the at least one of the first sensor may include any one of a temperature sensor, a pressure sensor, a pH sensor, an optical sensor, and a blood sensor. The blood sensor may measure data on pathogens present in the joint. The blood sensor may measure a glucose level in the joint.

Continuing in accordance with this aspect, at least one of the first sensor may measure the first type of data upon activation by a user.

In accordance with an aspect of the present disclosure, a method for monitoring an implant performance is provided. A method according to this aspect, may include the steps of providing a joint implant with a first sensor configured to measure a first type of data, tracking and outputting the first type of data over time to a network using a processor disposed within the implant, comparing the first type of data to a set of data received into the network from other implants, determining a state of the implant based on the comparison of the first type of data with the set of data received from other implants, and initiating a warning from the implant when the implant is determined to be in a first state.

Continuing in accordance with this aspect, the first state may be any one of the joint being inflamed, infected, or injured.

Continuing in accordance with this aspect, the first type of data may be compared to a predetermined value designated according to the set of data received into the network from the other implants. The predetermined value may include a range of predetermined values. The implant may be determined to be in the first state when the first type of data falls outside of the range of predetermined values. The predetermined value may be adapted to change when a new set of data from an implant is received in the network.

In accordance with an aspect of the present disclosure, a method for monitoring an implant performance is provided. A method according to this aspect, may include the steps of coupling a first implant to a first bone of a joint, coupling a second implant to a second bone of the joint, tracking and outputting the first type of data to an external source using a processor disposed within the implant, comparing the first type of data to a predetermined value formed based on a set of data obtained from other joint implants, and determining a state of the implant. The second implant may be configured to contact the first implant. The second implant may include a first sensor to measure a first type of data such that the implant may be determined to be in a first state when the first type of data is different than the predetermined value. The range of predetermined values may be adapted to change when new data is provided to the set of data.

Continuing in accordance with this aspect, the new data may include a first type of data measured by a first sensor of an implant. The new data may include a determination of a state of an implant as determined by a user.

Continuing in accordance with this aspect, the method may further comprise initiating an alert to a user when the implant is determined to be in the first state. The first state may be one of the joint being inflamed, infected, or injured.

Continuing in accordance with this aspect, the predetermined value may include a range of predetermined values. The implant may be determined to be in the first state when the first type of data is outside of the range of predetermined values.

Continuing in accordance with this aspect, the first sensor may be any one of a temperature sensor, a pressure sensor, a pH sensor, an optical sensor, and a blood sensor.

Disclosed herein are joint implants and methods for intra-operatively detecting joint implant gaps.

In accordance with an aspect of the present disclosure, a method for detecting joint implant gap is provided. A method according to this aspect, may include the steps of coupling a first implant to a first bone of a joint, the first implant may include at least one magnetic marker, coupling a second implant to a second bone of the joint, the second implant may be configured to contact the first implant, the second implant may include at least one magnetic sensor to detect a magnetic flux density of the magnetic marker, measuring an amplitude of the magnetic flux density using the magnetic sensor, and determining a gap between the first implant and the second implant from the measured amplitude of the magnetic flux density.

Continuing in accordance with this aspect, the steps of measuring the amplitude of the magnetic flux density and determining the gap between the first implant and the second implant may be performed intra-operatively. The step of determining the gap between the first implant and the second implant may be performed by comparing the measured amplitude of the magnetic flux density to a predetermined value. The predetermined value may be stored in a database. The database may include a library of magnetic flux density amplitude and corresponding gap distances.

Continuing in accordance with this aspect, the method may further include a step of initiating a warning when the measured amplitude of magnetic flux does not match the predetermined value. The joint implant may be any of a knee joint implant, shoulder implant, hip implant and spine implant.

Continuing in accordance with this aspect, the joint implant may be a knee joint implant. The first implant may be a femoral implant and the second implant may be a tibial implant.

Continuing in accordance with this aspect, the method may further comprise a step of performing a varus-valgus movement to determine femoral and tibial implant lift off.

Continuing in accordance with this aspect, the first implant may include a medial magnetic marker and a lateral magnetic marker and the second implant may include a medial magnetic sensor and a lateral magnetic sensor.

Continuing in accordance with this aspect, the step of measuring the amplitude may include measuring an amplitude of the medial magnetic flux of the medial magnetic marker by the medial magnetic sensor and an amplitude of the lateral magnetic flux of the lateral magnetic marker by the lateral magnetic sensor. The step of determining the gap may include determining a medial gap between a medial portion of the first implant and the second implant from the measured amplitude of the medial magnetic flux density and determining a lateral medial gap between a lateral portion of the first implant and the second implant from the measured amplitude of the lateral magnetic flux density.

Continuing in accordance with this aspect, the steps of measuring the amplitude of the magnetic flux density and determining the gap between the first implant and the second implant may be performed post-operatively.

In accordance with another aspect of the present disclosure, a method for detecting joint gap is provided. A method according to this aspect, may include the steps of coupling a first implant to a first bone of a joint, the first implant may include a light source, coupling a second implant to a second bone of the joint, the second implant may be configured to contact the first implant, the second implant may include a pattern, transmitting light from the light source through the pattern, reading the light passing through the pattern from a reader disposed on the first implant, and determining a gap between the first implant and the second implant from the light passing through the pattern.

Continuing in accordance with this aspect, the steps of transmitting the light, reading the light passing through the pattern and determining the gap between the first implant and the second implant may be performed intra-operatively. The step of determining the gap between the first implant and the second implant may be performed by comparing a formed pattern generated by the light passing through the pattern to a predetermined pattern. The predetermined pattern may be stored in a database. The database may include a library of predetermined patterns and corresponding gap distances.

Continuing in accordance with this aspect, the method may further include a step of initiating a warning when the formed pattern does not match the predetermined pattern. The joint implant may be any of a knee joint implant, shoulder implant, hip implant and spine implant.

Continuing in accordance with this aspect, the joint implant may be a knee joint implant. The first implant may be a femoral implant and the second implant may be a tibial implant.

Described herein is a joint implant having a sensor redundancy system for improving the accuracy, efficiency and effectiveness of the joint implant's ability to measure positioning and movement data of the implant and the joint within which the implant is implanted. The sensor redundancy system includes a group of sensors, preferably a plurality of the same type of sensor, which first measure and record a certain type(s) of data with respect to the operation of the implant and its performance after implantation. After such data is recorded, each of the sensors may wirelessly communicate with a processor to send the data to the processor. The processor may arrange the data from each sensor into respective packets of data to be handled and read in such groupings.

Typically, each sensor will provide accurate and valuable data to the processor to be used in for analysis of the implant's performance. Occasionally, however, one or more of the sensors may provide skewed or unusable data that may be an outlier from the other sensors and should not be incorporated into the analysis to produce accurate results. In such cases, the processor may tag the data packet containing the unusable data. The processor may be in wireless communication with a channel detector, which is arrange each of the data packets into separate channels, and also identify the data packet tagged by the processor and exclude said data packet from use in the final analysis. After exclusion of the unusable data packet(s), the channel detector can wirelessly connect with a neural network to process only the usable data and suppressing the data tagged for exclusion. From the neural network, the data can then be output to a user to provide accurate readings for proper analysis of the performance of the joint implant.

In one aspect of the disclosure, a join implant may include a first implant coupled to a first bone of a joint, and a second implant coupled to a second bone of the joint adjacent the first implant. The second implant may include a plurality of sensors configured to measure data, and a processor operatively coupled to the plurality of sensors and adapted to receive the data from the sensors. The processor may be adapted to communicate with a neural network and a detector configured to exclude a first portion of the data received from the processor and output a second portion of the data.

Further to the joint implant according to this aspect of the disclosure, the plurality of sensors may be Hall sensor assemblies. Each of the plurality of the Hall sensor assemblies may be configured to measure positioning and movement data of the joint implant. Each of the plurality of the Hall sensor assemblies may be configured to measure a coordinate in an X-direction, a coordinate in a Y-direction, and a coordinate in a Z-direction. The processor may be configured to identify data received from one of the plurality sensors that is inconsistent with data received from other sensors of the plurality of sensors. The processor may be configured to identify data received from one of the plurality sensors that is inconsistent with data received from other sensors of the plurality of sensors. The processor may be configured to tag the flawed data set. The first portion of the first type of data may be inaccurate data and the second portion of the first type of data may be accurate data. The channel detector may be configured to arrange data from each of the plurality of sensors into a corresponding channel. The channel detector may be configured to select channels based on a presence of a data tag with each channel. The channel detector may be configured to automatically omit a channel including the data tag. The channel detector may be configured to automatically omit a channel including improper data. The channel detector may be configured to output all channels excluding the channel including improper data to be viewed by a user. The processor may be configured to communicate with an external source including a channel detector. The external source may be adapted to communicate with the neural network. The channel detector may be disposed within the implant and operatively coupled to the processor. The plurality of sensors may be automatically activated according to a timed schedule. The plurality of sensors may be activated when brought into proximity with an external source. The plurality of sensors may be manually activated by a user.

According to another aspect of the disclosure a system for tracking a joint implant may include a joint implant including a first implant coupled to a first bone of a joint, a second implant coupled to a second bone of the joint and contacting the first implant, and a channel detector operatively coupled to the processor to detect the channels containing the data and select the channels containing the data to output to a user. The second implant may include a plurality of sensors configured to measure data and a processor operatively coupled to the plurality of sensors and adapted to arrange the data into channels. The channel detector may exclude a channel from selection to output remaining channels to the user.

Further to the system for tracking a joint implant according to this aspect of the disclosure, the system may include an external source operatively coupled to the processor of the joint implant, wherein the external source is connected to a neural network adapted to receive the data from the processor. The external source may include the channel detector disposed therein. The second implant may include an antenna configured to operatively couple the processor to the external source. The processor may be configured to arrange data measured by each of the plurality of sensors into corresponding data packets. The processor may be configured to identify inaccurate data measured by any one of the plurality of sensors. The processor may be configured to tag the inaccurate data measured by the any one of the plurality of sensors. The channel detector may identify the data tag. The channel detector may exclude the tagged data from selection.

According to another aspect of the disclosure, a method of monitoring implant performance may include measuring data with a plurality of sensors provided in a joint implant; identifying inaccurate data recorded by at least one of the plurality of sensors; and selecting a sensor or group of sensors among the plurality of sensors from which data will be used to output to a user; wherein the selecting step includes omitting at least one of the plurality of sensors having improper data as determined in the identifying step.

Further to the method of monitoring implant performance according to this aspect of the disclosure, the method may further include tagging the improper data with a data tag to be automatically identified among the data measured by the plurality of sensors. A channel detector may automatically omit the channel having the data tag. The method may further include arranging the data measured by each of the plurality of sensors into a corresponding channel. The method may further include detecting each of the channels and the corresponding data of each channel with a channel detector. The method may further include communicating the channel detector with a neural network. The step of selecting may include communicating the channel detector with the neural network to select which channels to output. The plurality of sensors may be Hall sensor assemblies configured to measure positioning and movement data. The data may be measured automatically according to a timed schedule. The data may be measured automatically when the joint implant is brought into proximity with an external device. The data may be measured upon manual activation by a user. The method may further include outputting the selected data to a user.

According to another aspect of the disclosure, a method for monitoring implant performance may include coupling a first implant to a first bone of a joint; coupling a second implant to a second bone of the joint, the second implant configured to contact the first implant, the second implant including a plurality of sensors; measuring data with the plurality of sensors; identifying improper data recorded by at least one of the plurality of sensors; and selecting a group of sensors among the plurality of sensors from which data will be used to output to a user. The selecting step may include omitting at least one of the plurality of sensors having improper data as determined in the identifying step. In accordance with an aspect of the present disclosure a joint implant is provided. A joint implant according to this aspect, may include a first implant coupled to a first bone of a joint and a second implant coupled to a second bone of the joint. The first implant may include at least one marker. The second implant may contact the first implant. The second implant may include at least one marker reader to detect a position of the marker to identify positional data of the first implant with respect to the second implant. The second implant may include at least one load sensor to measure load data between the first and second implants. A processor may be operatively coupled to the marker reader and the load sensor. The processor may simultaneously output the positional data and the load data to an external source.

Continuing in accordance with this aspect, the marker may be a magnet and the marker reader may be a magnetic sensor. The magnetic sensor may be a Hall sensor assembly including at least one Hall sensor. The magnet may be a magnetic track disposed along a surface of the first implant. The first implant may include a first magnetic track extending along a medial side of the first implant and a second magnetic track extending along a lateral side of the first implant.

Continuing in accordance with this aspect, the second implant may include a first Hall sensor assembly on a medial side of the second implant and a second Hall sensor assembly on a lateral side of the second implant. The first Hall sensor assembly may be configured to read a magnetic flux density of the first magnetic track and the second Hall sensor assembly configured to read a magnetic flux density of the second magnetic track.

Continuing in accordance with this aspect, a central portion of the first magnetic track may be narrower than an anterior end and a posterior end of the first magnetic track. The first magnetic track may include curved magnetic lines extending across the first magnetic track.

Continuing in accordance with this aspect, the magnetic sensor may be coupled to the load sensor by a connecting element. The connecting element may be a rod configured to transmit loads from the magnetic sensor to the load sensor. The load sensor may be a strain gauge.

Continuing in accordance with this aspect, the joint may be a knee joint. The first implant may be a femoral implant and the second implant may be a tibial implant. The tibial implant may include a tibial insert and a tibial stem. The marker reader and the processor may be disposed within the tibial insert.

Continuing in accordance with this aspect, the positional data may include any of a knee flexion angle, knee varus-valgus rotation, knee internal-external rotation, knee medial-lateral translation, superior-inferior translation, anterior-posterior translation, and time derivatives thereof. The load data may include any of a medial load magnitude, lateral load magnitude, medial load center and lateral load center. The tibial insert may include any of a pH sensor, a temperature sensor and a pressure sensor operatively coupled to the processor. The tibial insert may include a spectroscopy sensor. The tibial insert may be made of polyethylene.

Continuing in accordance with this aspect, the joint implant may include an antenna to transmit the positional data and the load data to an external source. The external source may be any of a tablet, computer, smart phone, and remote workstation.

In accordance with another aspect of the present disclosure, a joint implant is provided. A joint implant according to this aspect, may include a first implant coupled to a first bone of a joint and a second implant coupled to a second bone of the joint. The first implant may include a plurality of medial markers located on a medial side of the first implant, and a plurality of lateral markers located on a lateral side of the first implant. The second implant may contact the first implant. The second implant may include at least one medial marker reader to identify a position of the medial markers and at least one lateral marker reader to identify a position of the lateral markers. The position of the medial markers and the position of the lateral markers may provide positional data of the first implant with respect to the second implant. The second implant may include a medial load sensor to measure medial load data between the first and second implants on a medial side of the joint implant, a lateral load sensor to measure lateral load data between the first and second implants on a lateral side of the joint implant. A processor may be operatively coupled to the medial marker reader, the lateral marker reader, the medial load sensor, and the lateral load sensor. The processor may simultaneously output the positional data, the medial load data, and the lateral load data to an external source.

Continuing in accordance with this aspect, a number of medial markers may be different from a number of lateral markers. The medial markers and the lateral markers may include magnets located at discrete locations on the first implant. The medial marker reader and the lateral marker reader may include a Hall sensor assembly with at least one Hall sensor. The medial load sensor and the lateral load sensor may include piezo stacks.

Continuing in accordance with this aspect, the joint implant may include a battery disposed within the second implant. The joint implant may include a charging circuit disposed within the second implant to charge the battery using power generated by the piezo stacks during loading between the first and second implants.

Continuing in accordance with this aspect, the joint may be a knee joint. The first implant may be a femoral implant and the second implant may be a tibial implant. The tibial implant may include a tibial insert and a tibial stem. The marker reader and the processor may be disposed within the tibial insert. The positional data may include any of a knee flexion angle, knee varus-valgus rotation, knee internal-external rotation, knee medial-lateral translation, anterior-posterior translation, superior-inferior translation, and time derivatives thereof.

Continuing in accordance with this aspect, the medial load data may include a medial load magnitude and a medial load center. The tibial insert may include any of a pH sensor, a temperature sensor, accelerometer, gyroscope, inertial measure unit and a pressure sensor operatively coupled to the processor. The tibial insert may include a spectroscopy sensor.

In accordance with another aspect of the present disclosure, a joint implant system is provided. A joint implant system according to this aspect, may include a first implant coupled to a first bone of a joint, a second implant coupled to a second bone of the joint, and an external sleeve configured to be removably attached to the joint. The first implant may include at least one marker. The second implant may contact the first implant. The second implant may include at least one marker reader to detect a position of the marker to identify positional data of the first implant with respect to the second implant. The second implant may include at least one load sensor to measure load data between the first and second implants. A processor may be operatively coupled to the marker reader and the load sensor. The processor may be configured to simultaneously output the positional data and the load data to an external source.

Continuing in accordance with this aspect, the joint implant system may include a battery to power the marker reader and the processor. The battery may be disposed within the second implant and including a joint implant charging coil. The external sleeve may include an external charging coil to charge the battery. The battery may be configured to be charged by ultrasonic wireless charging or optical charging.

In accordance with another aspect of the present disclosure, a method for monitoring a joint implant performance is provided. A method according to this aspect, may include the steps of providing a first implant couplable to a first bone of a joint, providing a second implant couplable to a second bone of the joint, tracking magnetic flux density magnitudes over time using a magnetic sensor, and initiating a warning when a tracked magnetic flux density magnitude is different from a predetermined value. The first implant may include at least one magnetic marker. The second implant may be configured to contact the first implant. The second implant may include at least one magnetic sensor to detect the magnetic flux density of the magnetic marker. The magnetic flux density value may be proportional to a thickness of the second implant.

In accordance with another aspect of the present disclosure, a method for monitoring a joint implant performance is provided. A method according to this aspect, may include the steps of providing a first implant couplable to a first bone of a joint, providing a second implant couplable to a second bone of the joint, tracking a rate of change of a magnetic flux density over time using a magnetic sensor, and initiating a warning when a tracked rate of change of the magnetic flux density exceeds a predetermined value. The first implant may include at least one magnetic marker. The second implant may be configured to contact the first implant. The second implant may include at least one magnetic sensor to detect the magnetic flux density of the magnetic marker. The rate of change of the magnetic flux density may be proportional to a wear rate of the second implant.

In accordance with another aspect of the present disclosure, a method of monitoring implant performance is provided. A method according to this aspect, may include the steps of providing an implant with a first sensor to detect implant temperature, a second sensor to detect a fluid pressure, and a third sensor to detect implant alkalinity, tracking and outputting implant temperature, implant pressure and implant alkalinity over time to an external source using a processor disposed within the implant, and initiating a notification when any of the implant temperature, implant pressure and implant alkalinity, or any combination thereof, exceeds a predetermined value. The implant temperature, implant pressure and implant alkalinity may be related to any of an implant failure and an implant infection. The fluid pressure may be a synovial fluid pressure.

In accordance with an aspect of the present disclosure, a method for performing surgery is provided. A method according to this aspect, may include the steps of receiving first information related to a first implant, receiving second information related to a second implant, selecting an algorithm based on the first and second information, and receiving data from the first and second implants utilizing the algorithm.

Continuing in accordance with this aspect, the first information may be a size of the first implant and the second information may be a size of the second implant. The first implant may be implanted on a first bone and the second implant may be implanted on a second bone. The first implant may include a marker and the second implant may include a reader. The marker may be a magnet and the reader may be a magnetic sensor. The magnetic sensor may be a Hall sensor assembly including at least one Hall sensor. The first and second information may be manually inputted. The information as to the first and second sizes may be received from an RFID chip. The first and second information may be determined by magnetic readings.

Continuing in accordance with this aspect, the algorithm may be included in a software package in communication with the reader. The data may include kinematic information.

In accordance with another aspect of the present disclosure, a joint replacement system is provided. A joint replacement system according to this aspect, may include a first implant having a marker, a second implant having a reader to detect the marker, and a processor in communication with the second implant. The processor may include different algorithms based on the first and second implants. The processor may include different algorithms based on a size of the first and second implants.

Continuing in accordance with this aspect, the first implant may be a femoral implant and the second implant may be a tibial implant. The marker may be a magnet and the reader may be a magnetic sensor. The magnetic sensor may be a Hall sensor assembly including at least one Hall sensor. The processor may receive kinematic information from the reader. The first implant may include a first RFID chip and the second implant may include a second RFID chip. The first and second RFID chips may provide implant size information to the processor.

In accordance with another aspect of the present disclosure, a surgical procedure is disclosed. A surgical procedure according to this aspect, may include the steps of implanting a first implant on a first bone, implanting a second implant on a second bone, connecting a reader with a processor, providing the processor with a first size of the first implant and a second size of the second implant, and reviewing data obtained by the processor. The data may be based upon the first and second sizes. The first implant may include a marker. The second implant may include a reader. The reader may be configured to detect the marker.

Continuing in accordance with this aspect, the providing step may include manually inputting the first and second sizes. The providing step may include receiving the first and second sizes from RFID chips. The providing step may include receiving the first and second sizes from magnetic readings.

In accordance with an aspect of the present disclosure a joint implant is provided. A joint implant according to this aspect, may include a first implant coupled to a first bone of a joint and a second implant coupled to a second bone of the joint. The first implant may include at least one marker. The second implant may contact the first implant. The second implant may include at least one marker reader to detect a position of the marker to identify positional data of the first implant with respect to the second implant. The second implant may include at least one load sensor to measure load data between the first and second implants. A processor may be operatively coupled to the marker reader and the load sensor. The processor may simultaneously output the positional data and the load data to an external source.

Continuing in accordance with this aspect, the marker may be a magnet and the marker reader may be a magnetic sensor. The magnetic sensor may be a Hall sensor assembly including at least one Hall sensor. The magnet may be a magnetic track disposed along a surface of the first implant. The first implant may include a first magnetic track extending along a medial side of the first implant and a second magnetic track extending along a lateral side of the first implant.

Continuing in accordance with this aspect, the second implant may include a first Hall sensor assembly on a medial side of the second implant and a second Hall sensor assembly on a lateral side of the second implant. The first Hall sensor assembly may be configured to read a magnetic flux density of the first magnetic track and the second Hall sensor assembly configured to read a magnetic flux density of the second magnetic track.

Continuing in accordance with this aspect, a central portion of the first magnetic track may be narrower than an anterior end and a posterior end of the first magnetic track. The first magnetic track may include curved magnetic lines extending across the first magnetic track.

Continuing in accordance with this aspect, the magnetic sensor may be coupled to the load sensor by a connecting element. The connecting element may be a rod configured to transmit loads from the magnetic sensor to the load sensor. The load sensor may be a strain gauge.

Continuing in accordance with this aspect, the joint may be a knee joint. The first implant may be a femoral implant and the second implant may be a tibial implant. The tibial implant may include a tibial insert and a tibial stem. The marker reader and the processor may be disposed within the tibial insert.

Continuing in accordance with this aspect, the positional data may include any of a knee flexion angle, knee varus-valgus rotation, knee internal-external rotation, knee medial-lateral translation, superior-inferior translation, anterior-posterior translation, and time derivatives thereof. The load data may include any of a medial load magnitude, lateral load magnitude, medial load center and lateral load center. The tibial insert may include any of a pH sensor, a temperature sensor and a pressure sensor operatively coupled to the processor. The tibial insert may include a spectroscopy sensor. The tibial insert may be made of polyethylene.

Continuing in accordance with this aspect, the joint implant may include an antenna to transmit the positional data and the load data to an external source. The external source may be any of a tablet, computer, smart phone, and remote workstation.

In accordance with another aspect of the present disclosure, a joint implant is provided. A joint implant according to this aspect, may include a first implant coupled to a first bone of a joint and a second implant coupled to a second bone of the joint. The first implant may include a plurality of medial markers located on a medial side of the first implant, and a plurality of lateral markers located on a lateral side of the first implant. The second implant may contact the first implant. The second implant may include at least one medial marker reader to identify a position of the medial markers and at least one lateral marker reader to identify a position of the lateral markers. The position of the medial markers and the position of the lateral markers may provide positional data of the first implant with respect to the second implant. The second implant may include a medial load sensor to measure medial load data between the first and second implants on a medial side of the joint implant, a lateral load sensor to measure lateral load data between the first and second implants on a lateral side of the joint implant. A processor may be operatively coupled to the medial marker reader, the lateral marker reader, the medial load sensor, and the lateral load sensor. The processor may simultaneously output the positional data, the medial load data, and the lateral load data to an external source.

Continuing in accordance with this aspect, a number of medial markers may be different from a number of lateral markers. The medial markers and the lateral markers may include magnets located at discrete locations on the first implant. The medial marker reader and the lateral marker reader may include a Hall sensor assembly with at least one Hall sensor. The medial load sensor and the lateral load sensor may include piezo stacks.

Continuing in accordance with this aspect, the joint implant may include a battery disposed within the second implant. The joint implant may include a charging circuit disposed within the second implant to charge the battery using power generated by the piezo stacks during loading between the first and second implants.

Continuing in accordance with this aspect, the joint may be a knee joint. The first implant may be a femoral implant and the second implant may be a tibial implant. The tibial implant may include a tibial insert and a tibial stem. The marker reader and the processor may be disposed within the tibial insert. The positional data may include any of a knee flexion angle, knee varus-valgus rotation, knee internal-external rotation, knee medial-lateral translation, anterior-posterior translation, superior-inferior translation, and time derivatives thereof.

Continuing in accordance with this aspect, the medial load data may include a medial load magnitude and a medial load center. The tibial insert may include any of a pH sensor, a temperature sensor, accelerometer, gyroscope, inertial measure unit and a pressure sensor operatively coupled to the processor. The tibial insert may include a spectroscopy sensor.

In accordance with another aspect of the present disclosure, a joint implant system is provided. A joint implant system according to this aspect, may include a first implant coupled to a first bone of a joint, a second implant coupled to a second bone of the joint, and an external sleeve configured to be removably attached to the joint. The first implant may include at least one marker. The second implant may contact the first implant. The second implant may include at least one marker reader to detect a position of the marker to identify positional data of the first implant with respect to the second implant. The second implant may include at least one load sensor to measure load data between the first and second implants. A processor may be operatively coupled to the marker reader and the load sensor. The processor may be configured to simultaneously output the positional data and the load data to an external source.

Continuing in accordance with this aspect, the joint implant system may include a battery to power the marker reader and the processor. The battery may be disposed within the second implant and including a joint implant charging coil. The external sleeve may include an external charging coil to charge the battery. The battery may be configured to be charged by ultrasonic wireless charging or optical charging.

In another aspect of the present disclosure, a method for monitoring a joint implant performance is provided. A method according to this aspect, may include the steps of providing a first implant couplable to a first bone of a joint, providing a second implant couplable to a second bone of the joint, tracking magnetic flux density magnitudes over time using a magnetic sensor, and initiating a warning when a tracked magnetic flux density magnitude is different from a predetermined value. The first implant may include at least one magnetic marker. The second implant may be configured to contact the first implant. The second implant may include at least one magnetic sensor to detect the magnetic flux density of the magnetic marker. The magnetic flux density value may be proportional to a thickness of the second implant.

In accordance with another aspect of the present disclosure, a method for monitoring a joint implant performance is provided. A method according to this aspect, may include the steps of providing a first implant couplable to a first bone of a joint, providing a second implant couplable to a second bone of the joint, tracking a rate of change of a magnetic flux density over time using a magnetic sensor, and initiating a warning when a tracked rate of change of the magnetic flux density exceeds a predetermined value. The first implant may include at least one magnetic marker. The second implant may be configured to contact the first implant. The second implant may include at least one magnetic sensor to detect the magnetic flux density of the magnetic marker. The rate of change of the magnetic flux density may be proportional to a wear rate of the second implant.

In accordance with another aspect of the present disclosure, a method of monitoring implant performance is provided. A method according to this aspect, may include the steps of providing an implant with a first sensor to detect implant temperature, a second sensor to detect a fluid pressure, and a third sensor to detect implant alkalinity, tracking and outputting implant temperature, implant pressure and implant alkalinity over time to an external source using a processor disposed within the implant, and initiating a notification when any of the implant temperature, implant pressure and implant alkalinity, or any combination thereof, exceeds a predetermined value. The implant temperature, implant pressure and implant alkalinity may be related to any of an implant failure and an implant infection. The fluid pressure may be a synovial fluid pressure.

In accordance with another aspect of the present disclosure, a method of determining kinematic information of a joint is provided. A method according to this aspect, may include the steps of receiving data obtained from a sensor of an implanted joint implant, analyzing the data with a trained estimation model to simultaneously determine kinematic information of the joint in six degrees of freedom, and outputting the kinematic information.

Continuing in accordance with this aspect, the sensor may be a Hall sensor. The joint implant may further include at least one magnet.

Continuing in accordance with this aspect, the joint may be a knee joint and the implanted joint implant may include femoral and tibial components. The femoral component may include a plurality of magnets and the tibial component include a Hall sensor.

Continuing in accordance with this aspect, the method may include a step of training the estimation model. The step of training the estimation model may include obtaining data from a prototype. The data may pertain to different poses of the prototype. The data may be obtained through the use of a robot. The data may be obtained through the use of video motion capture. The step of training the estimation model may include creating a finite element analysis. The step of training the estimation model may further include obtaining data from a prototype.

Continuing in accordance with this aspect, the method may further comprise determining a model error.

Continuing in accordance with this aspect, the implanted joint implant may be any of a knee implant, shoulder implant, hip implant, and spine implant.

In accordance with another aspect of the present disclosure, a method of determining kinematic information of a joint is provided. A method according to this aspect, may include the steps of applying data obtained from a Hall sensor of an implanted joint implant to a trained estimation model to simultaneously determine kinematic information of the joint in six degrees of freedom, and outputting the kinematic information.

Continuing in accordance with this aspect, the joint implant may include at least one magnet.

Continuing in accordance with this aspect, the joint may be a knee joint and the implanted joint implant includes femoral and tibial components. The femoral component may include a plurality of magnets and the tibial component may include the Hall sensor.

Continuing in accordance with this aspect, the outputting step may include providing a visual model of the kinematic information. The visual model may be a graphical representation of the motion of bones of the joint.

Continuing in accordance with this aspect, the implanted joint implant may be any of a knee implant, shoulder implant, hip implant, and spine implant.

In accordance with another aspect of the present disclosure, a method of determining kinematic information of a knee joint is provided. A method according to this aspect, may comprise the steps of applying data obtained from the cooperation of a magnet of a femoral component and a Hall sensor of a tibial component to a trained estimation model to simultaneously determine kinematic information of the knee joint in six degrees of freedom, and outputting the kinematic information as a visual representation depicting the movement of the femur and the tibia.

In accordance with another aspect of the present disclosure, a method of determining kinematic information of a joint comprising is provided. A method according to this aspect, may include the steps of applying data obtained from a simulation of a Hall sensor on a joint implant model to a trained estimation model to simultaneously determine kinematic information of the joint in six degrees of freedom, and outputting the kinematic information.

In accordance with another aspect of the present disclosure, a kinematic tracking system is provided. A kinematic tracking system according to this aspect, may include a first tracker attached to a first bone of a joint, a second tracker attached to a second bone of the joint, and a wearable for the joint having first and second sensors. The first sensor may detect a first magnetic field of the first tracker and the second sensor may detect a second magnetic field of the second magnet.

Continuing in accordance with this aspect, the first tracker may include a first magnet. The second tracker may include a second magnet. The wearable may be a brace. The wearable may include first and second portions. The first portion may be located adjacent the first bone and the second portion may be located adjacent the second bone. The first and second trackers may be bone attachment members. The bone attachment members may be threaded shafts.

Continuing in accordance with this aspect, the first and second sensors may be Hall sensors. The brace may include first and second portions connected by a hinge mechanism. The joint may be a knee joint. The brace may include inner spaces for receiving the first and second sensors.

Continuing in accordance with this aspect, the joint may be a knee joint and the first tracker may be attached to the femur and the second tracker may be attached to the tibia. The kinematic tracking system may further include third and fifth trackers attached to the femur and fourth and sixth tackers attached on the tibia.

Continuing in accordance with this aspect, the kinematic tracking system may further include a third sensor for detecting movement of the third tracker, a fourth sensor for detecting movement of the fourth tracker, a fifth sensor for detecting movement of the fifth tracker and a sixth sensor for detecting movement of the sixth tracker.

Continuing in accordance with this aspect, the first sensor may detect a position of the first tracker via the first magnetic field and the second sensor may detect a position of the second tracker via the second magnetic field.

In accordance with another aspect of the present disclosure, a brace for a joint is provided. A brace according to this aspect, may include a first portion associated with a first bone of the joint, a second portion associated with a second bone of the joint, a first ultrasound sensor located in the first portion, and a second ultrasound sensor located in the second portion. The first and second ultrasound sensors may collect data pertaining to the motion of the joint.

Continuing in accordance with this aspect, the joint may be a knee joint and the first bone may be a femur and the second bone may be a tibia. The first and second portions may be connected by a hinge mechanism. The first portion may further include third, fourth and fifth ultrasound sensors and the second portion may further include sixth, seventh and eighth ultrasound sensors.

Continuing in accordance with this aspect, the brace may further include a power source. The power source may be a battery included in the brace.

Continuing in accordance with this aspect, the brace may further include a communication mechanism. The communication mechanism may be wired or wireless.

In accordance with another aspect of the present disclosure, a method for tracking kinematic movement of a joint of a patient is provided. A method according to this aspect, may include the steps of attaching a first magnet to a first bone of the joint, attaching a second magnet to a second bone of the joint, and providing the patient with instructions to wear a wearable on the joint. The wearable may have first and second sensors. The first sensor may detect movement of the first magnet and the second sensor may detect movement of the second magnet.

Continuing in accordance with this aspect, the method may further include a step of providing the patient with specific movements of the joint to perform. The method may further include a step of analyzing data received from the first and second sensors.

Disclosed herein are systems and methods for providing peripheral services for an implant with sensors. These services connect an implant with sensors to a remote monitoring platform, which is utilized to track and monitor the performance of the implant. The system and method disclosed herein enables the remote monitoring platform to receive data from the implant with sensors in real-time, allowing for a more accurate assessment of the implant's performance. Furthermore, this system and method provides a secure connection between the implant with sensors and the remote monitoring platform, ensuring the integrity of the data being transmitted. The system and method of the present disclosure offer a comprehensive solution for providing peripheral services between an implant with sensors and a remote monitoring platform for tracking implant performance.

In accordance with an aspect of the present disclosure a method for monitoring implant performance is provided. A method according to this aspect, may include the steps of creating a patient account on a patient monitoring platform, determining sensor information to be measured from one or more sensors disposed on an implant coupled to a patient using the patient account, determining a duration during which sensor information is collected and transferred from the one or more sensors to the patient monitoring platform, analyzing sensor information received from the one or more sensors on the patient account via an external device, and communicating corrective steps from the external device to the patient or the implant via the patient account. The corrective steps may be communicated to an HCP.

Continuing in accordance with this aspect, the step of determining sensor information to be measured may include the step of measuring sensor information from any of a pH sensor, a temperature sensor, an accelerometer, a gyroscope, an inertial measurement unit, a Hall sensor, and a pressure sensor disposed on the implant.

Continuing in accordance with this aspect, the implant may be a knee joint implant. The knee joint implant may include a femoral component coupled to the patient's femur and a tibial component coupled to the patient's tibia. The femoral component may include one or more magnets and the one or more sensors may be disposed in the tibial component. The sensor information may include any of a knee flexion angle, knee varus-valgus rotation, knee internal-external rotation, knee medial-lateral translation, superior-inferior translation, anterior-posterior translation, and time derivatives thereof. The superior-inferior translation may represent a physical gap between the tibial and femoral component for medial and lateral condyles. The sensor information may include any of a pH, temperature, and pressure value.

Continuing in accordance with this aspect, the implant may be any of a hip implant, shoulder implant, and ankle implant.

Continuing in accordance with this aspect, any of the steps of creating the patient account, determining sensor information to be measured and determining the duration may be performed by a health care professional or the patient.

Continuing in accordance with this aspect, the step of analyzing sensor information received from the one or more sensors may include using an algorithm to evaluate patient condition and implant condition from the sensor information.

Continuing in accordance with this aspect, the step of communicating corrective steps may include changing the sensor information to be measured from the one or more sensors.

Continuing in accordance with this aspect, the step of communicating corrective steps may include changing the duration during which sensor information is collected and transferred from the one or more sensors.

Continuing in accordance with this aspect, the step of communicating corrective steps may include alerting the patient and the HCP to perform corrective action. The step of communicating corrective steps may be communicated to a patient's personal device. The patient's personal device may be any of a smartphone, tablet, computer, watch, and fob.

Continuing in accordance with this aspect, the implant may include a communication interface to wirelessly communicate with the patient monitoring platform.

Disclosed herein are systems and methods for providing secure authentication and connection between an implant and a remote monitoring platform to track implant performance.

In accordance with an aspect of the present disclosure, a joint implant is provided. A joint implant according to this aspect, may include a first implant coupled to a first bone of a joint, a second implant coupled to a second bone of the joint. a first communication module, and a memory to store authentication information. The first communication module may be configured to wirelessly transfer the authentication information to a communication module of an external device when the external device is placed adjacent the joint implant.

Continuing in accordance with this aspect, the first communication module may be an NFC communication module. The NFC communication module may be configured to transfer the authentication information to the communication module of the external device via NFC. The joint implant may include at least one sensor to measure an interaction between the first and second implants. The authentication information may include joint implant data or patient data. The joint implant may be configured to change from a sleep mode to an advertising mode when the external device is placed adjacent the joint implant.

Continuing in accordance with this aspect, the joint implant may include a second communication module. The second communication module may be any of BLE, Z-wave or Zigbee module. The second communication module may be a BLE module. The BLE module may be configured to transfer the measured interaction between the first and second implants to the communication module of the external device via BLE in the advertising mode.

Continuing in accordance with this aspect, the joint implant may be configured to return to the sleep mode upon transferring the measured interaction. The measured interaction may be any of a load between the first and second implants and position of the first implant with respect to the second implant.

Continuing in accordance with this aspect, the joint implant may be a knee joint implant. The first implant may be a femoral implant and the second implant may be a tibial implant. The tibial implant may include a tibial insert and a tibial stem. The first communication module, the second communication module and the memory may be disposed within the tibial insert.

Continuing in accordance with this aspect, the position of the first implant with respect to the second implant may include any of a knee flexion angle, knee varus-valgus rotation, knee internal-external rotation, knee medial-lateral translation, superior-inferior translation, anterior-posterior translation, and time derivatives thereof.

Continuing in accordance with this aspect, the tibial insert may include any of a pH sensor, a temperature sensor and a pressure sensor operatively coupled to a processor.

Continuing in accordance with this aspect, the external device may be any of a smartphone, tablet, watch, and fob. The joint implant may be any of hip implant, shoulder implant, and ankle implant.

Continuing in accordance with this aspect, the measured interaction may include patient activity data. The patient activity data may include any of a patient's gait and a number of steps taken by the patient in a predetermined interval.

In accordance with another aspect of the present disclosure, an implant system is provided. An implant system according to this aspect, may include an implant coupled to a patient and an external device including a communication module. The implant may include a first communication module, and a memory to store authentication information. The first communication module may be configured to wirelessly transfer the authentication information to the communication module of an external device when the external device is placed adjacent the implant.

Continuing in accordance with this aspect, the communication module may be configured to communicate with a cloud-based service such that the authentication information from the first communication module is authenticated on the cloud-based service.

In accordance with another aspect of the present disclosure, a method for monitoring implant performance is provided. A method according to this aspect, may include the steps of placing an external device adjacent an implant coupled to patient to initiate a first communication between the implant and the external device, authenticating implant information via the first communication, initiating a second communication between the implant and the external device upon successful authentication of the first communication, and transferring implant data from the implant to the external device via the second communication.

Continuing in accordance with this aspect, the first communication may be an NFC communication and the second communication is a BLE communication.

In accordance with an aspect of the present disclosure, an implant system comprises a first implant coupled to a first bone of a joint; a second implant coupled to a second bone of the joint; an acoustic exciter configured to vibrate at least the first or second bones; a transducer to detect a vibration signal of the first implant and the second implant; and a processor operatively coupled to the transducer, the processor configured to output a vibration signature to an external source.

In another aspect, the first implant is a femoral component of a knee implant and the second implant is a tibial component of a knee implant.

In a different aspect, the system further includes an insert located between the femoral component and the tibial component.

In another aspect, the acoustic exciter is an ultrasound exciter.

In a further aspect, the transducer includes first and second transducers, each of the first and second transducers disposed in the tibial insert adjacent a condyle.

In a different aspect, the processor is disposed in the tibial insert.

In another aspect, the processor is configured to wirelessly communicate the vibration signature with the external source.

In a further aspect, the wireless communication is a Bluetooth communication.

In yet another aspect, the system further comprises an analog to digital converter, the converter configured to convert the vibration signal to the vibration signature.

In a different aspect, the vibration signature includes at least one of a response, peak, amplitude, and magnitude of the vibration signal.

In another aspect, a change in the vibration signature over time indicates implant loosening.

In another aspect, a change in the vibration signature over time indicates implant subsidence.

In a further aspect, the external source is any of a computer, tablet, and smartphone.

In a different aspect, the system further comprises a guidance system configured to position the acoustic exciter.

In a further aspect, the guidance system includes an inertial measurement unit.

In another aspect, the inertial measurement unit is located in the first or second implant.

In accordance with another aspect of the present disclosure, a method for monitoring implant movement comprises coupling a first implant to a first bone of a joint; coupling a second implant to a second bone of the joint; sensing a vibration signal emitted through the joint with a sensor positioned in the any of the first or second implants; and outputting a vibration signature from a processor to an external source, the vibration signature converted from the vibration signal.

In another aspect, the coupling steps include coupling the first implant to a femur and coupling the second implant to a tibia.

In a different aspect, the method further comprises a step of vibrating at least one of the first or second bones using an acoustic exciter.

In another aspect, the method further comprises converting the vibration signal to a vibration signature with an analog to digital converter.

In a different aspect, the outputting step includes outputting the vibration signal to a computer.

In another aspect, the outputting step includes outputting the vibration signal at least first time and a second time, the first time being different from the second time.

In a different aspect, the method further comprises creating an alert when a change in vibration signature is detected.

In accordance with another aspect of the present disclosure, a method of monitoring implant position over time comprises coupling a first implant to a first bone of a joint; coupling a second implant to a second bone of the joint, the second implant including an insert contacting the first implant; measuring a reference movement value at a first time; measuring a secondary movement value at a second time; and comparing the reference movement value to the secondary movement value.

In another aspect, the method further comprises measuring transducer data from a transducer embedded in the insert at the first time and at the second time to obtain a first sensor data and a second sensor data respectively.

In a further aspect, the transducer data includes vibration data.

In another aspect, the method further comprises creating an alert when a change between a first and second transducer data exceeds a predetermined value.

In a different aspect, the method further comprises creating an alert when a change between the reference movement value and the secondary movement value exceeds a predetermined value.

In another aspect, the method further comprises comparing at least one of the reference movement value, the secondary movement value, the first sensor data, and the second sensor data with a machine learning algorithm.

In a different aspect, the method further comprises creating an alert when the machine learning algorithm detects a change that exceeds a predetermined value in at least one of the reference movement value, the secondary movement value, the first sensor data, and the second sensor data.

In accordance with another aspect of the present disclosure, a method of measuring joint implant movement over time comprises disposing a first magnet in a first bone of a joint; disposing a second magnet in a second bone the joint; coupling a first implant to the first bone; coupling a second implant to the second bone, the second implant including an insert contacting the first implant; manipulating the joint at a first time such that a first magnetic sensor disposed in the insert registers the first magnet to create first sensor data and a second magnetic sensor disposed in the insert registers the second magnet to create second sensor data; repeating the manipulating movements at a second time; and outputting the first sensor data and the second sensor data from the first time and the second time to an external source.

In another aspect, the method further comprises drilling a hole into a first bone to receive the first magnet and a hole in the second bone to receive the second magnet.

In a different aspect, the method further comprises processing the first and second sensor data with a processor.

In another aspect, the method further comprises outputting the first and second sensor data to the external source with Bluetooth communication.

In a further aspect, the repeating step includes repeating identical manipulating movements of the joint.

In a different aspect, the repeating step includes repeating the manipulating movements at frequent intervals of time.

In another aspect, the magnetic sensor is a Hall sensor.

In a different aspect, the first bone is a femur and the second bone is a tibia.

In a further aspect, the joint is a hip joint.

In another aspect, a change in the first and second sensor data at the second time indicates implant loosening.

In a different aspect, a change in the first and second sensor data at the second time indicates implant subsidence.

In another aspect, the method further comprises comparing the first and second sensor data at the first time with the first and second sensor data at the second time.

In another aspect, the comparing step includes utilizing a finite element analysis model.

In a different aspect, the method further comprises recording the locations of the first and second magnets in the first and second bones.

Disclosed herein are joint implants with sensors and methods for activating sensors in joint implants.

In accordance with an aspect of the present disclosure a joint implant is provided. A joint implant according to this aspect, may include a first implant coupled to a first bone of a joint and a second implant coupled to a second bone of the joint. The second implant may include one or more sensors, a processor, a battery, and a switch. The switch may couple the battery to the processor to power the processor and the one or more sensors when the switch detects a magnetic field strength.

Continuing in accordance with this aspect, the first implant may include a magnet, the magnet generating the magnetic field strength detected by the switch.

Continuing in accordance with this aspect, the magnetic field strength may be generated by an external source. The magnetic field strength may be defined by a predetermined threshold. A distance between the first implant and the second implant may be directly proportional to the magnetic field strength detected by the switch.

Continuing in accordance with this aspect, the joint may be a knee joint. The first implant may be a femoral implant and the second implant may be a tibial implant. The tibial implant may be a tibial insert.

Continuing in accordance with this aspect, the one or more sensors may include at least one marker reader to detect a position of the magnet to identify positional data of the first implant with respect to the second implant. The marker reader may be a Hall sensor.

Continuing in accordance with this aspect, the one or more sensors may include any of a load sensor, pH sensor, a temperature sensor and a pressure sensor operatively coupled to the processor.

Continuing in accordance with this aspect, the joint implant may be any of a shoulder joint, and a hip joint.

Continuing in accordance with this aspect, the switch may be configured to decouple the battery from the processor to deactivate the processor and the one or more sensors when the detected magnetic field strength is below the predetermined threshold.

Continuing in accordance with this aspect, the joint may be a hip joint. The first implant may be a hip insert and the second implant may be a femoral head.

Continuing in accordance with this aspect, the joint may be a shoulder joint. The first implant may a glenoid sphere and the second implant may be a shoulder insert.

Continuing in accordance with this aspect, the switch may include a magnetic sensor to detect the magnetic field strength.

In accordance with another aspect of the present disclosure, a method of activating a processor of a joint implant is provided. A method according to this aspect, may include the steps of coupling a first implant to a first bone of a joint, the first implant may include at least one magnet, and placing a second implant adjacent the first implant to activate a switch in the second implant to couple a battery of the second implant to a processor of the second implant to power the processor and one or more sensors of the second implant. The switch may be activated by detecting a magnetic field strength generated by the magnet.

Continuing in accordance with this aspect, the magnetic field strength may be defined by a predetermined threshold. A distance between the first implant and the second implant may be directly proportional to the magnetic field strength detected by the switch.

Continuing in accordance with this aspect, the joint may be a knee joint. The first implant may be a femoral implant and the second implant may be a tibial implant. The tibial implant may be a tibial insert.

In accordance with an aspect of the present disclosure, a knee joint implant comprises: a femoral implant coupled to a femur of the patient, the femoral implant including at least one marker; a patellar implant coupled to a patella of a patient, the patellar implant including: at least one marker reader to detect a position of the marker to identify positional data of the patellar implant with respect to the femoral implant, and a processor operatively coupled to the marker reader, wherein the processor outputs the positional data to an external source.

In a different aspect, the marker is a magnet and the marker reader is a magnetic sensor.

In another aspect, the magnetic sensor is a Hall sensor assembly including at least one Hall sensor.

In a different aspect, the magnet is a magnetic track disposed along a surface of the femoral implant.

In another aspect, the femoral implant includes a first magnetic track extending along a medial side of the first implant and a second magnetic track extending along a lateral side of the femoral implant.

In a further aspect, the patellar implant includes a first Hall sensor assembly on a medial side of the patellar implant and a second Hall sensor assembly on a lateral side of the patellar implant, the first Hall sensor assembly configured to read a magnetic flux density of the first magnetic track and the second Hall sensor assembly configured to read a magnetic flux density of the second magnetic track.

In yet another aspect, a central portion of the first magnetic track is narrower than an anterior end and a posterior end of the first magnetic track.

In another aspect, the first magnetic track includes curved magnetic lines extending across the first magnetic track.

In a different aspect, the magnetic sensor is coupled to a load sensor by a connecting element.

In a further aspect, the patellar implant includes any of a pH sensor, a temperature sensor and a pressure sensor operatively coupled to the processor.

In a different aspect, the patellar implant includes a transmitter to transmit the positional data and the load data to an external source.

In another aspect, the external source is any of a tablet, computer, smart phone, and remote workstation.

In a further aspect, an antenna is positioned within the patellar implant.

In a different aspect, the positional data indicates at least one of patellar shift and patellar rotation.

In accordance with another aspect of the present disclosure, a method for monitoring a patellar implant may comprise the steps of coupling a femoral implant to a femur of a joint; coupling a patellar implant to a patella; sensing sensor data with a sensor positioned in the patellar implant, the sensor data indicating a relative position of the patellar implant with reference to the femoral implant; and outputting the sensor data from a processor to an external source.

In a further aspect, the sensing step includes sensing the sensor data from at least one Hall sensor positioned in the patellar implant.

In another aspect, the sensing step further includes sensing magnetic flux density caused by at least one magnet positioned within the femoral implant.

In a different aspect, the outputting step includes gathering sensor data from the sensor, analyzing the sensor data with the processor, storing the sensor data, and emitting the sensor data to an external source.

In another aspect, storing step includes storing the sensor data within a memory system, the memory system including one of RAM, ROM, and flash.

In a different aspect, the outputting step includes outputting the sensor data to the external source via near-field communication.

In another aspect, the method further includes analyzing the sensor data with a machine learning algorithm.

In a different aspect, the analyzing step includes analyzing a first sensor data from a first point in time and comparing it to a second sensor data at a second point in time to determine a change in sensor data.

In another aspect, a change in sensor data indicates patellar tendonitis.

In accordance with another aspect of the present disclosure, a method of monitoring implant position over time comprises: coupling a femoral implant to a first bone of a joint; coupling a patellar implant to a second bone of the joint, the patellar implant including a sensor, a microcontroller, and a power source; measuring a reference movement value at a first time; measuring a secondary movement value at a second time; and comparing the reference movement value to the secondary movement value.

In another aspect, the coupling steps include coupling the femoral implant to a femur and coupling the patellar implant to a patella.

In another aspect, the measuring steps include measuring a first magnetic flux from a Hall sensor corresponding to the reference movement and measuring a second magnetic flux from the Hall sensor corresponding to the second movement.

In a further aspect, the measuring steps further include measuring first and second magnetic fluxes caused by magnets imbedded within the femoral implant.

In another aspect, the measuring steps include manipulating the joint in the same orientations at the first time and the second time, the first and second times being different.

In accordance with another aspect of the present disclosure, a method of measuring joint implant movement over time comprises: coupling a femoral implant to a first bone, the femoral implant including a magnet; coupling a patellar implant to a second bone, the patellar implant including a sensor configured to sense a magnetic flux caused by the magnet of the first implant; manipulating the joint at a first time such that the sensor registers a first magnetic flux data; repeating the manipulating step at a second time, the second time being different than the first time such that the sensor registers a second magnetic flux data; and outputting the first and second magnetic flux data from the first time and the second time to an external source.

In another aspect, the method further comprises processing the first and second magnetic flux data with a microcontroller.

In a different aspect, the method further comprises powering the microcontroller with a battery.

In yet another aspect, the method further comprises outputting the first and second magnetic flux data to the external source with Bluetooth communication.

In a different aspect, the method further comprises powering the microcontroller with an inductive coil positioned adjacent the microcontroller.

In another aspect, the powering step includes positioning an external power source adjacent the inductive coil to provide power to the inductive coil and the microcontroller via near-field communication.

In a different aspect, the method further comprises charging a battery when the external power source is positioned adjacent the inductive coil.

In another aspect, the method further comprises outputting the first and second magnetic flux data to the external source via near field communication.

In another aspect, the repeating step includes repeating identical movements of the joint.

In a further aspect, the repeating step includes repeating the manipulating movements at frequent intervals of time.

In another aspect, the sensor is a Hall sensor.

In a different aspect, the first bone is a femur and the second bone is a patella.

In another aspect, the joint is a knee joint.

In a further aspect, a change in the first and second magnetic flux data at the second time indicates patellar shift or patellar rotation.

Disclosed herein are modular joint implants with sensors and methods for assembling modular joint implants with sensors.

In accordance with an aspect of the present disclosure a knee implant is provided. A knee implant according to this aspect, may include a femoral implant configured to be coupled to a femur, and a tibial implant configured to be coupled to a tibia. The tibial implant may include a tibial insert disposed between the femoral implant and a tibial baseplate. The tibial insert may comprise at least one sensor and a battery disposed within a void of the tibial insert, and a detachable case configured to seal an opening of the void. The detachable case may be configured to seal the opening of the void by engaging one or more projections with one or more corresponding recesses of the tibial insert.

Continuing in accordance with this aspect, the at least one sensor and the battery may be located away from a medial central region and a lateral central region of the tibial insert. The at least one sensor and the battery may be disposed with the void in a central region of the tibial insert between the medial central region and the lateral central region. The at least one sensor and the battery may be disposed within the void around a periphery of the detachable case when the detachable case is attached to the tibial insert.

Continuing in accordance with this aspect, the at least one sensor may include a Hall sensors and the femoral implant may include a magnet. The Hall sensor may be configured to track a location of the magnet. The at least one sensor may include a plurality of sensors. The plurality of sensors may include at least one load sensor. The plurality of sensors may include a temperature sensor, a pressure sensor, and a pH sensor. The at least one battery may include a plurality of batteries.

Continuing in accordance with this aspect, the tibial insert may further include a printed circuit board assembly, a processor, a charging coil, and an antenna, all of which are located away from a medial central region and the lateral central region.

Continuing in accordance with this aspect, the detachable case may include the one or more projections. The one or more projections may be any of a tab, barb, and rib. The tibial insert may include the one or more corresponding recesses. The one or more corresponding recesses may be any of a notch, groove and slit. The one or more projections may be living hinges and the one or more recesses may be notches. The living hinges may be configured to engage with a corresponding notch.

Continuing in accordance with this aspect, the detachable case may be configured to hermetically seal the opening.

In accordance with another aspect of the present disclosure, a method for assembling a tibial implant is provided. A method according to this aspect, may include the steps of placing at least one sensor and a battery within a void of a tibial insert, inserting a detachable case into the void, and sealing an opening of the void by engaging at least one projection with a corresponding recess.

Continuing in accordance with this aspect, the step of inserting the detachable case may include inserting the detachable case into an opening of the void located at a posterior end of the tibial insert. The step of sealing the opening may include engaging a living hinge extending from the detachable case with a corresponding notch on the tibial insert to lock the detachable case to the tibial insert and seal the opening of the void.

Continuing in accordance with this aspect, the step of placing the at least one sensor and the battery may be done intra-operatively. The step of placing the at least one sensor and the battery may include a step of placing a sensor module containing the at least one sensor and the battery into the void.

Continuing in accordance with this aspect, the method may further include a step of attaching the tibial insert to a tibial baseplate.

In accordance with an aspect of the present disclosure a shoulder implant is provided. A shoulder implant according to this aspect, may include a glenoid implant coupled to a scapula, the glenoid implant may include at least one marker, and a humeral implant coupled to a humerus and contacting the glenoid implant. The humeral implant may include at least one marker reader to detect a position of the marker to identify positional data of the glenoid implant with respect to the humeral implant, at least one sensor to measure kinematic data between the glenoid and humeral implants, and a processor operatively coupled to the marker reader and the at least one sensor. The processor may output the positional data and the kinematic data to an external source.

Continuing in accordance with this aspect, the processor may output post-operative positional data and post-operative kinematic data to the external source. The at least one sensor may include an inertial measurement unit. The marker may be a magnet and the marker reader may be a magnetic sensor. The magnetic sensor may be a Hall sensor assembly including at least one Hall sensor. The magnetic sensor may include three Hall sensor assemblies. The magnet may be a magnetic track disposed within the glenoid implant. The magnet may include two magnetic tracks coupled to each other within the glenoid implant.

Continuing in accordance with this aspect, the positional data and the kinematic data may include any of a flexion-extension, abduction-adduction, internal-external rotation, lift-off and direction vector of the lift-off of a patient's shoulder.

Continuing in accordance with this aspect, the at least one sensor may include any of a load sensor, pH sensor, temperature sensor and pressure sensor operatively coupled to the processor.

Continuing in accordance with this aspect, the shoulder implant may further include a transmitter to transmit the positional data and the kinematic data to an external source. The external source may be any of a tablet, computer, smart phone, and remote workstation.

In accordance with another aspect of the present disclosure, a method for monitoring a shoulder joint implant performance is provided. A method according to this aspect, may include the steps of coupling a glenoid implant to a first bone of the shoulder joint, the glenoid implant may include at least one magnetic marker, coupling a humeral implant to a second bone of the shoulder joint, the humeral implant may be configured to contact the glenoid implant, the humeral implant may include at least one magnetic sensor to detect a magnetic flux density of the magnetic marker and at least one sensor to measure kinematic data between the glenoid and humeral implants, tracking magnetic flux density magnitudes and kinematic data over time using the magnetic sensor and the at least one sensor, and initiating a warning when a tracked magnetic flux density magnitude and kinematic data differ from a predetermined value.

Continuing in accordance with this aspect, the warning may include any of shoulder dislocation and shoulder impingement.

Continuing in accordance with this aspect, the first bone may be a scapula and the second bone may be a humerus.

Continuing in accordance with this aspect, the at least one sensor may be an inertial measurement unit. The method may further include a step of tracking kinematic data measured by an external inertial measurement unit on the patient's body. The external inertial measurement unit may be located away from the glenoid implant and the humeral implant Continuing in accordance with this aspect, the positional data and the kinematic data may include any of a flexion-extension, abduction-adduction, internal-external rotation, lift-off and direction vector of the lift-off of a patient's shoulder.

Continuing in accordance with this aspect, the steps of tracking magnetic flux density magnitudes and kinematic data and initiating a warning may be performed post-operatively.

Continuing in accordance with this aspect, the method may include a step of transmitting the tracked magnetic flux density magnitudes and kinematic data to an external source. The tracked magnetic flux density magnitudes and kinematic data may be transmitted wirelessly to the external source.

BRIEF DESCRIPTION OF THE DRAWINGS

A more complete appreciation of the subject matter of the present disclosure and the various advantages thereof can be realized by reference to the following detailed description, in which reference is made to the following accompanying drawings:

FIG. 106 is an enlarged view of one of the attached trackers of FIG. 50;

FIG. 107 is a perspective partial view of a knee brace in accordance with another embodiment of the present disclosure disposed on a knee joint;

FIG. 108 is a schematic view of a first communication between an implant and an external device according to an embodiment of the present disclosure;

FIG. 109 is a schematic view of a second communication between the implant and the external device of FIG. 108 according to an embodiment of the present disclosure;

FIG. 110 is a flowchart showing steps of a peripheral service for an implant according to an embodiment of the present disclosure;

FIG. 111 is a flowchart showing steps of the first communication between the implant and the external device of FIG. 108;

FIG. 112 is a flowchart showing steps of the second communication between the implant and the external device of FIG. 108;

FIG. 113 is a flowchart showing steps of a first communication between an implant and an external device according to another embodiment of the present disclosure;

FIG. 114 is a flowchart showing steps of a second communication between the implant and the external device of FIG. 113;

FIG. 115 is a flowchart showing steps of a communication between an implant and a first responder device according to an embodiment of the present disclosure;

FIG. 116 is a front view of a knee joint implant according to an embodiment of the present disclosure;

FIG. 117 is a perspective view of a tibial implant of the knee joint implant of FIG. 116;

Figure 116:
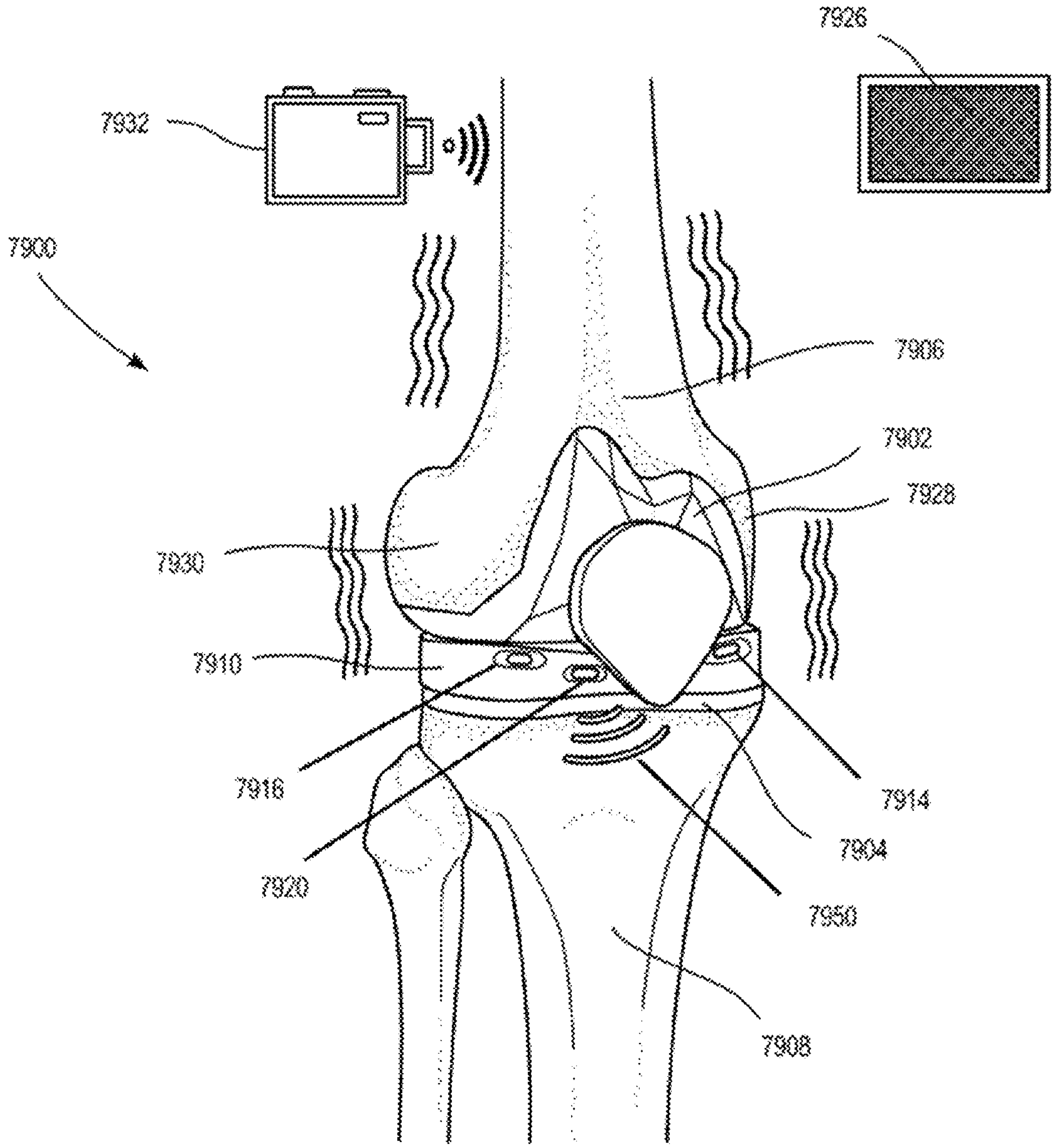
Figure 118:
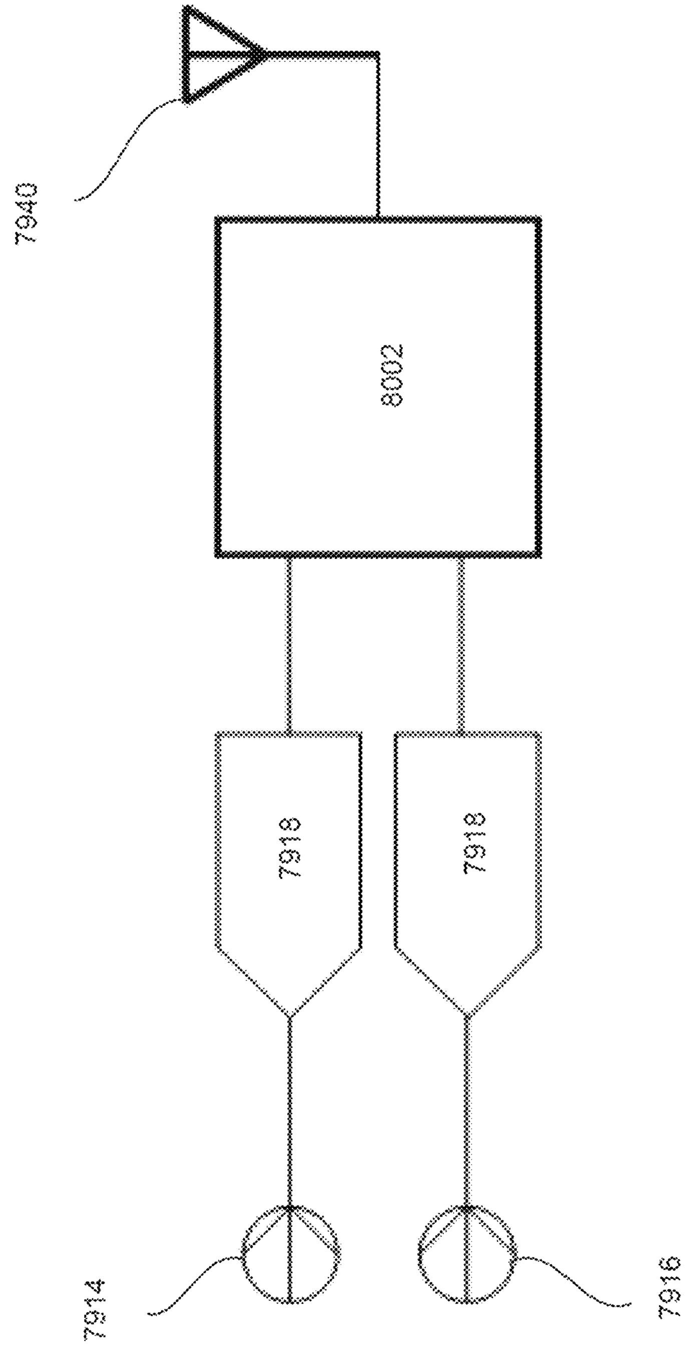
Figure 119:
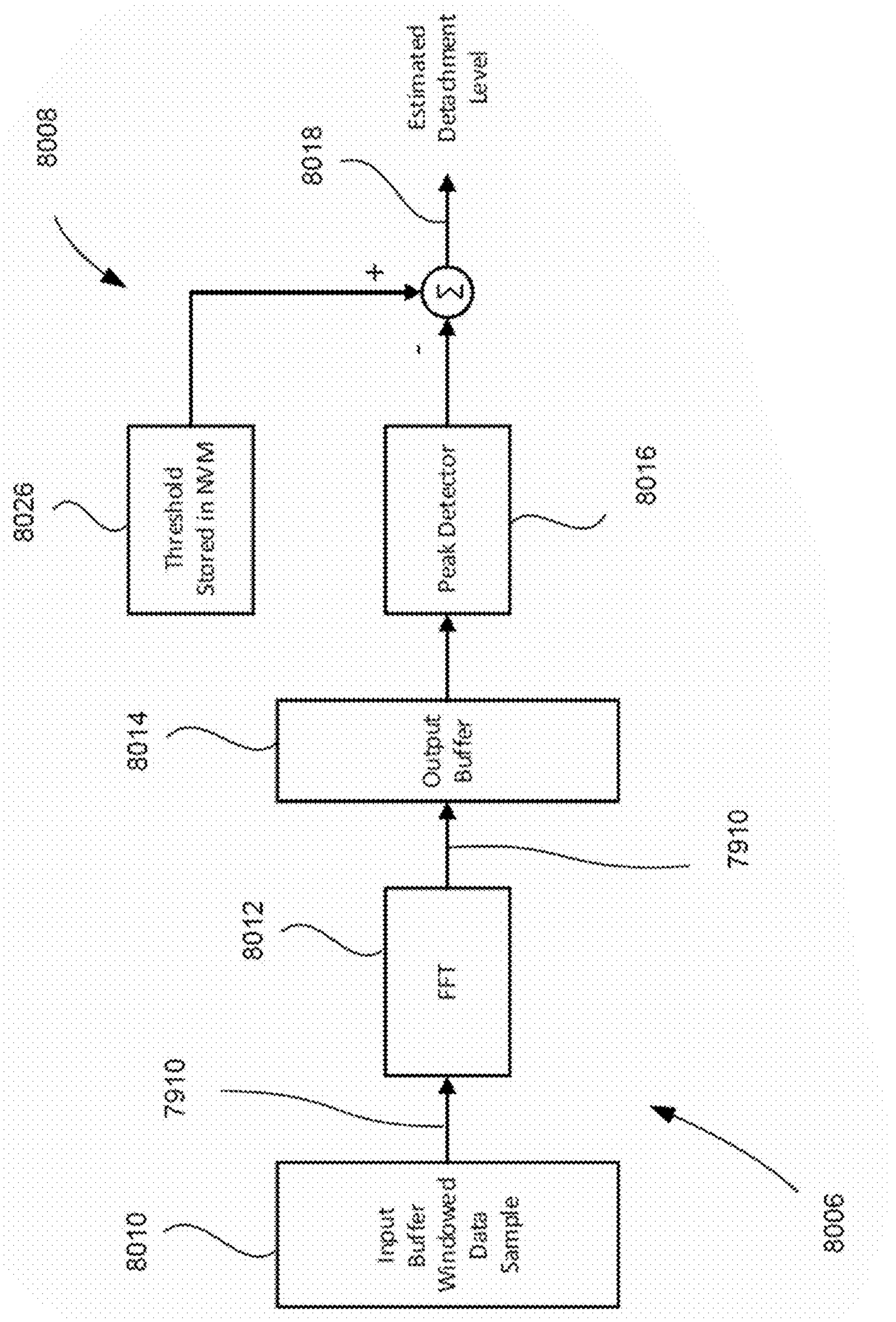
Figure 121:
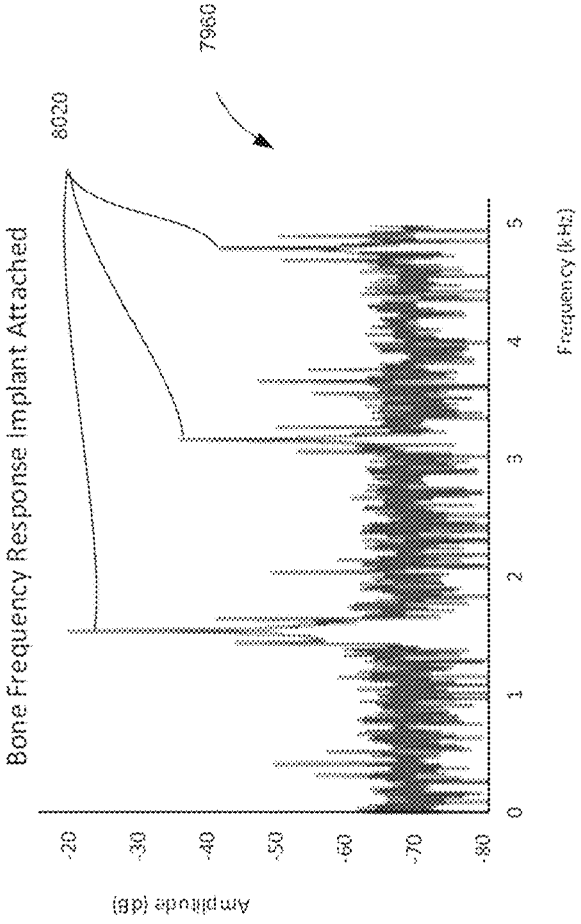
Figure 120:
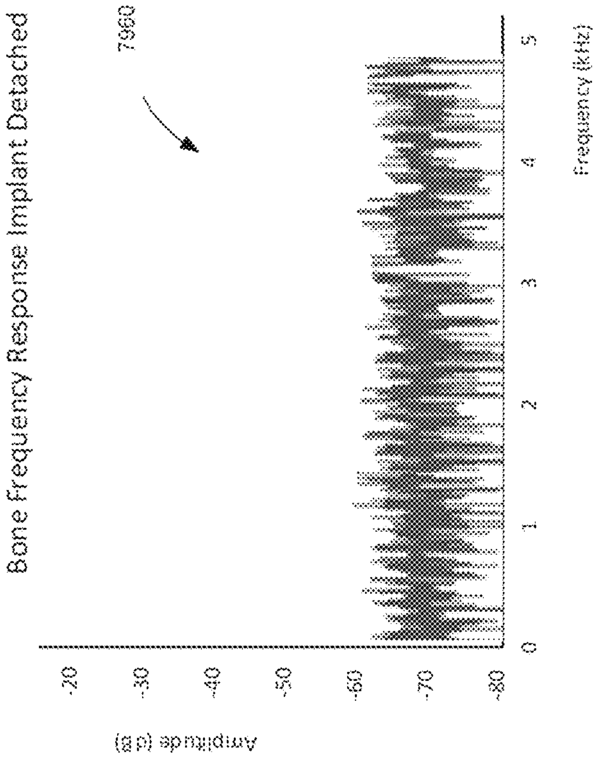
Figure 122:
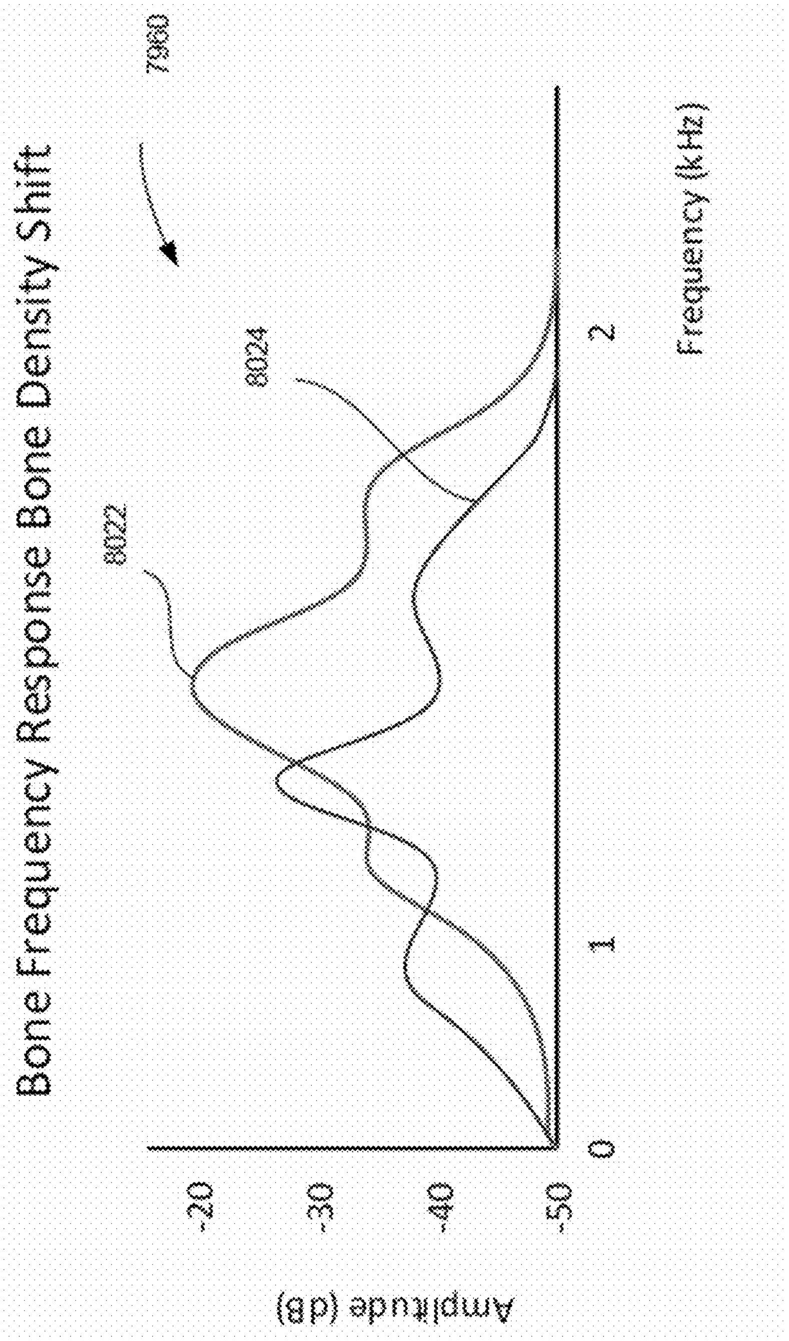
Figure 123:
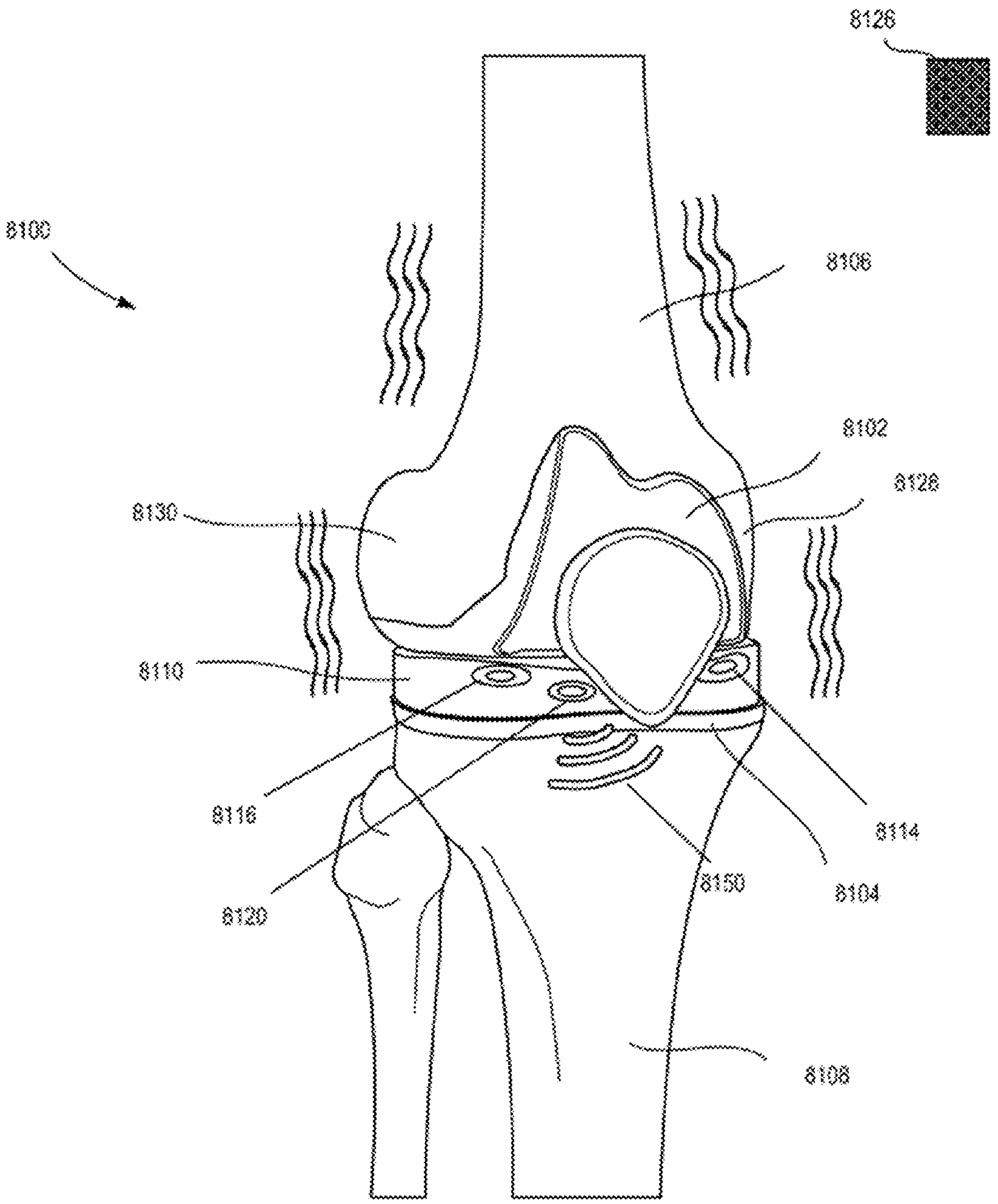
Figure 124:
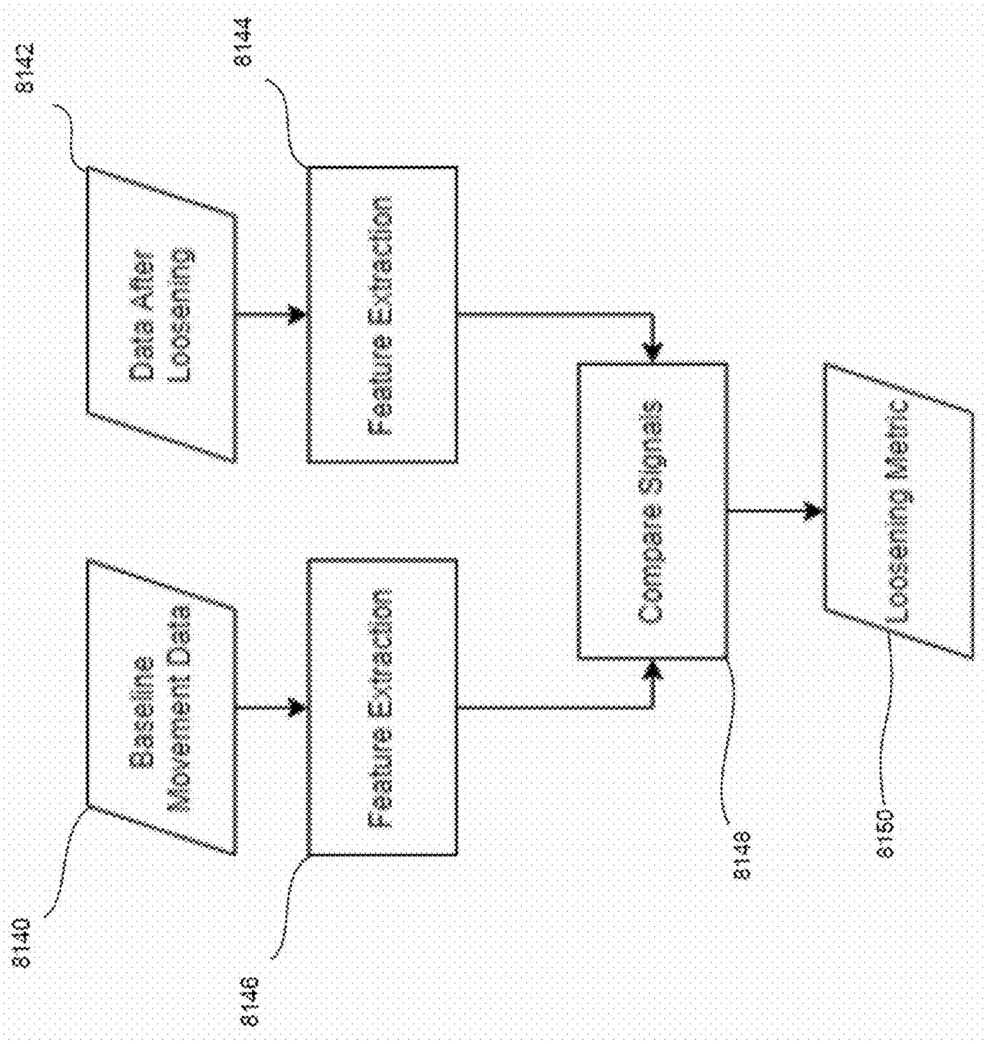
Figure 125:
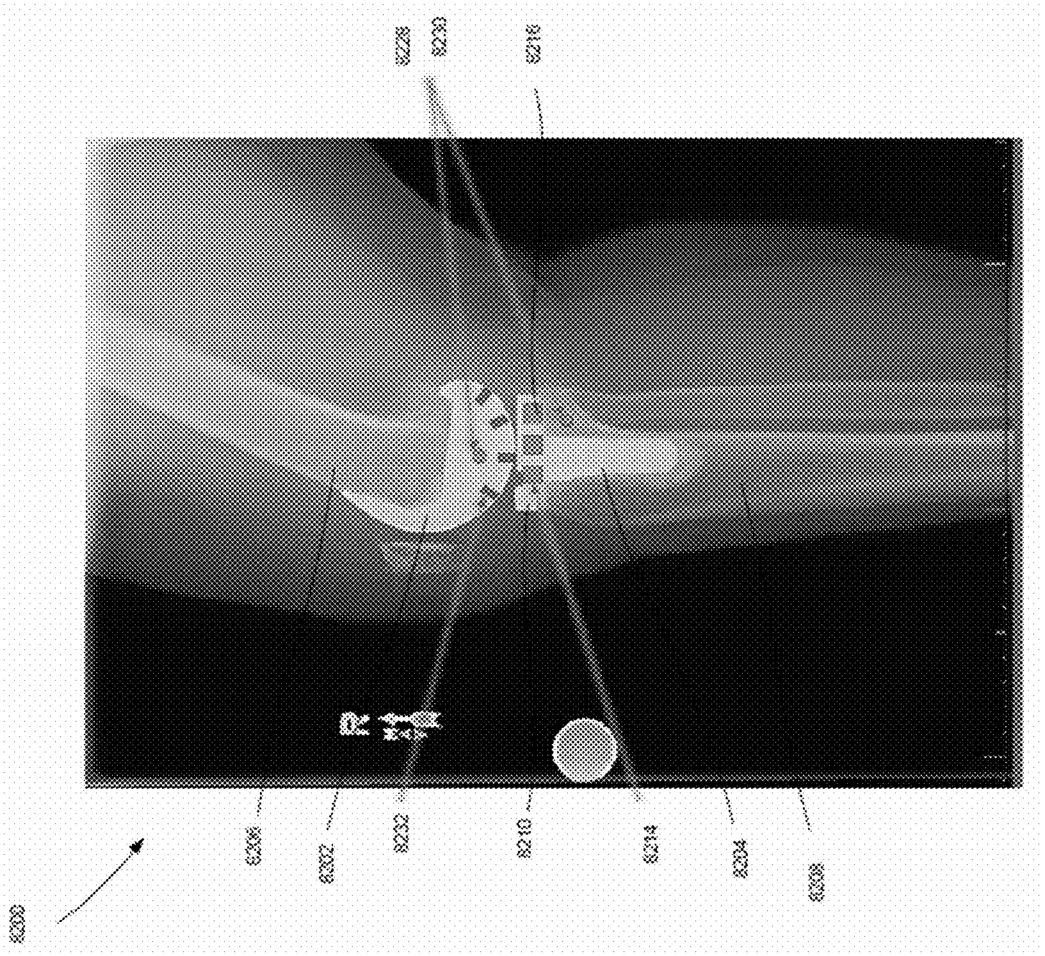
Figure 126:
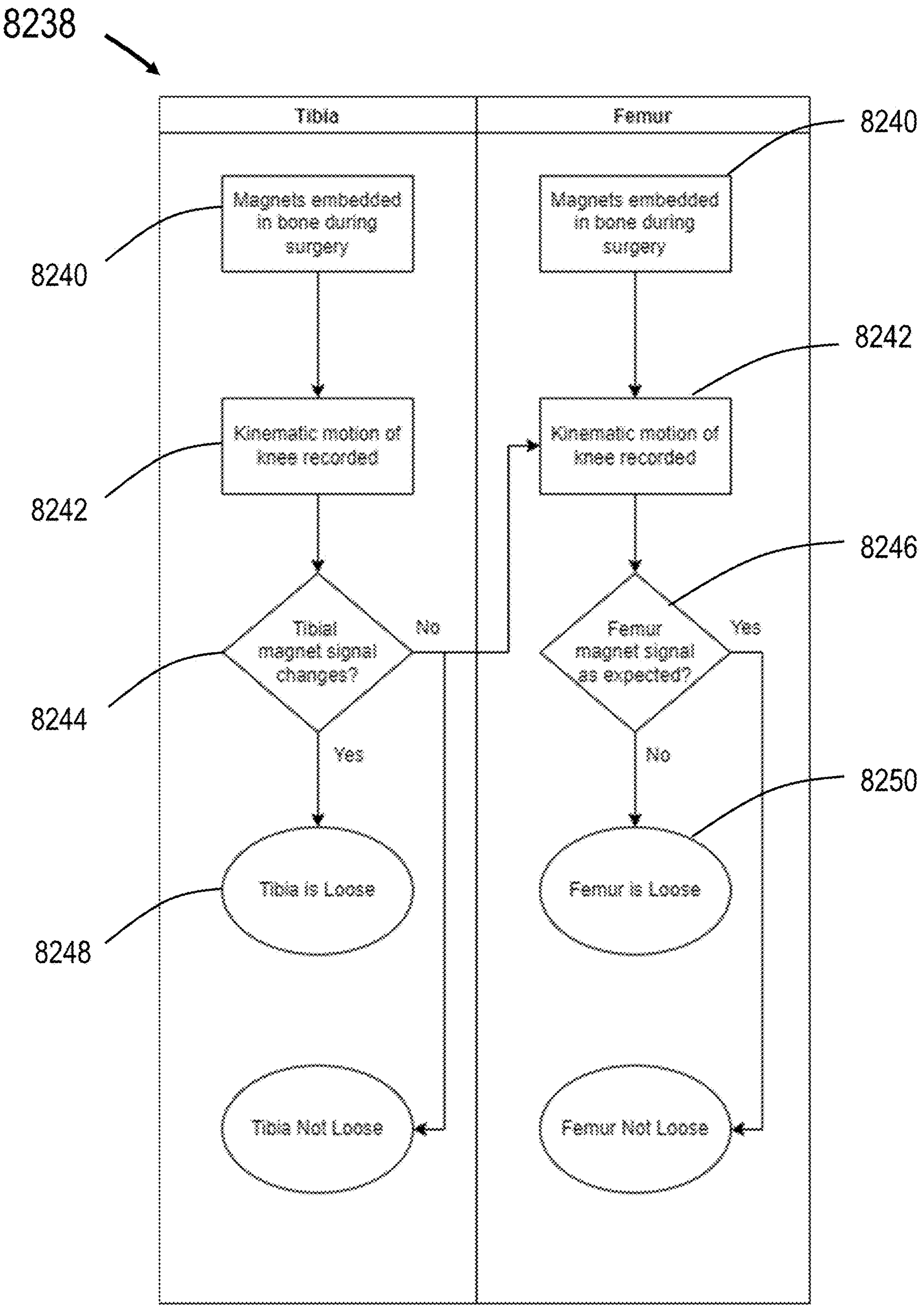
Figure 127:
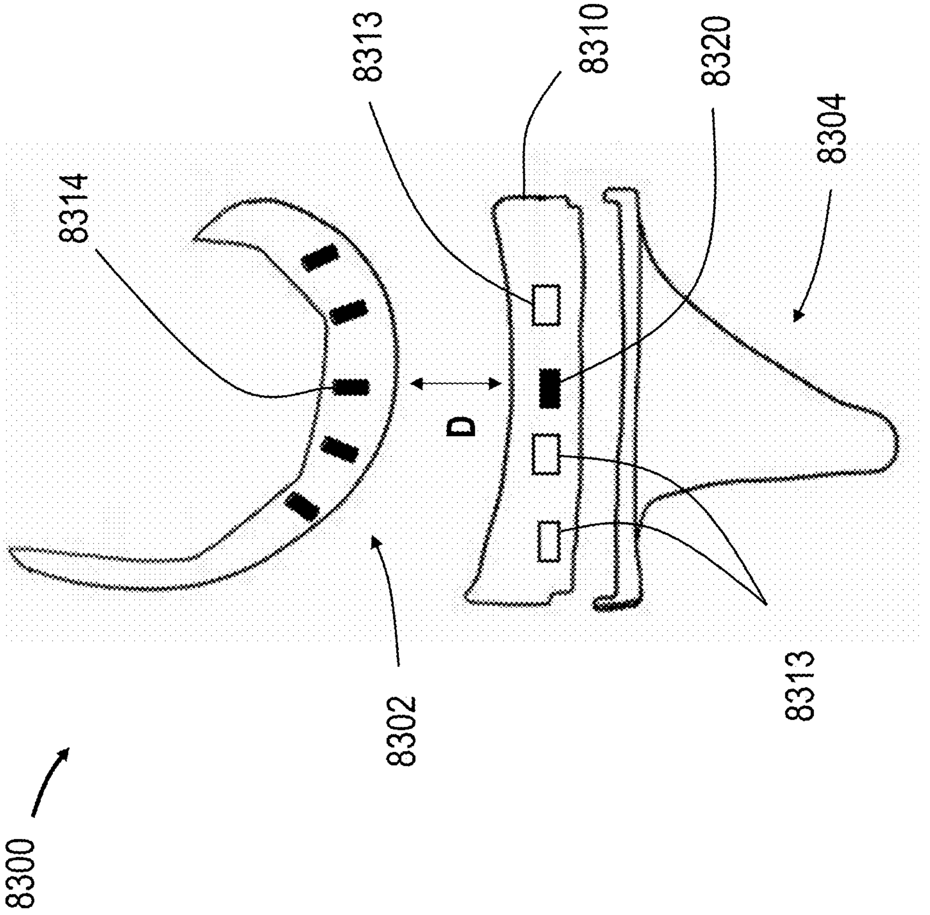
Figure 128:
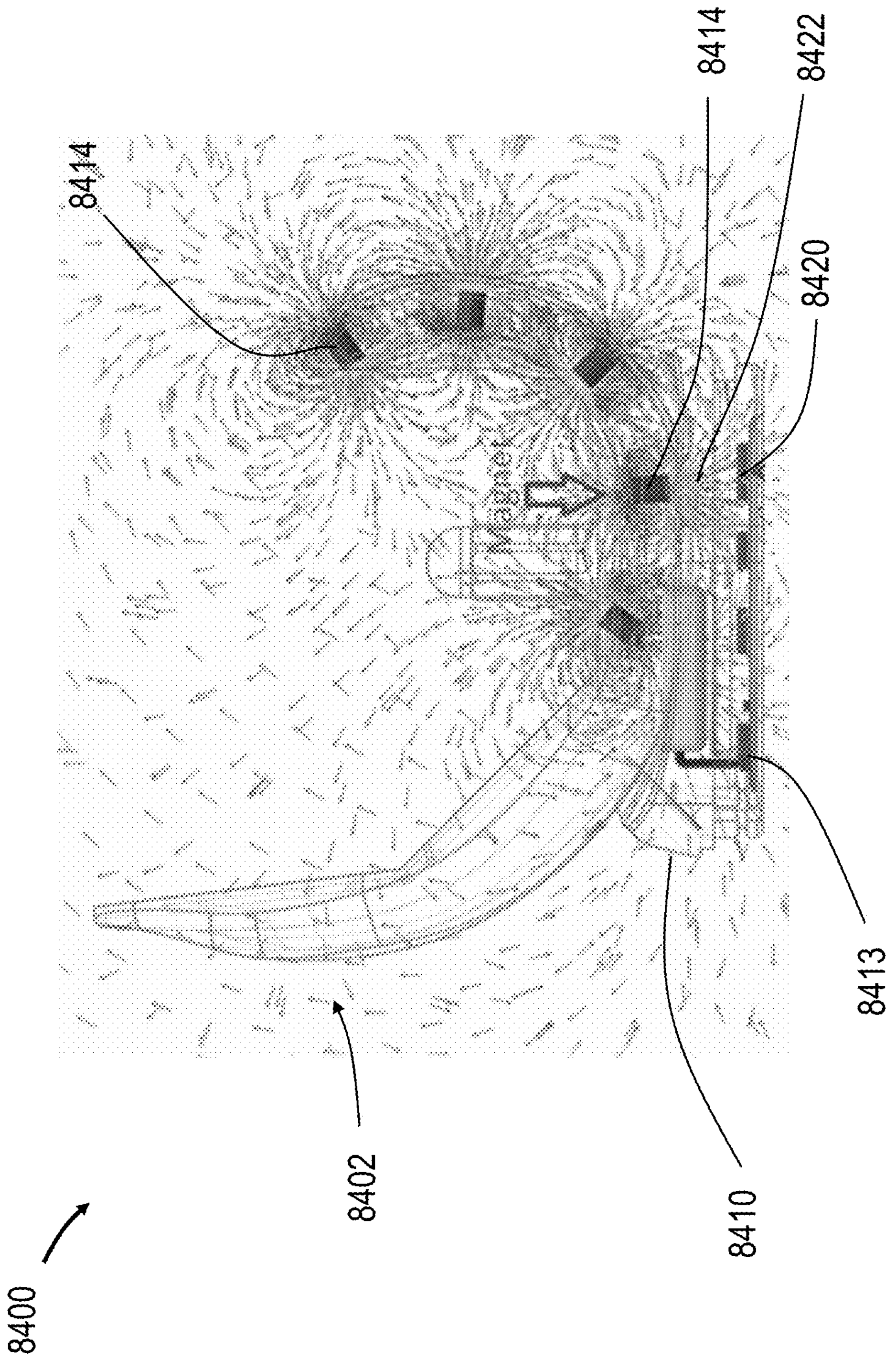
Figure 129:
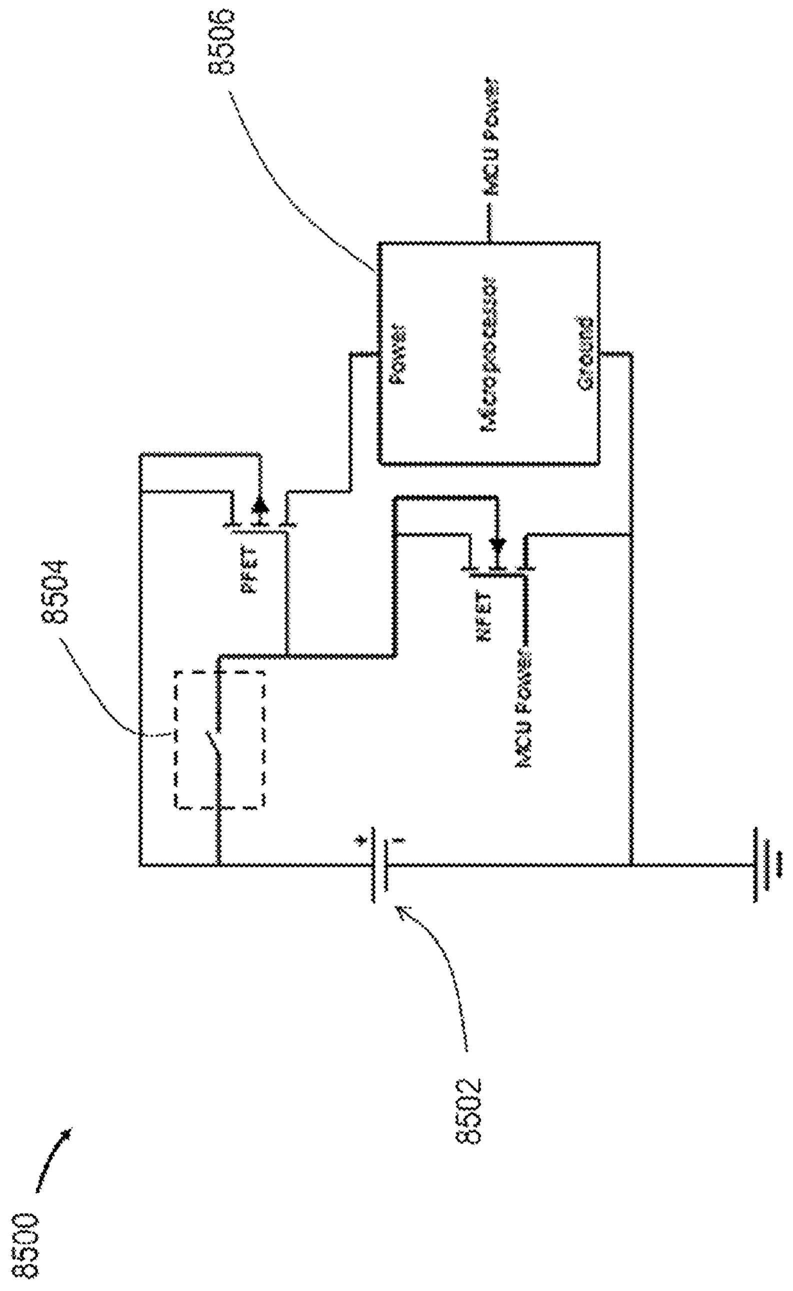
Figure 130:
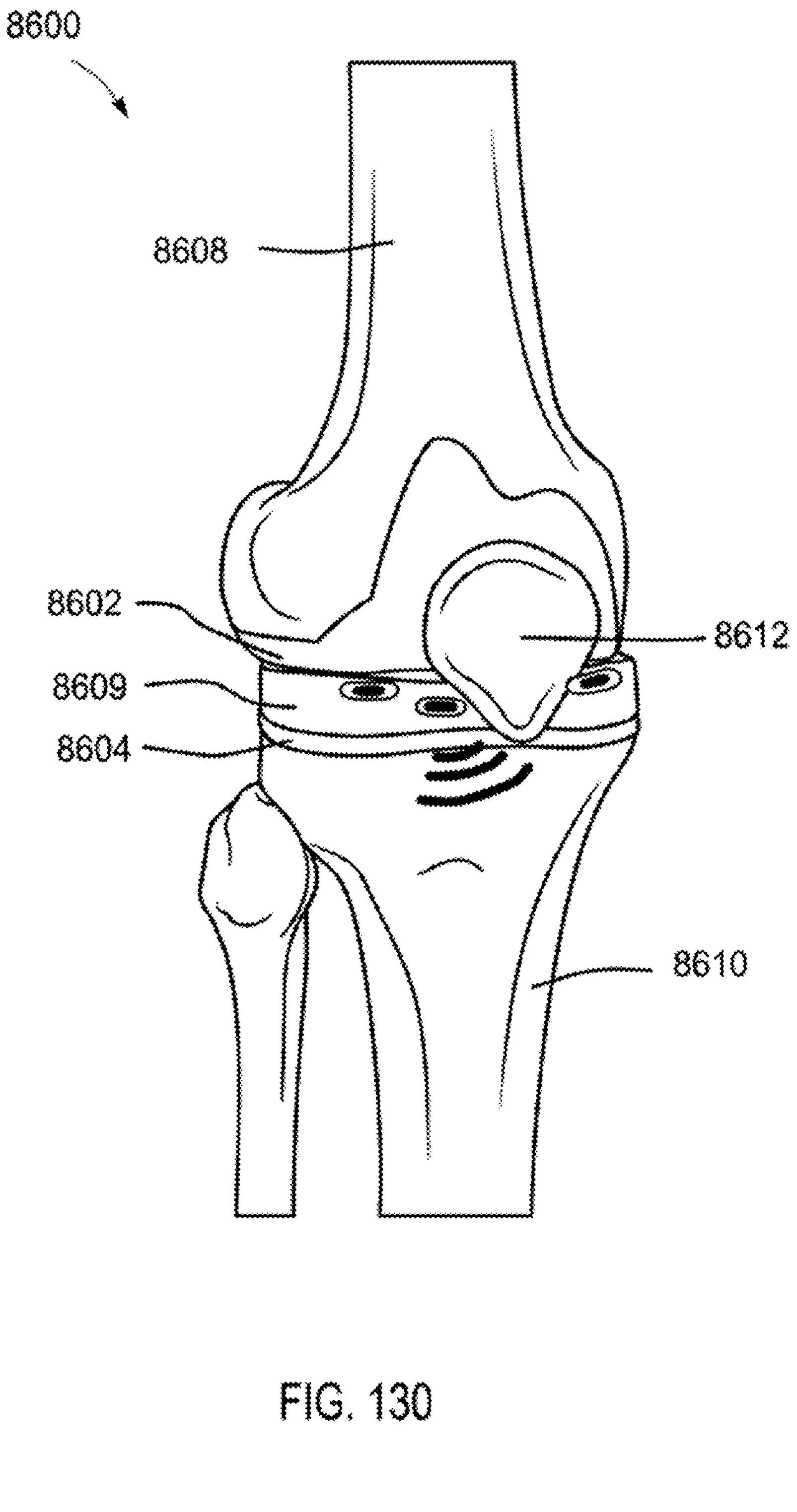
Figure 131:
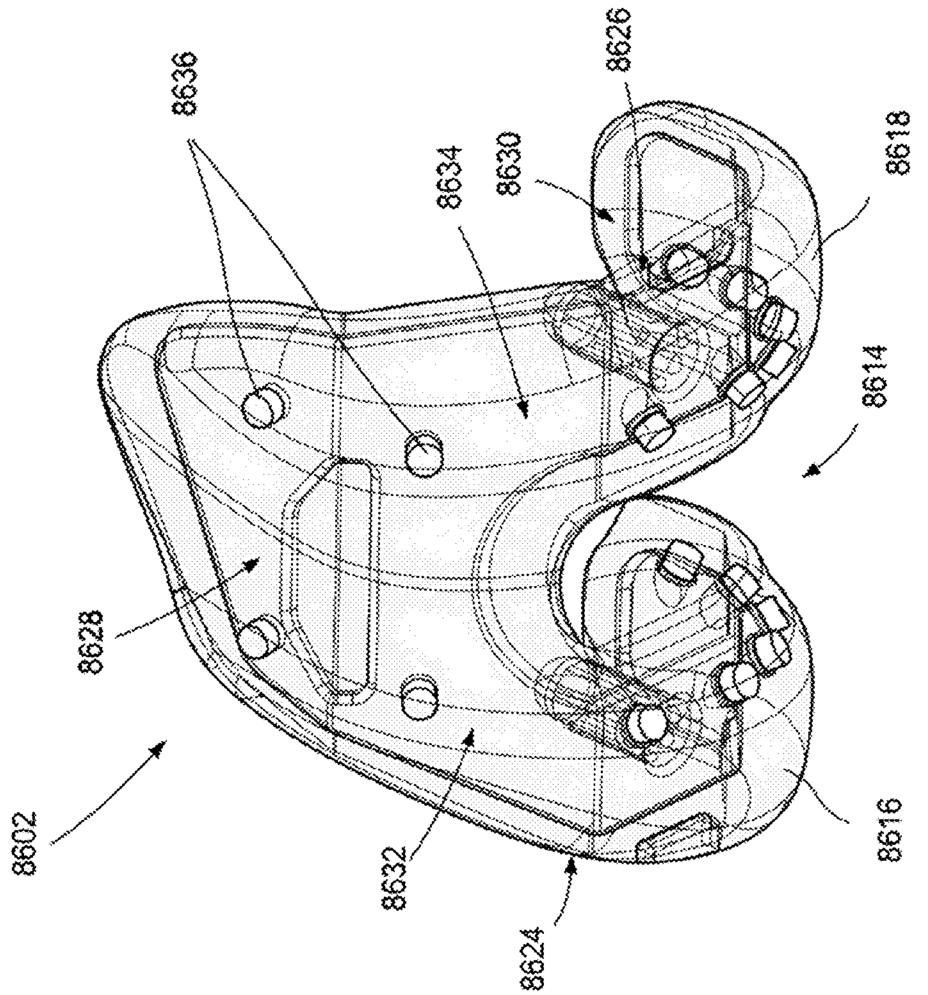
Figure 133:
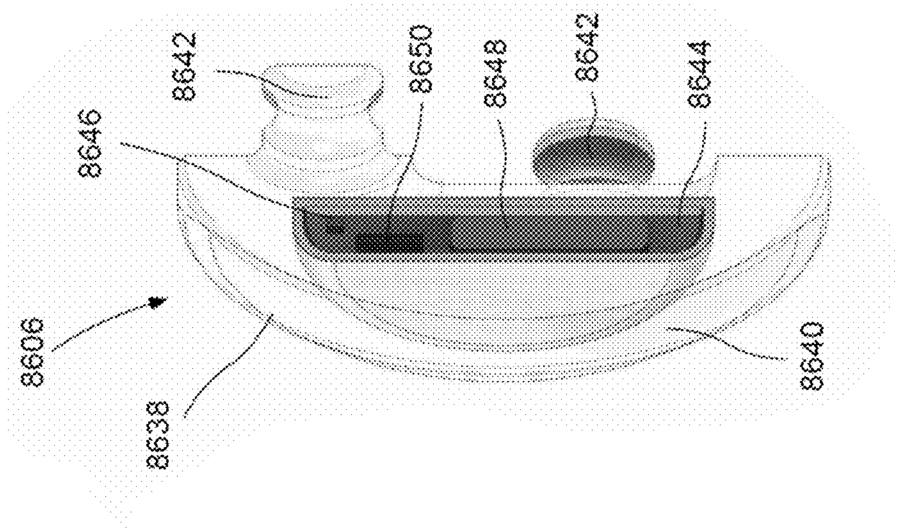
Figure 132:
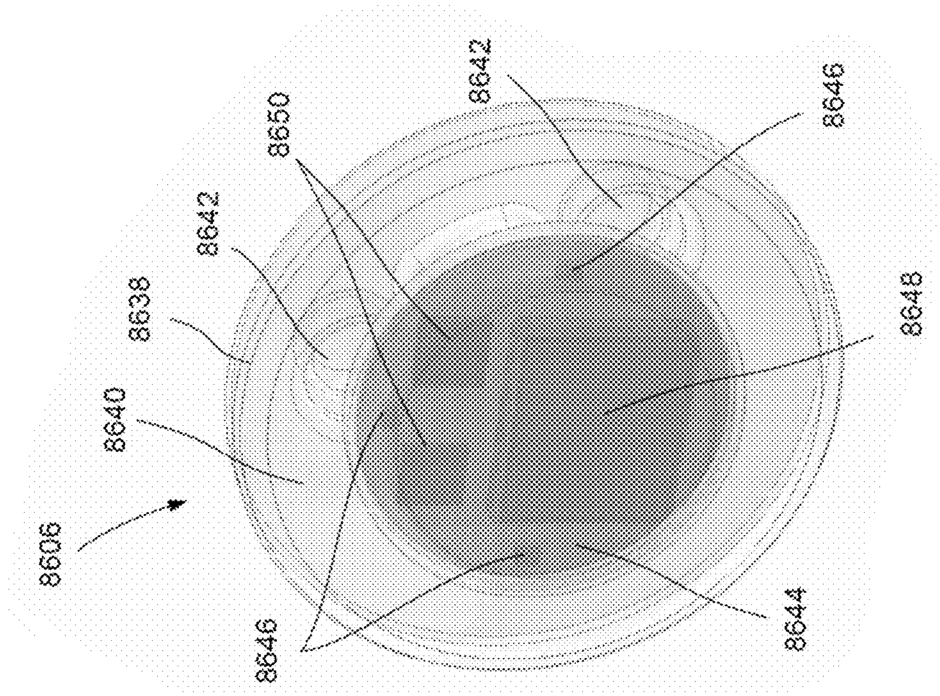
Figure 134:
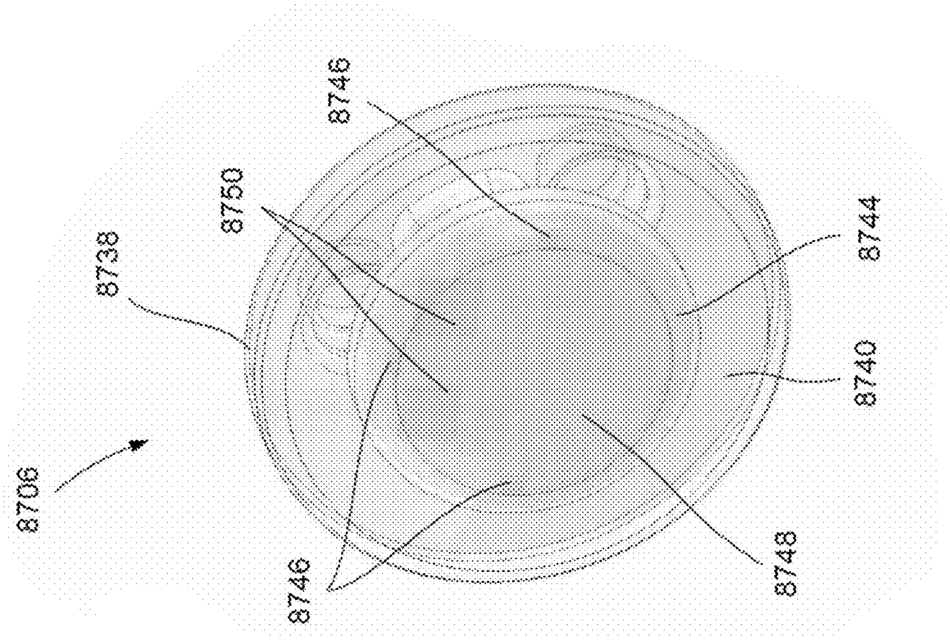
Figure 135:
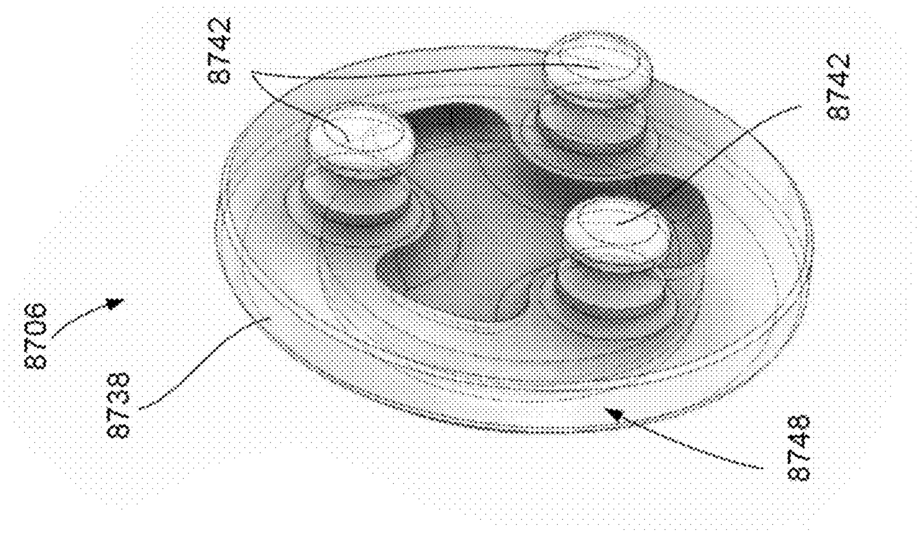
Figure 136:
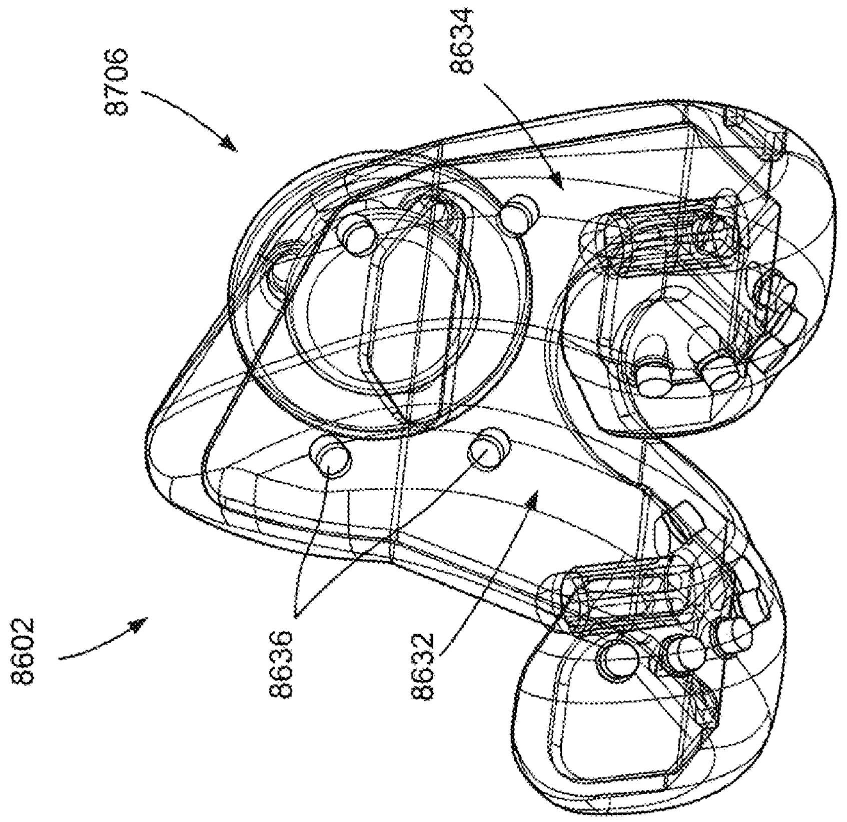
Figure 137:
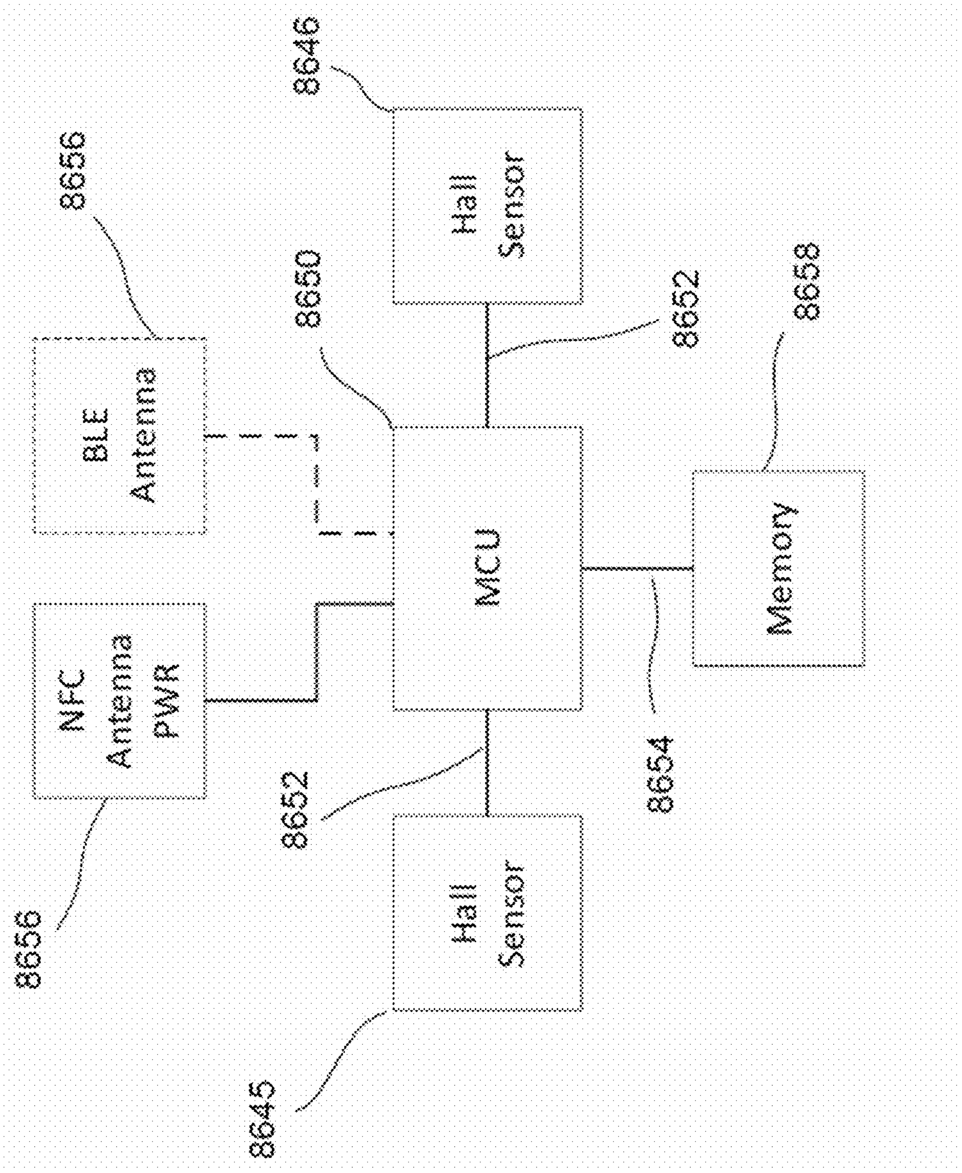
Figure 138:
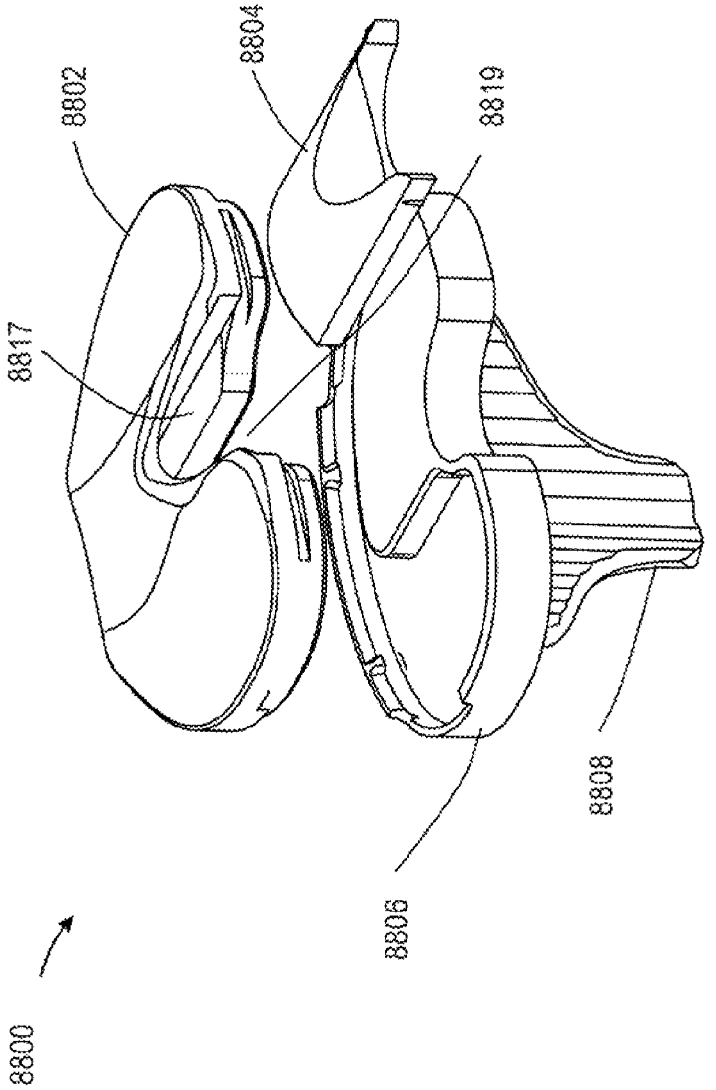
Figure 139:
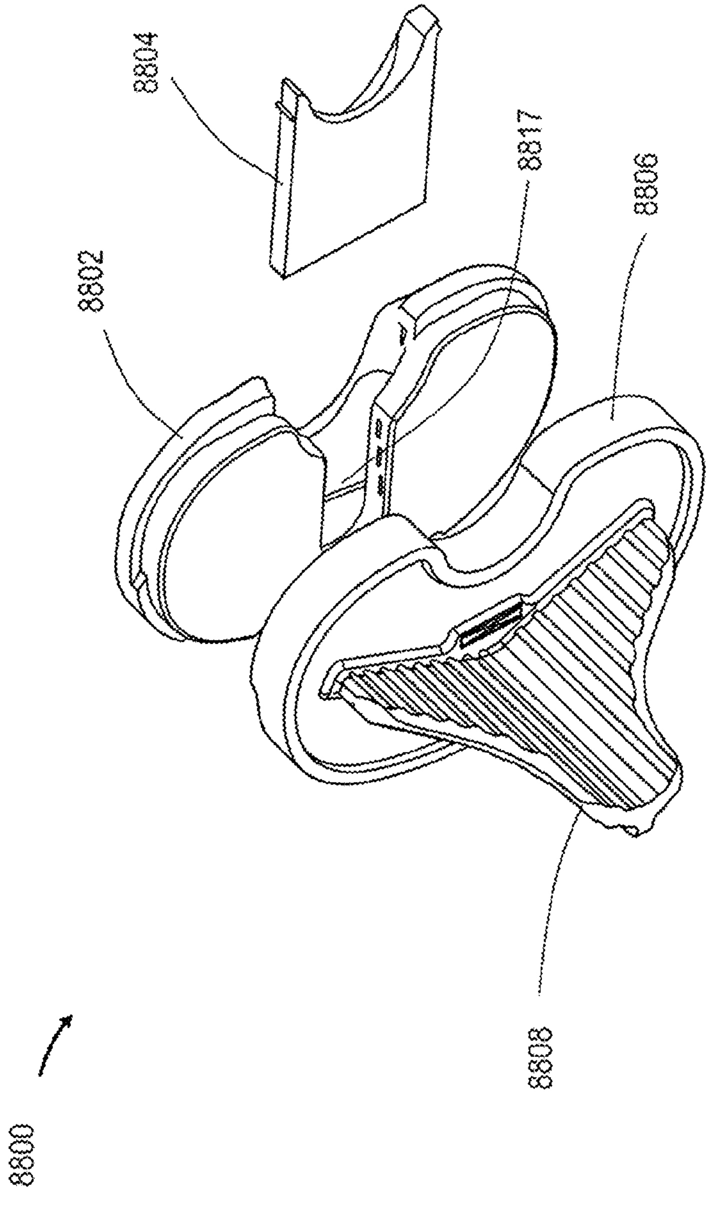
Figure 141:
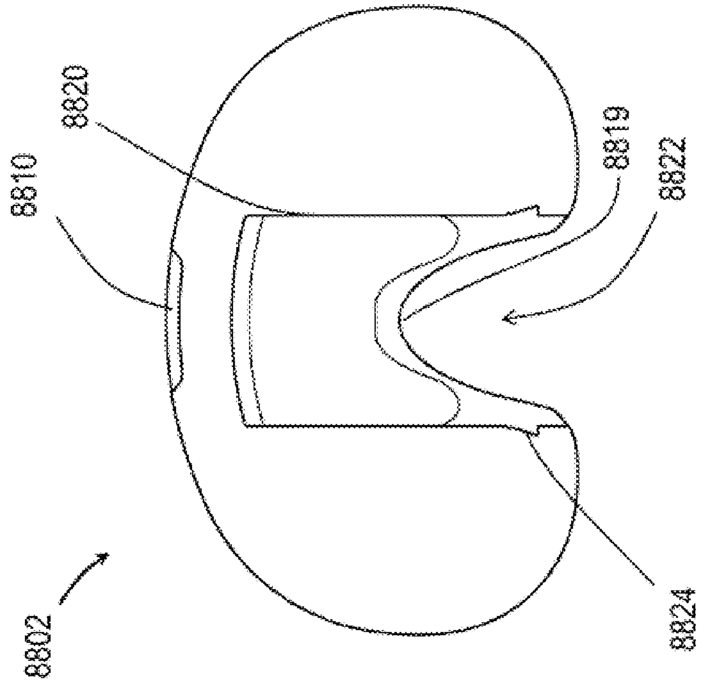
Figure 140:
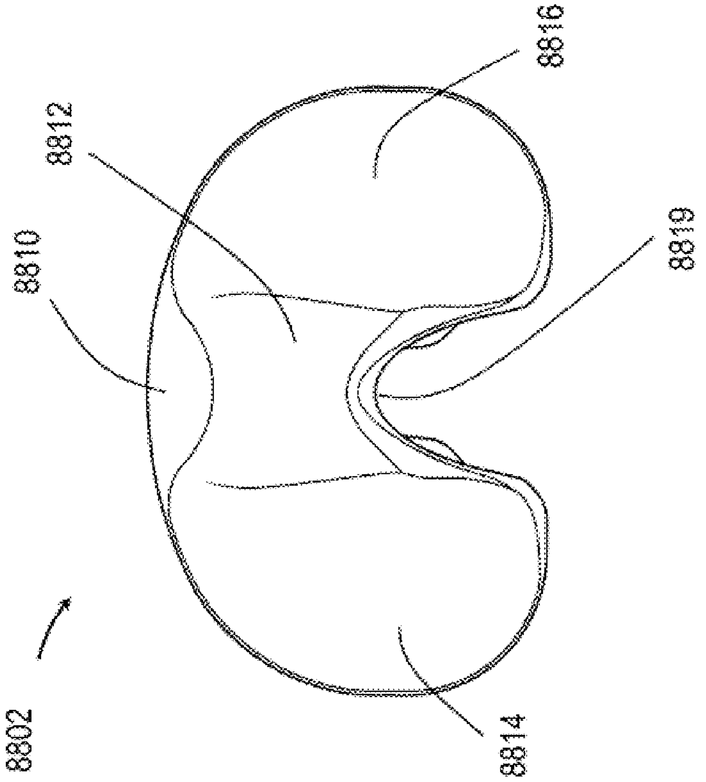
Figure 142:
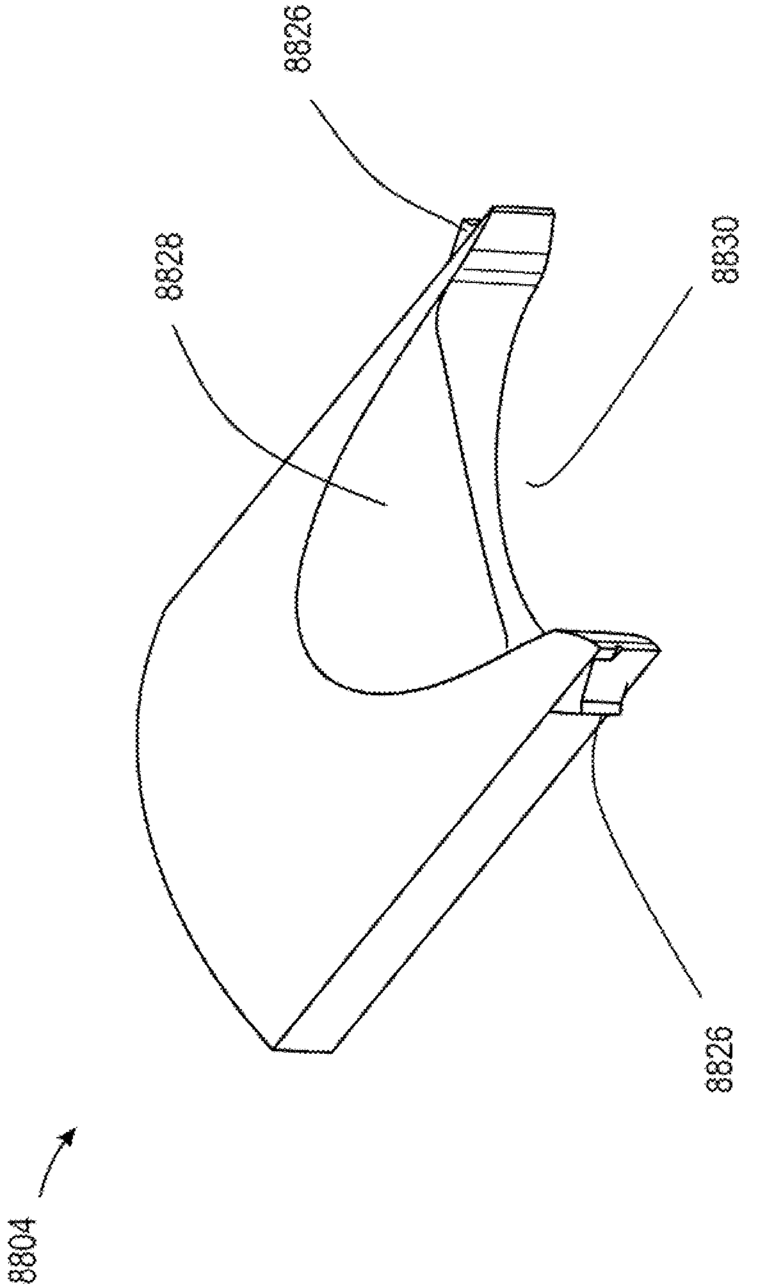
Figure 143:
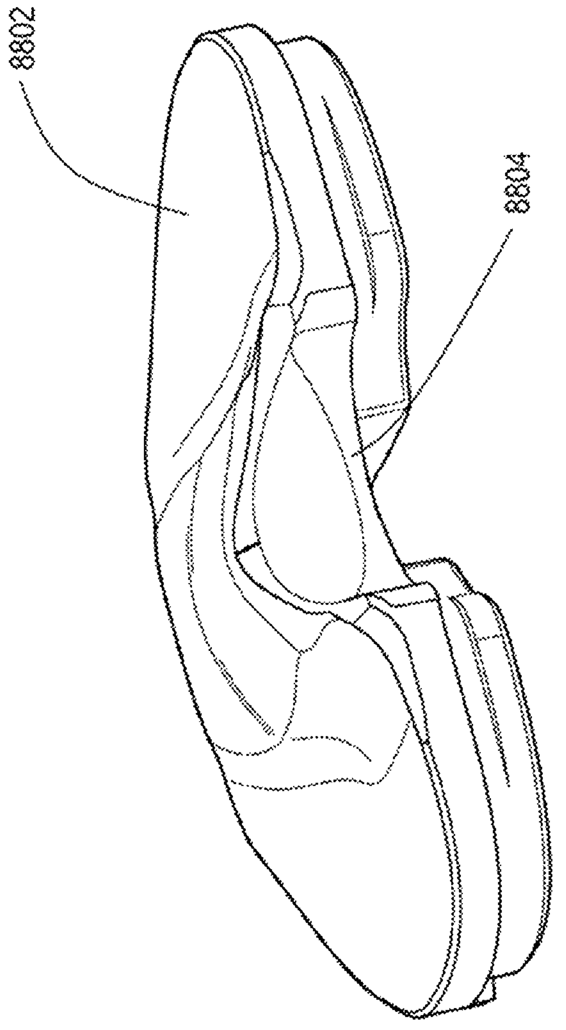
Figure 144:
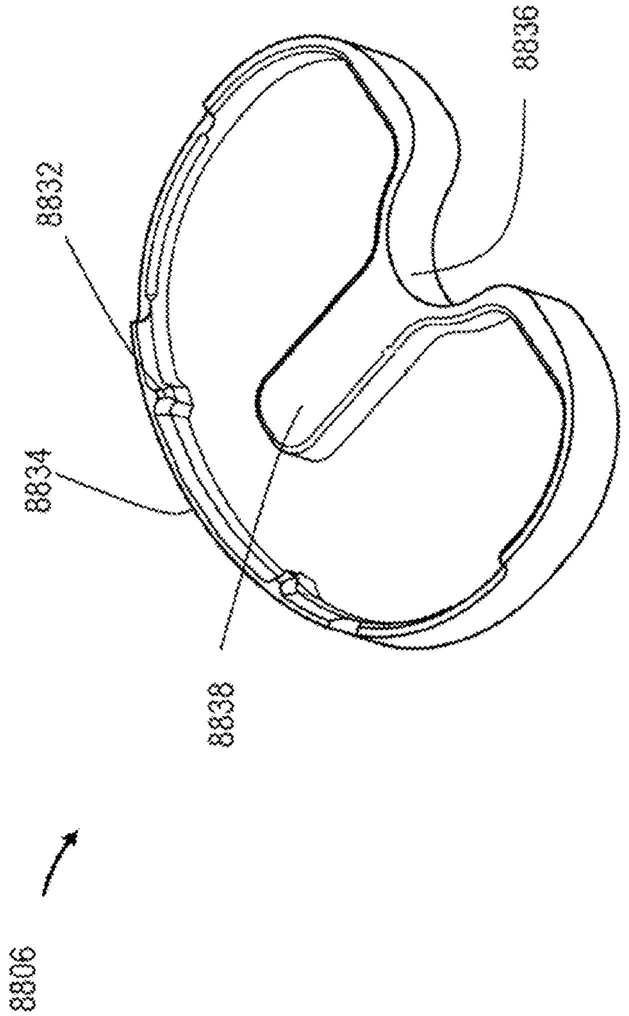
Figure 145:
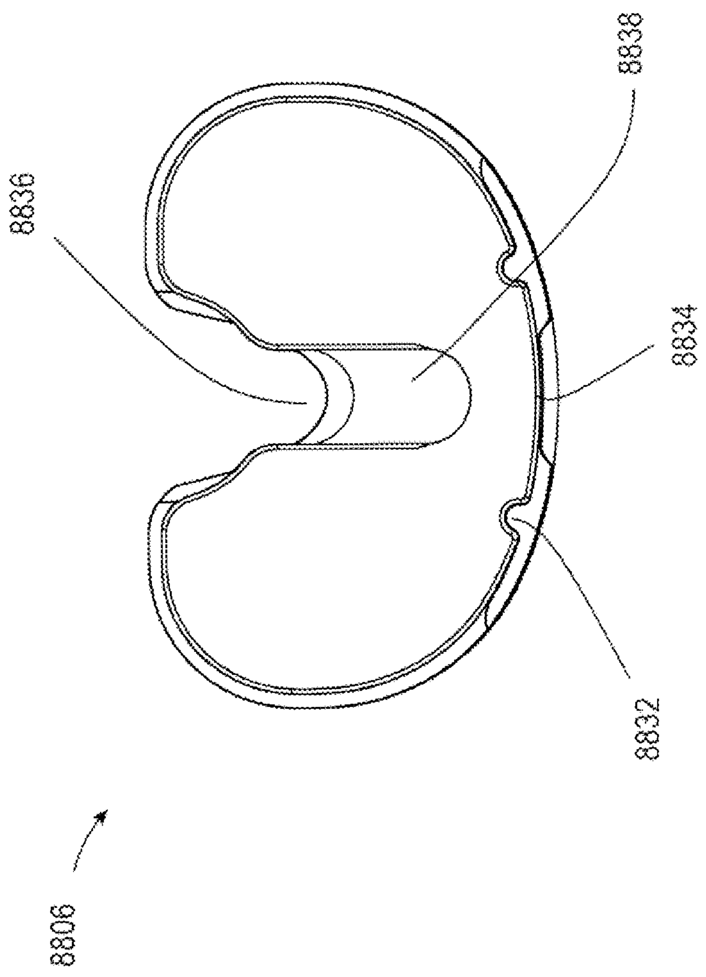
Figure 146:
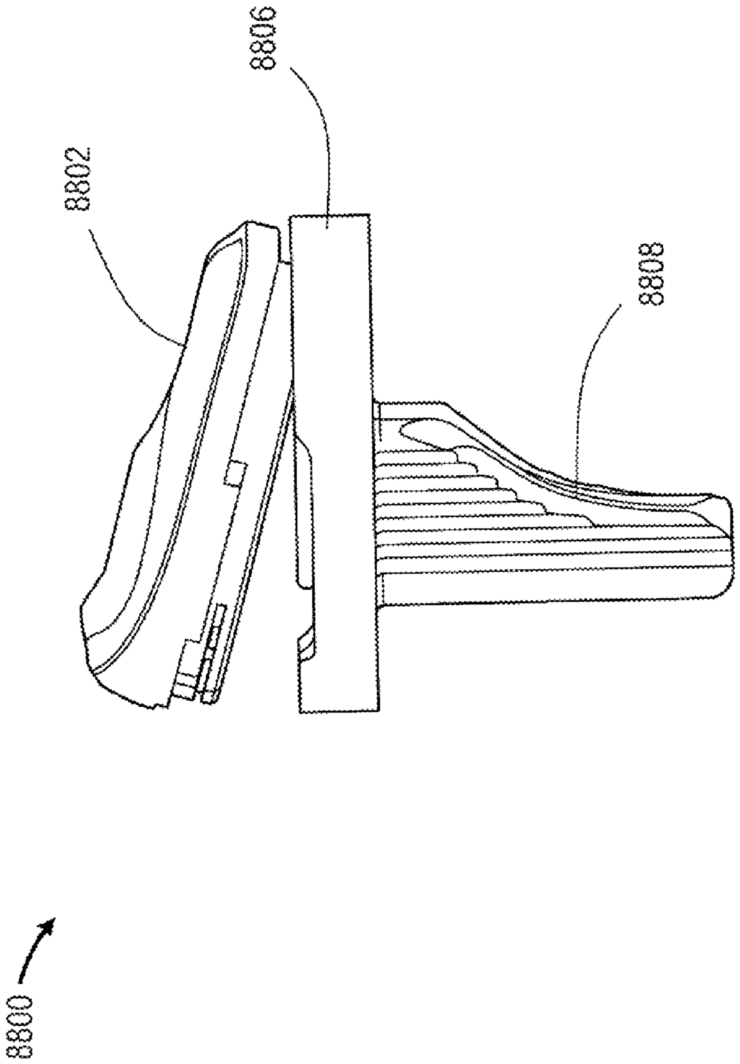
Figure 147:
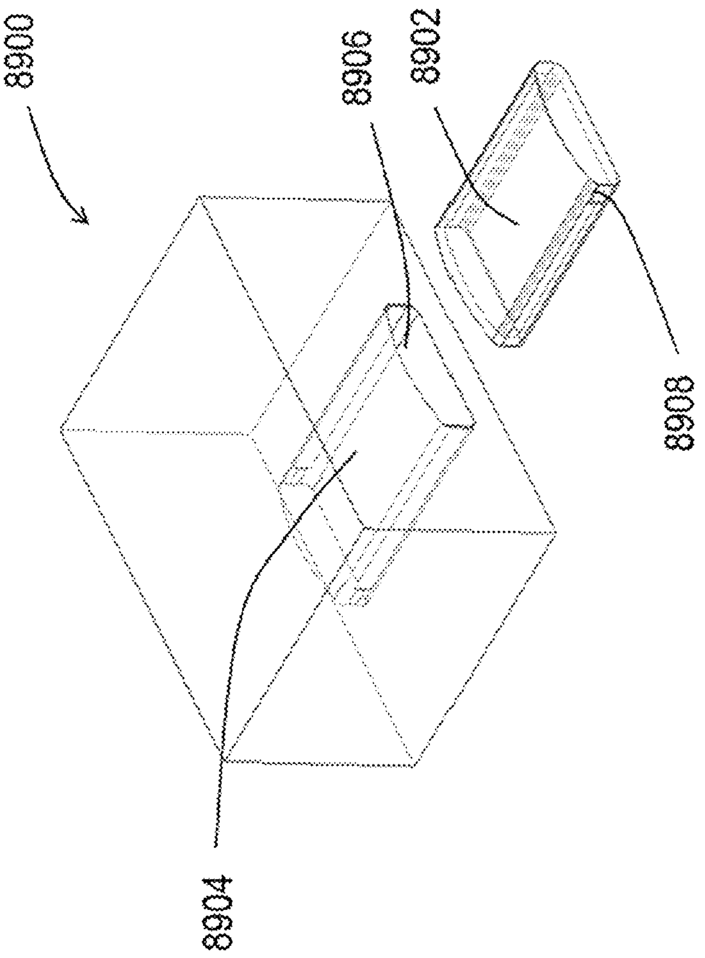
Figure 148:
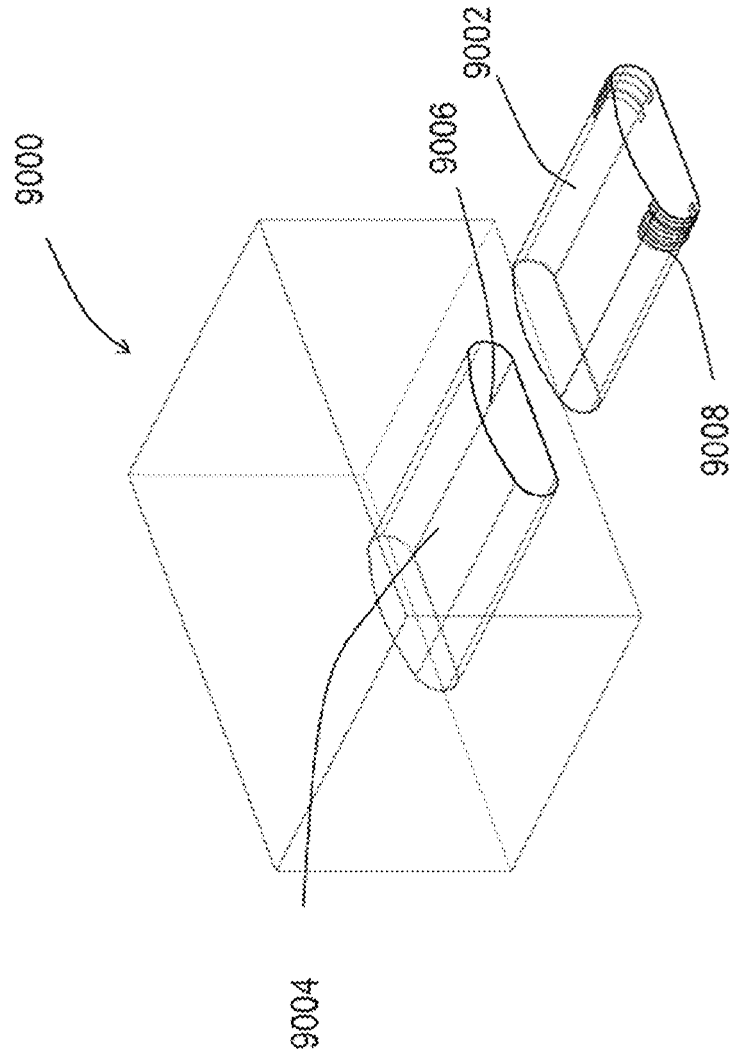
Figure 149:
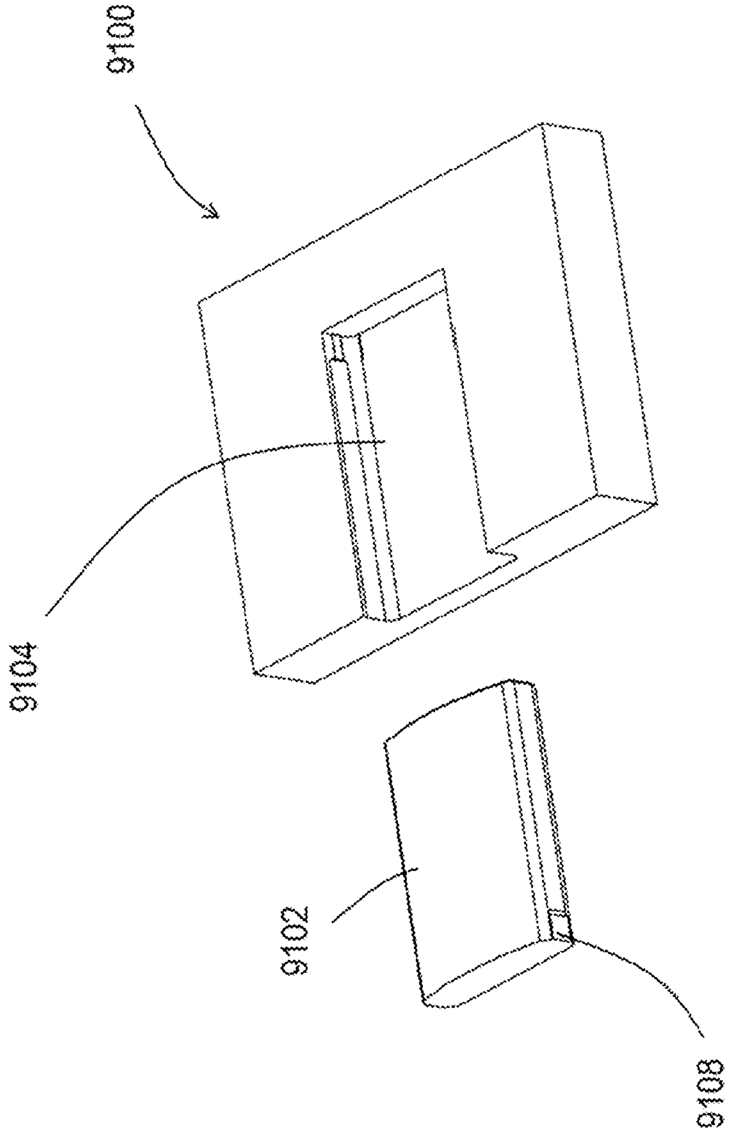
Figure 150:
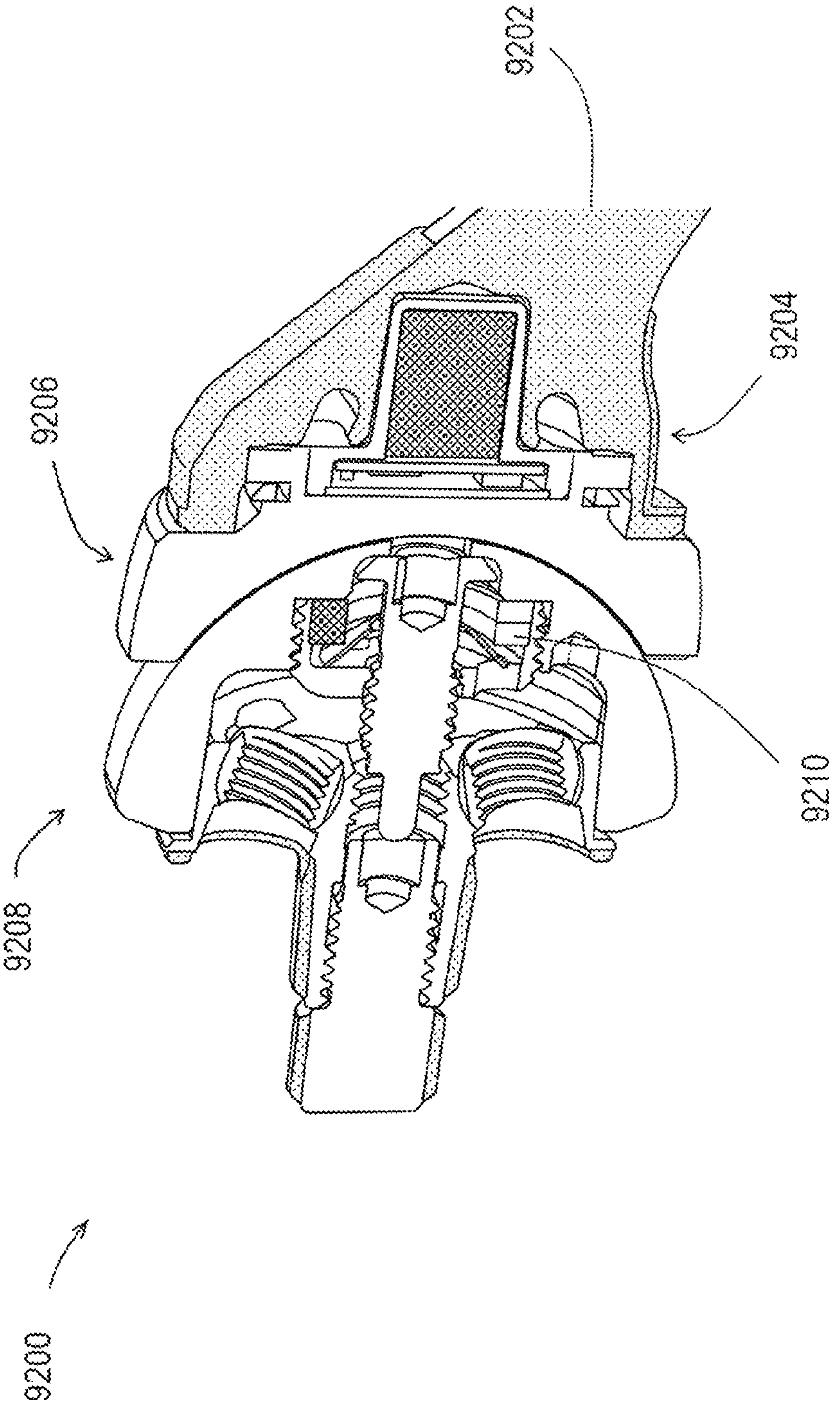
Figure 152:
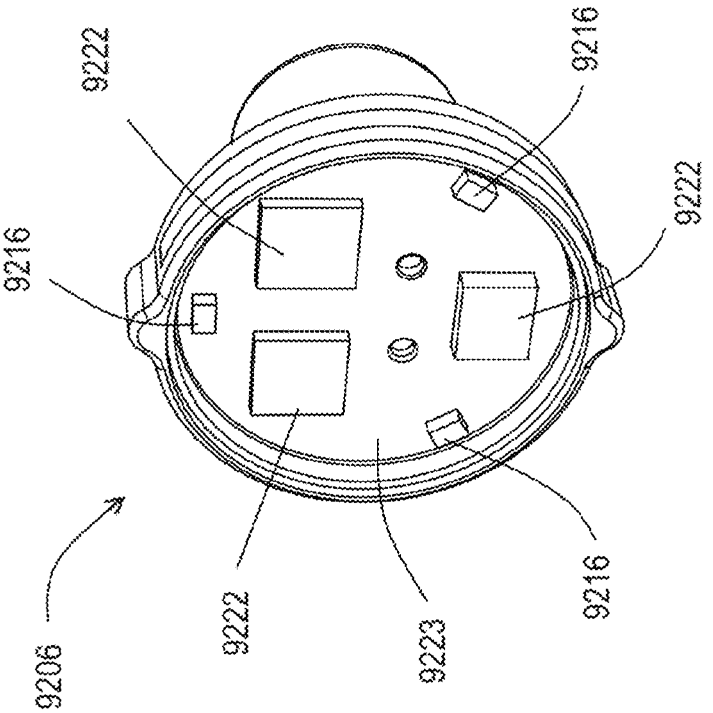
Figure 151:
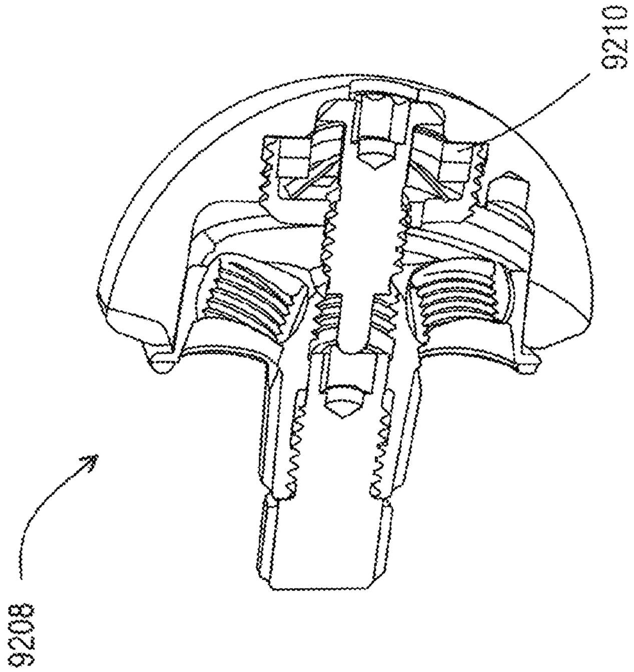
Figure 153:
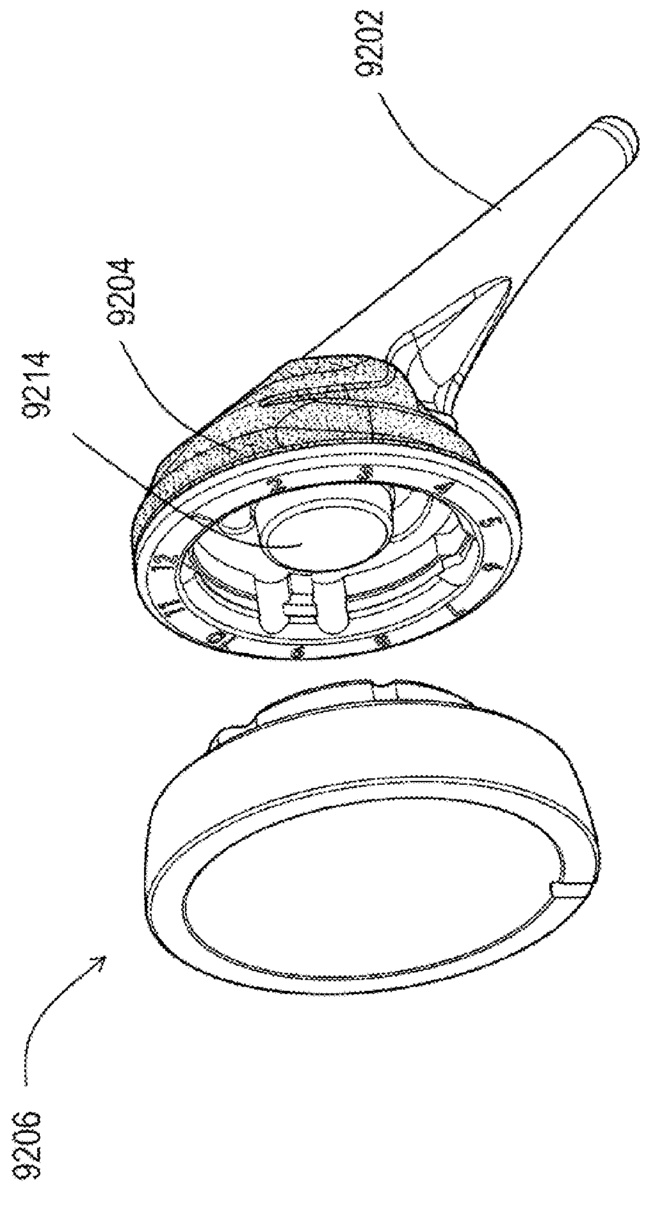
Figure 154:
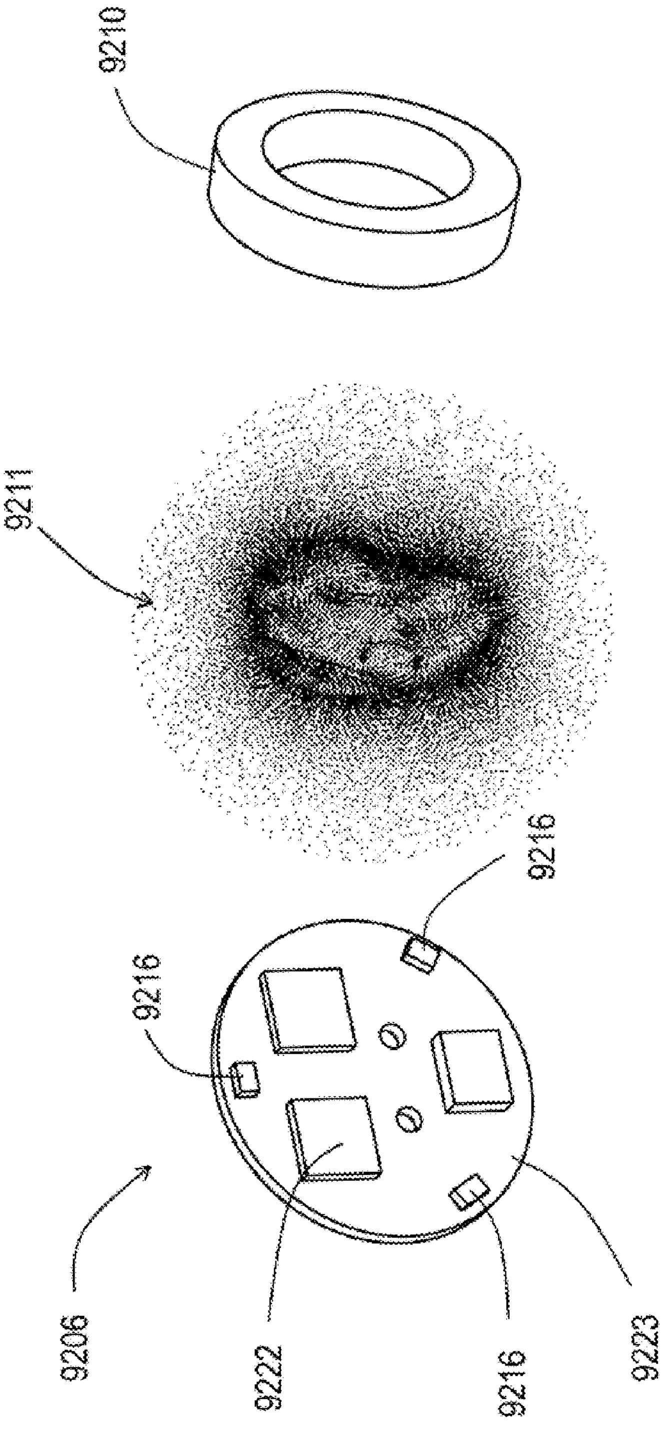
Figure 155:
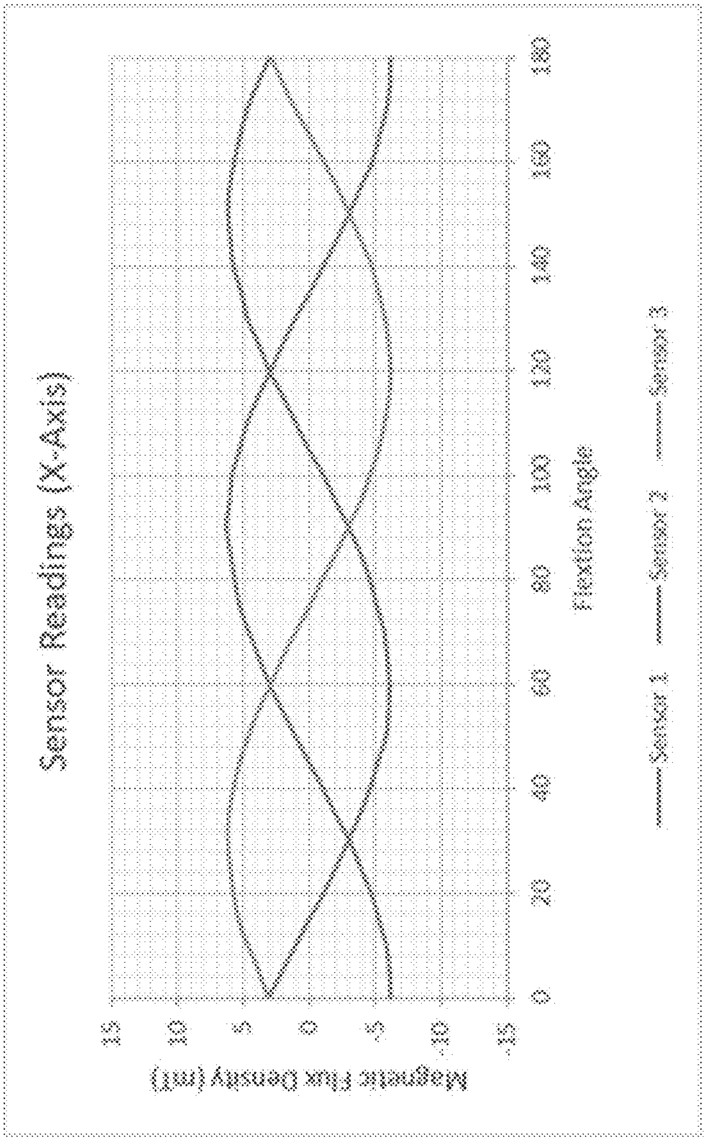
Figure 156:
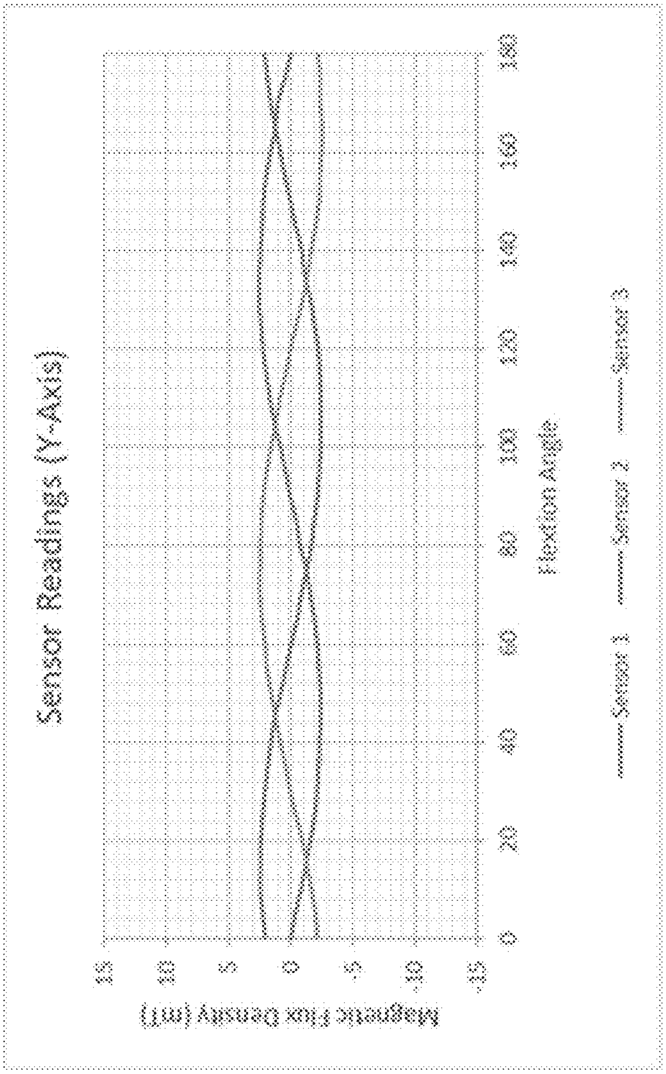
Figure 157:
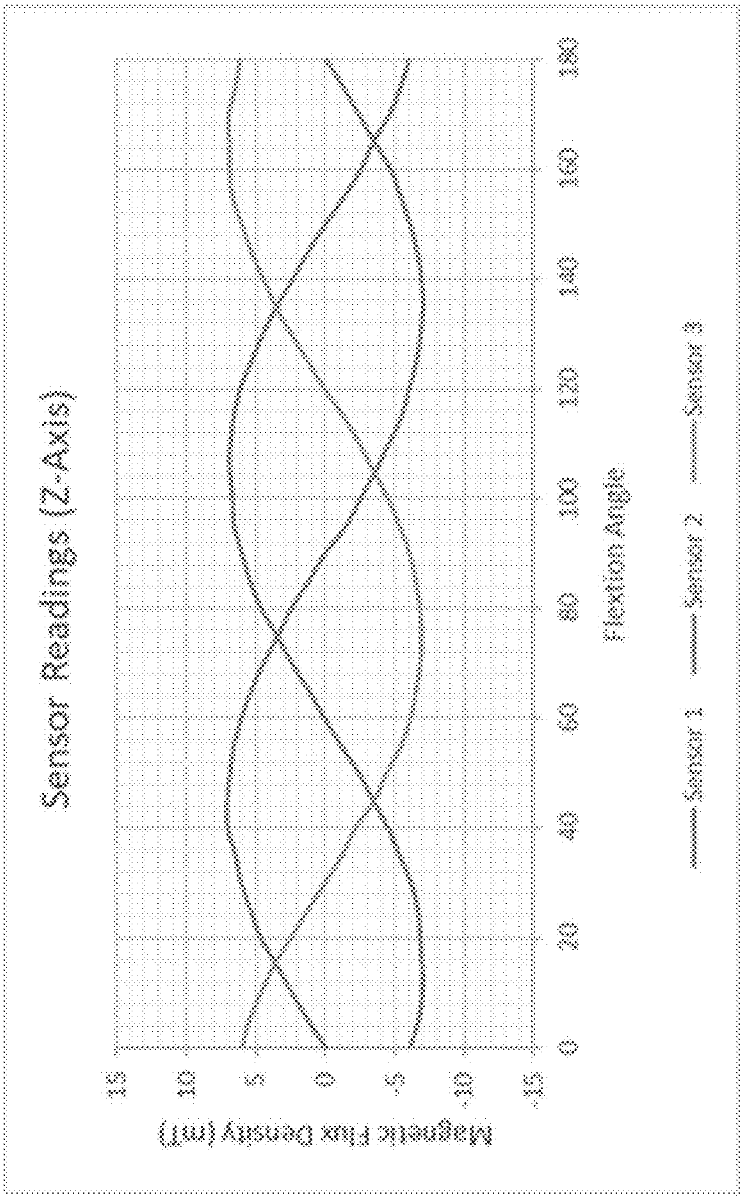
Figure 158:
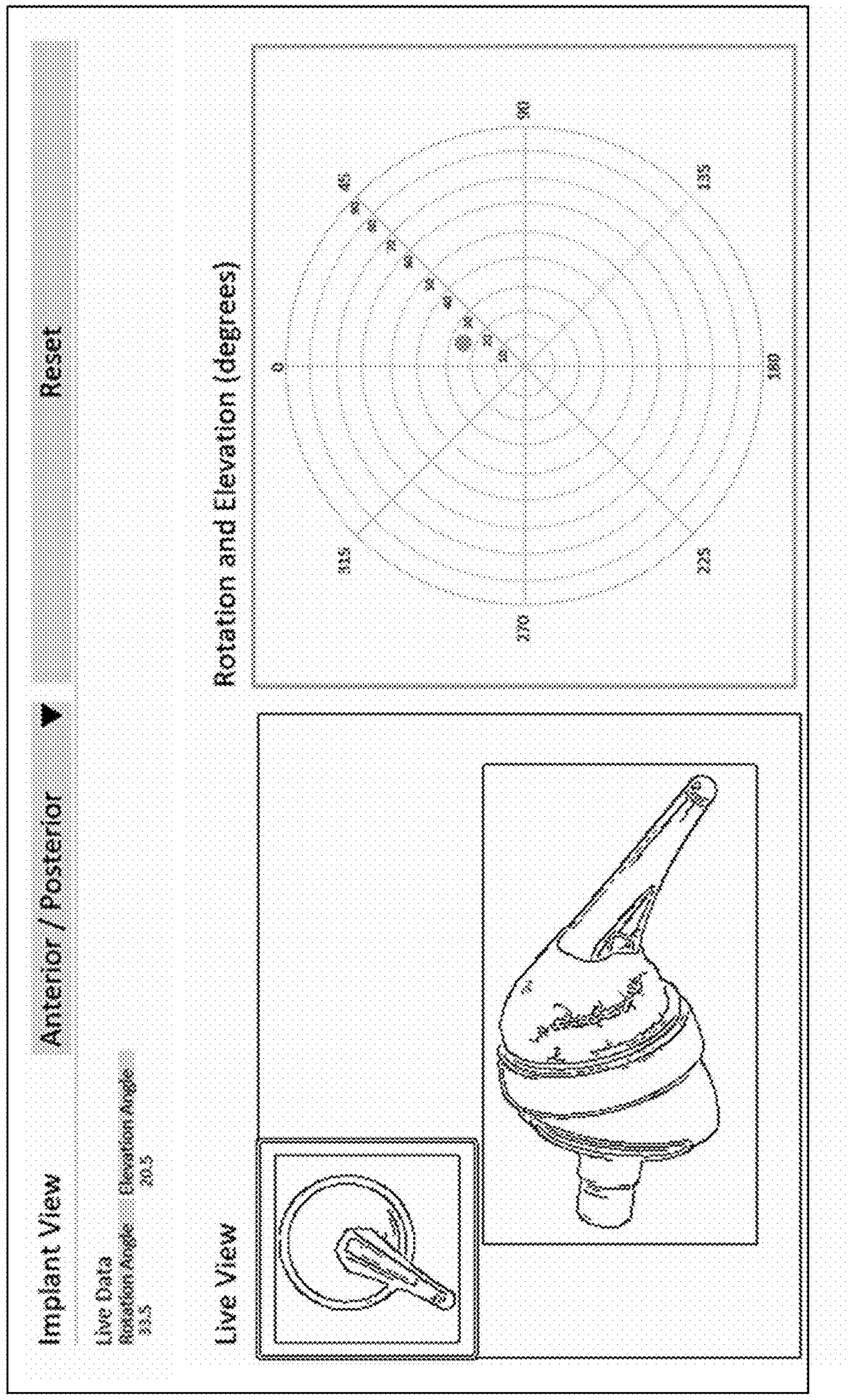
Figure 159:
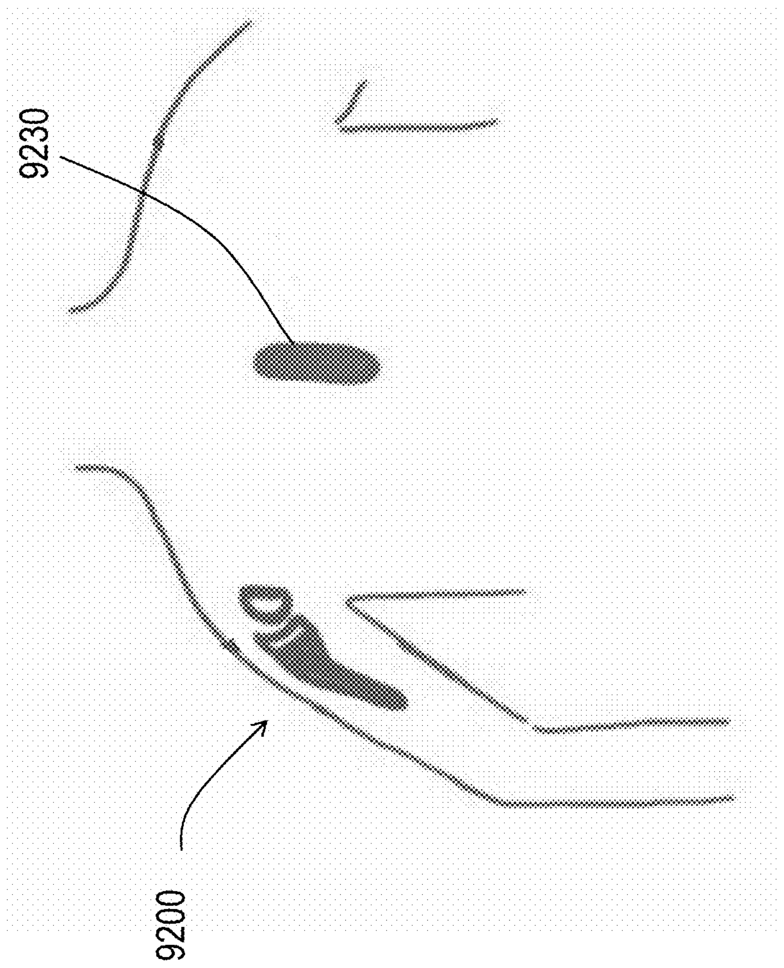
Figure 160:
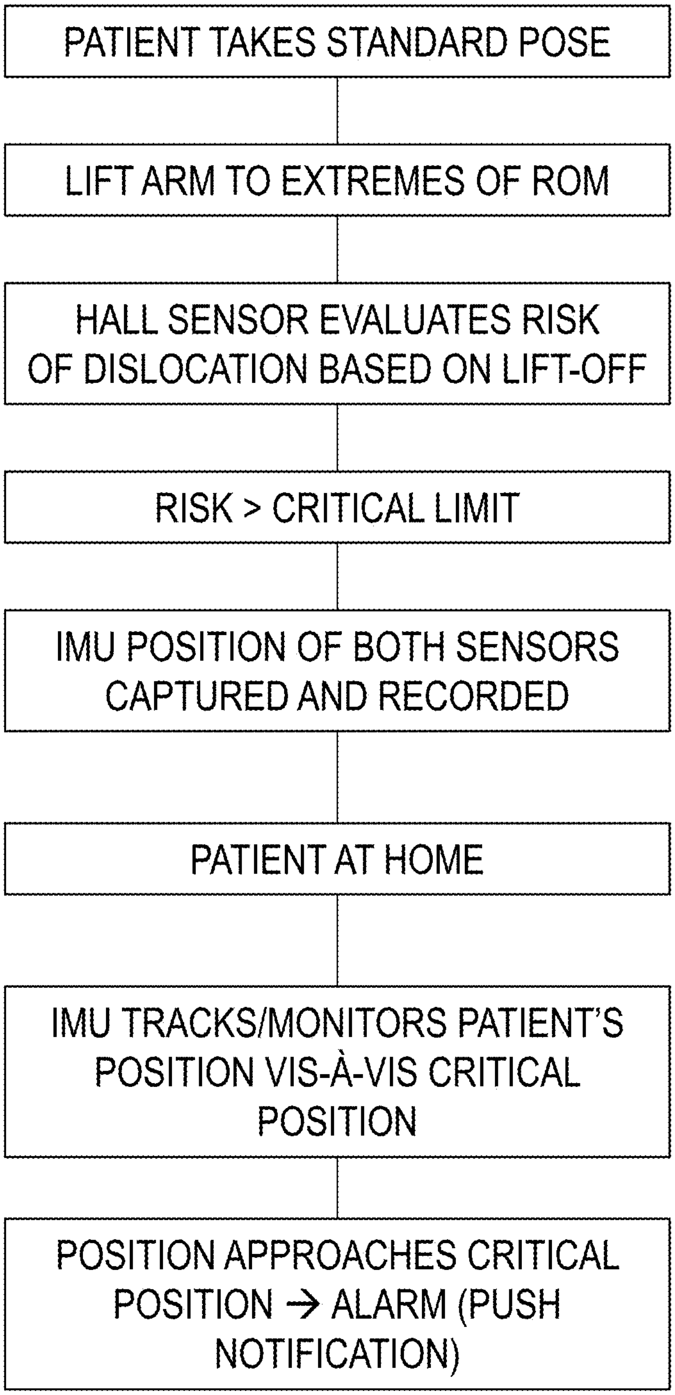

FIG. 118 is a schematic view of a vibration signal being processed by the knee joint implant of FIG. 116;

FIG. 119 is a schematic flowchart view of the processor of FIG. 116;

FIG. 120 is a graph of frequency plotted against amplitude when an implant is detached;

FIG. 121 is a graph of frequency plotted against amplitude when an implant is attached;

FIG. 122 is a graph of two frequencies plotted against two amplitudes;

FIG. 123 is a front view of a knee joint implant according to another embodiment of the present disclosure;

FIG. 124 is a schematic flowchart view of the data stream of the knee joint implant of FIG. 123;

FIG. 125 is a perspective view of a knee joint implant according to another embodiment of the present disclosure;

FIG. 126 is a schematic flowchart view of the logic used to determine if the implant of FIG. 125 is loose;

FIG. 127 is a schematic side view of a knee joint implant with a magnetic switch according to an embodiment of the present disclosure;

FIG. 128 is a schematic side view of partial knee joint implant with a magnetic switch according to another embodiment of the present disclosure;

FIG. 129 is a circuit diagram of a magnetic switch according to an embodiment of the present disclosure;

FIG. 130 is a front view of a knee joint implant according to an embodiment of the present disclosure;

FIG. 131 is a perspective view of a femoral implant of the knee joint implant of FIG. 130;

FIG. 132 is a perspective view of a patellar implant;

FIG. 133 is a side view of the patellar implant of FIG. 132;

FIG. 134 is perspective view of another embodiment of a patellar implant;

FIG. 135 is another perspective view of the patellar implant of FIG. 134;

FIG. 136 is a perspective view of the femoral implant of FIG. 131 with the patellar implant of FIGS. 134-135;

FIG. 137 is a schematic flowchart view of the data stream of the knee joint implant of FIG. 130;

FIG. 138 is an exploded perspective view of a tibial implant according to an embodiment of the present disclosure;

FIG. 139 is an exploded bottom view of the tibial implant of FIG. 138;

FIG. 140 is a top view of a tibial insert of the tibial implant of FIG. 138;

FIG. 141 is a top cross-sectional view of the tibial insert of FIG. 140;

FIG. 142 is a perspective view of a case of the tibial implant of FIG. 138;

FIG. 143 is a side perspective view of the case and the tibial insert of the tibial implant of FIG. 138;

FIG. 144 is a top view of a tibial baseplate of the tibial implant of FIG. 138;

FIG. 145 is a bottom view of the tibial baseplate of FIG. 144;

FIG. 146 is a side view of the tibial assembly of FIG. 138;

FIG. 147 is a perspective view of a tibial insert with a sensor module according to another embodiment of the present disclosure;

FIG. 148 is a perspective view of a tibial insert with a sensor module according to another embodiment of the present disclosure;

FIG. 149 is a perspective view of tibial insert with a sensor module according to another embodiment of the present disclosure;

FIG. 150 is a side cross-sectional view of a shoulder implant according to another embodiment of the present disclosure;

FIG. 151 is a side cross-sectional view of a glenoid sphere of the shoulder implant of FIG. 150;

FIG. 152 is a top view of an insert of the shoulder implant of FIG. 150;

FIG. 153 is a perspective view of the insert, a cup and a stem of the shoulder implant of FIG. 150;

FIG. 154 is a schematic view showing magnetic flux density between the glenoid sphere and the cup of the shoulder implant of FIG. 150;

FIG. 155 is a graph showing magnetic flux density readings of the shoulder implant of FIG. 150 along an x-axis;

FIG. 156 is a graph showing magnetic flux density readings of the shoulder implant of FIG. 150 along a y-axis;

FIG. 157 is a graph showing magnetic flux density readings of the shoulder implant of FIG. 150 along a z-axis;

FIG. 158 is graphical user interface for monitoring performance of the shoulder implant of FIG. 150 according to an embodiment of the present disclosure;

FIG. 159 is a schematic view of patient with the shoulder implant of FIG. 150 and an external inertial measurement unit according to an embodiment of the present disclosure, and FIG. 160 is a flowchart showing steps for monitoring a patient with the shoulder implant of FIG. 150.

DETAILED DESCRIPTION

Reference will now be made in detail to the various embodiments of the present disclosure illustrated in the accompanying drawings. Wherever possible, the same or like reference numbers will be used throughout the drawings to refer to the same or like features within a different series of numbers (e.g., 100-series, 200-series, etc.). It should be noted that the drawings are in simplified form and are not drawn to precise scale. Additionally, the term "a," as used in the specification, means "at least one." The terminology includes the words above specifically mentioned, derivatives thereof, and words of similar import. Although at least two variations are described herein, other variations may include aspects described herein combined in any suitable manner having combinations of all or some of the aspects described.

As used herein, the terms "load" and "force" will be used interchangeably and as such, unless otherwise stated, the explicit use of either term is inclusive of the other term. Similarly, the terms "magnetic markers" and "markers" will be used interchangeably and as such, unless otherwise stated, the explicit use of either term is inclusive of the other term.

As used herein, the terms "power" and "energy" will be used interchangeably and as such, unless otherwise stated, the explicit use of either term is inclusive of the other term. Similarly, the terms "implant" and "prosthesis" will be used interchangeably and as such, unless otherwise stated, the explicit use of either term is inclusive of the other term. The term "joint implant" means a joint implant system comprising two or more implants. Similarly, the terms "energy generator" and "energy harvester" will be used interchangeably and as such, unless otherwise stated, the explicit use of either term is inclusive of the other term.

In describing preferred embodiments of the disclosure, reference will be made to directional nomenclature used in describing the human body. It is noted that this nomenclature is used only for convenience and that it is not intended to be limiting with respect to the scope of the present disclosure. As used herein, when referring to bones or other parts of the body, the term "anterior" means toward the front part of the body or the face, and the term "posterior" means toward the back of the body. The term "medial" means toward the midline of the body, and the term "lateral" means away from the midline of the body. The term "superior" means closer to the head, and the term "inferior" means more distant from the head.

Figure 1:
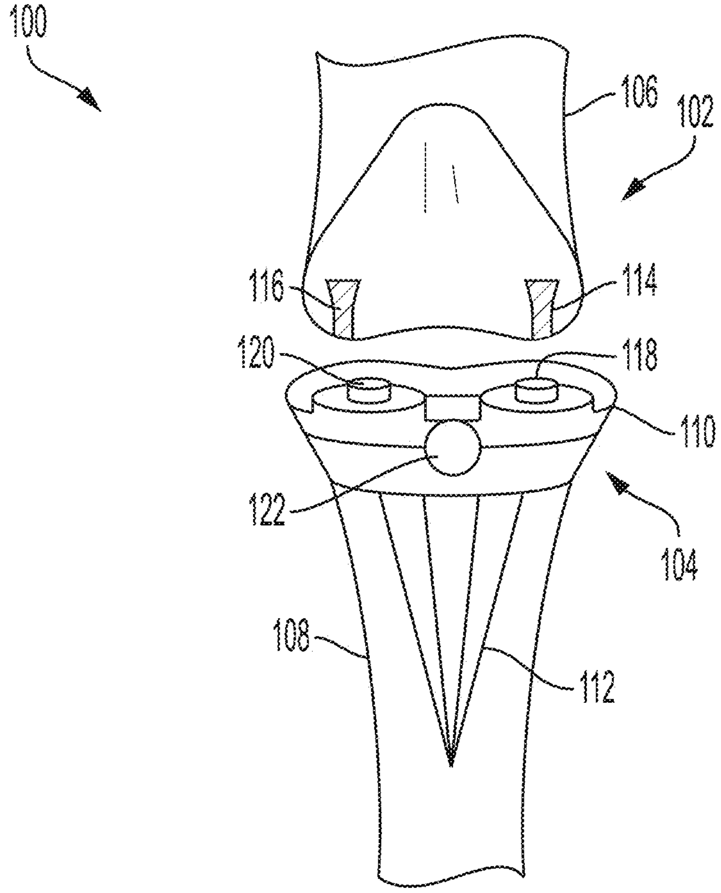
FIG. 1 is a front view of a knee joint implant according to an embodiment of the present disclosure.

FIG. 1 is a front view of a knee joint implant 100 according to an embodiment of the present disclosure. Knee joint implant 100 includes a femoral implant 102 located on a femur 106 and a tibial implant 104 located on a tibia 108. Tibial implant 104 has a tibial insert 110 configured to contact femoral implant 102, and a tibial baseplate or tibial stem 112 extending distally into tibia 108. Femoral implant 102 includes a medial encoder track 114 located on a medial side and a lateral encoder track 116 on a lateral side of the femoral implant. While the encoder tracks are shown along a surface of femoral implant 102 in FIG. 1, these tracks can be located within or partially within a femoral implant on the medial and lateral sides thereof in other embodiments. The encoder tracks can be made of various structures, including magnetic tape of varying lengths and magnetic markers positioned at discrete locations. The resolution of the encoder track can be adjusted depending on the required precision of the measured parameters such as joint displacement, joint rotation, joint slip, etc. Tibial insert 110 includes a medial read head 118 and lateral read head 120 to read a magnetic flux density from medial encoder track 114 and lateral encoder track 116, respectively. Medial read head 118 and lateral read head 120 can be any suitable magnetometer configured to detect and measure magnetic flux density, such as a Hall effect sensor. As tibia 108 rotates with reference to femur 106 during knee flexion and extension, medial encoder track 114 and lateral encoder track 116 move along medial read head 118 and lateral read head 120, respectively. This movement causes a change in magnetic flux density which is detected by read heads 118, 120, and can be utilized to measure knee joint implant 100 movement, rotation, speed and range of articulation, motion/activity, joint slip, and other motion related information. The magnetic-mechanic coupling of the read heads with the encoder tracks allows for direct, instantaneous, and continuous measurements of these knee joint implant parameters. A data transmitter such as an antenna 122 located on tibial insert 110 transmits the knee joint implant parameters measured by the read heads via Bluetooth or other similar wireless means to an external source such as a smart phone, tablet, monitor, network, etc. to allow for real time review of the knee joint implant performance.

Figure 2:
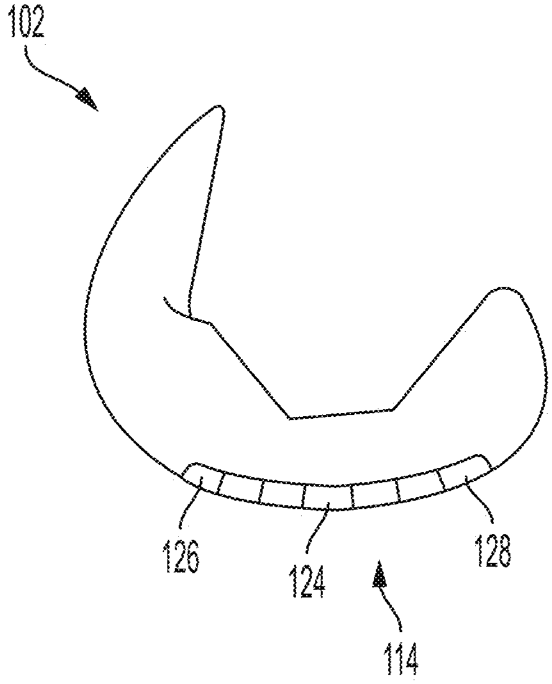
FIG. 2 is a side view of a femoral implant of the knee joint implant of FIG. 1.
Figure 3B:
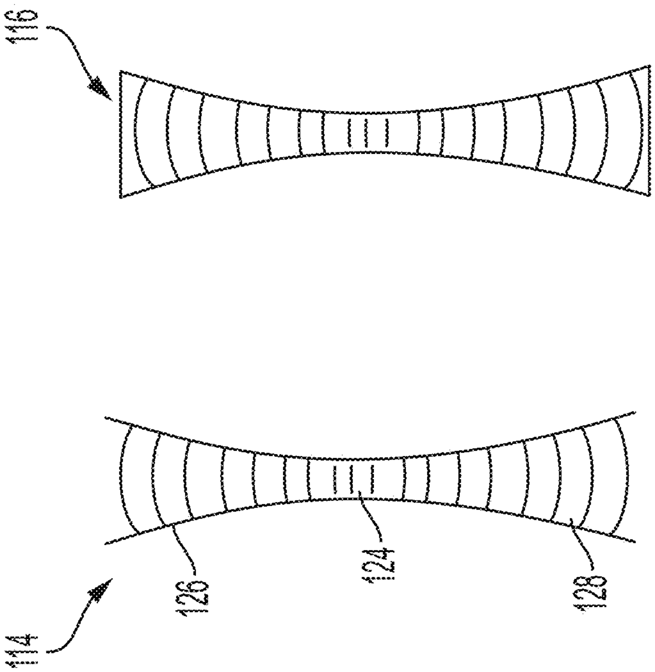
FIG. 3B is schematic view of encoder tracks of the femoral implant of FIG. 2.
Figure 3A:
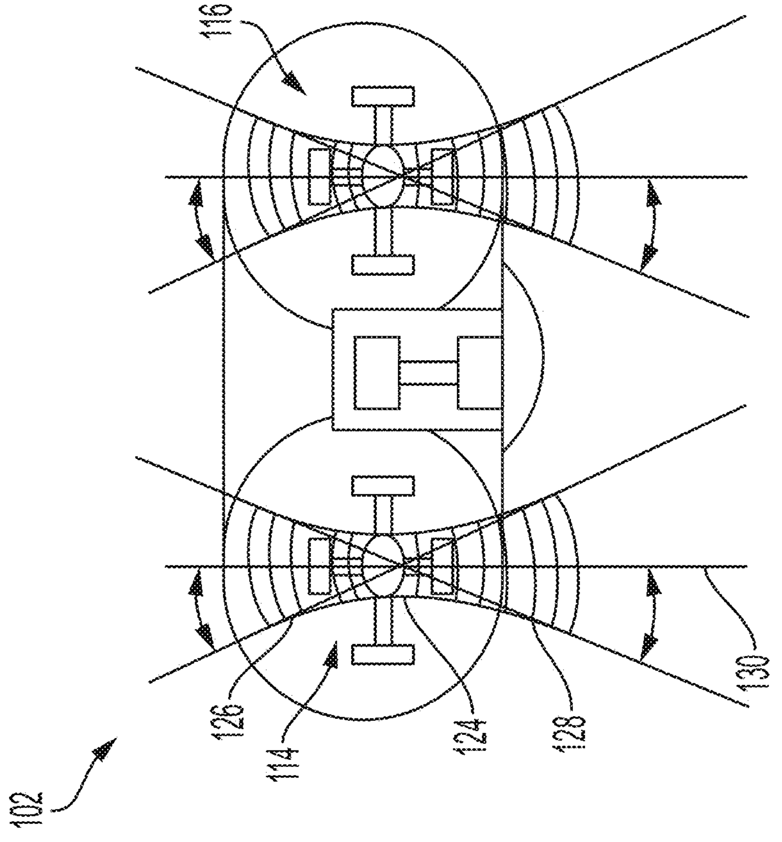
FIG. 3A is a bottom view of the femoral implant of FIG. 2.

FIGS. 2-3B illustrate additional details of femoral implant 102, medial encoder track 114 and lateral encoder track 116. As shown in FIG. 2, medial encoder track 114 extends from an anterior portion 126 of femoral implant 102 to a posterior portion 128 of the femoral implant along a track axis 130. Medial encoder track 114 includes a central portion 124 which is narrower than anterior and posterior portions 126, 128 as shown in FIG. 3A. As shown in FIG. 3B, medial encoder track 114 includes arched or curved magnetic lines to compensate for joint rotations in order to maintain uniform readings during a full range of motion of the knee joint. Similarly, lateral encoder track 116 extends from an anterior portion to a posterior portion of the femoral implant and includes a narrow central portion relative to the anterior and posterior portions with arched or curved magnetic lines. The conical profile and curved magnetic lines of the encoder tracks are configured to compensate for joint rotational motion and maintain alignment and coupling between the read heads and the tracks. This maximizes measurement collection and measurement accuracy during a full range of motion of the knee joint. The shape, size and location of the encoder tracks can vary depending on the implant.

Figure 4:
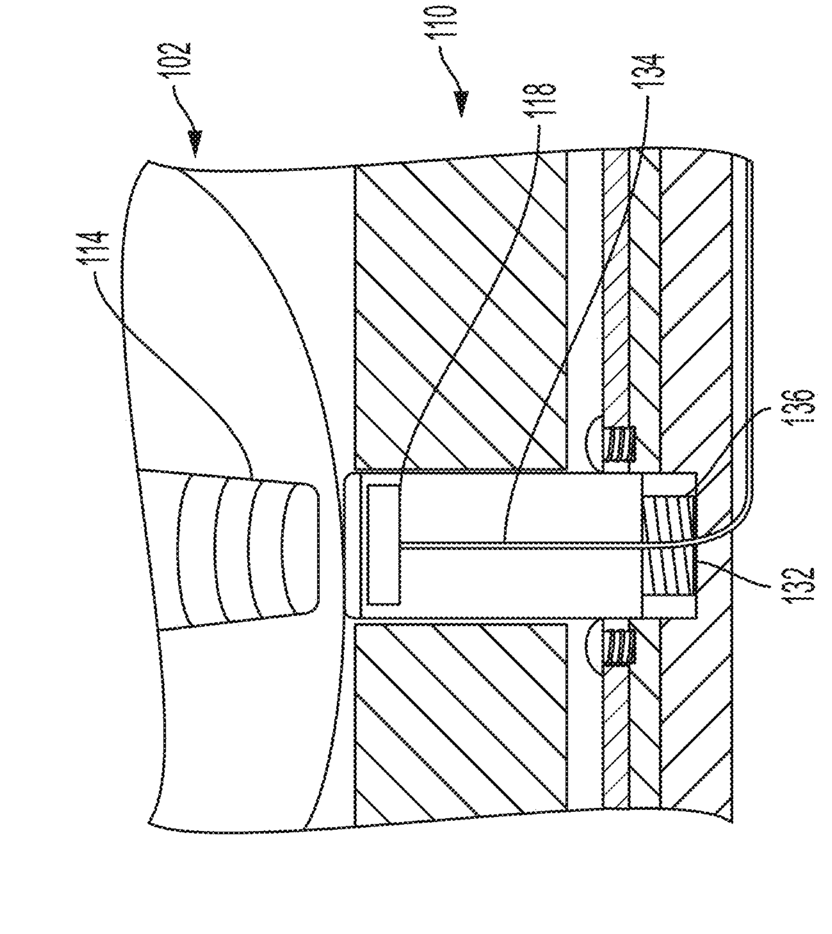
FIG. 4 is a partial view of an encoder read head and a load sensor of a tibial implant of the knee joint implant of FIG. 1.

FIG. 4 shows details of a medial side of tibial insert 110. Tibial insert 110 includes a medial load sensor 132 in connection with medial read head 118 via a medial connector 134. Medial load sensor 132 is a load measuring sensor such as a strain gauge or piezoelectric sensor configured to measure loads or forces transmitted from medial read head 118 via medial connector 134. Medial connector 134 can be a rigid member such as a connecting rod to transmit loads from medial read head 118 to medial load sensor 132. As shown in FIG. 4, a portion of the medial side of femoral implant 102 directly contacts medial read head 118 to transmit loads (medial side loads), which is then measured by medial load sensor 132. Medial read head 118 is spring-loaded by a medial load spring 136 located below medial load sensor 132 to ensure contact between medial read head 118 and femoral implant 102. Similarly, a lateral side of tibial insert 110 includes a lateral load sensor, a lateral connector, and a lateral load spring. The lateral load sensor is configured to measure lateral loads between femoral implant 102 and tibial implant 104. Measured medial and lateral loads are transmitted via antenna 122 to an external source. Thus, knee joint implant 100 can simultaneously provide knee motion information (rotation, speed, flexion angle, etc.) and knee load (medial load, medial load center, lateral load, lateral load center, etc.) in real time to an external source.

Figure 5A:
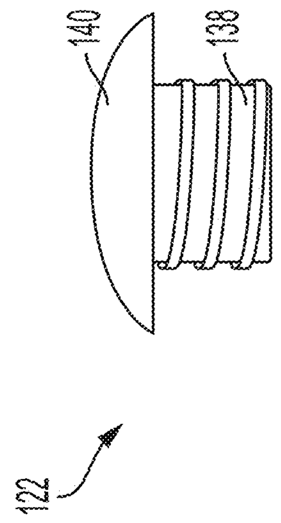
FIG. 5A is a front view of an antenna of the knee joint implant of FIG. 1.
Figure 5B:
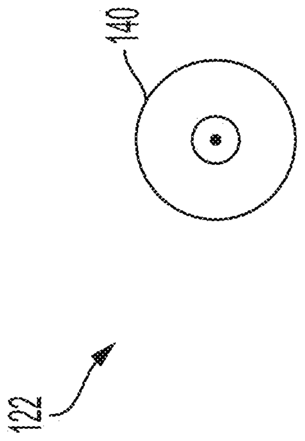
FIG. 5B is a top view of the antenna of FIG. 5A.

Details of antenna 122 are shown in FIGS. 5A and 5B. Antenna 122 includes screw threads configured to be attached to tibial insert 110. Antenna 122 can include a coax interface to shield knee joint and improve transmission between knee joint implant 100 and the external source. A battery is located adjacent antenna 122 (not shown) to power knee joint implant 100. Antenna 122 can serve as a charging port via radio frequency (RF) or inductive coupling if a rechargeable battery is used. The location of battery and antenna 122 in tibial insert 110 allow for convenient access to remove and replace these components if necessary. Various other sensors such as a temperature sensor, pressure sensor, accelerometer, gyroscope, magnetometer, pH sensor, etc., can be included in knee joint implant 100 as more fully described below.

Figure 6:
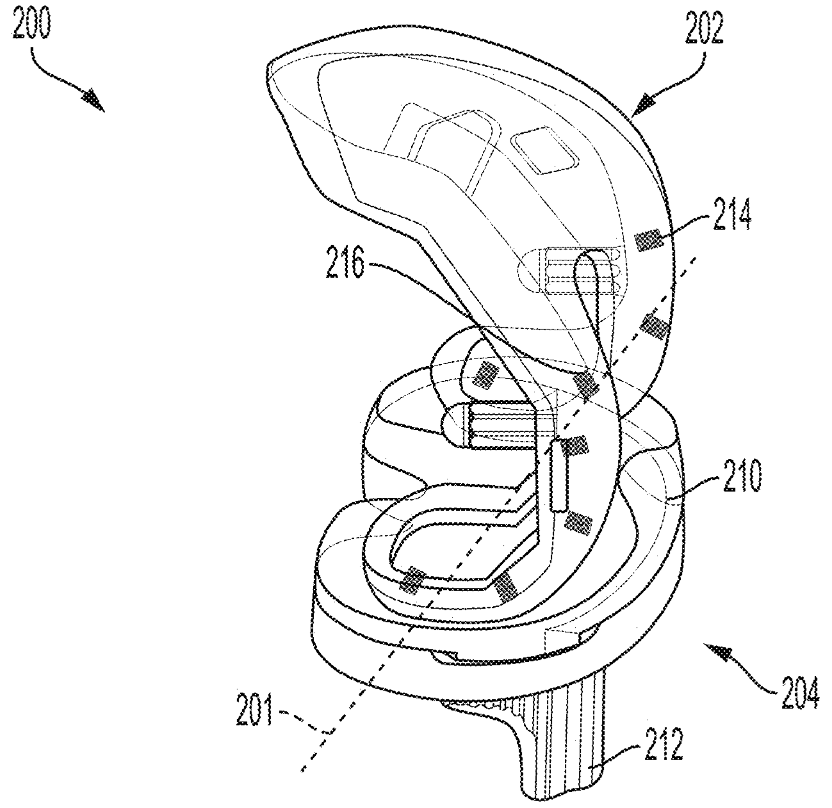
FIG. 6 is a perspective side view of a knee joint implant according to another embodiment of the present disclosure.
Figure 7:
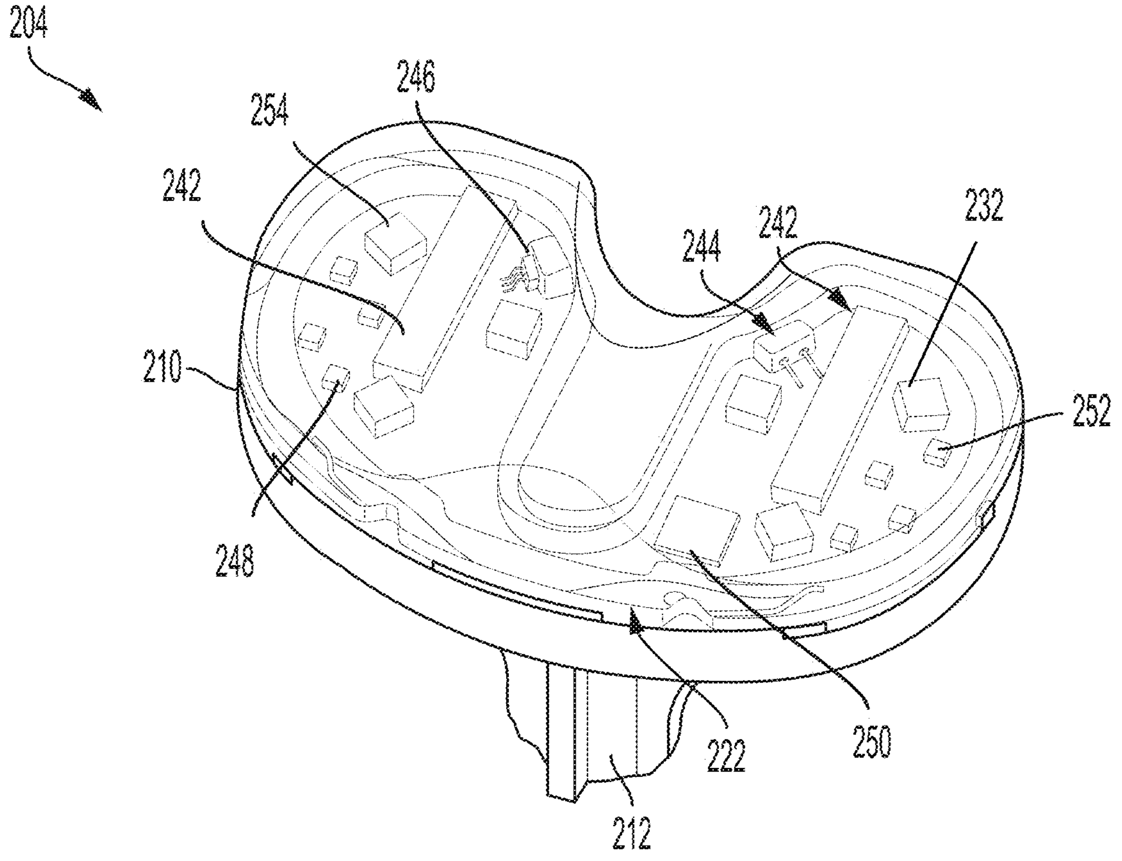
FIG. 7 is a perspective front view of a tibial implant of the knee joint implant of FIG. 6.
Figure 8:
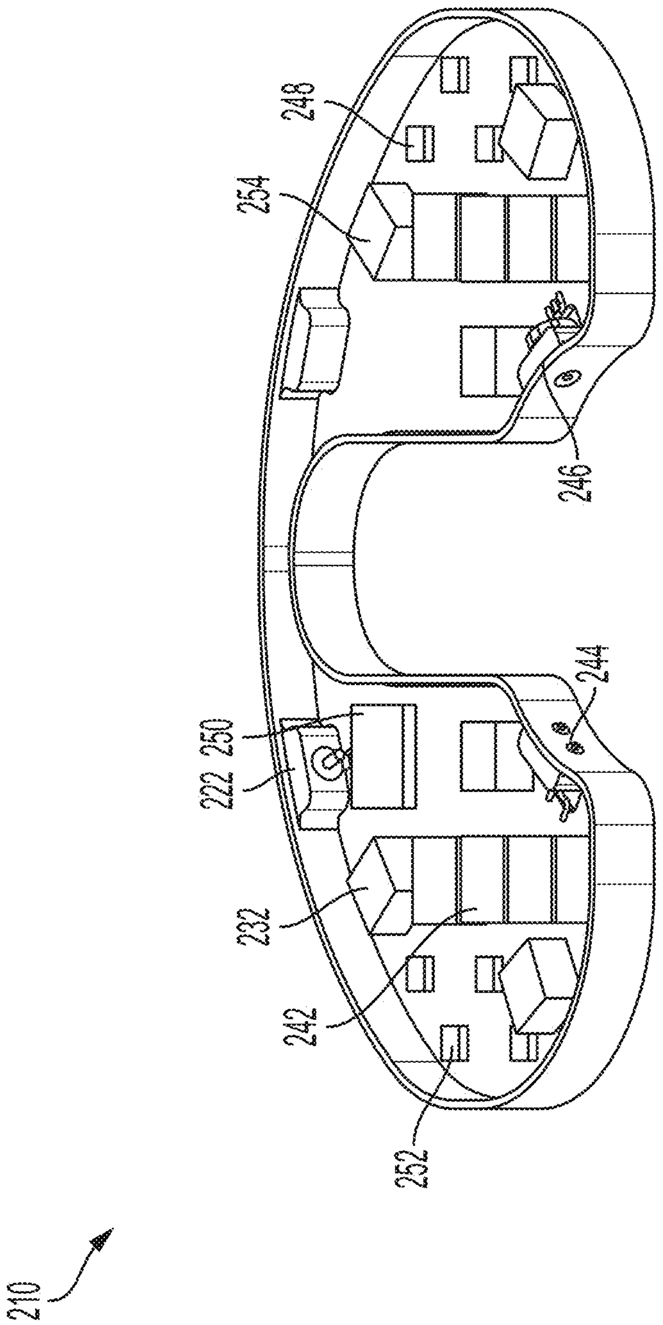
FIG. 8 is a partial perspective view of an insert of the tibial implant of FIG. 6

FIG. 6 is a perspective side view of a knee joint implant 200 according to another embodiment of the present disclosure. Knee joint implant 200 is similar to knee joint implant 100, and therefore like elements are referred to with similar numerals within the 200-series of numbers. For example, knee joint implant 200 includes a femoral implant 202, a tibial implant 204 with a tibial insert 210 and a tibial stem 212. However, knee joint implant 200 includes magnetic medial markers 214 and magnetic lateral markers 216 located at discrete locations along the medial and lateral sides of femoral implant 202, respectively.

Figure 9:
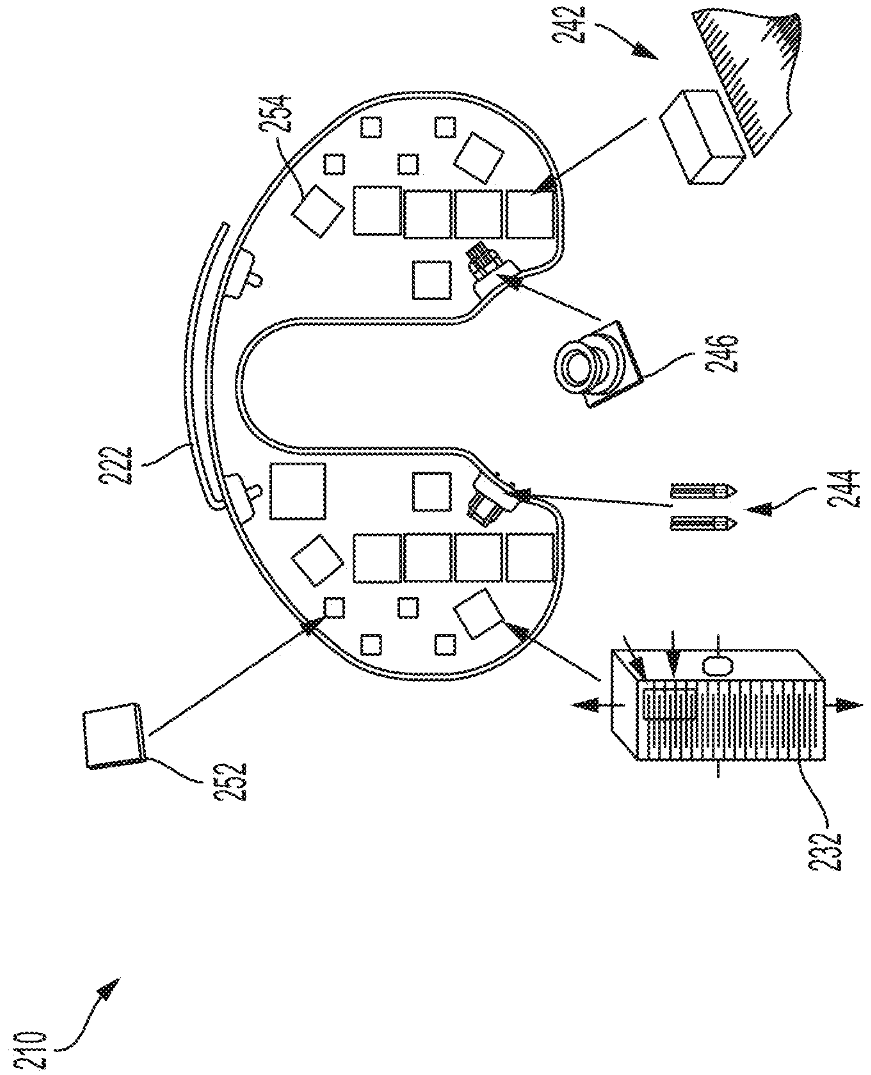
FIG. 9 is a partial top view of the insert of FIG. 8 showing details of various insert components.

Details of tibial insert 210 are shown in FIGS. 7-11. Tibial insert 210 includes batteries 242 on both medial and lateral sides. Batteries 242 can be solid state batteries, lithium ion batteries, lithium carbon monofluoride batteries, lithium thionyl chloride batteries, lithium ion polymer batteries, etc. As best shown in FIG. 9, Hall sensor assemblies, with each assembly including at least one Hall sensor, are used as a medial marker reader 252 and a lateral marker reader 248 to read medial markers 214 and lateral markers 216, respectively. Each Hall sensor assembly can include multiple Hall sensors arranged in various configurations and orientations. For example, the Hall sensor assembly can include Hall sensors oriented in Cartesian coordinates. As the tibia rotates with reference to the femur during knee flexion and extension, medial markers 214 and lateral markers 216 move along medial marker reader 252 and lateral marker reader 248, respectively. This movement causes a change in magnetic flux density, which is detected by marker readers 252, 248, to measure knee joint implant 200 movement, rotation, speed and range of articulation, motion/activity, joint slip, and other motion related information. The magnetic-mechanic coupling of the marker readers with the markers allows for direct, instantaneous, and continuous measurements of these knee joint implant parameters without the need to process this information via an algorithm or other means. While eight Hall sensor assemblies (four on each side) are shown in this embodiment, other embodiments can have more than eight or less than eight Hall sensor assemblies positioned at various locations. The arrangement of marker readers and markers provide absolute positions of knee joint implant 200 supporting wake-up-and-read kernels. Thus, no inference of movement by data synchronization techniques is required to obtain absolute position data of knee joint implant 200. The number of medial markers 214 can be different from the number of lateral markers 216 to account for variation in signal fidelity between these sides. For example, seven magnetic markers can be provided on the medial side and only four magnet markers can be provided on the lateral side to improve signal fidelity and motion detection precision on the medial side.

As best shown in FIG. 9, three piezo stacks on the medial side serve as medial load sensors 232, and three piezo stacks on the lateral side serve as lateral load sensors 254. The staggered or non-linear arrangement of the three piezo stacks on the medial and lateral sides allow for net load measurements and identification of resultant load centers at the medial and lateral sides. Thus, knee joint implant 200 can simultaneously provide knee motion information (joint rotation, joint speed, joint flexion angle, joint slippage, etc.) and knee load (medial load, medial load center, lateral load, lateral load center, etc.) in real time to an external source. The piezo stacks are configured to generate power from the patient's motion by converting pressure on the piezo stacks to charge batteries 242 as more fully described below. Thus, knee joint implant 200 does not require external charging devices or replacement batteries for the active life of the implant.

Tibial insert 210 includes an infection or injury detection sensor 244. For example, the infection or injury detection can be a pH sensor configured to measured bacterial infection by measuring the alkalinity of synovial fluid to provide early detection of knee joint implant 200 related infection. A temperature and pressure sensor 246 is provided in tibial insert 210 to monitor knee joint implant 200 performance. For example, any increase in temperature and/or pressure may indicate implant-associated infection. Pressure sensor 246 is used to measure synovial fluid pressure in this embodiment. Temperature and/or pressure sensor 246 readings can provide early detection of knee joint implant 200 related infection. Thus, injury detection sensors 244 and 236 provide extended diagnostics with heuristics for first level assessment of infections or injury related to knee joint implant 200. An onboard processor 250 such as a microcontroller unit ("MCU") is used to read sensors 244 and 236 and process results for transmission to an external source. This data can be retrieved, processed, and transferred by the MCU via antenna 222 continuously, at predefined intervals, or when certain alkalinity, pressure, and/or temperature thresholds, or any combinations thereof, are detected.

Figure 10:
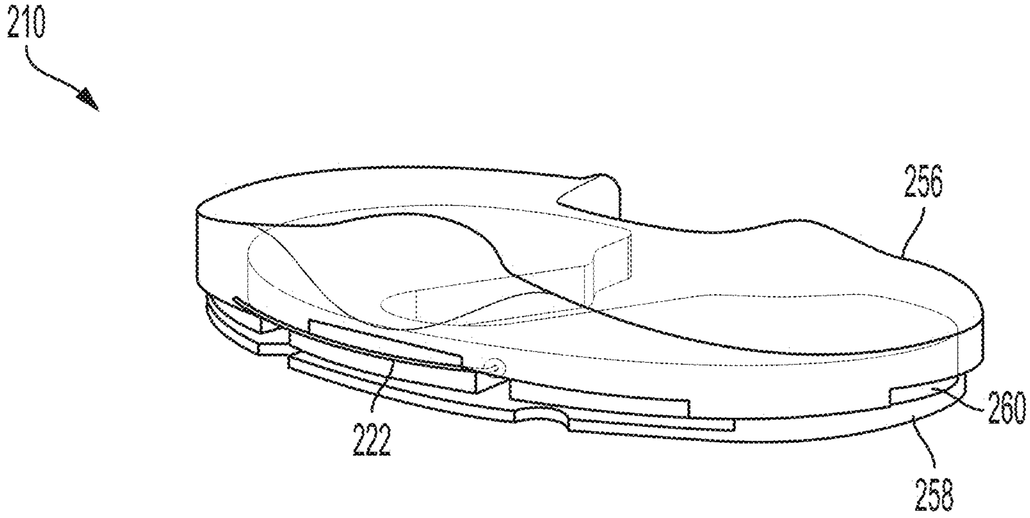
FIG. 10 is a perspective side view of the insert of the tibial implant of FIG. 7.
Figure 11:
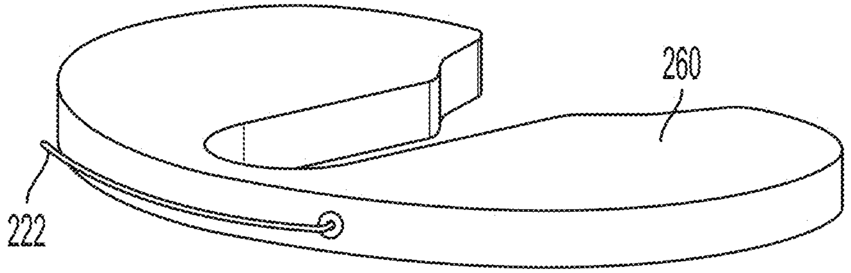
FIG. 11 is a perspective side view of a cover of the insert of FIG. 10.

The various sensors and electronic components of tibial insert 210 are contained within an upper cover 256 and a lower cover 258 as shown in FIG. 10. The upper and lower covers can be made from a polymer. Antenna 222 is located on an anterior portion of knee joint implant 200 to provide better line of site for transmitting data with less interference. The antenna is fixed inside the polymer covers to provide predictable inductance and capacitance. A cover 260 encloses the sensors and electronic components of tibial insert 210 as shown in FIG. 11. Cover 260 can be a hermetic cover to hermetically seal tibial insert 210. Cover 260 is preferably made of metal and provides radio frequency ("RF") shielding to the knee joint.

The modular design of knee joint implant 200 provides for convenient maintenance of its components. For example, an in-office or outpatient procedure will allow a surgeon to access the tibia below the patella (an area of minimal tissue allowing for fast recovery) to access component of knee joint implant 200. The electronic components and sensors of knee joint are modular and connector-less allowing for convenient replacement of tibial insert 210 or upgrades to same without impacting the femoral implant or the tibial stem.

Figure 12:
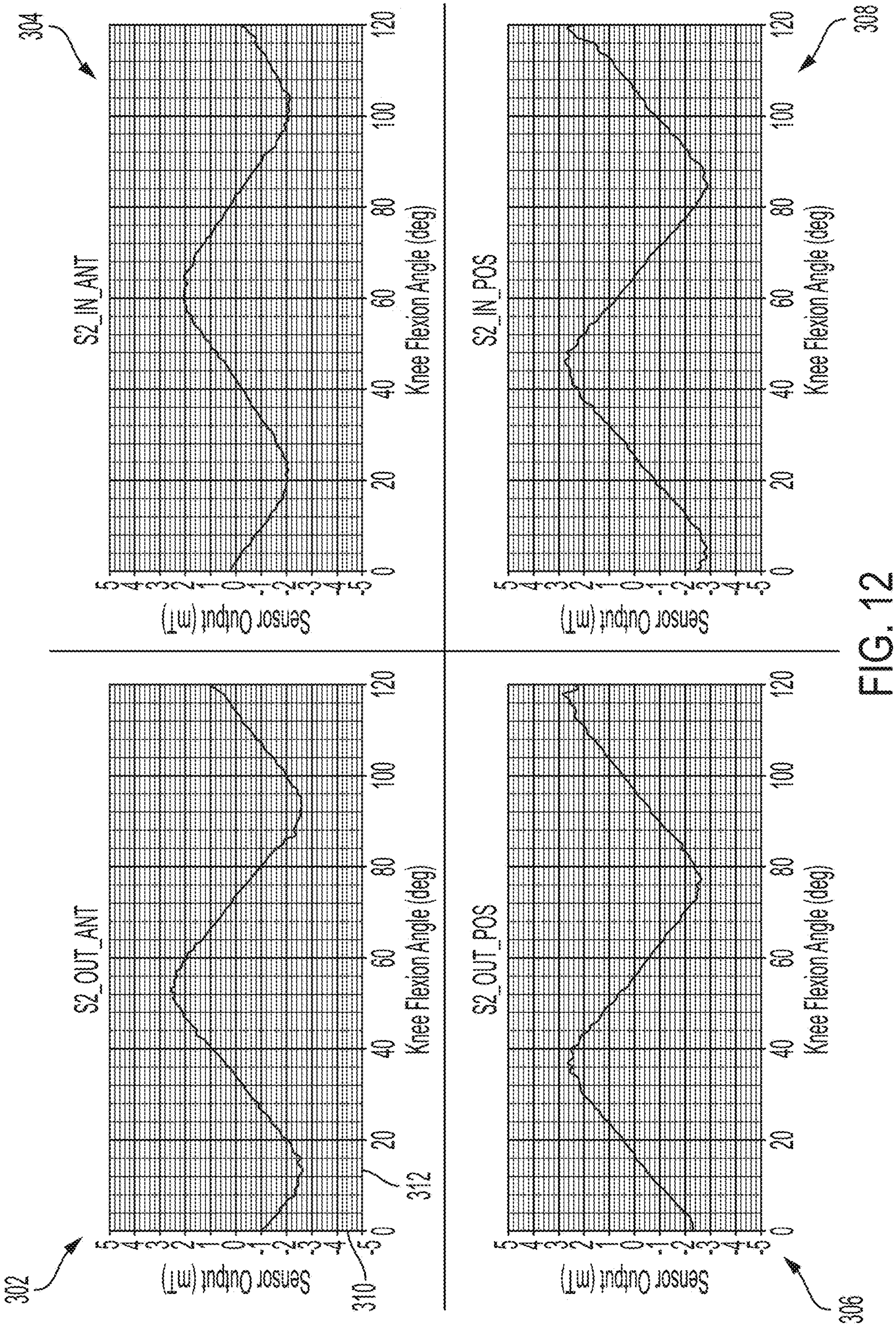
FIG. 12 are graphs showing magnetic flux density measurements of the implant sensors and knee flexion angles.

Graphs plotting magnetic flux density measurements 310 and knee flexion angles 312 are shown in FIG. 12. Magnetic flux density measurements 310 are generated from the magnetic-mechanic coupling of marker readers 248, 252 with the markers 214, 216 as more fully described above. Graphs 302 and 304 show magnetic flux density (mT) measurements from two Hall sensor assemblies (medial marker reader 252 or lateral marker reader 248) for a first range of motion of the knee joint. Similarly, graphs 306 and 308 show magnetic flux density (mT) measurements from two Hall sensors (medial marker reader 252 or lateral marker reader 248) for a second range of motion of the knee joint. The placement of magnetic markers 214, 216 on the femoral component create a sinusoidal magnetic flux density around femoral implant 202. As the femoral implant 202 rotates around an axis of rotation 201 shown in FIG. 6, the marker readers read sine and cosine waveforms. The magnitude of the sine and cosine waves are interpolated to a near linear knee flexion angle. Placing the individual magnetic markers of medial markers 214 and lateral markers 216 at different separation angles on each condyle of femoral implant 202 creates a phase shift in the measurements from one condyle to the next as the knee rotates. This phase shift can then be used to correct for any rollovers in the interpolated waveform. Thus, marker readers 248, 252 and markers 214, 216 serve as an absolute rotation sensor measuring knee flexion through a full range of motion of knee joint implant 200. In addition to the two Hall sensor assemblies on the lateral and medial side of tibial insert 210, the remaining Hall sensor assemblies of marker readers 248, 252 allow for 6-degrees of freedom movement measurements of knee joint implant 200 as more fully explained below. While an absolute magnetic encoder is disclosed in this embodiment, other embodiments can include a knee joint implant with an incremental magnetic encoder.

Figure 13:
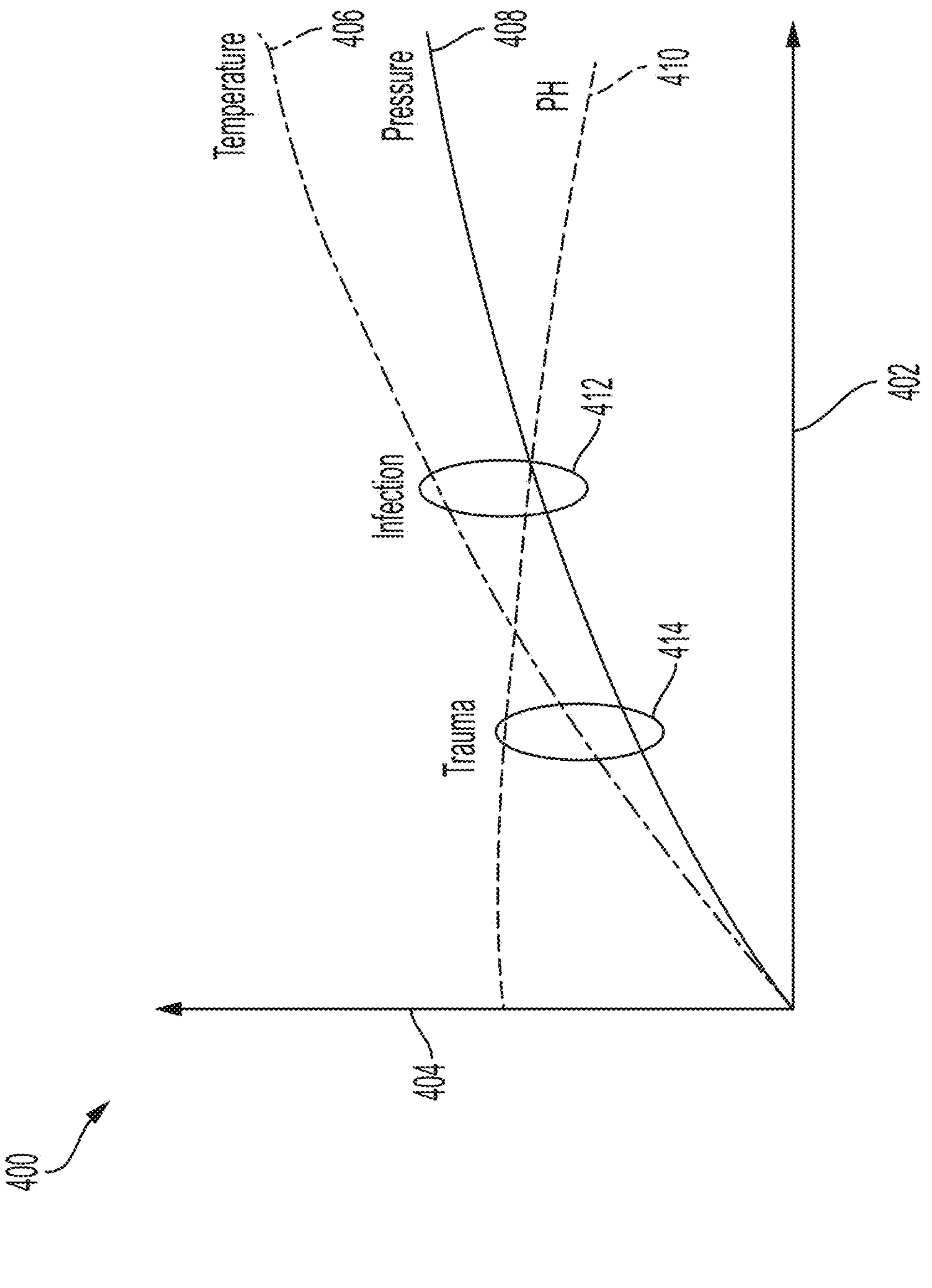
FIG. 13 is a graph showing various implant sensor readings of the knee joint implant of FIG. 6.
Figure 14:
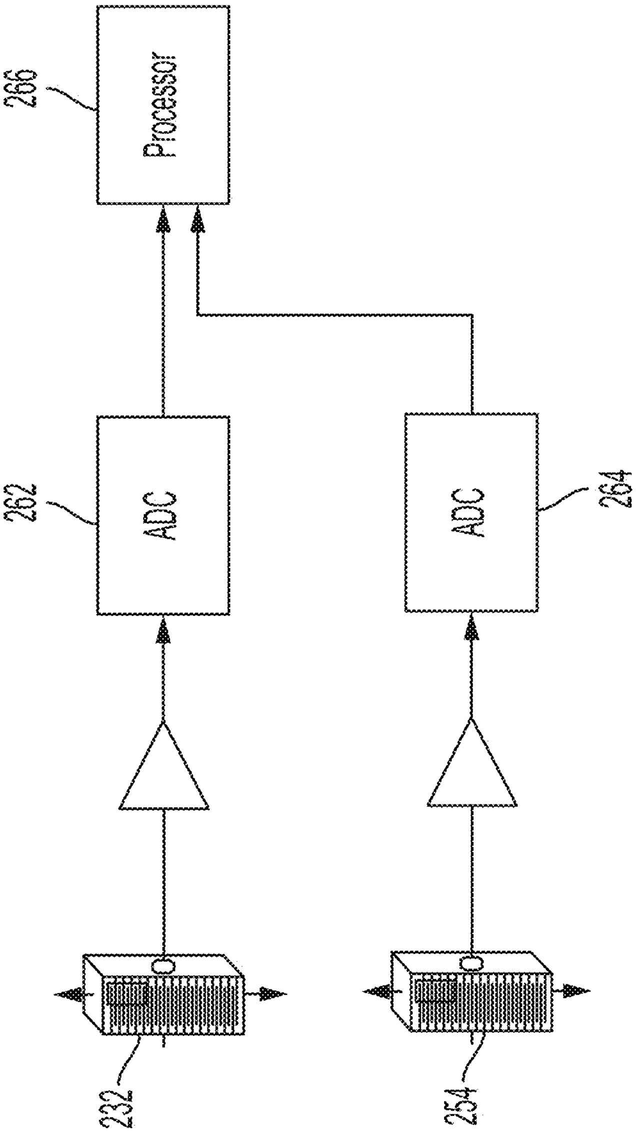
FIG. 14 is a schematic view of implant sensors of the knee joint implant of FIG. 6 in communication with a processor.

FIG. 13 is a graph showing various implant injury detection sensor readings 404 of knee joint implant 200 for early detection of knee joint implant related infection and/or failure. Pressure 408 and temperature 406 are measured using temperature and pressure sensor 246, and alkalinity 410 is measured using pH sensor 244 over time 402. As more fully explained above, alkalinity 410 measurements of joint synovial fluid can indicate bacterial infection to provide early detection of knee joint implant 200 related infection. Increase in pressure 408 and temperature 406 readings may indicate implant-associated infection. Variation or change in synovial fluid pressure 408 may indicate implant malfunction. In addition to predetermined absolute thresholds of the temperature, pressure and alkalinity readings indicating impending infection or implant failure, collective analysis of these readings can offer early detection warning ahead of the failure/infection thresholds. As shown in FIG. 14, a combination of temperature, pressure and alkalinity may indicate early detection of trauma 414 or infection 412. Thus, injury detection sensor readings provide extended diagnostics with heuristics for first level assessment of infections or injury related to knee joint implant 200.

In addition to the sensors described above, particularly with reference to knee joint implants 100 or 200, it is contemplated that the implant may include any type and any number of sensors useful for detecting signs of infection, inflammation, injury, etc. within the knee joint. For example, knee joint implant 200 may include an optical sensor capable of measuring the turbidity of the synovial fluid, and/or a blood sensor or analyzer capable of capturing data on pathogens present in the joint, which may allow for a more accurate treatment in the case of infection. Still further, the blood analyzer may include other functions such as glucose analysis, which may be useful for cases of diabetes in joint replacement.

Figure 86:
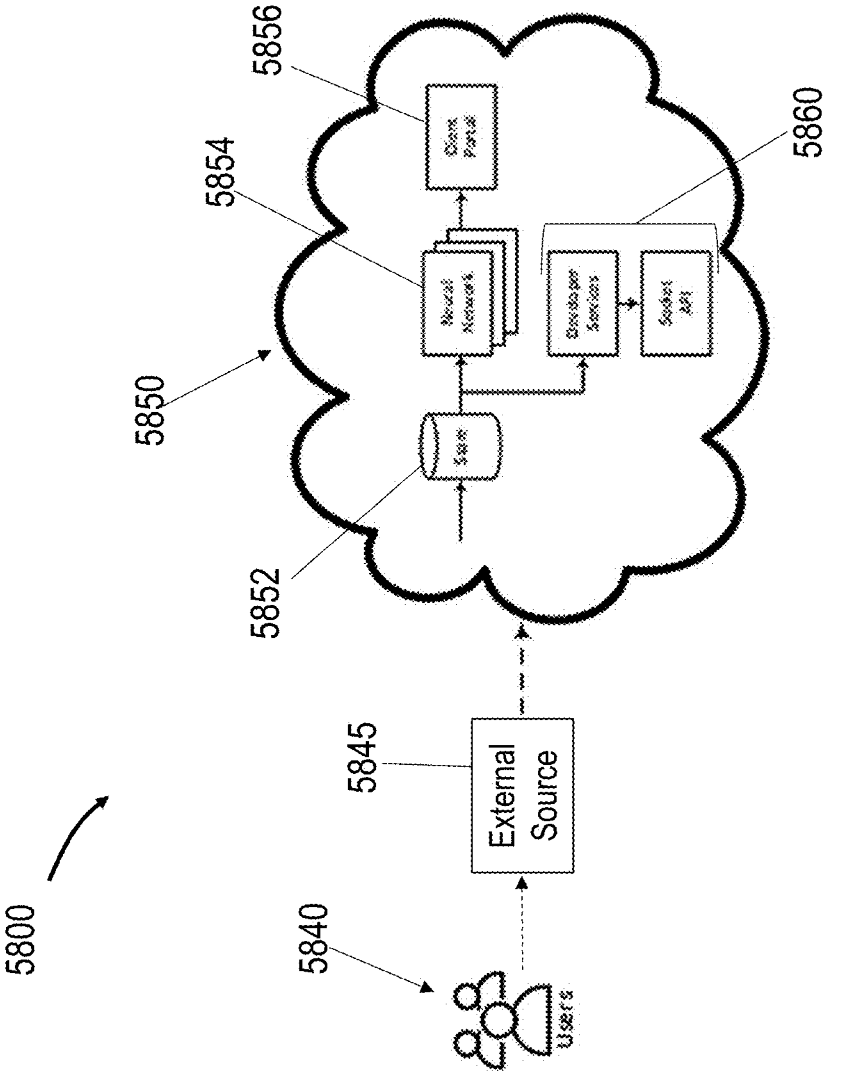
FIG. 86 is a diagram showing the communication between an implanted knee joint implant and a cloud network.

As noted above, the data measured and gathered by the various sensors are read by the processor 250, such as an MCU, to process and transfer the measurements to an external source 5845 via the antenna 222. Processor 250 can send data in packets arranged by data types. For example, data packets containing Hall sensor position, IMU gyro, accelerometer, pH, pressure, temperature, etc. can be each transmitted under unique IDs. The type of data and frequency of measurement can be defined by a physician via a platform such as OrthoLogIQ, and sent over the air to the implant by a paired mobile device. During normal operation, the processor can be configured to run a particular task (such as a list of measurements assigned by a physician) at a defined rate (the frequency). The data can then be stored in local FRAM. The processor can then go to sleep until it is woken up by a timer interrupt to read, make readings, store data in memory, and return to sleep status as scheduled. Data upload can be during a defined period (primary) or on first chance (secondary). As shown in FIG. 86, the external source 5845 may be any device, such as one of the devices identified above, and is connected to a network such as a cloud network 5850. That is, the stream of data relayed from the processor 250 to the external source 5845 is fed into storage 5852 of the cloud 5850 and incorporated into a single or a plurality of neural network functions 5854, thus passing from a user 5840 to the cloud 5850 as shown in FIG. 86. For ease of description, all data obtained by a single implant in a respective user 5840 or patient will be referred to as a single set of data. Thus, when a first type of data is measured by the sensors and transmitted from the processor 250 to the external source 5845, the external source 5845 stores that data in the neural network 5854 of the cloud 5850. This process may then be repeated with a second user 5840 or patient, such that a second set of data is measured by the sensors of a knee joint implant 200 implanted in the knee joint of second user 5840 or patient, processed by the processor 250, and transmitted to the same external source 5845 by the antenna 222 of the second knee joint implant 200 to then be stored in the neural network 5854 of the cloud 5850. It is also contemplated that the second set of data may be conveyed to a second external source different from the first external source to which the first set of data was conveyed, however, all external sources may be connected to the same neural network 5854. This process may continue for additional users 5840, thereby storing and accumulating a plurality of data sets in the neural network 5854.

Some of the content stored in the neural network 5854 of the cloud 5850 includes, as described above, a set of data from each knee joint implant 200. Each set of data may include several types of data. That is, a first type of data may be obtained from a first type of sensor (e.g., temperature readings may be obtained from a temperature sensor, or pH readings may be obtained from a pH sensor). From such readings of each type and/or set of data, a clinician makes a diagnosis of the state of the knee joint or knee joint implant 200, either based on the set of data or on other factors (such as information provided by the patient), or a combination thereof. The clinician's diagnosis includes the determination of the knee joint or knee joint implant 200 being in any one of a variety of states, such as a healthy state, an infected state, an inflamed state, an injured state, or the like. The diagnosis may be manually entered into the external source 5845 by the clinician and thereby associated with the corresponding set of data in the neural network 5854.

After a first set of data from a first knee joint implant 200 in a first user 5840 is provided in the neural network 5854 with an associated diagnosis of the state of the knee joint implant 200 or knee joint, such a process may be repeated for a second set of data from a second knee joint implant 200 in a second user 5840, and may continue thereafter for any number of patients and sets of data which the cloud 5850 is capable of holding. As shown in FIG. 86, the neural network 5854 is operatively coupled to a software system 5860 which analyzes the various existing sets of data and associated diagnoses stored in the neural network 5854 to make inferences and estimations on the state of the knee joint and/or the knee joint implant 200. That is, the software system 5860 interprets each type of data within each set of data in view of the corresponding diagnoses of the respective implant which already exists within the neural network 5854 of the cloud 5850 to then comes to a conclusion about the state of another patient's knee joint implant 200. For example, based on existing sets of data stored in the neural network 5854, the software 5860 may define certain predetermined values with which the software 5860 will determine that if any of the types of data were to match such predetermined values, the software 5860 would deem a new patient's knee joint implant 200 to be in a certain state. In other examples, the software 5860 may define a range of predetermined values with which the software 5860 will determine that if any of the types of data were to fall outside of the predetermined range, the software 5860 would deem the new patient's knee joint implant 200 to be in a certain state, and alternatively may be deemed to be in a different state if the sensor measurements were to fall inside the predetermine range of values. For instance, the software 5860 might conclude that when the temperature of a knee joint implant 200 falls between X and Y, the knee joint is in a healthy state. However, when the measured temperature of a knee joint implant 200 falls outside of (e.g., above) the range between X and Y or above a threshold temperature, the knee joint may be determined to be in an inflamed state. As described above, the software 5860 takes into account a combination of the different types of data (e.g., temperature, pressure, pH, etc.) to conclude that a knee joint or a knee joint implant 200 is in a particular state. For instance, as shown by the graph in FIG. 13, the software system 5860 takes multiple types of data from multiple sensors and formulates a determination of the state of the joint or joint implant while factoring in each the measurements from each sensor.

Upon determining the state of a knee joint or a knee joint implant 200, the software 5860 may then initiate an alert or a warning, depending on the type of state it has determined the knee joint or implant 200 to be in. For example, if the knee joint or implant 200 is determined by the software 5860 to be in an infected state, the software 5860 initiates a warning notifying the clinician of the patient state, or notifying the client of the same through the client portal 5856. In some scenarios, such an alert is provided prior to the patient's feeling of pain or discomfort and therefore prior to a clinician's diagnosis would have occurred had the knee joint implant 200 not provided the alert. It is contemplated that the processor 250 of the implant 200 may communicate with the external source when prompted or activated by the patient (e.g., in the patient's home) or by the clinician (e.g., in the clinician's office). It is also contemplated that the processor 250 may communicate with the external source 5845 automatically when within a certain proximity of the external source 5845, allowing the software 5860 to issue a warning to the client portal 5856 even when unsuspected by the patient. In some examples, the client portal 5856 is accessible through the external source 5845. In further examples, if the software 5860 determines that the knee joint and the knee joint implant 200 are in a healthy state, the software 5860 may issue a notice to the patient/clinician indicating such condition (e.g., when the patient or clinician activates communication between the implant 200 and the external 5845 source), or the implant 200 may issue nothing at all.

The set of data of each patient implant 200 stored in the neural network 5854 of the cloud 5850 will remain in the neural network 5854 for as long as permitted by the clinician. However, it is also contemplated that the software 5860 may be capable of detecting an outlier set of data based on an associated diagnosis or manual input from the clinician, and the software 5860 may be capable of disregarding such outliers from its interpretations or removing such data from the neural network 5854 altogether. Generally, with each additional set of data from each patient implant 200 that is added to the neural network 5854, the software 5860 uses artificial intelligence to update its reference points and further refine its ability to detect the state a joint or joint implant 200. For example, with each addition of a new set of data from an implanted implant 200 determined to be in a healthy state, or a new set of data from an implanted implant 200 determined to be in an infected state, etc., the software 5860 may modify its predetermined values or the predetermined ranges of values which it uses to determine the state of a knee joint or implant 200, thereby further enhancing its accuracy of detection with each addition of new data. Therefore, the software 5860 is able to draw conclusions from an aggregate of data history stored within the neural network 5854, and the knowledge base of the neural network 5854 continuously improves over time.

Figure 96A:
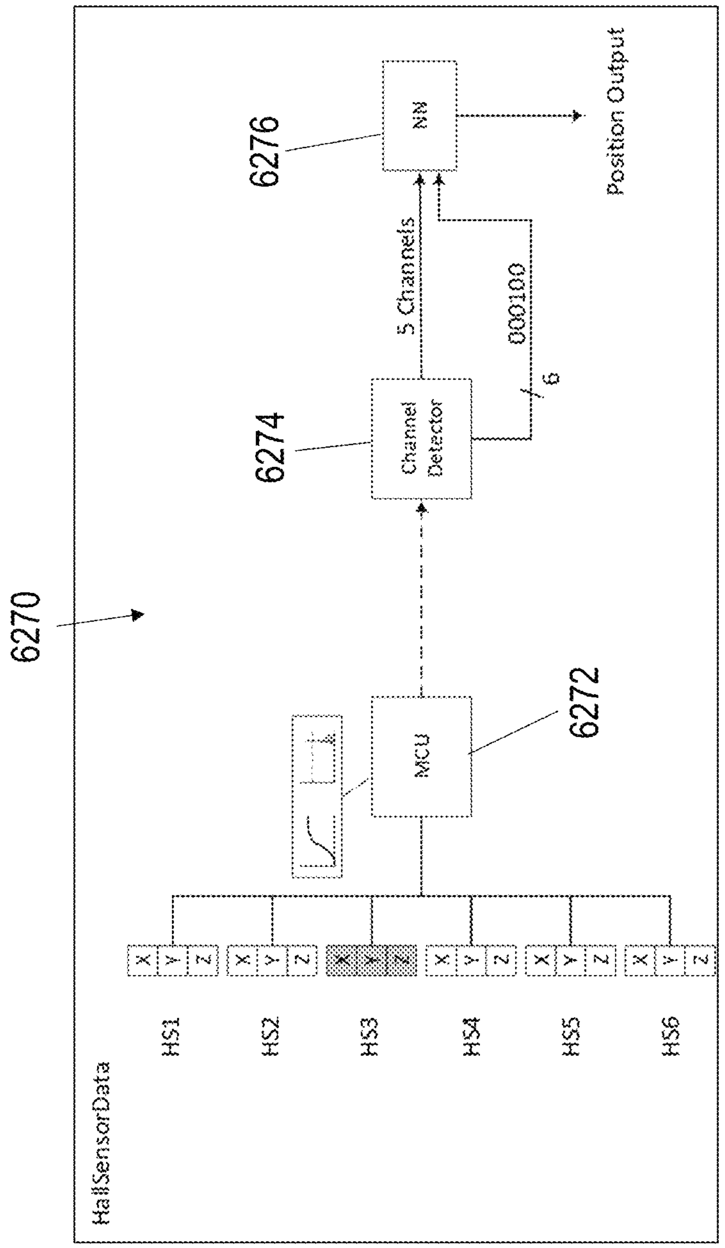
FIG. 96A is a flowchart showing elements of a sensor redundancy system.

In some examples, knee joint implant 200 employs a sensor redundancy system 6270 to filter the measured data using sensor redundancy, as shown in FIGS. 96A-96D, which helps to optimize and ensure accurate data measurements. In the example described herein, the plurality of redundant sensors is detailed with respect to the Hall sensors included in knee joint implant 200, however, it is contemplated that this concept may apply to any other type of sensor included in knee joint implant 200, such as temperature sensors, pressure sensors, accelerometers, gyroscopes, magnetometers, pH sensors, etc., specifically when more than one of the same type of sensor is included in the implant. Although knee joint implant 200 is described above as including eight Hall sensors assemblies, the example described herein with respect to FIGS. 96A-96D includes six Hall sensors, labeled sequentially as HS1-HS6. Each Hall sensor HS1-HS6 detects at least a positioning coordinate in each of an X-direction, a Y-direction, and a Z-direction as shown in FIG. 96A, which may be used to sense movement, rotation, speed and range of articulation, motion/activity, joint slip, and other motion related information as described above. Each Hall sensor is operatively and electrically coupled to a processor or microcontroller unit ("MCU") 6272 so that the data obtained by each of the sensors can be processed into information to be output by the knee joint implant 200. The data read from each Hall sensor is marked with a poison value and arranged into data packets, or packetized, by the MCU 6272 which can be later interpreted as described below in more detail.

Figure 96B:
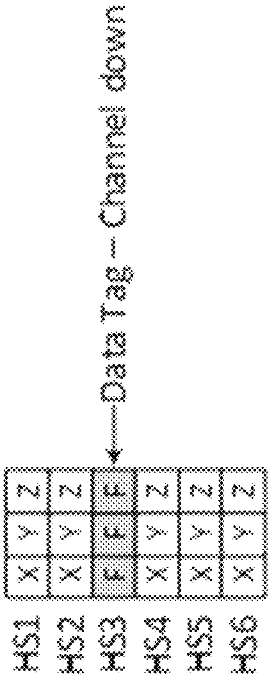
FIG. 96B is a schematic arrangement of data recorded by Hall effect sensors in the sensor redundancy system of FIG. 96A.
Figure 96C:
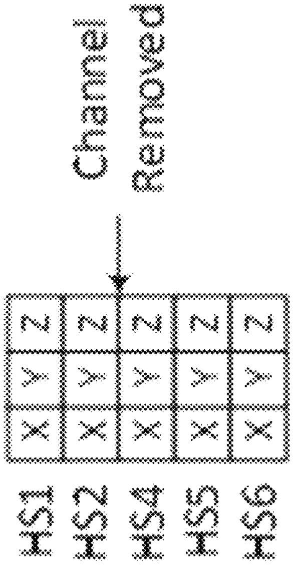
FIG. 96C is a schematic arrangement of the data of FIG. 96B excluding a sensor having inaccurate data.
Figure 96D:
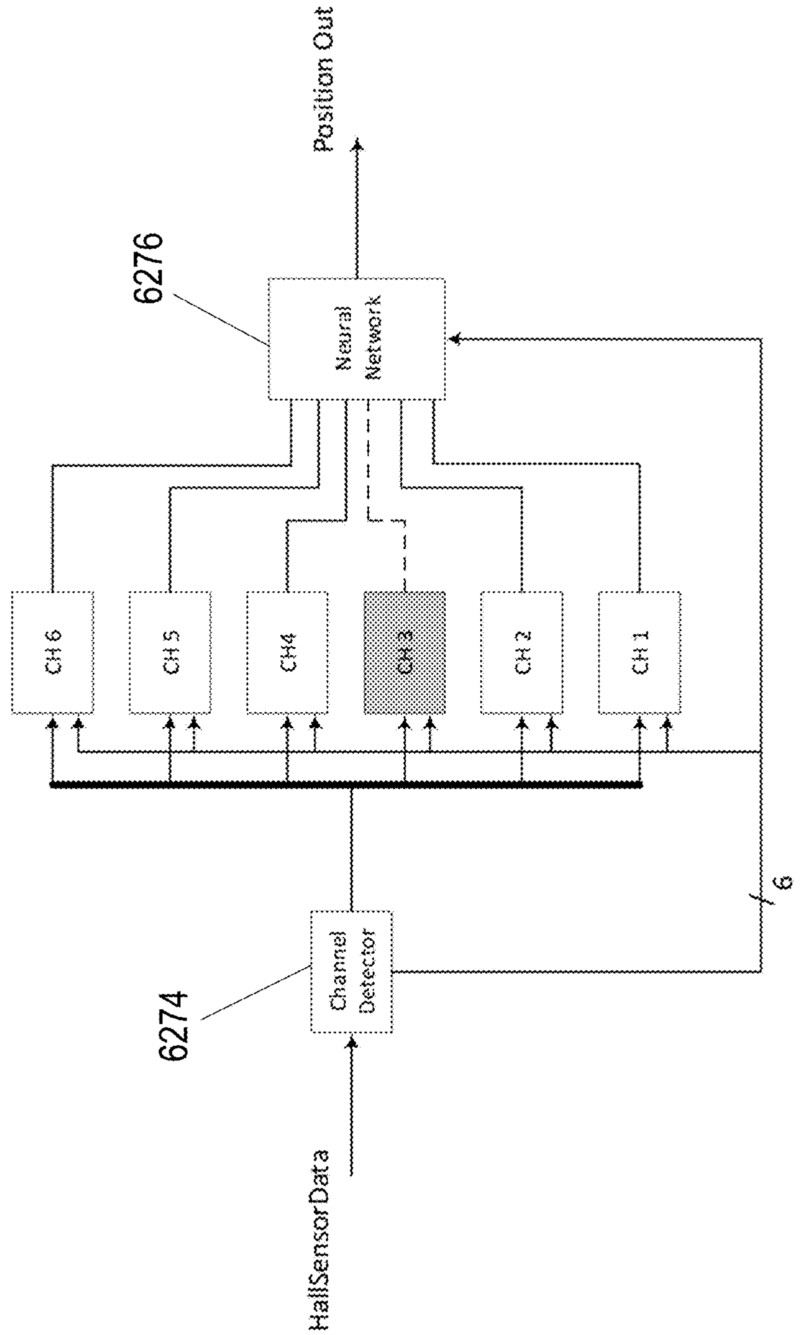
FIG. 96D is a flowchart showing a relationship between a channel detector and a neural network of the sensor redundancy system of FIG. 96A.

The MCU 6272, disposed within the knee joint implant 200, is operatively coupled to a channel detector 6274, e.g., via a wireless connection such as Bluetooth, which is able to read the data processed by the MCU 6272 from each Hall sensor HS1-HS6. In the illustrated example, the MCU 6272 is configured to communicate with an external source disposed outside of the knee joint implant 200 via, for example, an antenna disposed within the implant. The channel detector 6274 may be either included in or coupled to the external source. In some situations, all of the Hall sensors may measure and record consistent and generally accurate data, and the data from all six sensors can be used to determine the positioning and movement of knee joint implant 200. However, in other situations, any one or a plurality of the Hall sensors HS1-HS6 may produce inaccurate data for any reason, such as electrical noise. For example, in FIGS. 96A-96C, HS3 is outputting flawed or excludable data which preferably would not be considered in the collective positioning data gathered by the Hall sensors. Thus, the excludable data recorded by Hall sensor HS3 is tagged as having inaccurate data that should not be considered (as indicated in FIG. 96B wherein the "X-Y-Z" coordinates for HS3 are replaced with "F-F-F.") As shown in FIG. 96D, the channel detector 6274 is operatively coupled to, e.g., via a wireless connection such as Bluetooth, and can automatically engage a neural network 6276 including various channels to process only the valid channel data suppressing the data tagged for exclusion. The measurements from each Hall sensor are each fed into a corresponding channel That is, the data from HS1 is associated with channel 1, HS2 with channel 2, HS3 with channel 3, HS4 with channel 4, HS5 with channel 5, and HS6 with channel 6. The channel detector 6274 can be external to knee joint implant 200, and may be included in, for example, the external source communicating with the implant. The channel detector may communicate with the neural network 6276, which may be configured to communicate with various implants or other devices to accumulate and store data points from such devices. Thus, the MCU 6272 may compare and analyze only the data received from the Hall sensors of knee joint implant 200 to determine that one of the sensors has provided flawed data, or alternatively, the MCU 6272 may compare the data received from the Hall sensors with data contained and accumulated within the neural network to identify a flawed measurement.

In the illustrated example, HS3 is passing inaccurate data through channel 3. After the channel outputting inaccurate data is affirmatively identified and tagged, e.g., channel 3, the channel is automatically removed from consideration by the detector 6274 based on its data tag so that only the remaining channels outputting accurate data are selected by the detector 6274 for consideration of their respective data, which in this example includes channel 1, channel 2, channel 4, channel 5 and channel 6. In other words, the detector 6274 chooses the five remaining channels having accurate measurements to compile and output the positioning information collectively detected by the properly functioning Hall sensors.

In alternative embodiments, the channel detector may be included in the implant itself. The implant may have its own internal neural network in which it collects and accumulates data from the implant over time, or in which data can be uploaded and stored within the implant's internal neural network to allow the implant itself to detect and tag inaccurate data measurements.

The sensor redundancy system 6270 may be activated automatically, e.g., in accordance with a timed schedule or when brought into proximity with an external source. Alternatively, the sensor redundancy system 6270 may be activated manually by a user, such as the patient or a clinician. In either example, the sensor redundancy system 6270 may be optimized for power savings such that the system is powered off when not in use.

It should be understood that the exclusion of inaccurate data using sensor redundancy system 6270 is not limited to the example described herein in which the knee joint implant 200 includes six Hall sensors and one of the Hall sensors produces inaccurate data. Sensor redundancy may be applied in any implant having at least two Hall sensors, and preferably more than two sensors to further ensure the accurate measurements and the inaccurate measurements are correctly identified. For instance, knee joint implant 200 may indeed have eight Hall sensors gathering data relating to the movement of the knee joint, wherein any one or more of those eight sensors may malfunction at any given moment, which will then be tagged by the processor, detected and excluded by the channel detector 6274. It is contemplated that more than one sensor among the group of sensors may experience noise or produce unusable data, and that more than one channel can be identified and excluded from the selection of data. In such examples, a greater number of sensors may be advantageous so that inaccurate data can be confidently identified in the one, two, etc. malfunctioning sensors while still having a majority of the sensors, e.g., six or seven, still functioning properly and collecting useful positioning data. That is, incorporation of a greater number of sensors may help the MCU or the detector identify which channels have inaccurate data and should be excluded.

It should also be understood that the Hall sensors in the illustrated example may be replaced with any other type of sensor, and the same operations as described above may be performed to filter out inaccurate data from a plurality of such sensors. It should also be understood that the sensor redundancy system is not limited to use in knee joint implant 200, but may be used in any type of implant, including alternative implants described throughout this application, or outside the context of implants for measuring any type of data.

The sensor redundancy system 6270 provides for resilient operation of the knee joint implant's ability to measure and output data about the knee joint and/or the implant. That is, by identifying and removing improper data, the sensor redundancy system 6270 reinforces the implant's ability to output data either automatically or upon request, and also reduces the likelihood of the implant from outputting incorrect or misleading data, e.g., a situation in which a sensor is interrupted or otherwise recording wrongly affected data, and such data would have been factored into the movement or positioning information provided by the implant. Thus, the system provides redundancy and resiliency to ensure functioning operations in the face of component failure. Additionally, the system reduces processing requirements and improves efficiency by removal of the channel That is, once a channel is removed, the data processing associated with that channel decreases, thereby reducing the processing requirement.

In another embodiment, the sensor redundancy system can be used to control engagement/activity of the plurality of sensors manually or automatically. For example, the sensor redundancy system can deactivate Hall sensors by turning off the device for power savings, perform individual access tests, manage responses in noisy environments, etc. The sensor redundancy system can be used to target and use only specific sensors or rely more on specific sensors instead of using/relying on all sensors for data collection in particular applications such as characterizing movement with specific points of interest.

Figure 15:
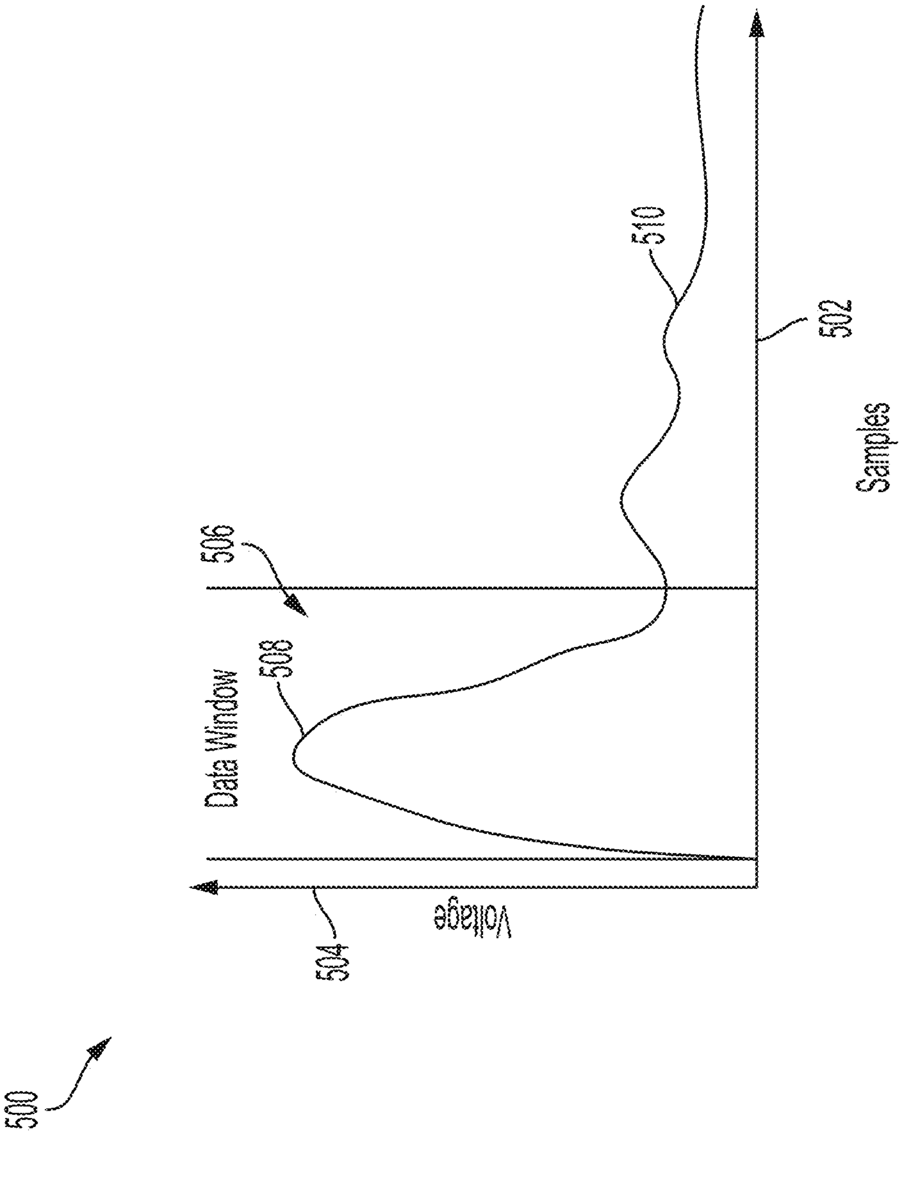
FIG. 15 is a graph showing voltage measurements of the implant sensors.

FIG. 14 is a schematic view of piezo stacks of medial load sensors 232 and lateral load sensor 254 in communication with a processor 266. Analog impulses generated by the piezo stacks when subjected to loading are converted to continuous digital signals via analog-to-digital converters 262 and 264 as shown in FIG. 14. The continuous digital signals (voltage) 508 can be serially loaded into a shift register and measured as shown in a graph 500 of FIG. 15. A sampling window 506 is selected to identify a peak reading 508 to detect knee joint motion. For continuous loading case, such as when a patient is standing, additional sensors such as an inertial measurement unit ("IMU") located in the tibial insert or other locations on knee joint implant 200 can be used to detect or confirm knee joint position. Load data from piezo stacks and IMU measurements can be used to create load and motion profiles for patient-specific or patient-independent analyses.

Figure 16:
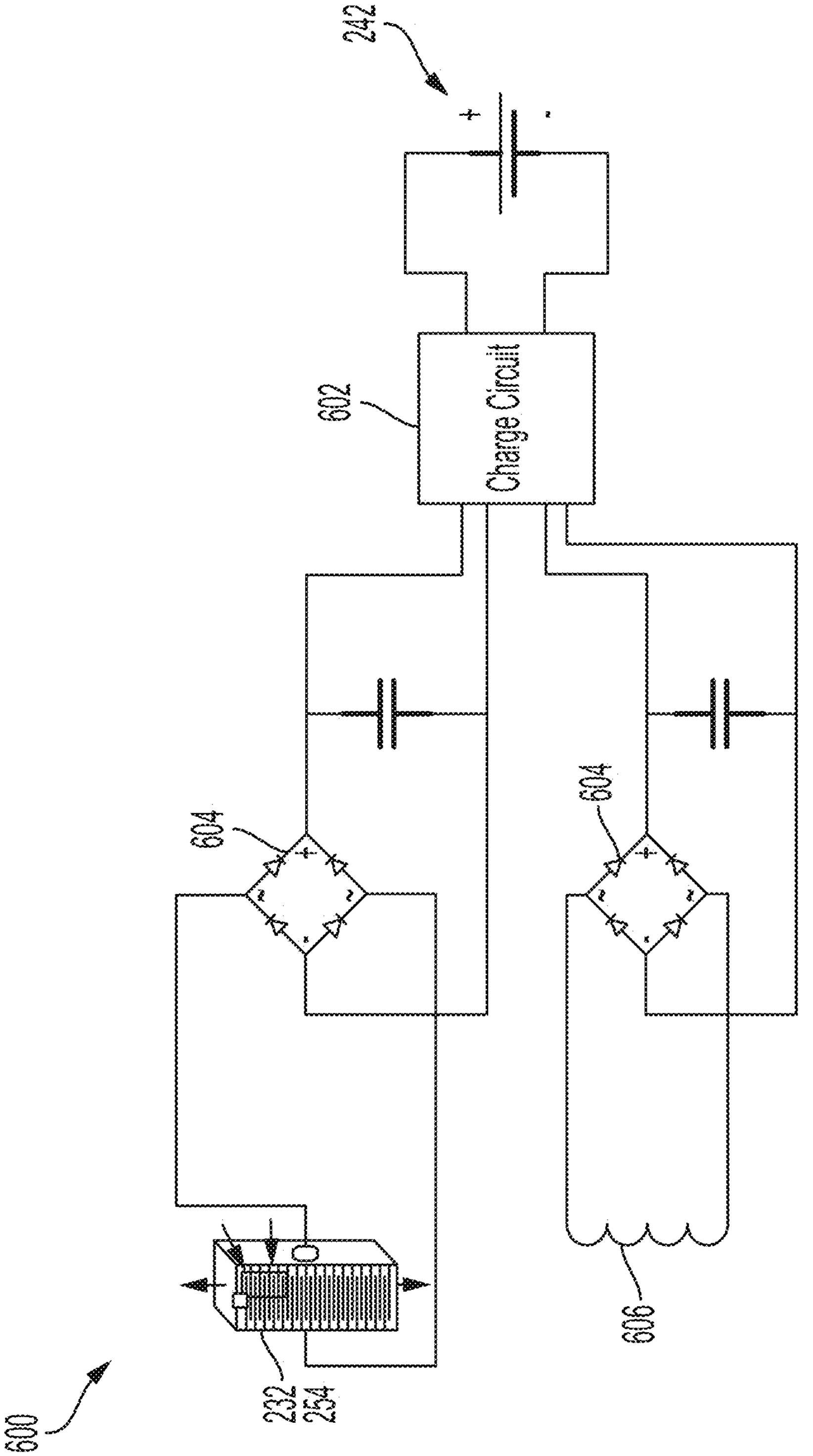
FIG. 16 is a schematic view of a charging circuit for the knee joint implant of FIG. 6.
Figure 17B:
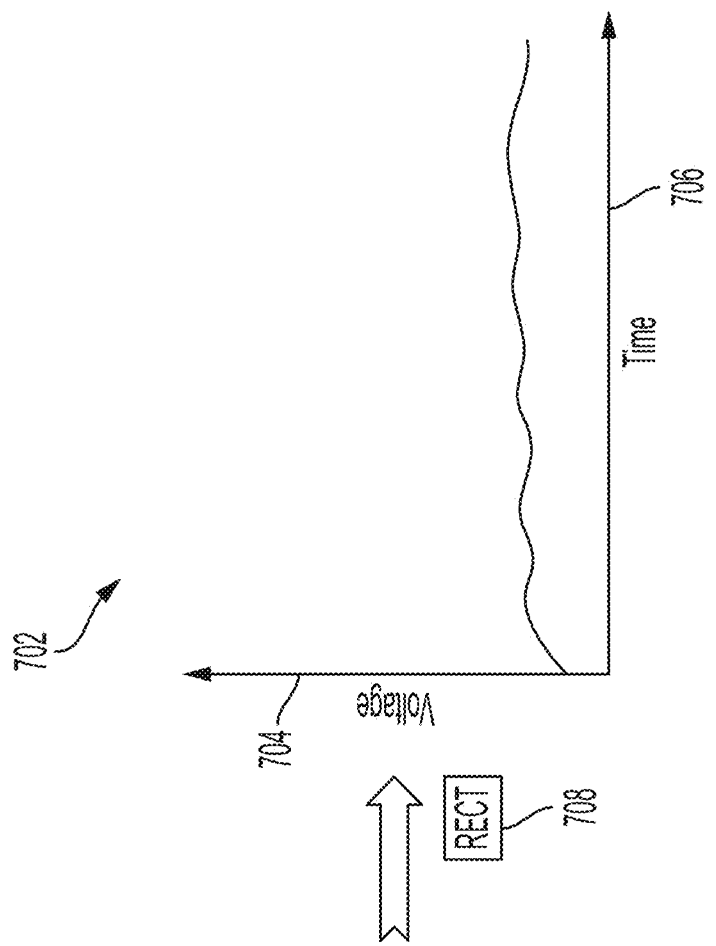
FIG. 17B is a graph showing rectified voltage of the implant sensors.
Figure 17A:
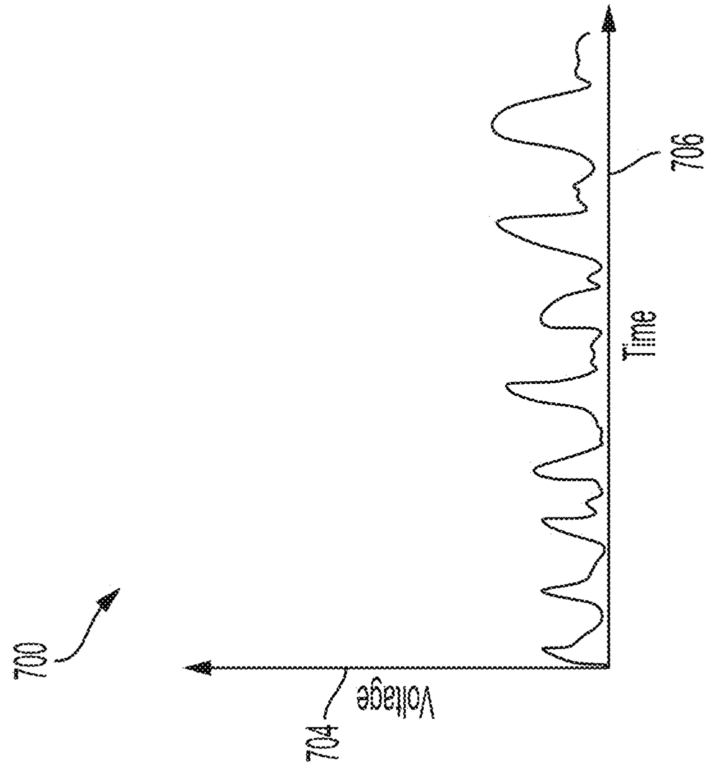
FIG. 17A is a graph showing measured voltage of the implant sensors.

FIG. 16 is a schematic view of a charging circuit 600 for charging battery 242 of knee joint implant 200. The charging circuit includes a charge circuit 602 connected to a charging coil 606 and piezo stacks of medial load sensors 232 and lateral load sensors 254 via bridge rectifier 604. Charging circuit is configured to direct charge to battery 242 utilizing inputs from one or more piezo stacks from the medial or lateral load sensors. This allows for singular or combined charging using individual or multiple piezo stacks. A minimum voltage output threshold of the piezo stacks can be predetermined to initiate battery charging. For example, when a patient is asleep, low piezo stack pulses will not be used to charge battery 242. Raw piezo stack pulses (voltage 704) as shown in a graph 700 of FIG. 17 over time 706 are rectified by a voltage rectifier 708 to produce a rectified and smoothed voltage output (voltage 704) shown in a graph 702 of FIG. 17B. The rectified and smoothed voltage output from the piezo stacks is used to charge battery 242. Thus, power harvesting from motion of knee joint implant 200 is achieved by using the pulses generated by the piezo stacks.

Figure 18:
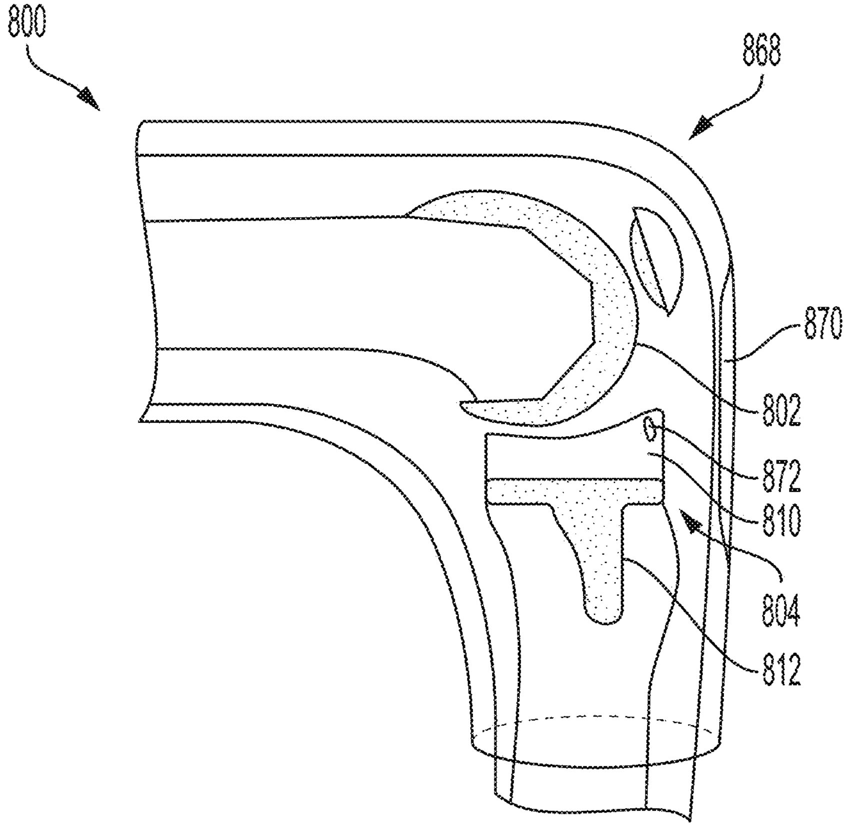
FIG. 18 is a schematic view of a knee joint implant with a charging sleeve according to an embodiment of the present disclosure.

FIG. 18 is a schematic view of a knee joint implant 800 according to another embodiment of the present disclosure. Knee joint implant 800 is similar to knee joint implant 200, and therefore like elements are referred to with similar numerals within the 800-series of numbers. For example, knee joint implant 800 includes a femoral implant 802, a tibial implant 804 with a tibial stem 812 and a tibial insert 810. However, knee joint implant 800 includes a chargeable implant coil 872 located in tibial insert 810 which can be charged by an external coil 870 contained in an external sleeve 868 as shown in FIG. 18.

Figure 19:
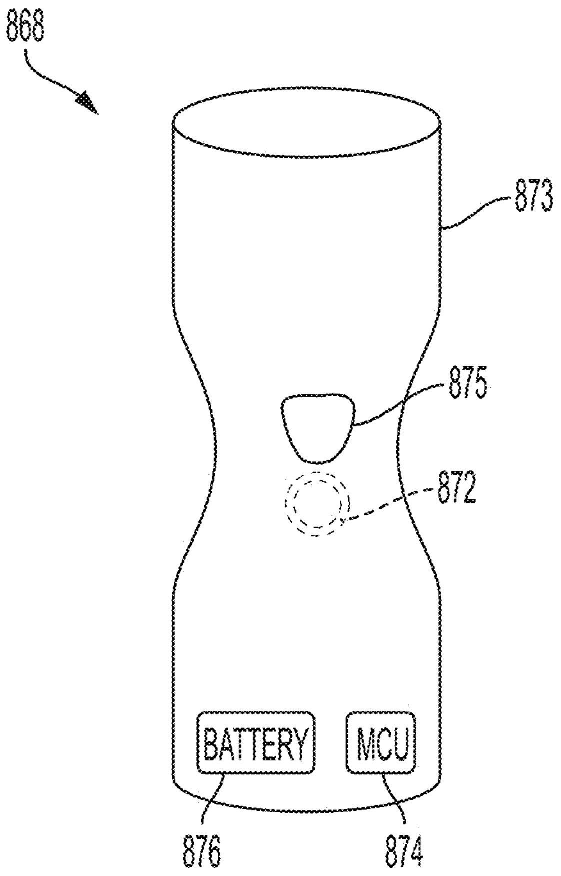
FIG. 19 is a front view of the charging sleeve of the knee joint implant of FIG. 17.

External sleeve 868 shown in FIG. 19 includes an outer body 873 made of stretchable fabric or other material. Outer body 873 is configured to be a ready-to-wear pull-on knee sleeve which a patiently can conveniently put on and remove. A kneecap indicator 875 allows the patient to conveniently align sleeve 868 with knee joint implant 800 for proper placement of external coil 870 with reference to implant coil 872 for charging. As shown in FIG. 18, when a patient aligns external sleeve 868 using kneecap indicator 875 and assumes a flexion position, external coil 870 is adjacent to implant coil 872 for proper charging. External sleeve 868 includes a battery 876 and a microcontroller 874 as shown in FIG. 19. Battery 876, which can be conveniently replaced, provides power to external coil 870. In another embodiment, external coil 870 may be charged by an external source not located on sleeve 868.

Figure 21:
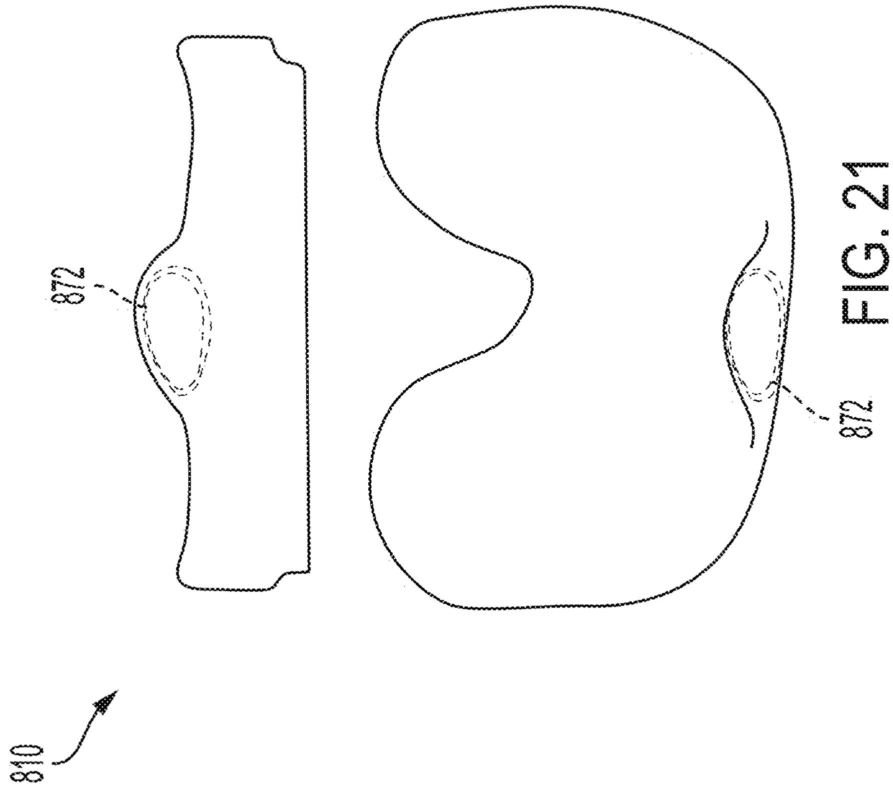
FIG. 21 shows top and front views of the insert of FIG. 19.
Figure 20:
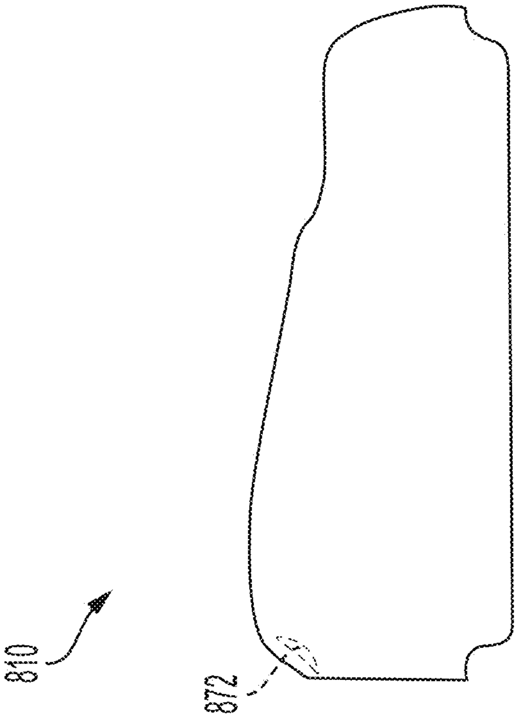
FIG. 20 is a side view of an insert of the knee joint implant of FIG. 17.

FIG. 20 shows a side view of tibial insert 810 of knee joint implant 800. Tibial insert 810 is made of a polymer or other suitable to facilitate charging of implant coil 872. Implant coil 872 is located within tibial insert 810 at an indent or depression at a proximal-anterior corner of the tibial insert as show in FIG. 20 and FIG. 21 (top and front views of tibial implant 810). The proximal-anterior location of implant coil 872 maximizes access to external coil 870 for efficient and convenient charging.

Figure 22B:
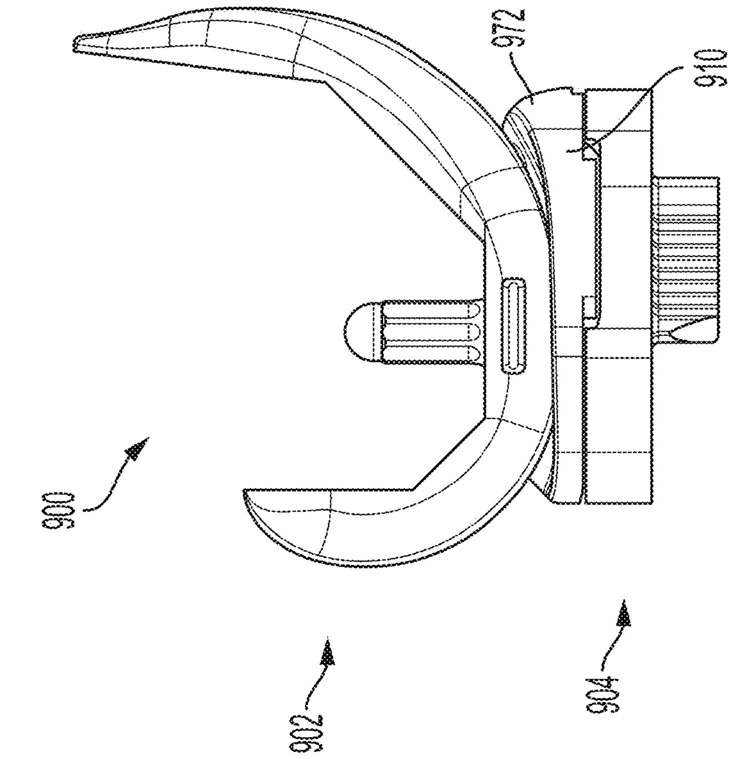
FIG. 22B is a side view of the knee joint implant of FIG. 22A.
Figure 22A:
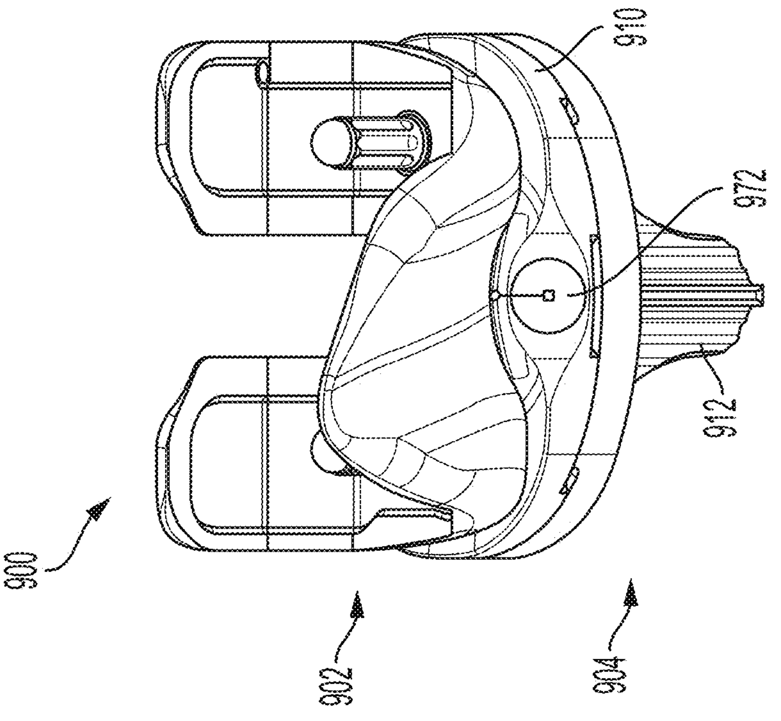
FIG. 22A is front view of a knee joint implant according to another embodiment of the present disclosure.

FIGS. 22A and 22B show a knee joint implant 900 according to another embodiment of the present disclosure. Knee joint implant 900 is similar to knee joint implant 800, and therefore like elements are referred to with similar numerals within the 900-series of numbers. For example, knee joint implant 900 includes a femoral implant 902, a tibial implant 904 with a tibial stem 912 and a tibial insert 910. However, knee joint implant 900 includes a chargeable implant coil 972 located at anterior end of tibial insert 910 which can be charged by an external coil 970 (not shown). An external sleeve as described with reference knee joint implant 900, or another charging mechanism can be used to conveniently charge implant coil 972.

Figure 23B:
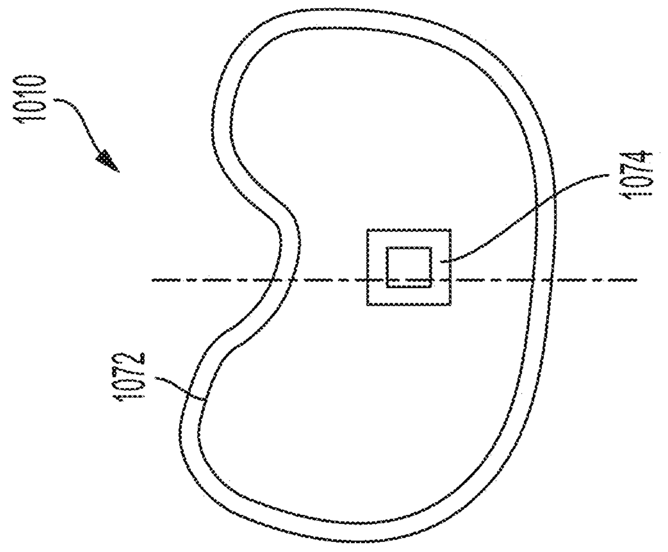
FIG. 23B is a top view of an insert of the tibial implant of FIG. 22A.
Figure 23A:
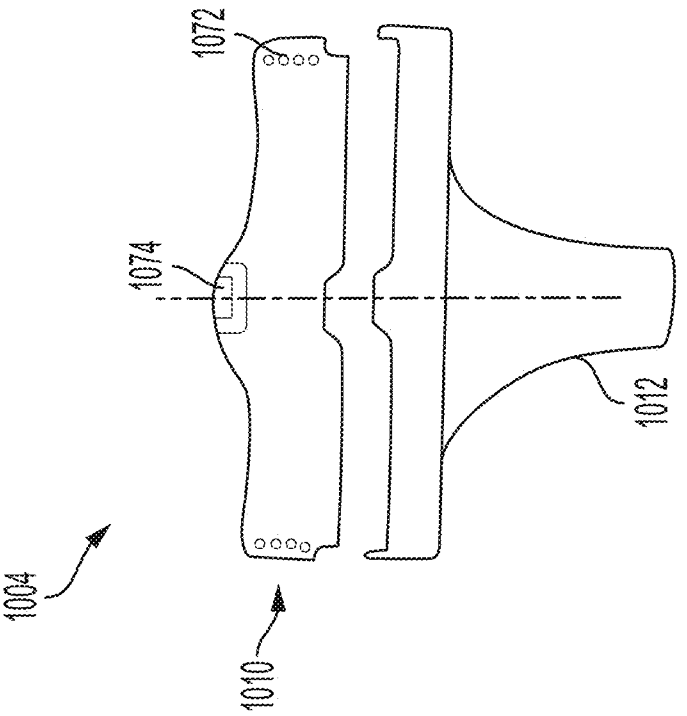
FIG. 23A is a front view of a tibial implant according to another embodiment of the present disclosure.

FIG. 23A is a front view of a tibial implant 1004 according to an embodiment of the present disclosure. Tibial implant 1004 is similar to tibial implant 204, and therefore like elements are referred to with similar numerals within the 1000-series of numbers. For example, tibial implant 1004 includes a tibial stem 1012 and a tibial insert 1010. However, tibial insert 1010 includes a charging coil 1072 located around a periphery of the tibial insert 1010 as shown in FIG. 23B. A spectroscopy sensor 1074 in tibial insert 1010 serves as an infection detection sensor for tibial implant 1004. Spectroscopy sensor 1074 is configured to identify the onset of biofilm on tibial implant (or a corresponding femoral implant) to provide early detection of implant related infection.

Figure 24A:
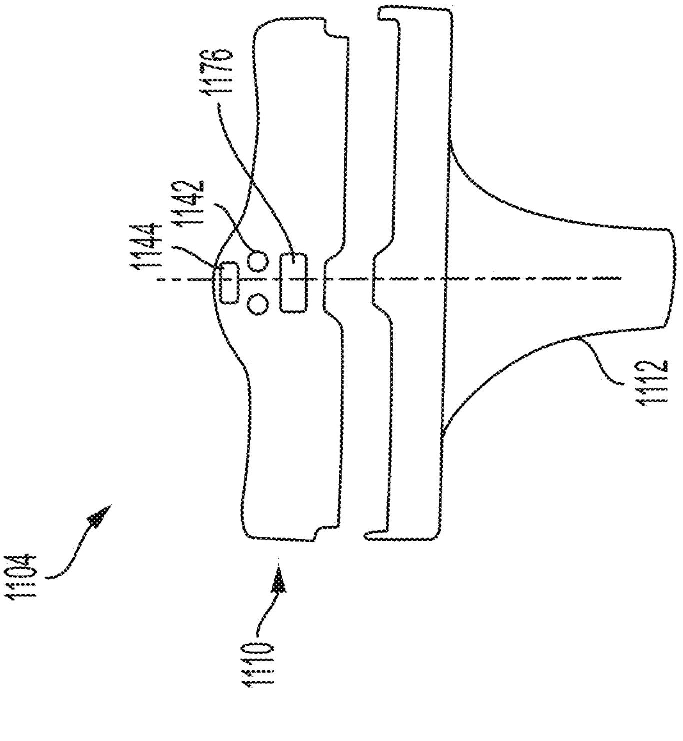
FIG. 24A is a front view of a tibial implant according to another embodiment of the present disclosure.
Figure 24B:
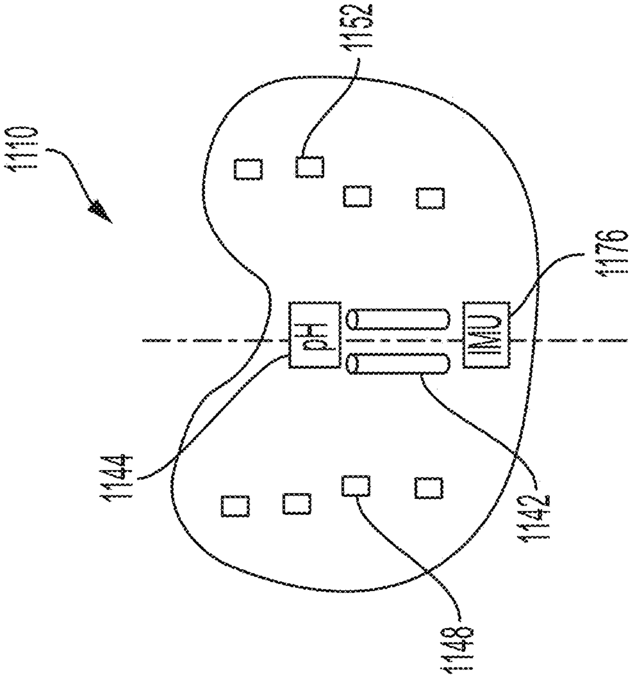
FIG. 24B is a top view of an insert of the tibial implant of FIG. 24A.

FIG. 24A is a front view of a tibial implant 1104 according to an embodiment of the present disclosure. Tibial implant 1104 is similar to tibial implant 204, and therefore like elements are referred to with similar numerals within the 1100-series of numbers. For example, tibial implant 1104 includes a tibial stem 1112 and a tibial insert 1110. However, tibial insert 1110 includes an IMU 1176 and five Hall sensor assemblies for each of the medial and lateral marker readers. The arrangement of the Hall sensor assemblies differ from tibial insert 210. Sensor data from IMU 1176 provides additional knee implant joint movement data as more fully explained above. For example, IMU 1176 can detect or confirm knee joint position during continuous loading positions of a patient such as standing. IMU data can reveal, or support measurements related to gait characteristics, stride, speed, etc., of a patient. pH sensor 1144 of tibial insert 1110 is located adjacent to a proximal face of the tibial insert at a central location as shown in FIG. 24B. All sensors of tibial implant 1104 are powered by batteries located in tibial insert 1110.

Figure 25B:
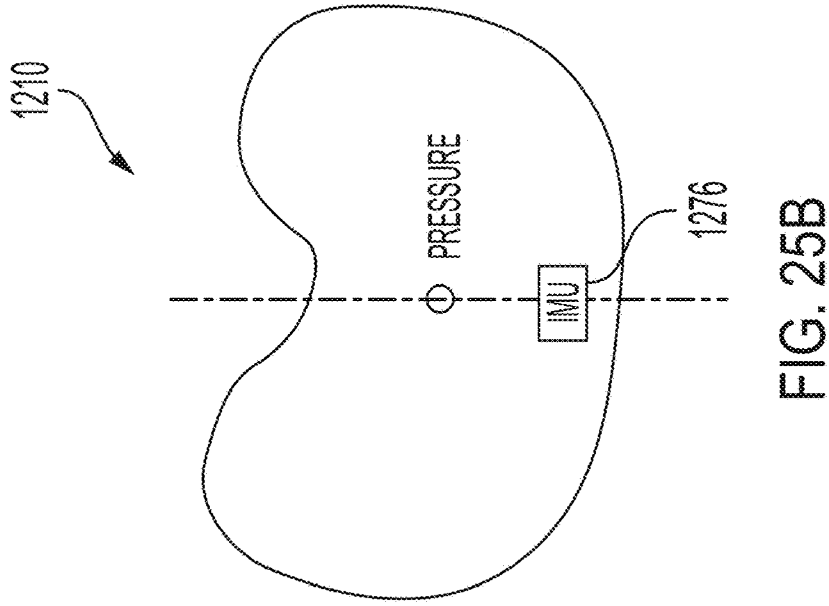
FIG. 25B is a top view of an insert of the tibial implant of FIG. 25A.
Figure 25A:
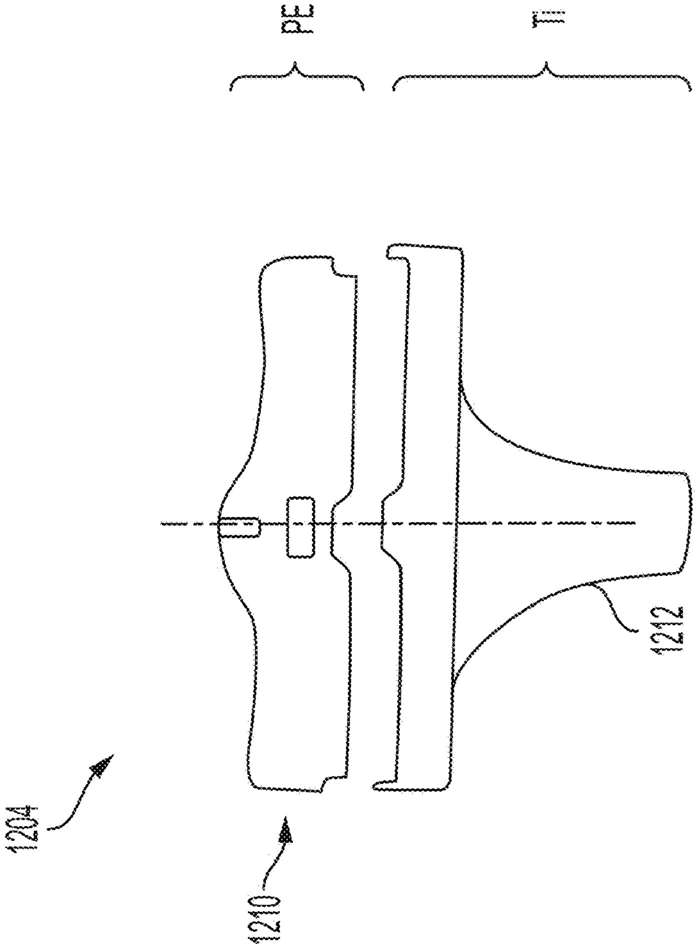
FIG. 25A is a front view of a tibial implant according to another embodiment of the present disclosure.

A tibial implant 1204 according to another embodiment of the present disclosure is shown in FIGS. 25A and 25B. Tibial implant 1204 is similar to tibial implant 204, and therefore like elements are referred to with similar numerals within the 1200-series of numbers. For example, tibial implant 1204 includes a tibial stem 1212 and a tibial insert 1210. However, tibial insert 1210 includes an IMU 1276 and a pressure sensor. Tibial insert 1210 is made of polyethylene and tibial stem 1212 is made of titanium in this embodiment.

Figure 26:
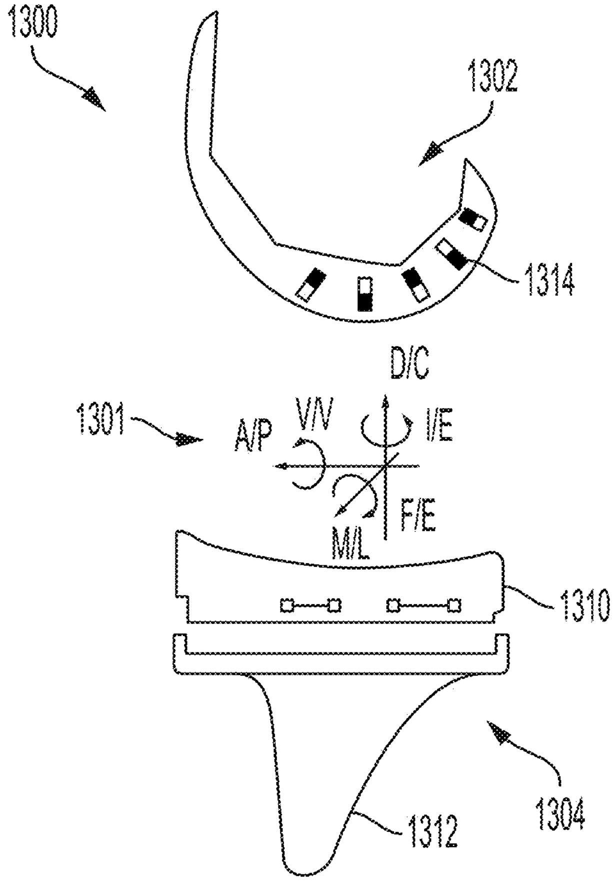
FIG. 26 is a side view of a knee joint implant according to another embodiment of the present disclosure.
Figure 27:
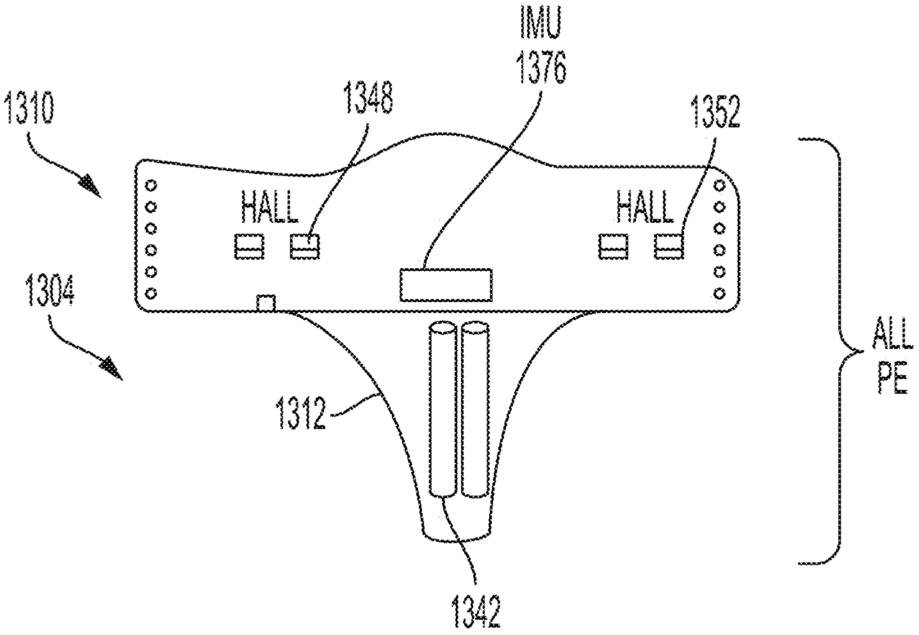
FIG. 27 is a front view of a tibial implant of the knee joint implant of FIG. 26.

FIG. 26 is a side view of a knee joint implant 1300 according to another embodiment of the present disclosure. Knee joint implant 1300 is similar to knee joint implant 200, and therefore like elements are referred to with similar numerals within the 1300-series of numbers. For example, knee joint implant 1300 includes a femoral implant 1302, a tibial implant 1304 with a tibial stem 1312 and a tibial insert 1310. However, battery 1342 of knee joint implant 1300 are located in tibial stem 1312 as best shown in FIG. 27. Locating batteries 1342 in tibial stem provides room for additional sensors in tibial insert 1310. The tibial stem and tibial insert 1310 can be made of polyethylene in this embodiment. Various knee joint implant motion data 1301 collected by magnetic markers and marker readers is shown in FIG. 26. Motion data 1301 can include internal-external rotation, medial-lateral rotation, varus-valgus rotation, etc.

Figure 28:
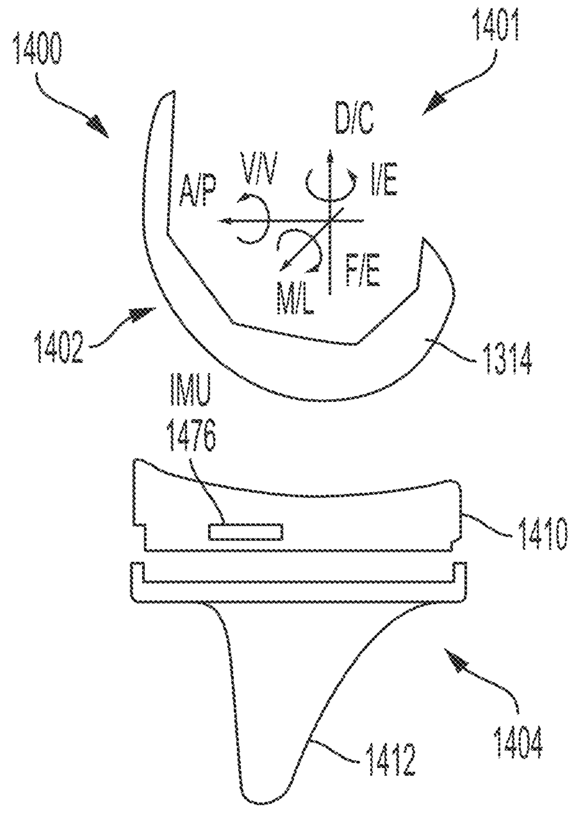
FIG. 28 is a schematic side view of a knee joint implant illustrating various measurements according to another embodiment of the present disclosure.

A knee joint implant 1400 according to another embodiment of the present disclosure is shown in FIG. 28. Knee joint implant 1400 is similar to knee joint implant 200, and therefore like elements are referred to with similar numerals within the 1400-series of numbers. For example, knee joint implant 1400 includes a femoral implant 1402, a tibial implant 1404 with a tibial stem 1412 and a tibial insert 1410. However, tibial insert 1410 includes an IMU 1476. Sensor data from IMU 1476 provides additional knee implant joint motion data 1401. Motion data 1401 can include internal-external rotation, medial-lateral rotation, varus-valgus rotation, etc. for reviewing knee joint implant 1400 performance. For example, internal-external rotation measurements exceeding a predetermined threshold can indicate knee joint implant lift-off (instability), medial-lateral rotation measurements exceeding predetermined thresholds can indicate knee joint implant stiffness. Combining these measurements with inputs from the various other sensors of tibial insert 1410 will provide a detailed assessment of knee joint implant 400 performance.

Figure 29:
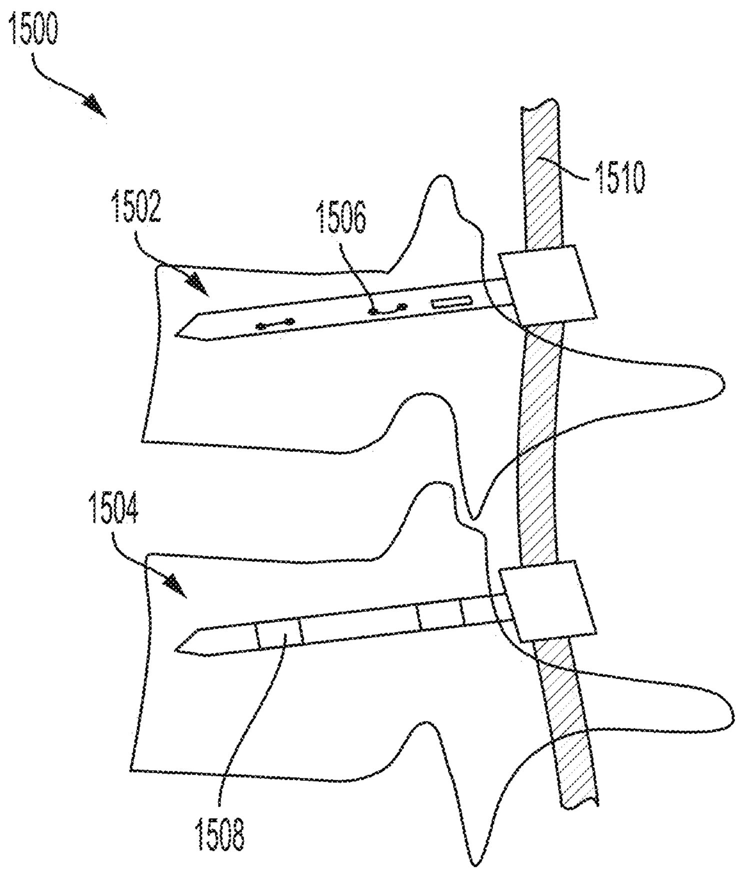
FIG. 29 is a schematic side view of a spinal implant assembly according to another embodiment of the present disclosure.

Referring now to FIG. 29, a spinal implant assembly 1500 is shown according to an embodiment of the present disclosure. Spinal implant assembly 1500 includes a spinal implant 1510 such as a plate, rod, etc., secured to first and second vertebrae by a first fastener 1502 and a second fastener 1504, respectively. The first and second fasteners can be screws as shown in FIG. 29. First fastener 1502 includes magnetic flux density detectors such as Hall sensor assemblies 1506 located along a body of the fastener 1502. Second fastener 1504 includes magnetic markers 1508 located along a body of the fastener. Any movement of second fastener 1504 with respect to the first fastener is detected and measured by Hall sensor assemblies 1506. Thus, the first and second fasteners function as an absolute or incremental encoder to detect spinal mobility of a patient during daily activity. As described with reference to the knee joint implants disclosed above, various other sensors such as temperature, pressure, pH, load, etc., can be included in fast fastener 1502 to provide additional measurements related to spinal implant assembly 1500 performance during a patient's recovery and rehabilitation. Ideally, there should be little to no movement between the first and second vertebrae for successful for spinal fusion. Therefore, any movement detected between the first and second fastener may indicate a compromised spinal implant assembly.

Figure 30:
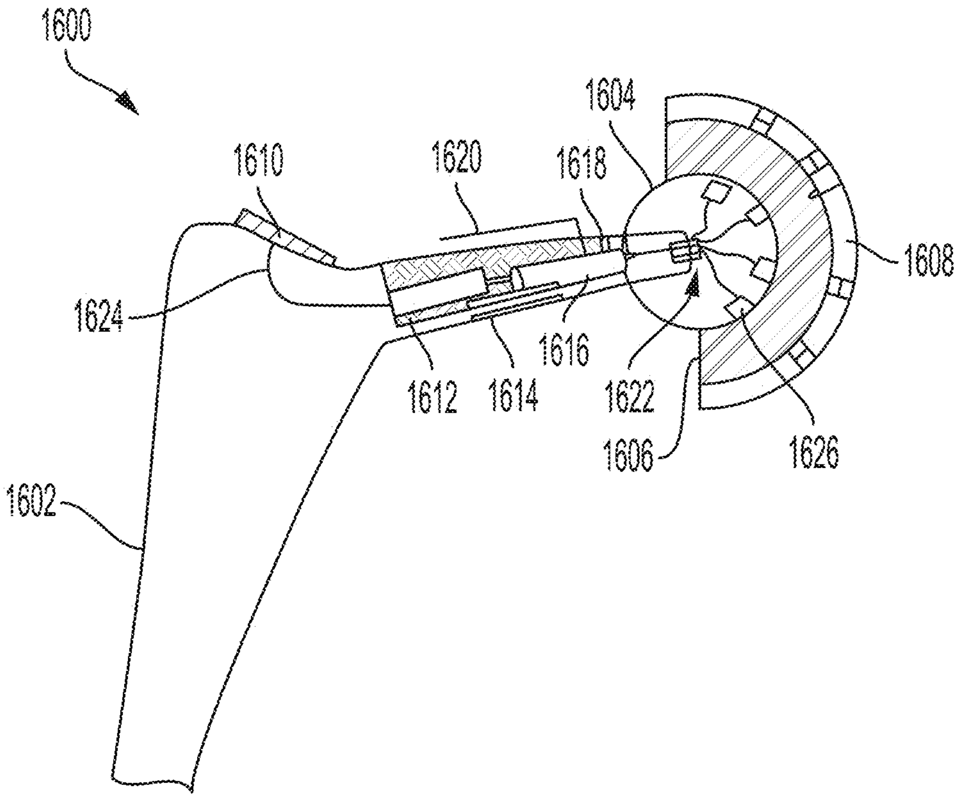
FIG. 30 is side view of a hip implant according to another embodiment of the present disclosure.
Figure 31C:
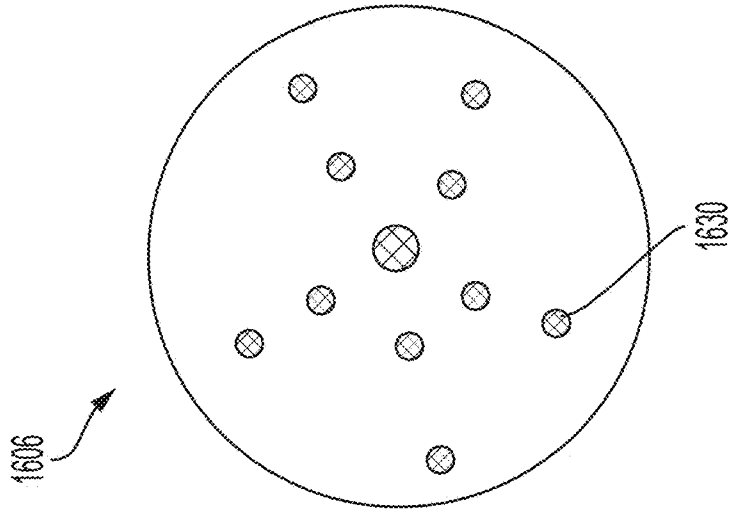
FIG. 31C is a top view of the sensor assembly and the insert of FIG. 31B.
Figure 31B:
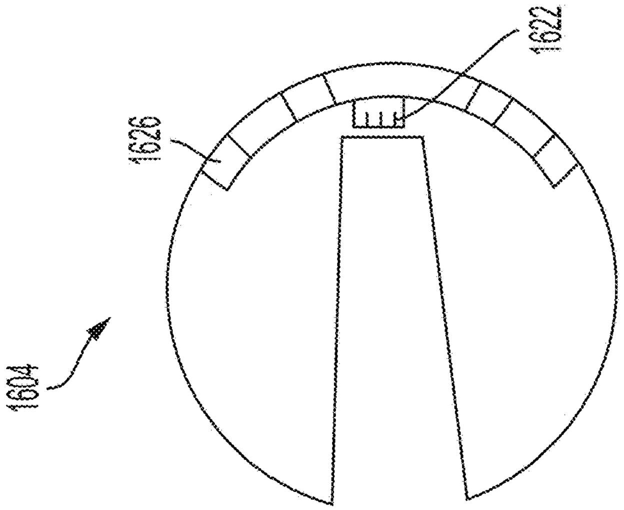
FIG. 31B is a side view of the sensor assembly and an insert of the hip implant of FIG. 31A.
Figure 31A:
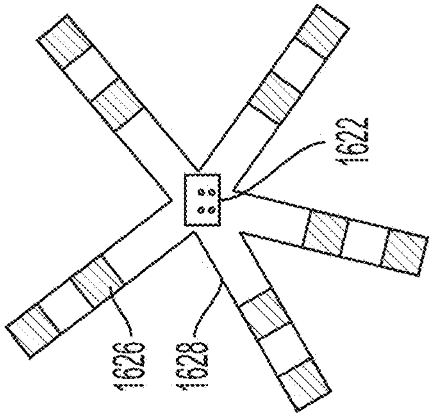
FIG. 31A is a schematic view of a sensor assembly of the hip implant of FIG. 30.

FIG. 30 is side view of a hip implant 1600 according to an embodiment of the present disclosure. Hip implant 1600 includes a stem 1602, a femoral head 1604, an insert 1606 and an acetabular component 1608. Magnetic flux density sensors such as Hall sensor assemblies 1626 are located on a flex connect 1628 and placed around femoral head 1604 as shown in FIGS. 31A and 31B. A connector 1622 on flex connect 1628 allows for convenient connection of femoral head 1604 with stem 1602. Magnetic markers 1630 are located on insert 1606 as best shown in FIG. 31C. Any motion of insert 1606 is detected by Hall sensor assemblies 1626 by measuring the change in magnetic flux density. Thus, Hall sensor assemblies 1626 and markers 1630 function as an absolute or incremental encoder to detect hip movement of a patient during daily activity.

Hip implant 1600 includes a charging coil 1610 located on stem 1602 as shown in FIG. 30. Charging coil 1610 charges a battery 1612 via a connector 1624 to power the various sensors located in hip implant 1600. A load sensor 1614 such a strain gauge detects forces between stem 1602 and acetabular component 1608 to monitor and transmit hip loads during patient rehabilitation and recovery. Various electronic components 1616, including sensors described with reference to knee joint implants, are located in stem 1602. A pH sensor 1618 located on stem can measure alkalinity and provide early detection notice of implant related infection. Data from these sensors is transmitted to an external source via an antenna 1620 as described with reference to the knee joint implants disclosed above.

Figure 32:
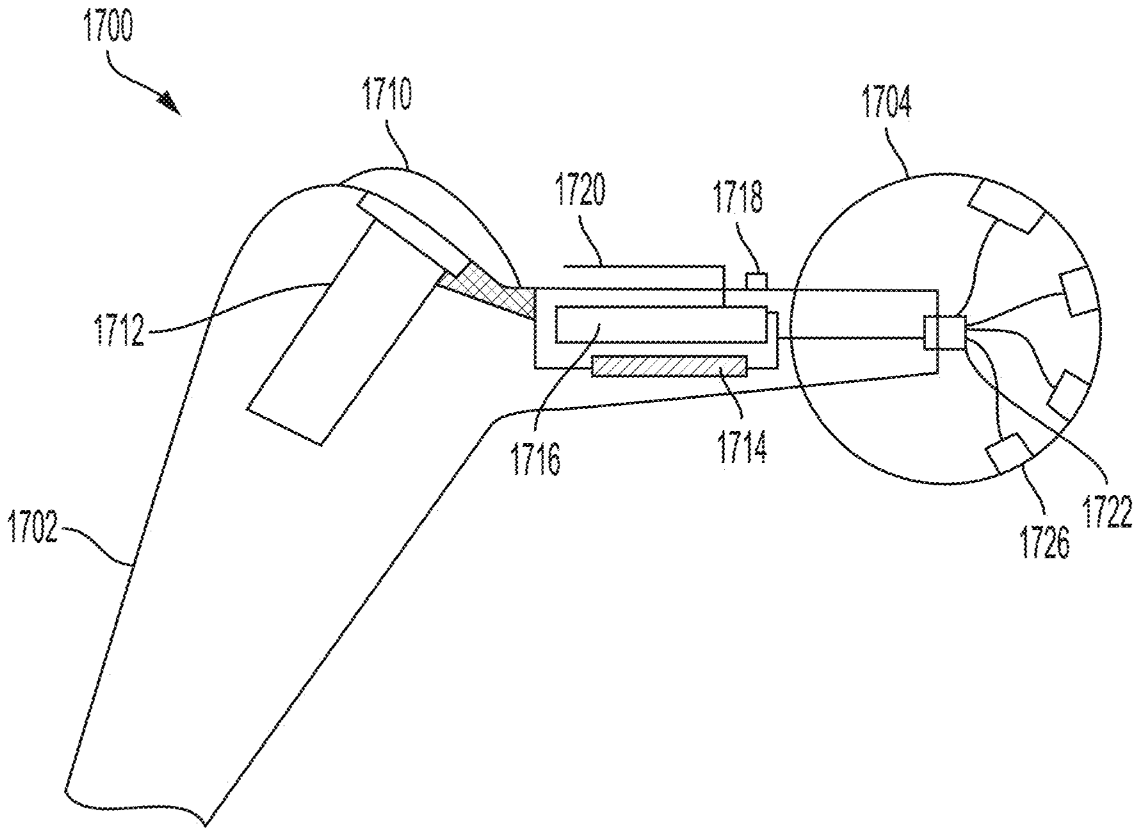
FIG. 32 is a side view of a hip implant according to another embodiment of the present disclosure.
Figure 33:
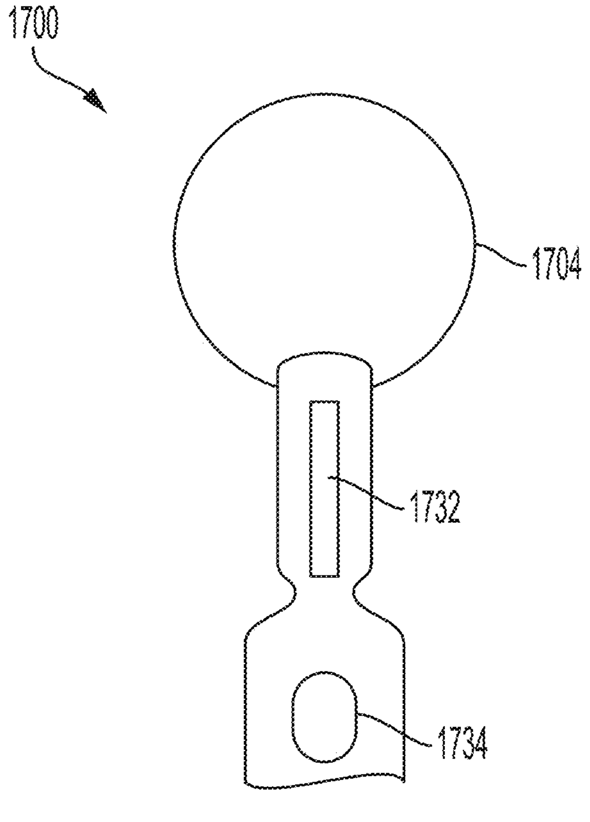
FIG. 33 is a partial top view of the hip implant of FIG. 32.

FIG. 32 is a side view of a hip implant 1700 according to another embodiment of the present disclosure. Hip implant 1700 is similar to hip implant 1600, and therefore like elements are referred to with similar numerals within the 1700-series of numbers. For example, hip implant 1700 includes a stem 1702, a femoral head 1704 and an acetabular component (not shown). However, battery 1712 of hip implant 1700 is located away from electric components 1716 as best shown in FIG. 32. Battery 1712 can be conveniently inserted into hip implant 1700 via a slot 1734 as shown in FIG. 33. Similarly, electric components 1716 can be inserted into hip implant 1700 via a slot 1732. This allows for convenient replacements and upgrades to the battery and electric components without disturbing hip implant 1700.

Figure 34:
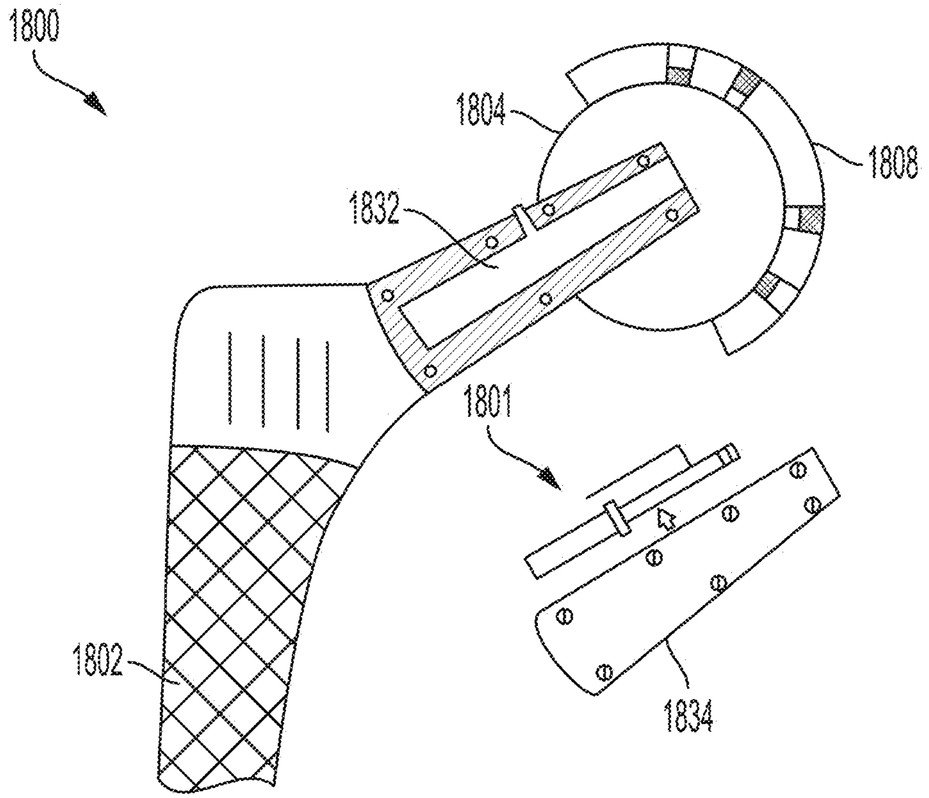
FIG. 34 is a side view of a hip implant according to another embodiment of the present disclosure.

FIG. 34 is a side view of a hip implant 1800 according to another embodiment of the present disclosure. Hip implant 1800 is similar to hip implant 1600, and therefore like elements are referred to with similar numerals within the 1800-series of numbers. For example, hip implant 1800 includes a stem 1802, a femoral head 1804 and an acetabular component (not shown). However, slot 1832 of hip implant 1800 is configured to receive all electronic components structured as a modular electronic assembly 1801 or a sensor assembly. A slot cover 1834 ensures that electronic assembly 1801 is secured and sealed in slot 1832. Thus, hip implant 1800 can be easily provided with replacement or upgrades to the electric components without disturbing hip implant 1800.

Figure 35:
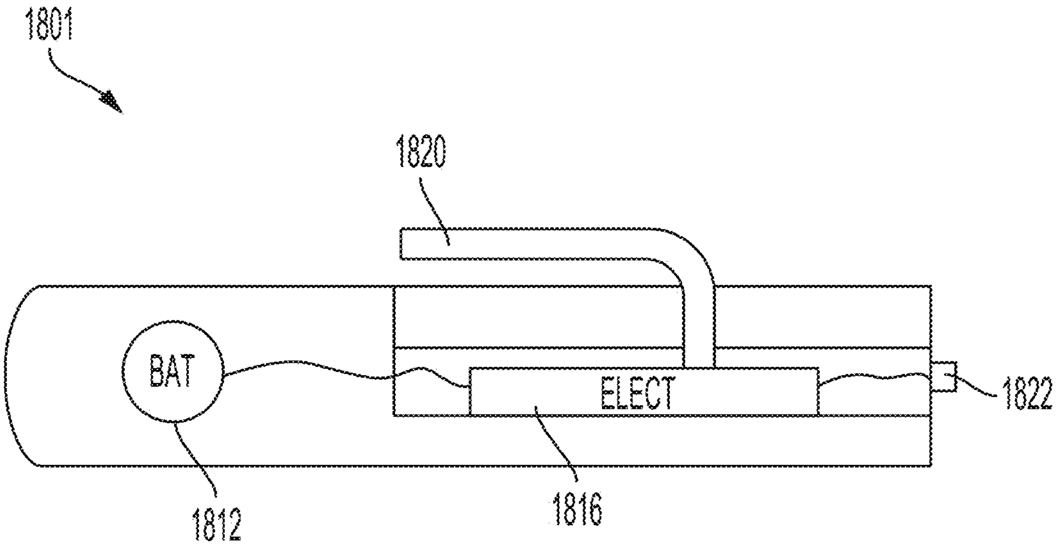
FIG. 35 is a side view of an electronic assembly of the hip implant of FIG. 34 according to another embodiment of the present disclosure.
Figure 36:
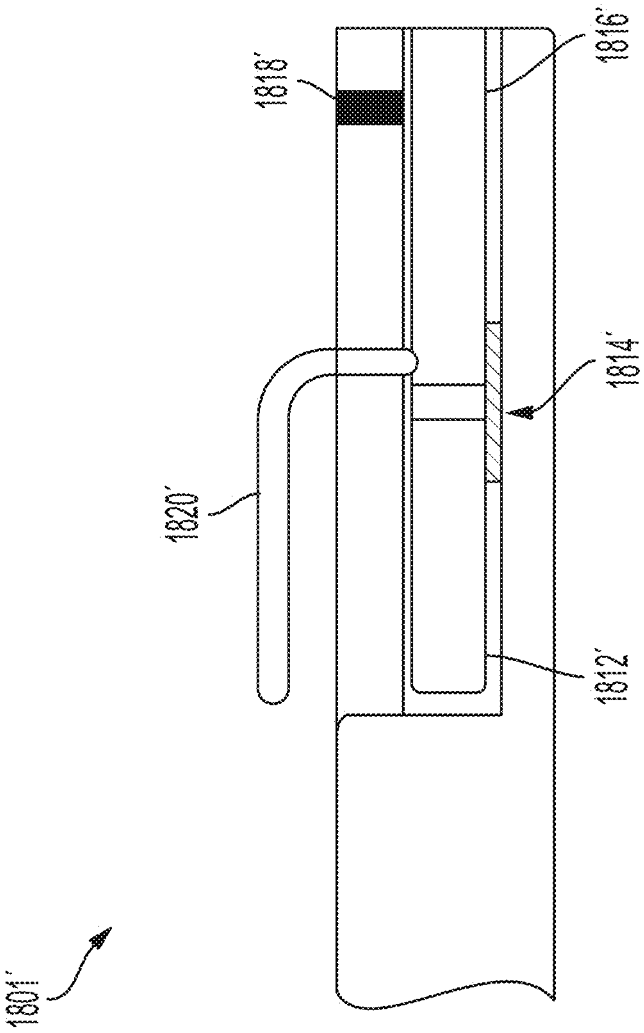
FIG. 36 is a side view of an electronic assembly of the hip implant of FIG. 34 according to another embodiment of the present disclosure.

A first embodiment of a modular electronic assembly 1801 is shown in FIG. 35. Electronic assembly includes a connector 1822 to connect to femoral head 1804, various electronic components 1816, a battery 1812 and an antenna 1820. Another embodiment of a modular electronic assembly 1801' is shown in FIG. 36. Electronic assembly 1801' includes various electronic components 1816', a battery 1812', a load sensor such as a strain gauge 1814' and an antenna 1820'. Electronic assembly 1801' includes a pH sensor 1818' to provide early detection of implant related infection.

Figure 37:
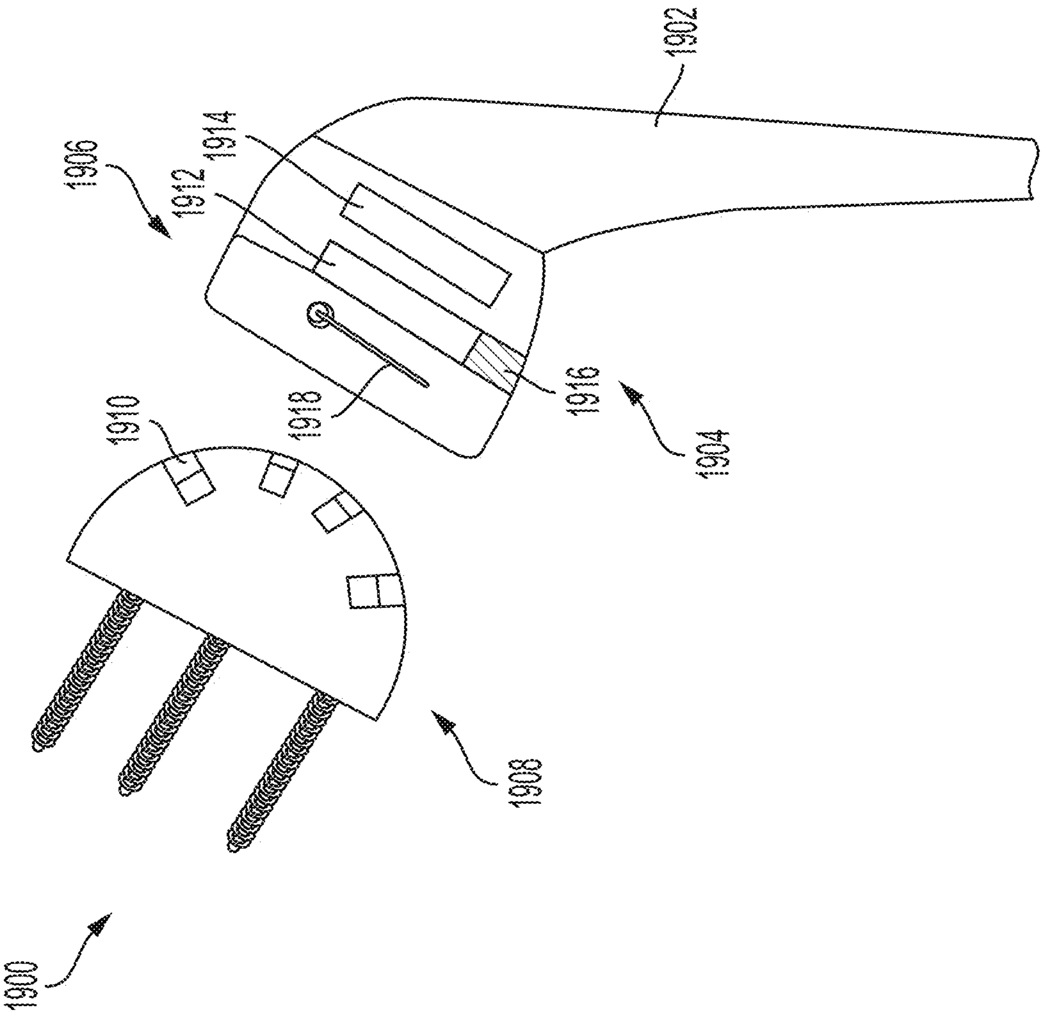
FIG. 37 is a side view of a shoulder implant according to another embodiment of the present disclosure.
Figure 39:
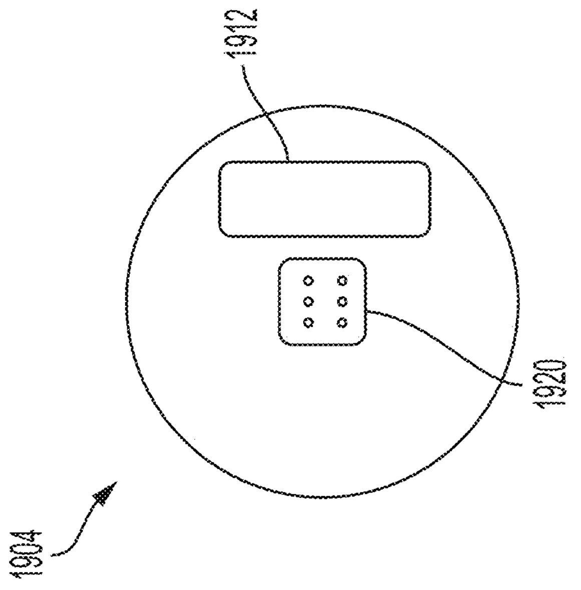
FIG. 39 is a top view of a cup of the shoulder implant of FIG. 37.
Figure 38:
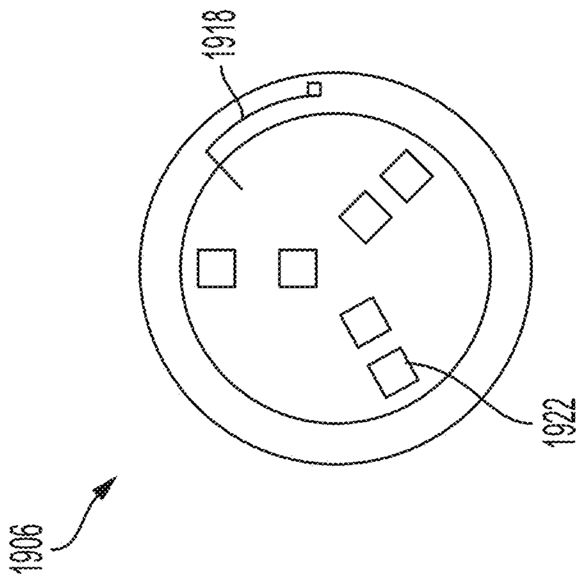
FIG. 38 is top view of an insert of the shoulder implant of FIG. 37.

FIG. 37 is a side view of a reverse shoulder implant 1900 according to an embodiment of the present disclosure. Shoulder implant 1900 includes a stem 1902, a cup 1904, an insert 1906 and a glenoid sphere 1908. Magnetic flux density sensors such as Hall sensor assemblies 1922 are located on insert 1906 as shown in FIG. 38. A connector 1920 on cup 1904 as shown in FIG. 39 allows for attachment of the cup to insert 1906. Magnetic markers 1910 are located on glenoid sphere 1908 as best shown in FIG. 37. Any motion of glenoid sphere 1908 is detected by Hall sensor assemblies 1922 by measuring the change in magnetic flux density. Thus, Hall sensor assemblies 1922 and markers 1910 function as an absolute or incremental encoder to detect shoulder movement of a patient during daily activity.

Shoulder implant 1900 includes a battery 1914 and an electronic assembly 1912 located within cup 1904. A pH sensor 1916 is located on cup 1904 to measure alkalinity and provide early detection notice of implant related infection. An antenna 1918 located on insert 1906 is provided to transmit sensor data to an external source to monitor and transmit shoulder implant 1900 performance during patient rehabilitation and recovery. Various electronic components of electronic assembly 1912, including sensors described with reference to knee joint implants, are located in cup 1904.

Figure 41:
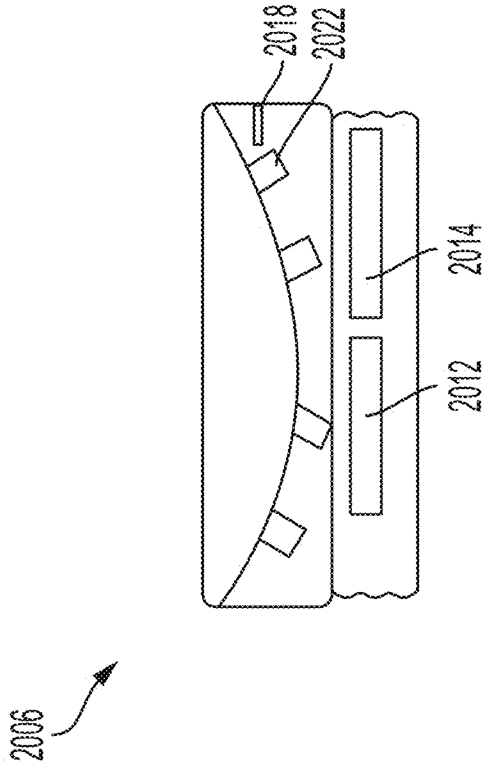
FIG. 41 is a side view of an insert of the shoulder implant of FIG. 40.
Figure 40:
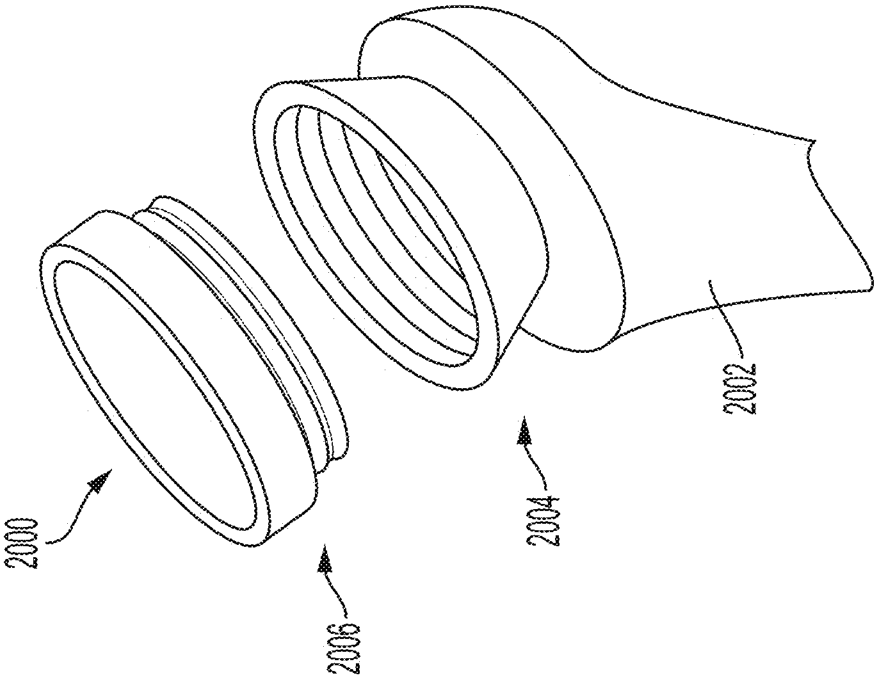
FIG. 40 is side view of a shoulder implant according to another embodiment of the present disclosure.

FIG. 40 is a side view of a reverse shoulder implant 2000 according to another embodiment of the present disclosure. Shoulder implant 2000 is similar to shoulder implant 1900, and therefore like elements are referred to with similar numerals within the 2000-series of numbers. For example, shoulder implant 2000 includes a stem 2002, a cup 2004 and an insert 2006. However, electronic assembly 2012, battery 2014 and pH sensor 2018 are located in insert 2006 as shown in FIG. 41. Thus, only a single component—i.e., the cup, of shoulder implant 2000 can be replaced or upgraded to make changes to sensor collection and transmission of the shoulder implant performance data.

Figure 42:
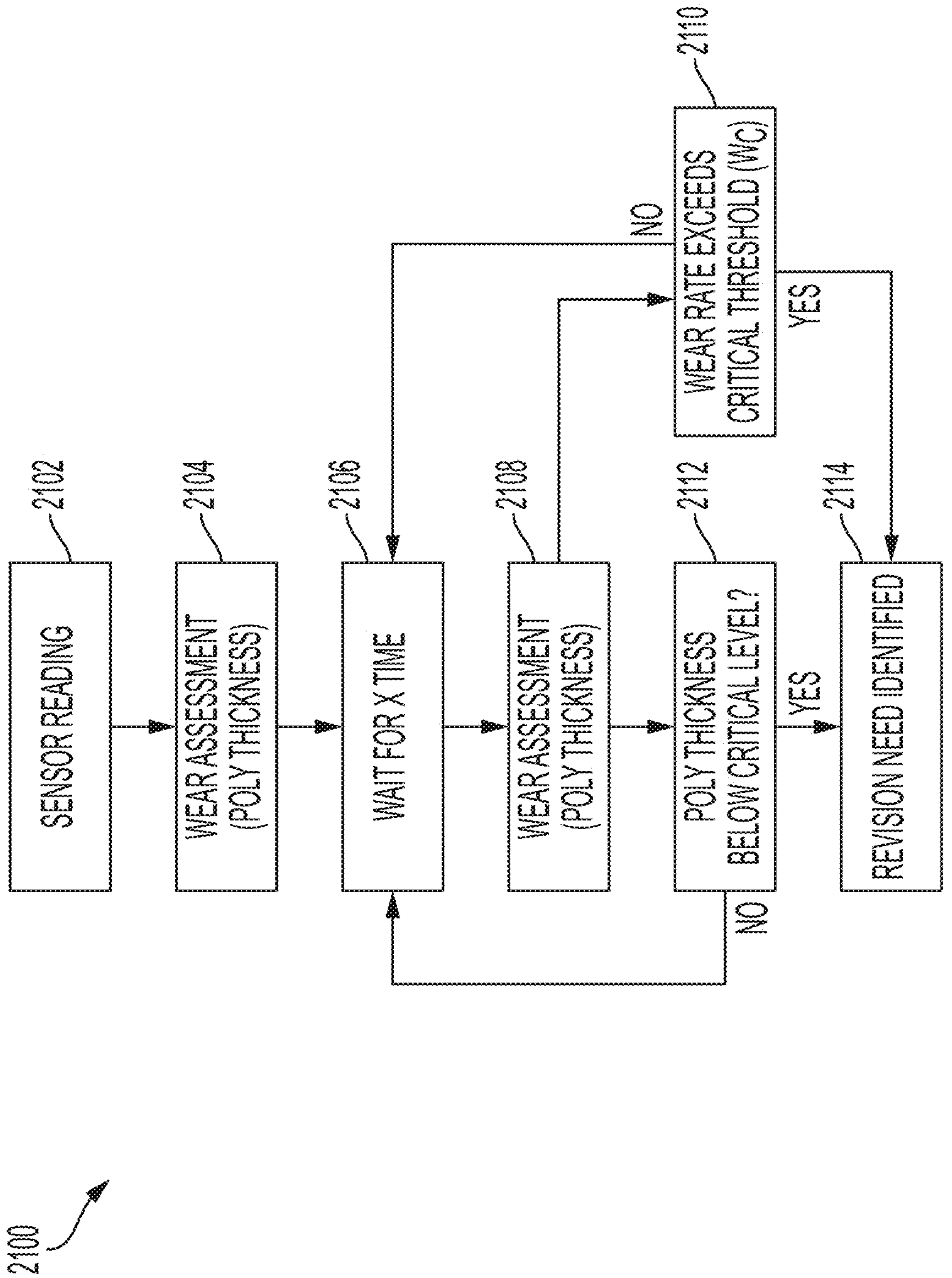
FIG. 42 is a flowchart showing steps to determine implant wear according to another embodiment of the present disclosure.

FIG. 42 is a flowchart showing steps of a method 2100 to determine implant wear according to an embodiment of the present disclosure. While method 2100 is described with reference to a knee joint implant below, method 2100 can be applied to any implant with sensors described in the present disclosure, including all of the implants disclosed above. In a first step 2102, the initial thickness of the knee joint implant (such as thickness of the tibial insert) is recorded. This can be obtained by measuring the tibial insert prior to implantation, or measured based on the magnetic flux density generated by the magnetic markers as measured by the Hall sensor assemblies. Once the knee joint implant is implanted, periodic measurements of tibial insert thickness are determined in a step 2104 by evaluating the magnetic flux density. As the polyethylene housing of tibial insert degrades over time, the distance between the markers and Hall sensor assemblies are reduced as measured in a step 2106. This results in increased magnetic flux density values, which are used to estimate tibial insert wear in a step 2108.

Figure 43:
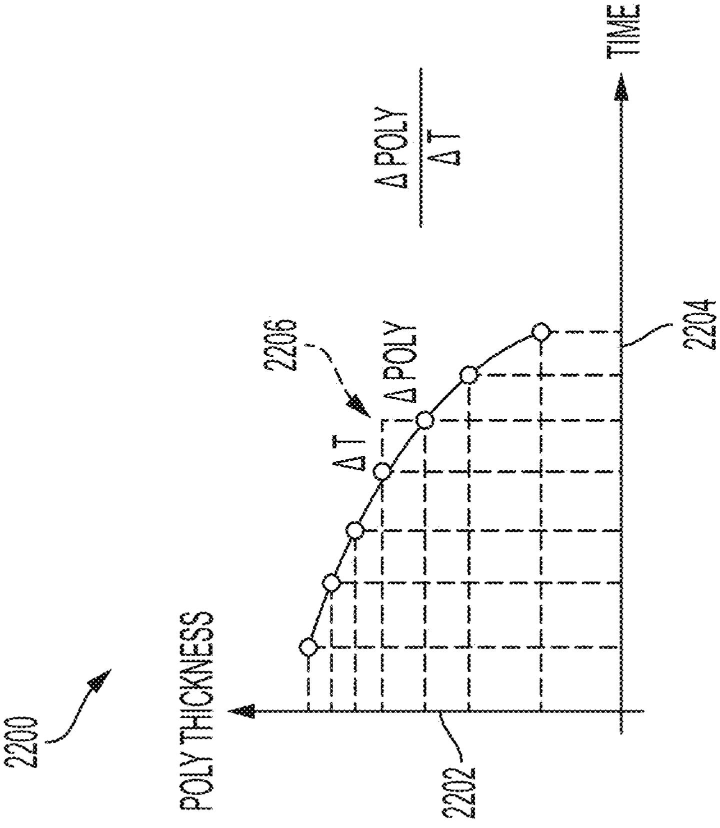
FIG. 43 is a first graph showing implant thickness over time.
Figure 44:
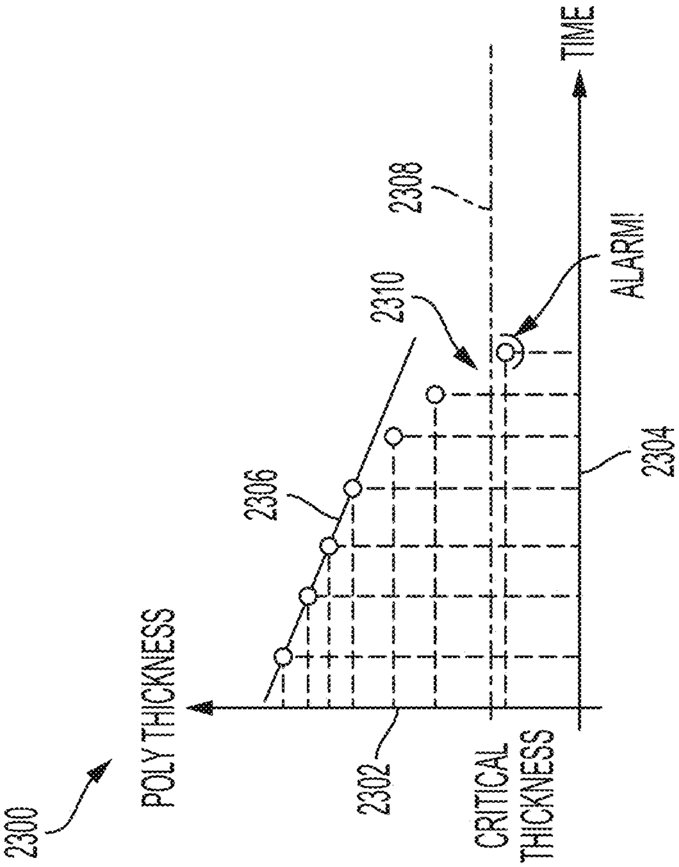
FIG. 44 is a second graph showing implant thickness over time.

The decision to replace the tibial insert can be based on a rate of wear threshold 2206 as shown in graph 2200 of FIG. 43 in a step 2110, or a critical thickness value 2308 as shown in graph 2300 of FIG. 44 in a step 2112. Graph 2200 plots tibial insert thickness 2202 over time 2204. A change in slope 2206 denotes the rate of wear of tibial insert. When slope 2206 exceeds the predetermined rate of wear threshold, notification to replace the tibial insert is triggered in a step 2114. Graph 2300 plots tibial insert thickness 2302 over time 2304. When the tibial insert thickness is less than a predetermined critical thickness value 2308, a notification 2310 is triggered to replace the tibial insert in step 2114.

Figure 45:
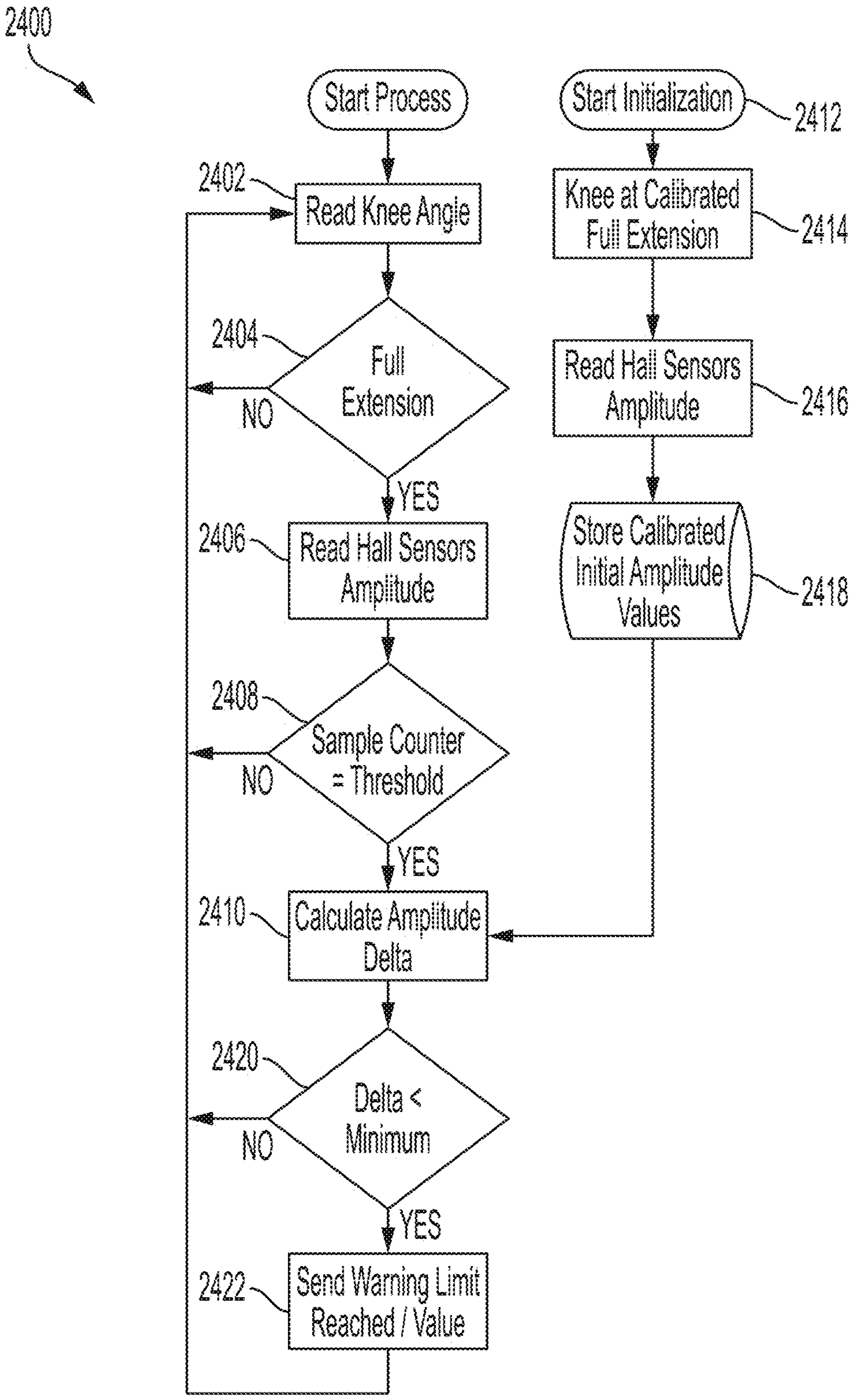
FIG. 45 is a flowchart showing steps to determine implant wear according to another embodiment of the present disclosure.

FIG. 45 is a flowchart showing steps of a method 2400 to determine implant wear according to another embodiment of the present disclosure. While method 2400 is described with reference to a knee joint implant below, method 2400 can be applied to any implant with sensors described in the present disclosure, including all of the implants disclosed above. In a first step 2402, a knee angle of a patient with the knee joint implant is measured. The knee is then placed in full extension in a step 2404. Hall sensor amplitudes are measured in a step 2408. This process is repeated over time to track the Hall sensor amplitude. These values are then compared with initial Hall sensor amplitude values obtained when the knee implant joint template was implanted (obtained by performing steps 2412 to 2418). As the Hall sensor amplitudes are directly related to a distance between the markers and the marker readers—i.e., a tibial insert thickness, a difference between the initial Hall sensor amplitudes and current Hall sensor amplitudes from step 2408 represent wear of the tibial insert in a step 2420. When a predetermined minimum implant thickness is reached in a step 2420, a notification to replace the tibial insert is triggered in a step 2422.

Figure 46:
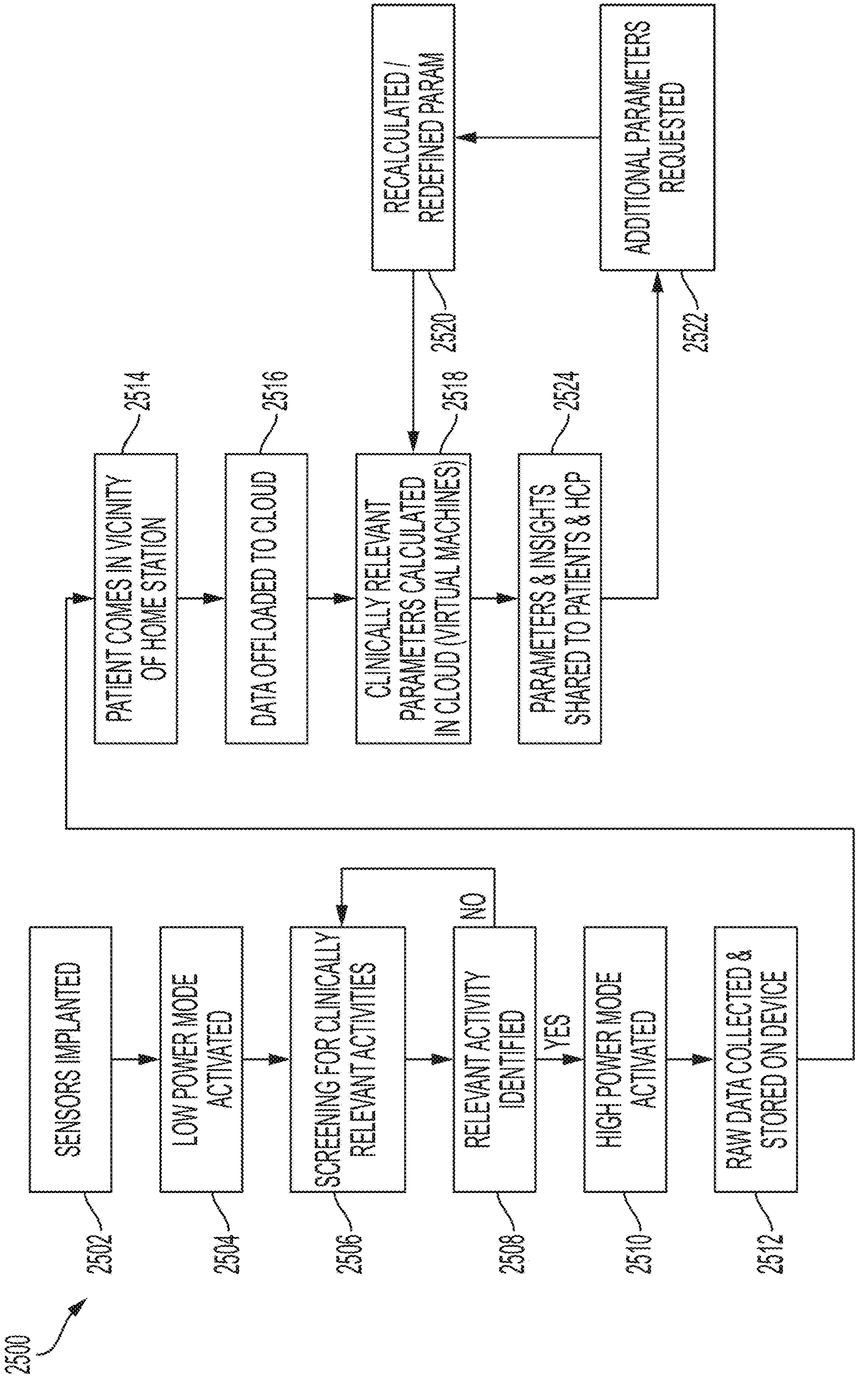
FIG. 46 is a flowchart showing for implant data collection according to another embodiment of the present disclosure.

FIG. 46 is a flowchart showing steps of a method 2500 for implant data collection according to an embodiment of the present disclosure. While method 2500 is described with reference to a knee joint implant below, method 2500 can be applied to any implant with sensors described in the present disclosure, including all of the implants disclosed above. In a first step 2502, a patient is implanted with a knee joint implant. The knee joint implant is in a low-power mode (to conserve battery power) until relevant activity is detected (steps 2504 and 2506). Once the relevant activity is identified by the sensor(s) of the knee joint implant (step 2508), the implant shifts to a high-power mode. Relevant activity to trigger the high-power mode can be patient-specific, and may include knee flexion speed, gait, exposure to sudden impact loads, temperature thresholds, alkalinity levels, etc. Upon identifying the relevant activity and switching over to the high-power mode, various sensors in the knee joint implant record and store sensor measurements on the device (step 2512). This data can be transferred from the patient to a home station when the patient is in the vicinity of the home station or a smart device (step 2514). The data is then transferred from the home station or the smart device to the cloud 5850 to be reviewed and analyzed by the software 5860 or virtual machines and/or by experts (steps 2518, 2520). Relevant information for patient rehabilitation and recovery uncovered from the sensor data is sent back to the patient (steps 2523, 2522) via the client portal 5856. Thus, method 2500 preserves and extends battery life of the knee joint implant by shifting the implant from low-power to high-power mode when required, and shifting the implant back to the low-power mode to conserve energy during other periods.

In some examples, the relevant patient information may be that the knee joint and knee joint implant are in a healthy state, or alternatively that the knee joint is in an infected state. If the knee joint is determined to not be in a healthy state, the clinician can then take steps to review the condition more closely and prepare a plan for treatment if necessary. After review, the clinician can input the state of the joint as determined by the clinician so that the confirmed diagnosis is then associated with the data provided by the joint implant. The diagnosis data combined with corresponding sensor data is then stored in the cloud 5850 and henceforth considered in the software's future determinations of the state of a joint and joint implant. In some examples, the software is adapted to adjust and further refine its parameters and/or thresholds used in determining the state of an implant upon receipt of the diagnosis data.

Figure 47A:
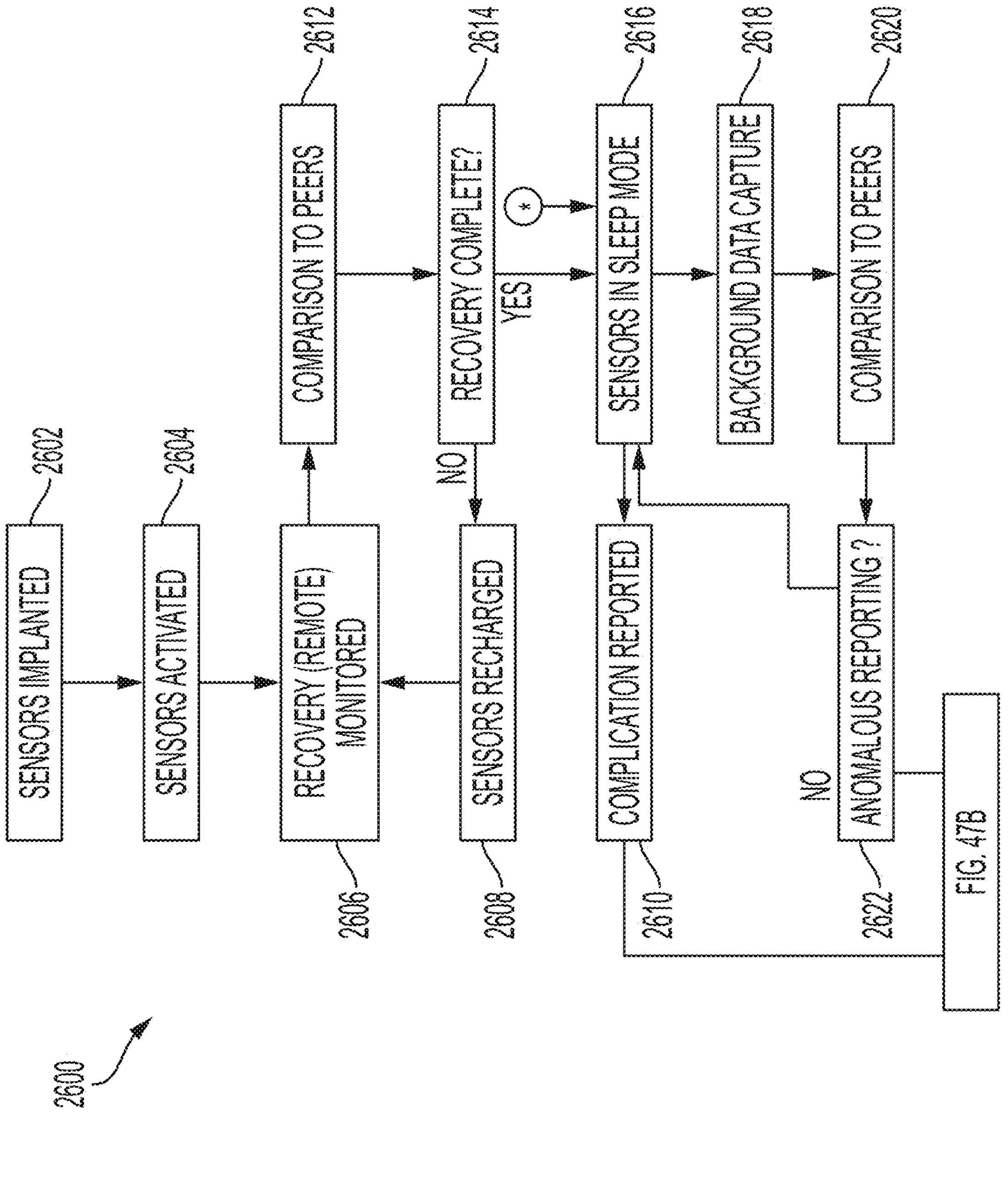
FIGS. 47A and 47B is a flowchart showing steps for patient monitoring according to another embodiment of the present disclosure.
Figure 47B:
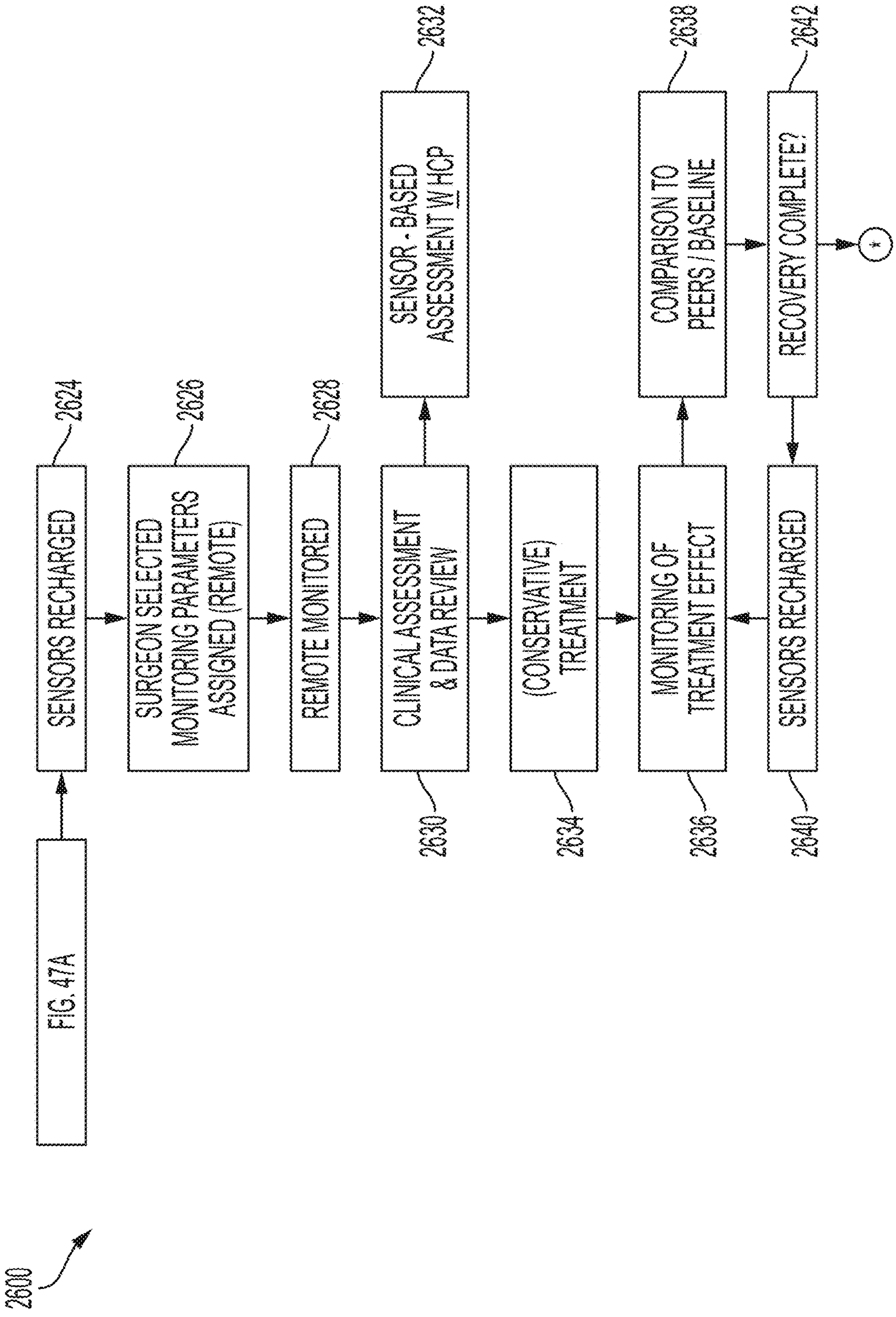

FIGS. 47A and 47B shows steps of a method 2600 for patient monitoring according to an embodiment of the present disclosure. While method 2600 is described with reference to a knee joint implant below, method 2600 can be applied to any implant with sensors described in the present disclosure, including all of the implants disclosed above. After installing the knee joint implant, various sensors within the sensor are activated (steps 2624, 2626) to track and monitor patient rehabilitation and recovery (step 2628). When the tracked data indicates that the desired recovery parameters are achieved, some of the sensors in the knee joint implant are deactivated or turned to a "sleep mode" (step 2616). For example, the recovery target can be a desired range of motion of the knee joint. Once a patient exhibits the desired knee flexion-extension range, some of the sensors on the knee joint implant can be turned off. Alternatively, peer data can be used to identify recovery thresholds (step 2612). If the recovery threshold or milestones are not achieved, the knee joint implant continues to charge and use all sensors (step 2608). Some sensors in the knee joint implant will be periodically used even after achieving the recovery milestones to monitor for early identification of improper implant performance (step 2610, 2618, 2620). For example, after turning off the magnetic readers upon achieving the desired flexion-extension range of motion, the pH or temperature sensors can be used to periodically measure alkalinity and temperature to identify infection or implant failure. Upon identification of an anomalous condition, the knee joint implant can be configured to fully recharge and turn on the previously turned off sensors to provide additional implant performance measurements (step 2624). A surgeon can customize the sensor readings and frequency based on the observed condition (steps 2626 and 2628). Additional rehabilitation steps for patient recovery can be provided to the patient at this point. The impact of the new rehabilitation steps can be monitored and compared with peers to observe patient recovery (steps 2636-2642).

Figure 48:
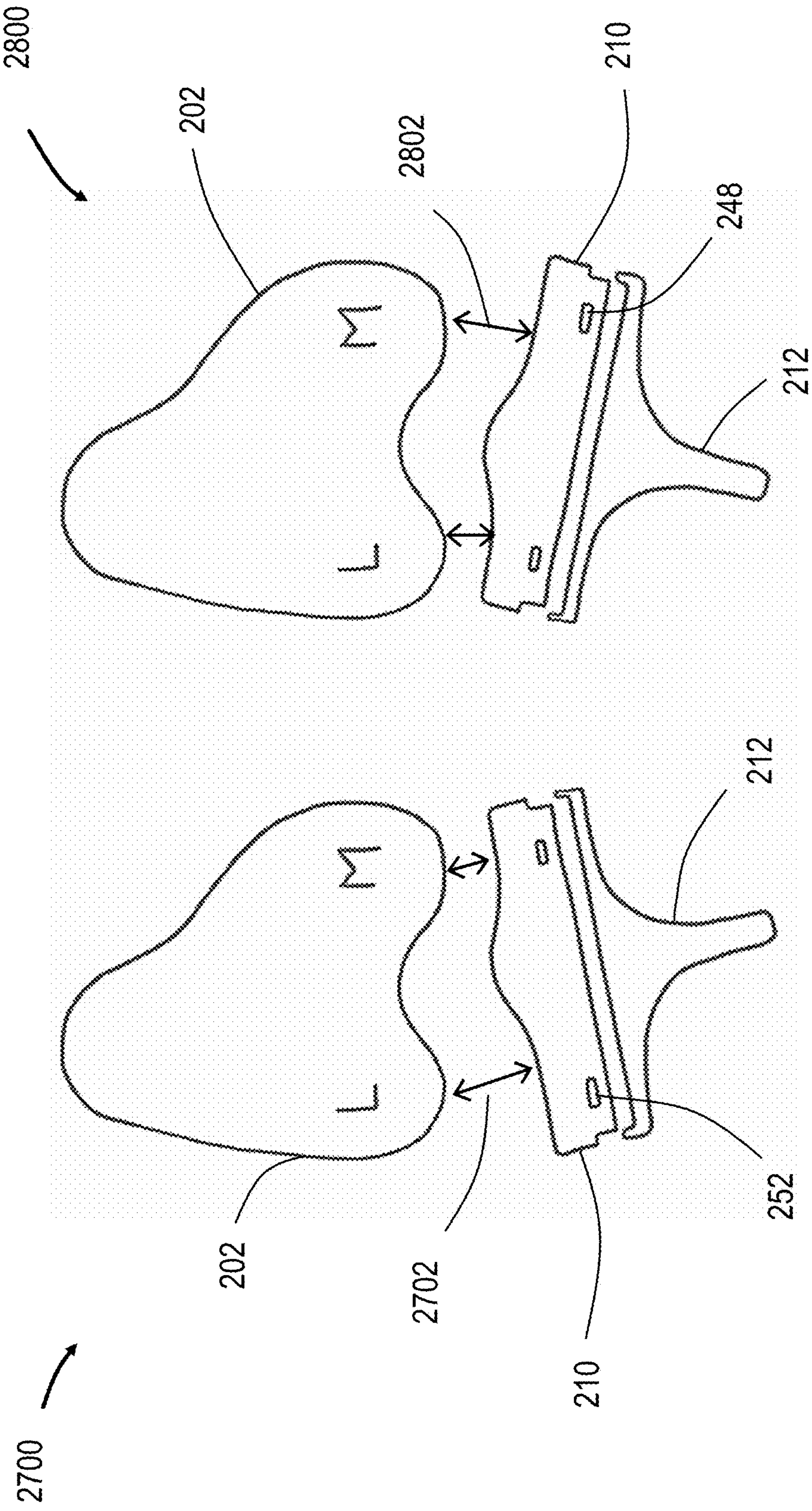
FIG. 48 is a schematic view of varus and valgus stress test results using the knee joint implant of FIG. 6 according to an embodiment of the present disclosure.

FIG. 48 is a schematic view of a varus stress test 2700 and a valgus stress test 2800 performed on knee implant joint 200 according to an embodiment of the present disclosure. Knee joint implant 200 allows a surgeon or an operator (including the patient) to conveniently perform a varus and valgus stress test and accurately record the results using the sensors of knee implant 200. As shown in FIG. 48, a patient implanted with knee joint implant 200 can be subjected to a varus stress test 2700 in extension during which medial marker reader 252 detects the tibiofemoral gap 2702 between femoral implant 202 and tibial insert 210. Tibiofemoral gap 2702 indicates the integrity of the lateral structures of the patient's knee joint to provide stability to the knee joint. While a varus stress test 2700 in extension is shown in FIG. 48, it should be understood that knee joint implant 200 allows for varus and valgus stress tests to be performed and recorded through a full range of motion of the patient's knee. Medial marker reader 252 accurately measures tibiofemoral gap 2702 by detecting the position of magnetic marker (not shown) in femoral implant 202. Similarly, a tibiofemoral gap 2802 is measured by lateral marker reader 248 during a valgus stress test 2800 as shown in FIG. 48. Tibiofemoral gap 2802 indicates the integrity of the medial structures of the patient's knee joint and consequently the stability of the patient's knee joint. Thus, knee joint implant 200 allows an operator or the patient to conveniently conduct and record the results of varus and valgus stress tests to evaluate knee stability. The varus and valgus stress tests can be performed intra-operatively to confirm proper placement, alignment, ligament tension, etc. of knee joint implant 200 to ensure sufficient knee stability and establish an intra-operative baseline of tibiofemoral gaps 2702, 2802. Varus and valgus stress test can now be conveniently performed during patient recovery using the sensors of knee joint implant 200 to track patient recovery. After patient recovery, these tests can be conducted at various intervals during the lifespan of the implant to track implant performance for patient knee stability and other parameters. Deviations from the intra-operative baseline values beyond predetermined thresholds can serve as an early warning of knee instability and allow for timely solutions as more fully explained below.

Figure 49:
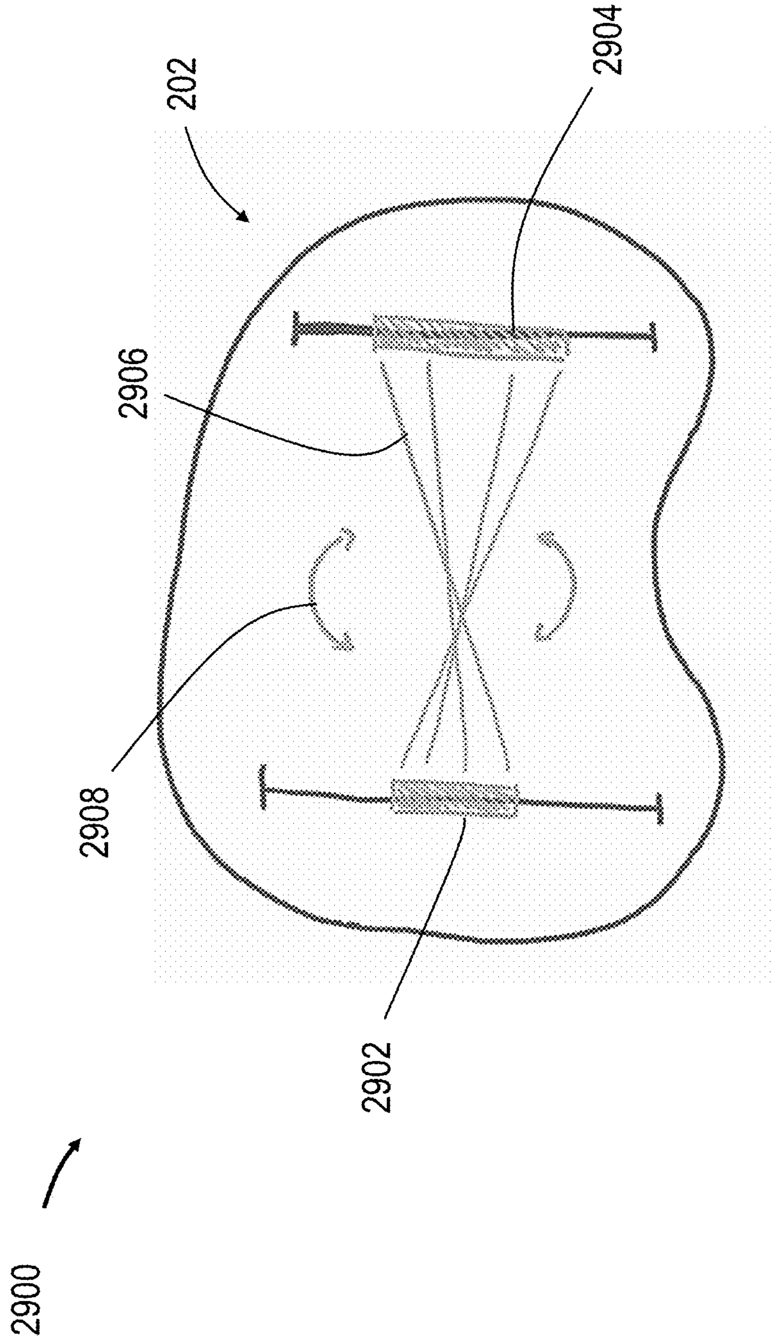
FIG. 49 is a schematic view of an internal-external rotational torque test result using the knee joint implant of FIG. 6 according to an embodiment of the present disclosure.

FIG. 49 shows an internal-external rotation torque test 2900 conducted on knee joint implant 200. Knee joint implant 200 allows a surgeon or an operator (including the patient) to conveniently perform an internal-external rotation torque test on the tibia to accurately record the results using the sensors of the knee implant. As shown in FIG. 49, a patient implanted with knee joint implant 200 can be subjected to an internal-external rotation torque test 2900 during which medial load sensors 232 and lateral load sensors 254 identify contact points between femoral implant 202 and tibial insert 210. A medial box 2902 represents contact points between the medial condyle of femoral implant 202 and tibial insert 210, and a lateral box 2904 represents contact points between the lateral condyle of femoral implant 202 and tibial insert 210 during the application of an internal-external rotation torque 2908 as shown in FIG. 49. Lines 2906 joining a medial contact point to a corresponding lateral contact point during the test are shown in FIG. 49. The size of the medial box and the lateral box represent the integrity of the ligaments and consequently the stability of knee. Small box sizes indicate stable knee joint and large box sizes indicate unstable knee joints. Thus, knee joint implant 200 allows an operator or the patient to conveniently conduct and record the results of internal-external rotational torque tests to evaluate knee stability. The internal-external rotational torque tests can be performed intra-operatively to confirm proper placement, alignment, ligament tension, etc. of knee joint implant 200 to ensure sufficient knee stability and establish an intra-operative baseline of medial and lateral box sizes for a fixed torque. Internal-external rotational torque tests can now be conveniently performed during patient recovery using the sensors of knee joint implant 200 to track patient recovery. After patient recovery, these tests can be conducted at various intervals during the lifespan of the implant to track implant performance for patient knee stability and other parameters. Deviations from the intra-operative baseline values beyond predetermined thresholds can serve as an early warning of knee instability.

Figure 50:
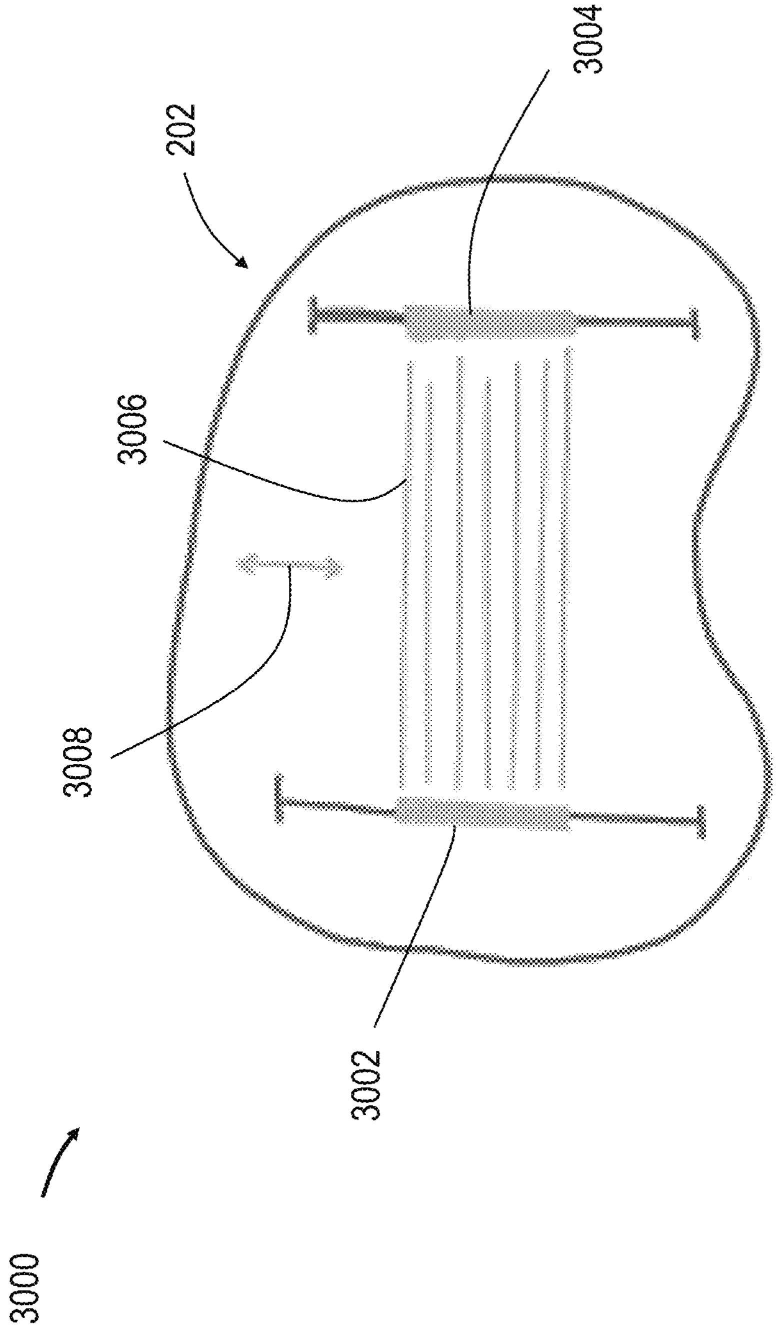
FIG. 50 is a schematic view of an anterior-posterior shear force test result using the knee joint implant of FIG. 6 according to an embodiment of the present disclosure.

Referring now to FIG. 50, there is shown results of an anterior-posterior shear force test 3000 conducted on knee joint implant 200. Knee joint implant 200 allows a surgeon or an operator (including the patient) to conveniently perform an anterior-posterior shear force test on the patients' knee joint to accurately record the results using the sensors of the knee implant. As shown in FIG. 50, a patient implanted with knee joint implant 200 can be subjected to an anterior-posterior shear force test 3000 during which medial load sensors 232 and lateral load sensors 254 identify contact points between femoral implant 202 and tibial insert 210. A medial box 3002 represents contact points between the medial condyle of femoral implant 202 and tibial insert 210, and a lateral box 3004 represents contact points between the lateral condyle of femoral implant 202 and tibial insert 210 during the application of an anterior-posterior shear force 3008 as shown in FIG. 50. Lines 3006 joining a medial contact point to a corresponding lateral contact point during the test are shown in FIG. 50. The size of the medial box and the lateral box represent the integrity of the ligaments and consequently the stability of knee. Small box sizes indicate stable knee joint and large box sizes indicate unstable knee joints. Thus, knee joint implant 200 allows an operator or the patient to conveniently conduct and record the results of anterior-posterior shear force tests to evaluate knee stability. The anterior-posterior shear force tests can be performed intra-operatively to confirm proper placement, alignment, ligament tension, etc. of knee joint implant 200 to ensure sufficient knee stability and establish an intra-operative baseline of medial and lateral box sizes for a known anterior-posterior shear force. Anterior-posterior shear force tests can now be conveniently performed during patient recovery using the sensors of knee joint implant 200 to track patient recovery. After patient recovery, these tests can be conducted at various intervals during the lifespan of the implant to track implant performance for patient knee stability and other parameters. Deviations from the intra-operative baseline values beyond predetermined thresholds can serve as an early warning of knee instability.

Figure 51:
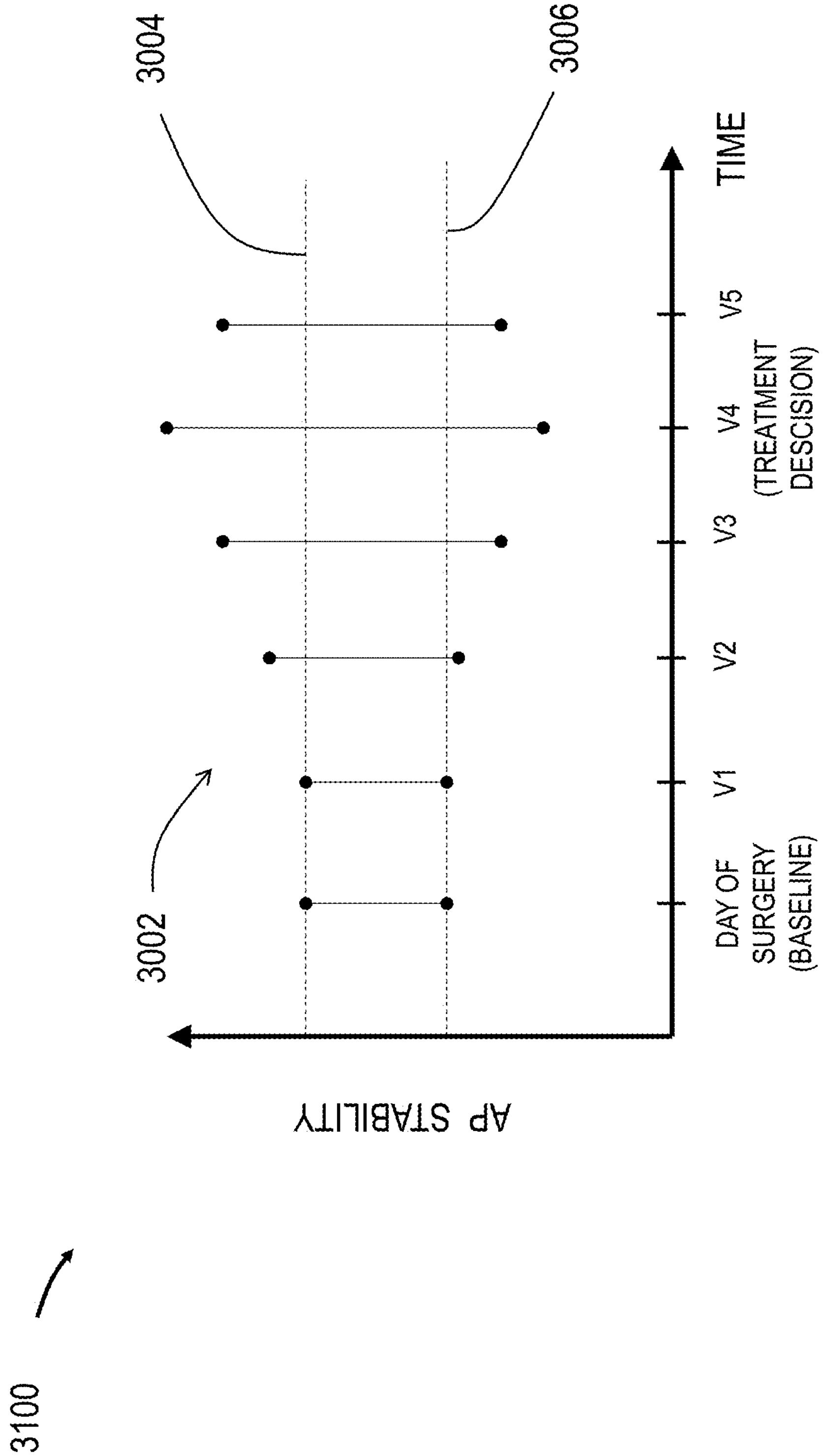
FIG. 51 is a graph showing a knee joint implant stability over time.

A graph 3100 plotting knee stability over time to track and treat potential knee stability is shown in FIG. 51. Knee stability metrics such as anterior-posterior stability measurements 3002 obtained from anterior-posterior shear force tests described above can be tracked over time using knee joint implant 200. An intraoperative baseline defined by an anterior threshold 3004 and a posterior threshold 3006 is established on the day of the surgery as shown in FIG. 51. Subsequent follow-up tests at discrete times V1-V5 are performed to ensure knee stability. The anterior-posterior translation recorded at V1 shows no deviation from the intra-operative baseline and thus indicates no anterior-posterior knee instability. Subsequent tests at V2, V3 and V4 show increasing deviation from the intra-operatively baseline indicating progressive anterior-posterior knee instability. Based on these readings, a surgeon can initiate a conservative treatment plan at V4 for example to prevent and reverse the knee instability. Conservative treatment options can include wearing a brace, performing muscle strengthening exercises, etc. In other words, the conservative treatment options are intended to prevent the patient from undergoing surgical intervention such as a revision knee surgery by early identification and correction of the knee instability. For example, when a patient shows increased anterior laxity in the medial column over time, PT exercises to increase muscular strength to stabilize the medial column by training the Vastus Medialis Obliquus (VMO) can be prescribed as a conservative treatment plant. As shown in FIG. 51, functional stability at $V_5$ stops progressing, indicating that the conservative treatment was successful in halting and reversing knee instability. Conservative treatment plans can be initiated after a trend is observed based on sensor data of the knee joint implant captured in the background without the requiring any particular knee stability tests or clinic visits.

Figure 52:
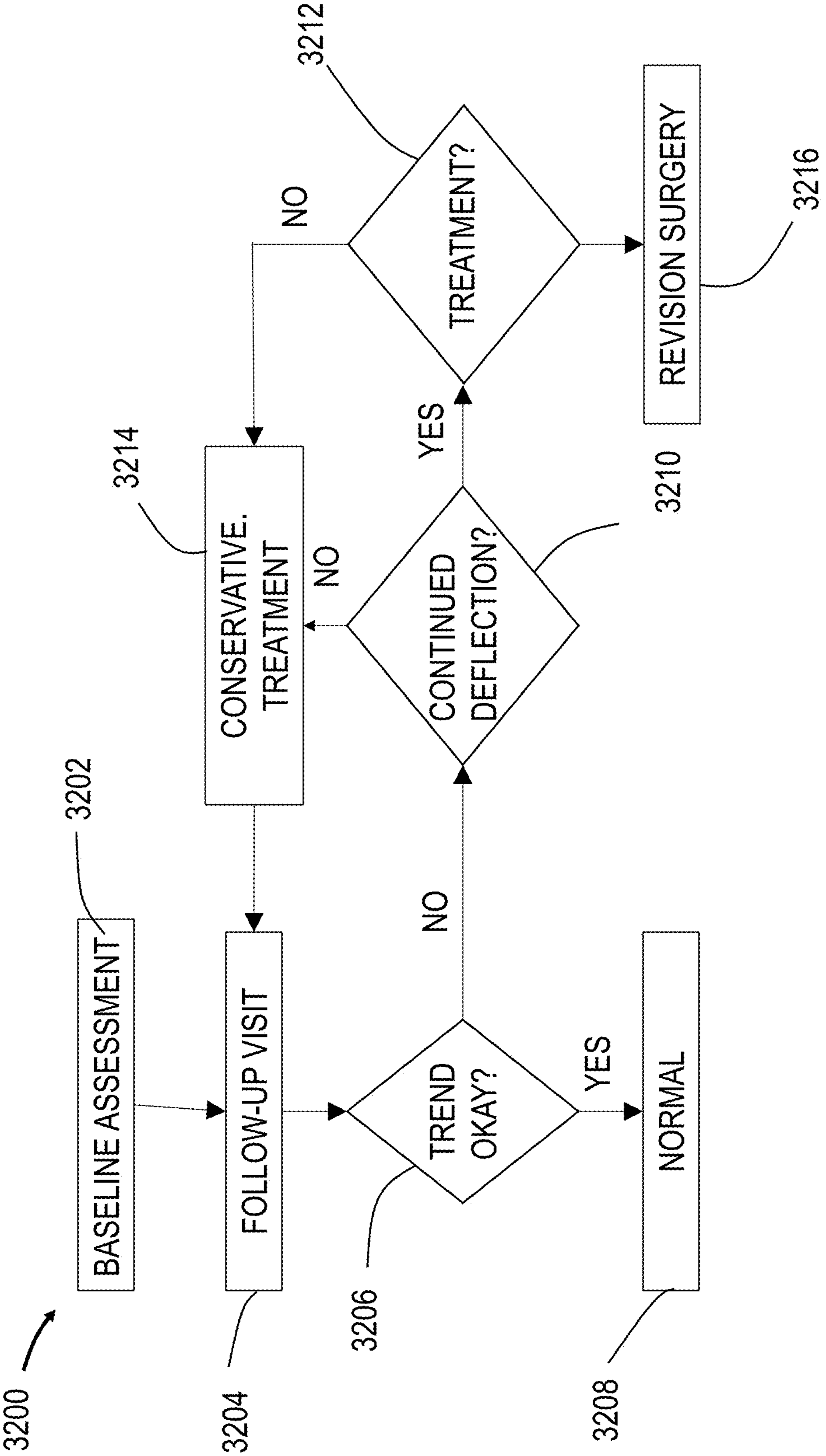
FIG. 52 is a flowchart showing steps for patient monitoring according to an embodiment of the present disclosure.

FIG. 52 shows a method 3200 for patient monitoring according to an embodiment of the present disclosure. A joint stability baseline is created in a first step 3202. This baseline can be based on intra-operative measurements or generated from peers by comparing patients with similar characteristics such as intra-operative stability and hence project a recovery trajectory for these patients. As such, a normal recovery performance versus an anomalous performance can be evaluated. Joint stability measurement are recorded during the patient's follow-up clinic visits in a step 3204. The joint stability measurements can be generated automatically by the joint implant and transmitted to the surgeon for analysis without requiring the patient to visit a clinic in another embodiment. The joint stability measurements recorded in step 3204 are compared with the baseline in a step 3206 to determine if the joint stability measurements are within expected baseline threshold indicating a stable joint (step 3208) or deviating from the baseline thresholds in a step 3210. Depending on the magnitude of deviation, a conservative treatment plan (step 3214) if the deviation is within predetermined levels or to a step 3212 if the deviation is greater than the predetermined levels. If conservative treatment has already been tried or if the deviation exceeds the predetermined levels, a surgical intervention such as a revision surgery is performed in a step 3216.

Figure 53:
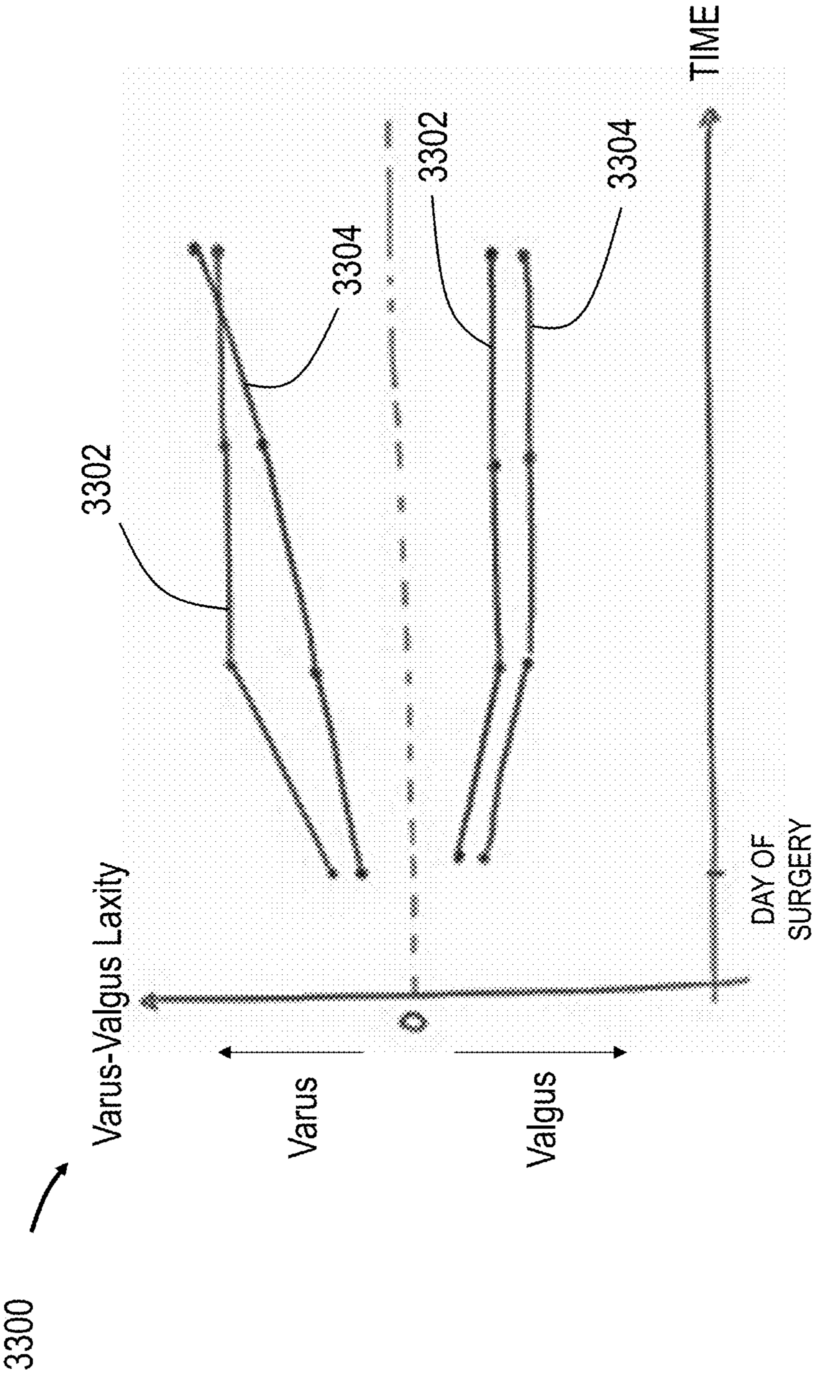
FIG. 53 is a graph showing a knee joint implant performance over time.

FIG. 53 shows a graph 330 depicting a first patient's varus-valgus laxity measurements 3302 and a second patient's varus-valgus laxity measurements over time. As shown here, varus and valgus measurements for first patient 3302 stabilize over time indicating a stable knee joint. While the valgus measurements of second patient 3304 stabilize over time, the varus measurement continue to diverge from the baseline (day of surgery) indicating a potentially unstable knee requiring an intervention. As accurate joint stability measurement are readily available from the sensors of the joint implant, the second patient can be treated with a conservative treatment plan early on in this process and thus prevent the need for surgical intervention.

Figure 54:
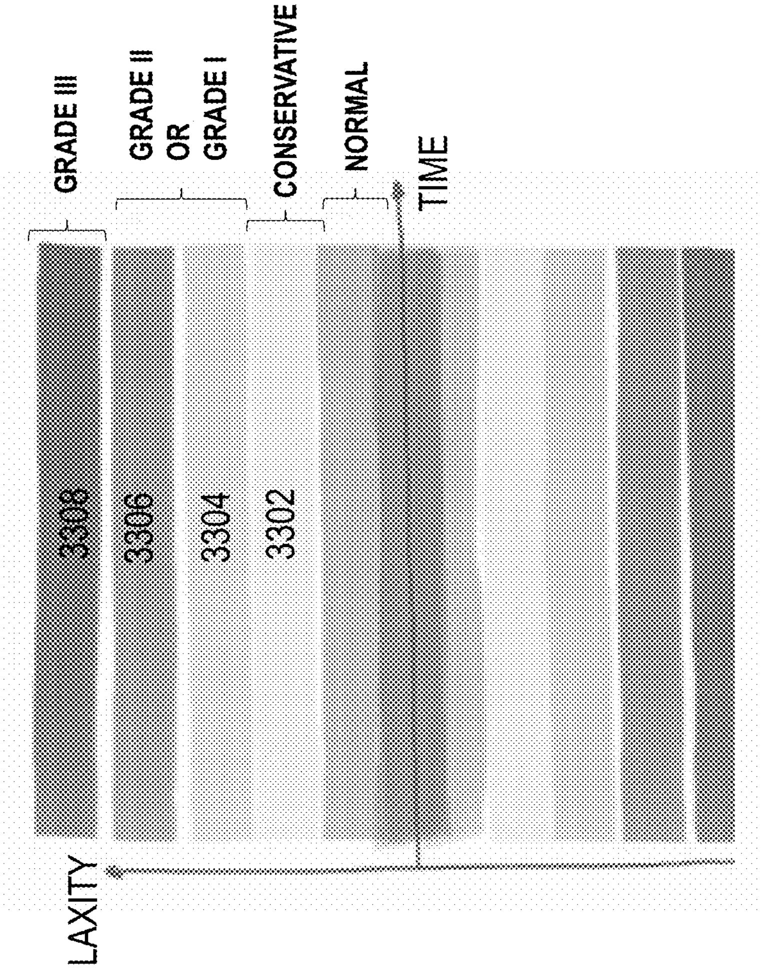
FIG. 54 is a graph showing a knee joint implant performance over time.

A graph 3300 showing laxity over time is shown in FIG. 54. As shown here, depending on the extent of the joint instability (shown as laxity in this embodiment), various treatments can be assigned depending on the level of laxity. For example, a mild instability zone 3302 can be treated with a conservative treatment plan such a wearing a brace or augmenting a patient's physiotherapy program. When more excessive instability is observed, revision surgery may be indicated. For example, when an isolated instability zone 3304 is observed and ligaments are still functional, i.e.—instability magnitudes are not excessive, the tibial insert can be replaced (Grade I). For medial instability, a thicker tibial insert can be introduced, and lateral structures can be released to facilitate the thicker component. However, when instability is substantial in a zone 3306, a single component revision (such as a tibial insert) is insufficient to correct the instability, and may require multiple components or all components of the joint implant to be replaced (Grade II). However, ligaments are still functional in zone 3306 and hence a hinged prosthesis is not required. When a maximum instability zone 3308 is detected, a Grade III revision is required whereby the existing joint implant is changed to a hinged prosthesis. Ligament function is no longer required—i.e., total ligament insufficiency. This can be identified during clinic or surgical assessment.

Figure 55:
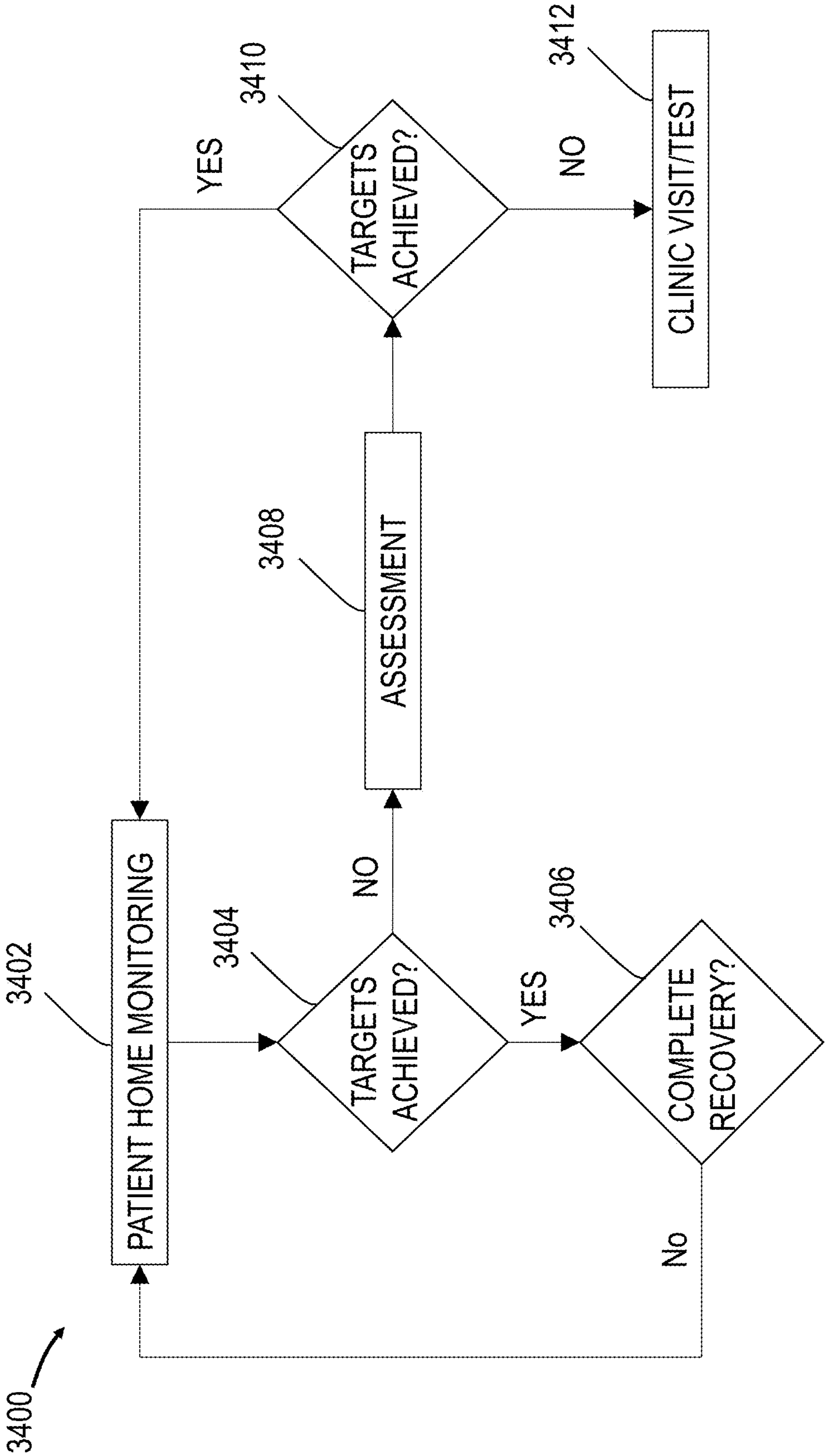
FIG. 55 is a flowchart showing steps for patient monitoring according to an embodiment of the present disclosure.

Referring now to FIG. 55, there is shown a method 3400 for patient home monitoring according to an embodiment of the present disclosure. Method 3400 discloses a workflow whereby a patient is monitored at home using the sensors of the joint implant (step 3402), without the need to engage in any focused activity subject to achieving predetermined targets (step 3404). When the targets are not achieved, a more detailed analysis is initiated to determine whether the same or new targets are to be set (step 3408). If these new targets are met, the patient can continue their daily activity (step 3410). If not, the patient is called in for clinic visit where additional tests under supervision of a surgeon is conducted (step 3412). For example, a range of motion test can be measured by the implantable system in the background without active interaction of the patient. When the extension-flexion targets are not achieved, the patient can be asked to complete another dedicated assessment to determine maximum flexion and extension. If this still does not meet the recovery targets, the patient is called in for a clinic visit.

Figure 56:
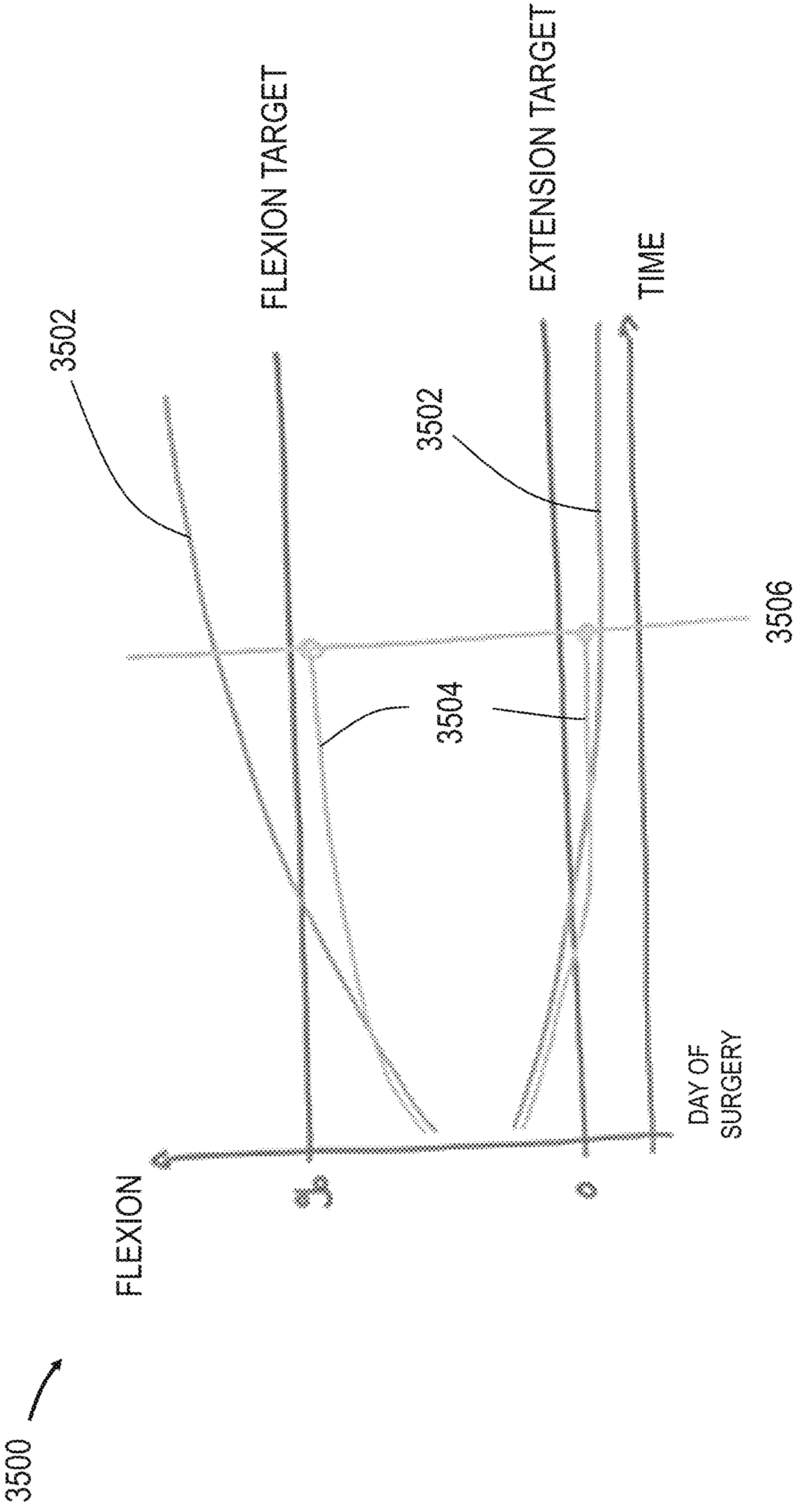
FIG. 56 is a graph showing a knee joint implant performance over time.

FIG. 56 is a graph 3500 showing flexion-extension results for a first patient 3502 and a second patient 3504 over time. First patient 3502 flexion and extension targets exceed the predetermined targets over the course of this patient's recovery as shown in graph 3500. While the second patient's extension target is achieved, this patient's flexion is below the flexion target as depicted by a line 3506. Consequently, second patient 3504 will require a conservative plan to achieve the predetermined flexion target.

Figure 57:
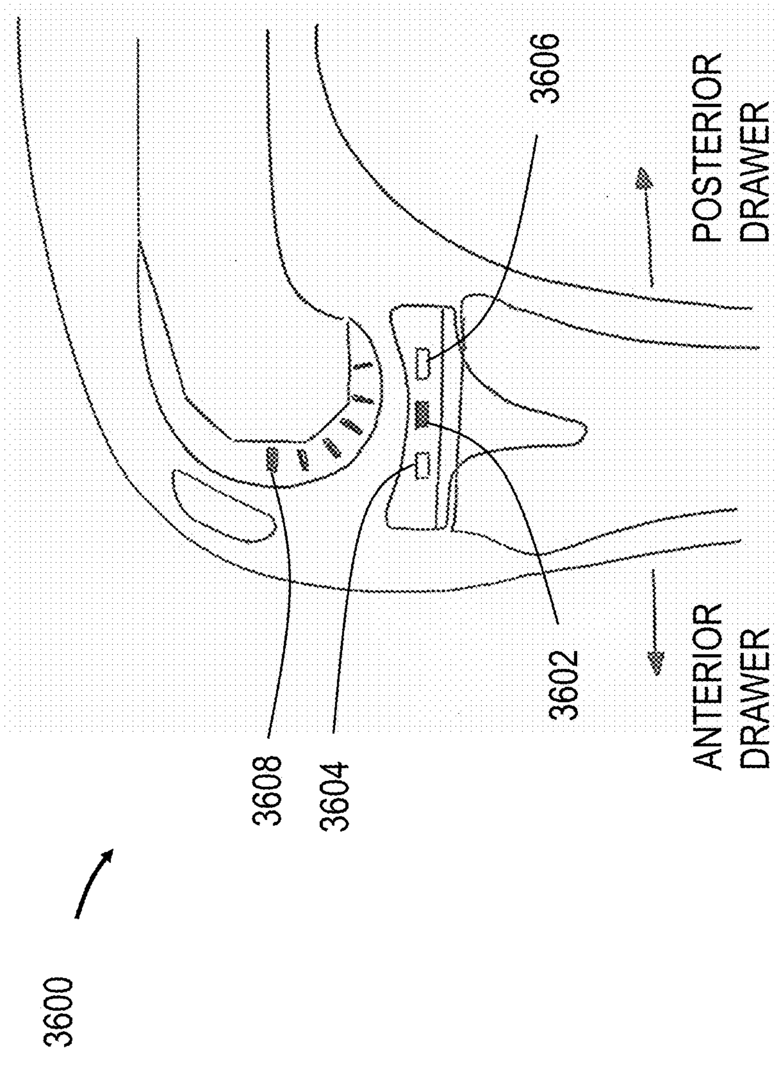
FIG. 57 is a side view an implanted knee joint implant.

An implanted knee joint implant 3600 in a flexion position is shown in FIG. 57. Magnets 3608 placed in the femoral implant allow accurate measurement of the femoral implant position via Hall sensors 3602-3606 embedded in the tibial component. In another embodiment, sensors can be located in the tibial baseplate or tibial stem. More than one sensor per condyle is used to cover a wide range of motion and contact areas between the implant component to track and record kinematics measurements for all degrees of freedom. However, when considering a single stability assessment such as the embodiments described above, Hall sensors away from the contact point can be switched off to increase the sensitivity of the system. For example, during an antero-posterior drawer test shown in FIG. 57, only Hall sensor 3602 is activated and Hall sensors 3604 and 3606 are deactivated to improve accuracy of readings and reduce power consumption of the knee joint implant.

Figure 58:
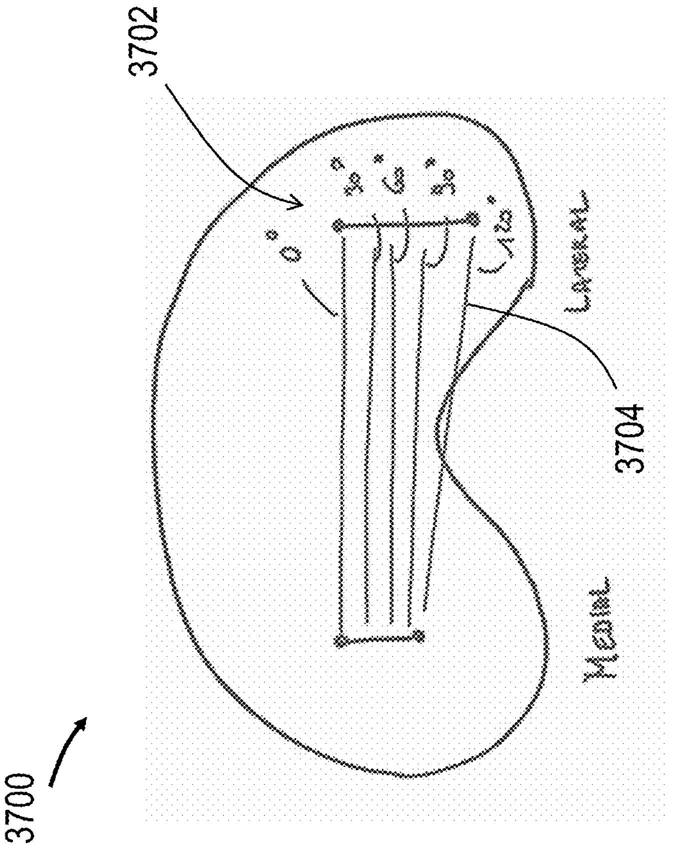
FIG. 58 is a schematic view of knee flexion-extension monitoring results of a first patient using the knee joint implant of FIG. 6.
Figure 59:
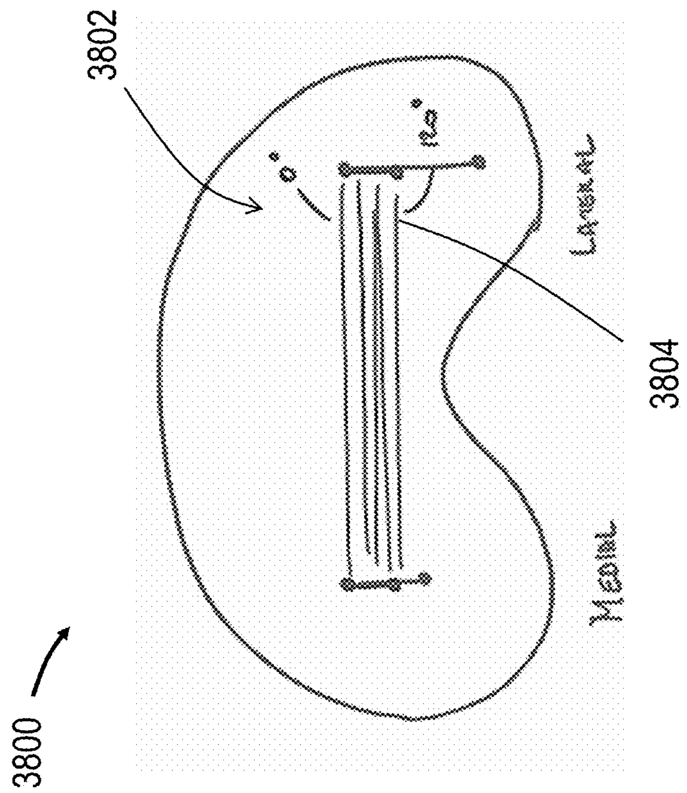
FIG. 59 is a schematic view of knee flexion-extension monitoring results of a second patient using the knee joint implant of FIG. 6.

FIG. 58 is a schematic view of knee flexion-extension monitoring results 3700 of a first patient and FIG. 59 is a schematic view of knee flexion-extension monitoring results 3800 of a second patient using knee joint implant 200 according to another embodiment of the present disclosure. First patient's knee flexion-extension measurements indicate an intact PCL showing stable progress of contact points through the range of motion and contact point rolling back 3704 in flexion 3702 as shown in FIG. 58. The second patient's knee flexion-extension measurement reveal an inefficient PCL as the rollback 3804 is reduced in flexion 3802 and contact points stay more centralized as best shown in FIG. 59. These measurements can be observed remotely as the patients performs daily or targeted activities (tests).

Figure 60:
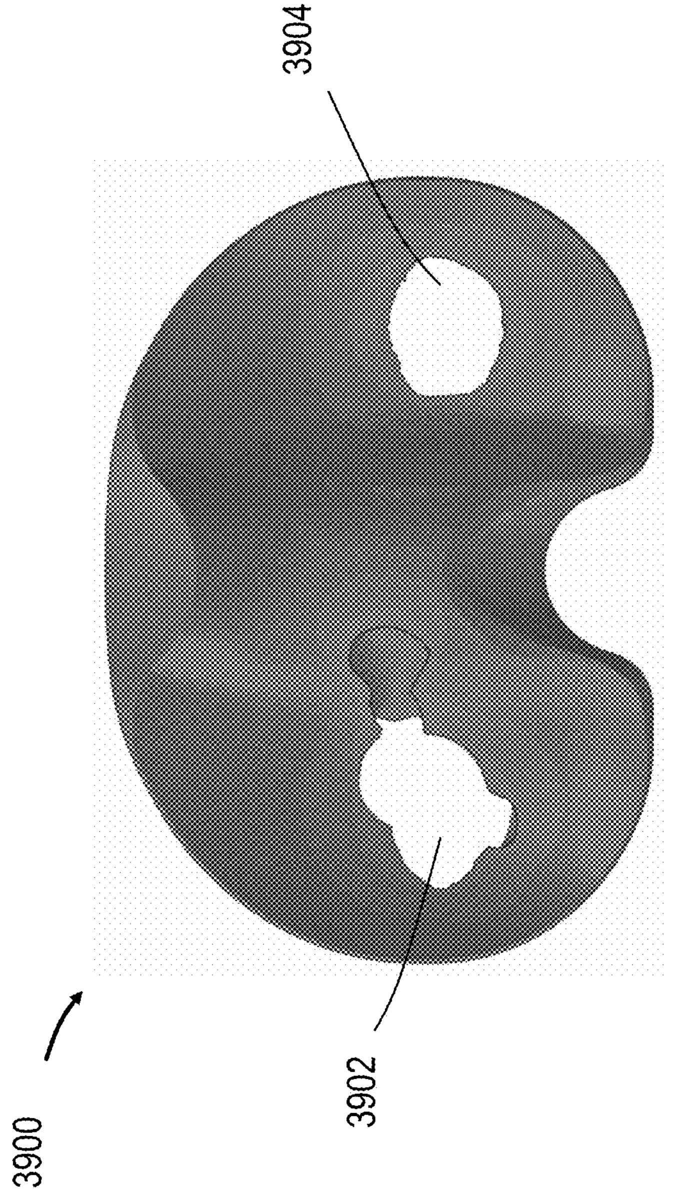
FIG. 60 shows results of a loading simulation on a tibial insert.

FIG. 60 shows the results of a dynamic load simulation on a tibial insert 3900 performed using an FEA analysis. As shown here, dynamic loading on tibial insert 3900 during patient use (such as walking, standing, etc.) is not uniform across the tibial insert. Instead, high loading is concentrated specifically on medial 3902 and lateral 3904 centers of the tibial insert (shown as unshaded regions in FIG. 60). These locations are subjected to high loads and represent 20-100% of the peak von Mises stress and consequently are more vulnerable to failure than the rest of the tibial insert. Hence, reducing the thickness of the tibial inserts at the high stress locations to accommodate sensors, batteries, and other components for any of the implant disclosed herein (such as tibial implant 204) will weaken the tibial insert. Areas at the middle (between medial and lateral sides) and periphery of the tibial insert experience less loading than other areas as shown in FIG. 60.

Figure 61:
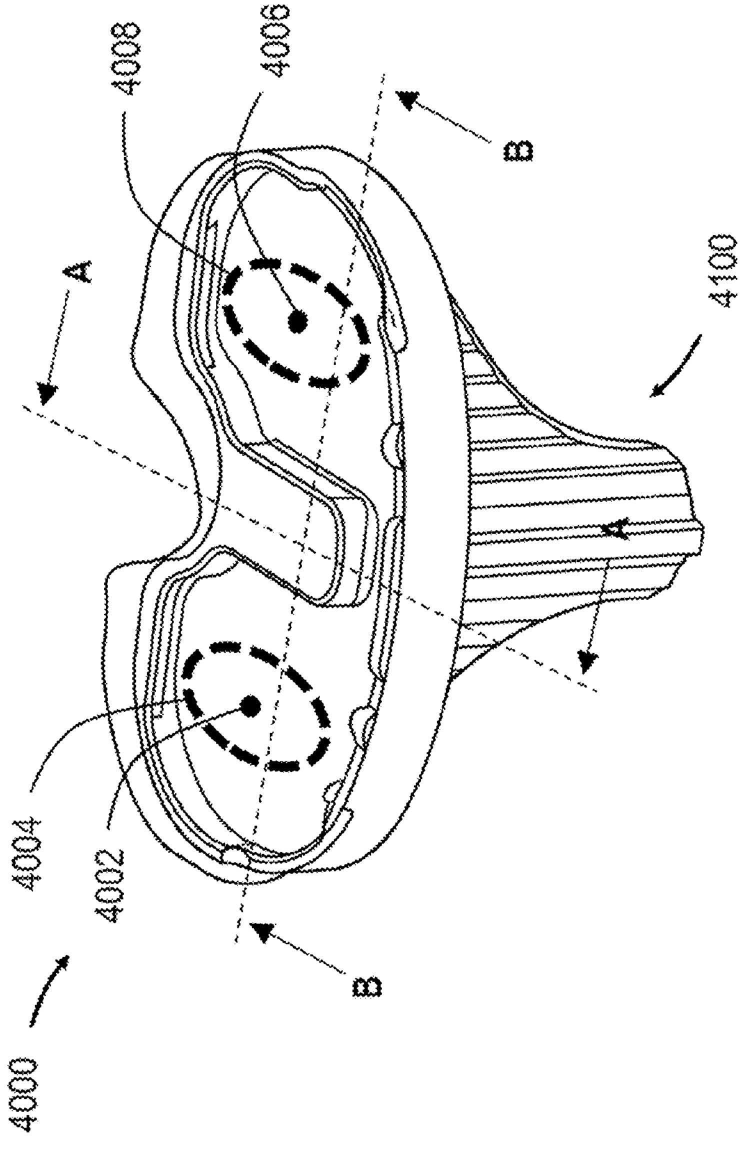
FIG. 61 is an isometric view of a tibial insert and a tibial stem according to an embodiment of the present disclosure.
Figure 62:
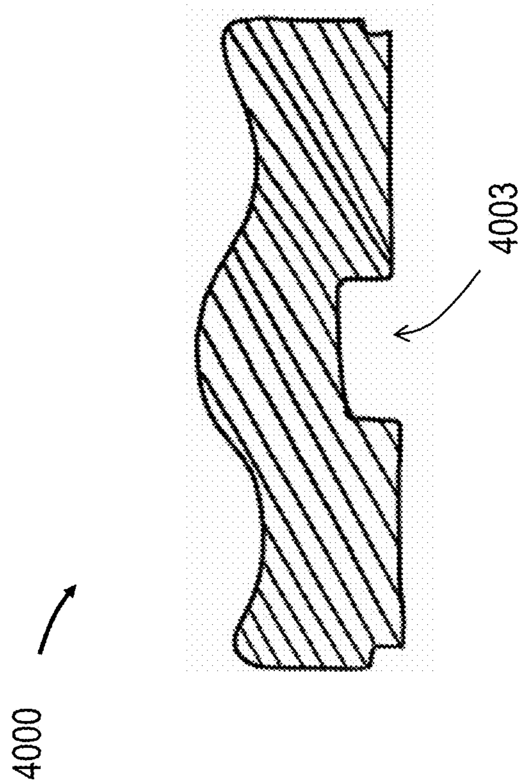
FIG. 62 is a cross-sectional view of a tibial insert according to an embodiment of the present disclosure taken along line B-B of FIG. 61.
Figure 63:
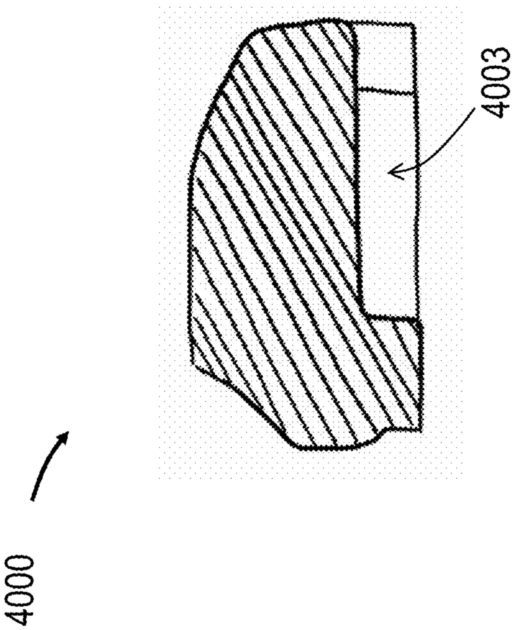
FIG. 63 is a cross-sectional view of the tibial insert of FIG. 62 taken along a line A-A of FIG. 49.

FIGS. 61-63 show a tibial insert 4000 and a tibial stem 4100 having a tibial baseplate according to another embodiment of the present disclosure. Tibial insert 4000 includes an opening 4003 to receive and couple with a complementary projection (not shown) of tibial stem 4100. As shown in the cross-sections of FIGS. 62 and 63, sensors, batteries and other components of the knee joint implant can be located within the body of tibial insert 4000. Tibial insert 4000 includes a medial side with a medial center 4002 and a lateral side with a later center 4006 as best shown in FIG. 61. A medial central portion 4004 defined by an oval or circular region around medial center 4002 and a lateral central portion 4008 defined by an oval or circular region around lateral center 4006 indicate the areas of tibial insert 4000 experiencing high/peak loading during implant life. Thus, the tibial inserts disclosed below are specifically configured to maximize strength, wear and fatigue resistance of these high loading areas by locating electronic and non-electronic component outside the high loading areas. While a circular or oval region is shown in this embodiment, other embodiments may have high loading areas defined by other shapes.

Figure 65:
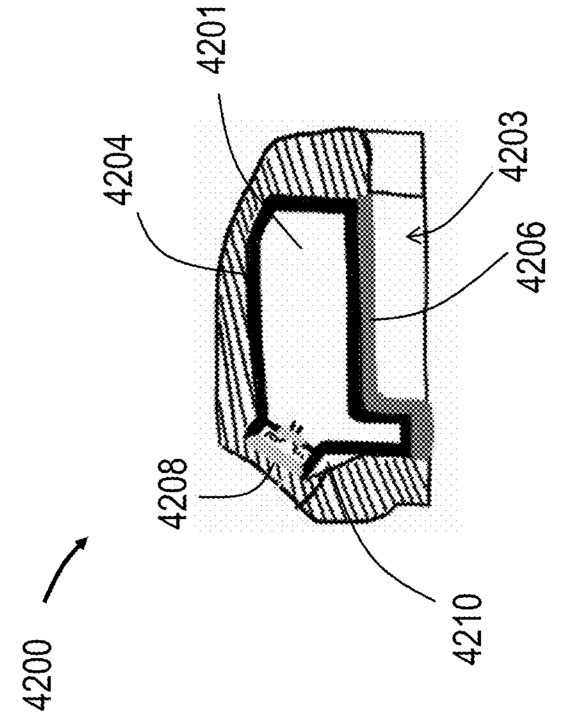
FIG. 65 is a cross-section view of the tibial insert of FIG. 64 taken along a line A-A of FIG. 61.
Figure 64:
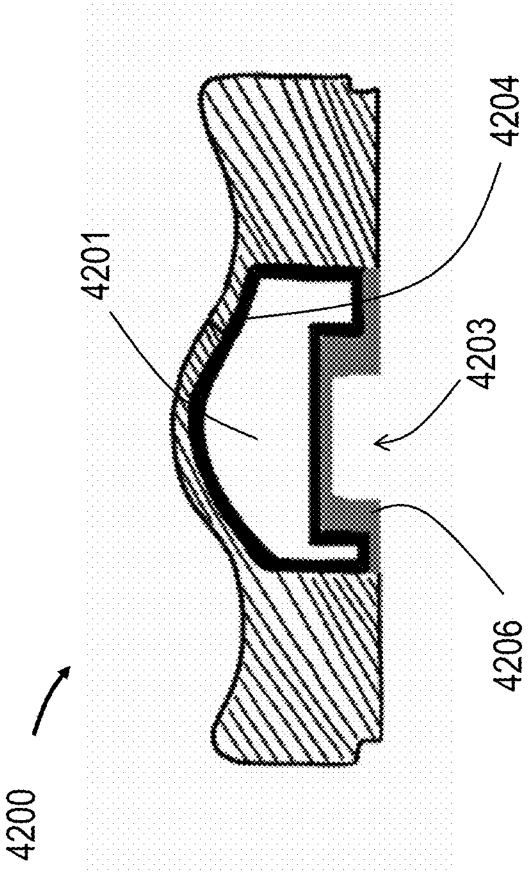
FIG. 64 is a cross-sectional view of a tibial insert according to another embodiment of the present disclosure taken along line B-B of FIG. 61.

Referring now to FIGS. 64 and 65, there is shown a tibial insert 4200 according to an embodiment of the present disclosure. Tibial insert is configured to accommodate the various electronic and non-electronic components of the smart implant within the tibial insert without weakening or otherwise comprising the structural strength and wear resistance of the implant during implant life. As shown in FIGS. 64 and 65, electronic and non-electronic components are embedded within a sealed cavity 4201 defined by a layer 4204 located above opening 4203. Thus, as the medial and lateral centers of tibial insert 4200 (shown in FIG. 61) are not weakened by removing tibial insert material (cross-linked polyethylene or other suitable material) to accommodate electronic and non-electronic components, structural strength of tibial insert 4200 is maximized Layer 4204 can be cobalt-chromium, titanium, or other suitable material to form a hermetic seal and protect the electronic components from impact, subsidence, etc. during implant life. A cross-linked polyethylene material or other suitable material can be used to form a layer 4206 below cavity 4201 as best shown in FIGS. 64 and 65. Layer 4206 can be reinforced to ensure improved coupling with the tibial baseplate and stem. Underlaying layer 4206 prevents metal on metal contact between the electronic components in cavity 4201 and the tibial stem/baseplate, and the formation of any wear particles resulting from the micromotion between these components. A void 4210 between layer 4204 and the body of tibial insert 4200 as shown in FIG. 65 allows for convenient mounting of layer 4204 within the tibial insert. For example, after locating all electronic and non-electronic components within cavity 4201, layer 4204 can be conveniently press-fit into tibial insert 4200 during assembly. A ceramic seal 4208 above a charging coil above a Bluetooth or RF antenna (not shown) allows for induction charging and wireless transmission of data while hermetically sealing cavity 4201.

Figure 67:
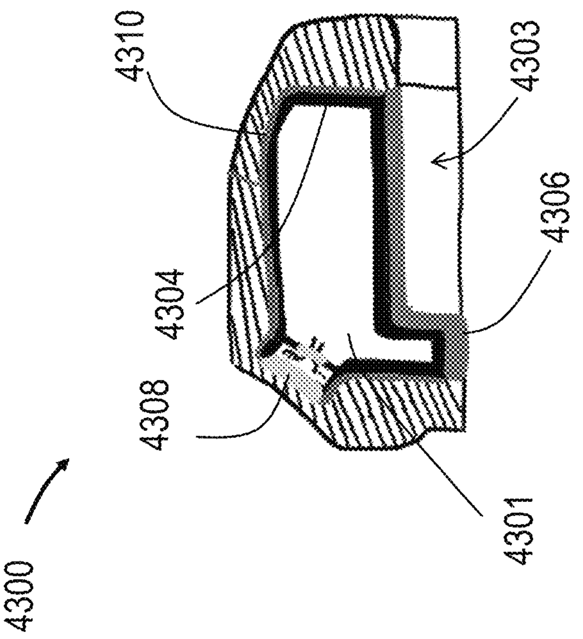
FIG. 67 is a cross-sectional view of the tibial insert of FIG. 66 taken along a line B-B of FIG. 61.
Figure 66:
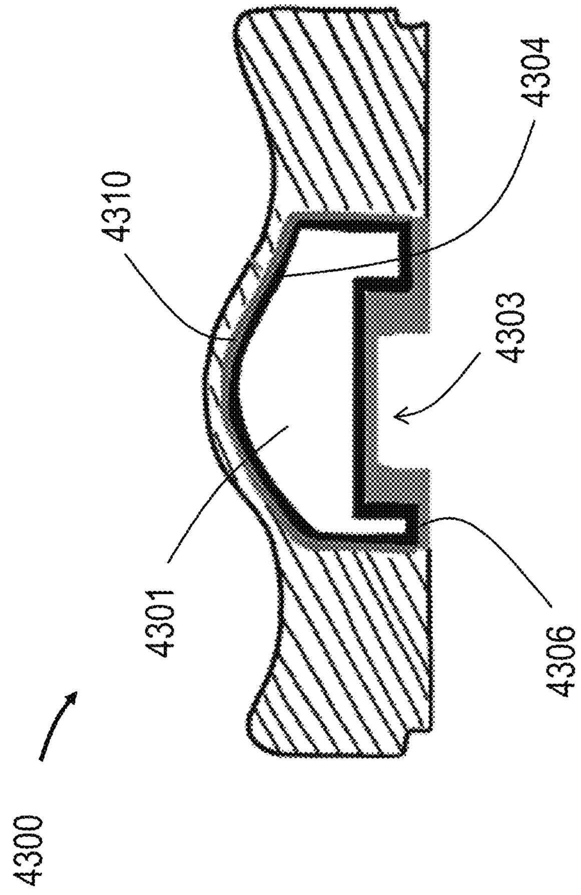
FIG. 66 is a cross-sectional view of a tibial insert according to another embodiment of the present disclosure taken along a line B-B of FIG. 61.

FIGS. 66 and 67 show a tibial insert 4300 according to another embodiment of the present disclosure. Tibial insert 4300 is similar to tibial insert 4200, and therefore like elements are referred to with similar numerals within the 4300-series of numbers. For example, a cavity 4301 formed by a layer 4304 to accommodate and protect the electronic and non-electronic components of tibial insert 4300 therein. However, tibial insert 4300 includes a porous layer 4310 covering layer 4304 as best shown in FIGS. 66 and 67. Porous layer 4310 can be bonded to the tibial insert (XLPE) articular surface. This bonding can be achieved by creating a porous structure on an interface, whereby the XLPE can be added to the metallic layer 4304 by over compression molding or other similar techniques.

Figure 68:
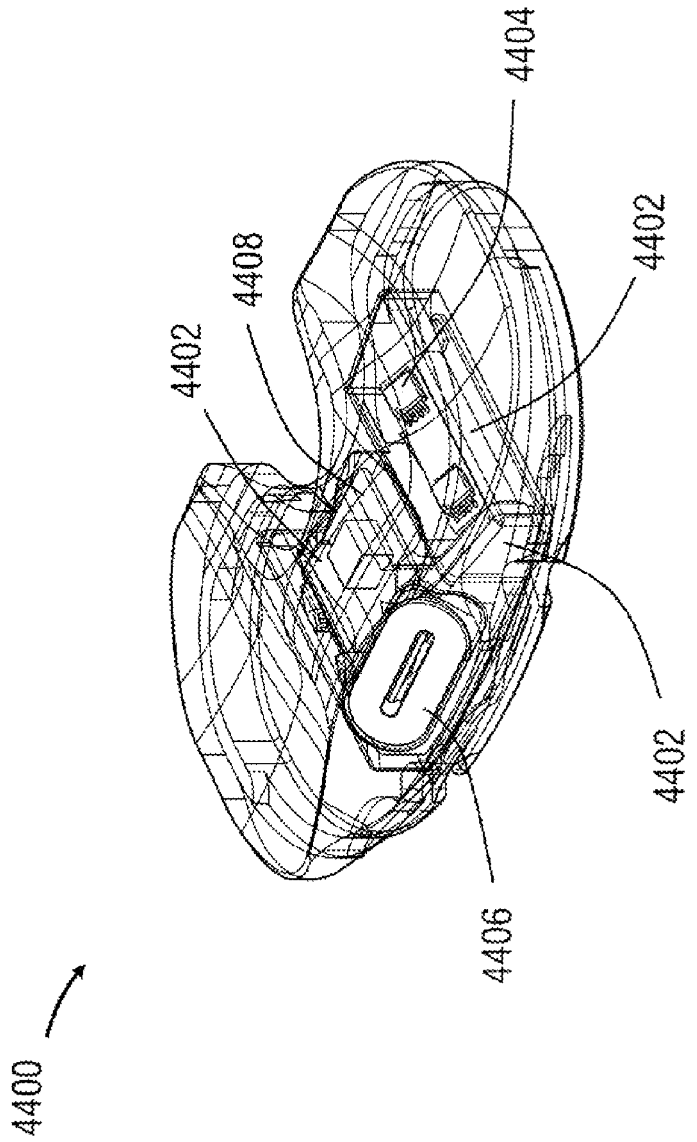
FIG. 68 is an isometric view of a tibial insert according to another embodiment of the present disclosure.

FIG. 68 shows a tibial insert 4400 according to another embodiment of the present disclosure. Tibial insert 4400 includes a printed circuit board assembly 4408, a battery 4402, Hall sensors 4404, and a charging coil 4406. Battery 4402 is made of three sections: a first section extending along a posterior end of tibial insert 4400 and second and third sections extending from the posterior end to an anterior end of the tibial insert as best shown in FIG. 68. In another embodiment, each of the battery sections can be separate batteries connected to each other or separate from each other to power particular components of the tibial insert. For example, a first battery can be used to power Hall sensors 4404, a second battery can be used to power the other sensors, and a third battery can be used to power data processing and transmission. All of the electronic and non-electronic components in tibial insert 4400 are located away from the medial and lateral centers which correspond to the high loading regions of the insert. These components are specifically located at areas within the tibial insert which experience minimum loading and forces as shown in FIGS. 60 and 61. Thus, the medial and lateral centers of tibial insert 4400 are composed of entirely solid areas—i.e., with no cavities to accommodate electronic and non-electronic components. This ensures that the medial and lateral centers are of maximum thickness and strength to withstand high loading and impact forces that the tibial insert will experience during the life of the implant.

Figure 69:
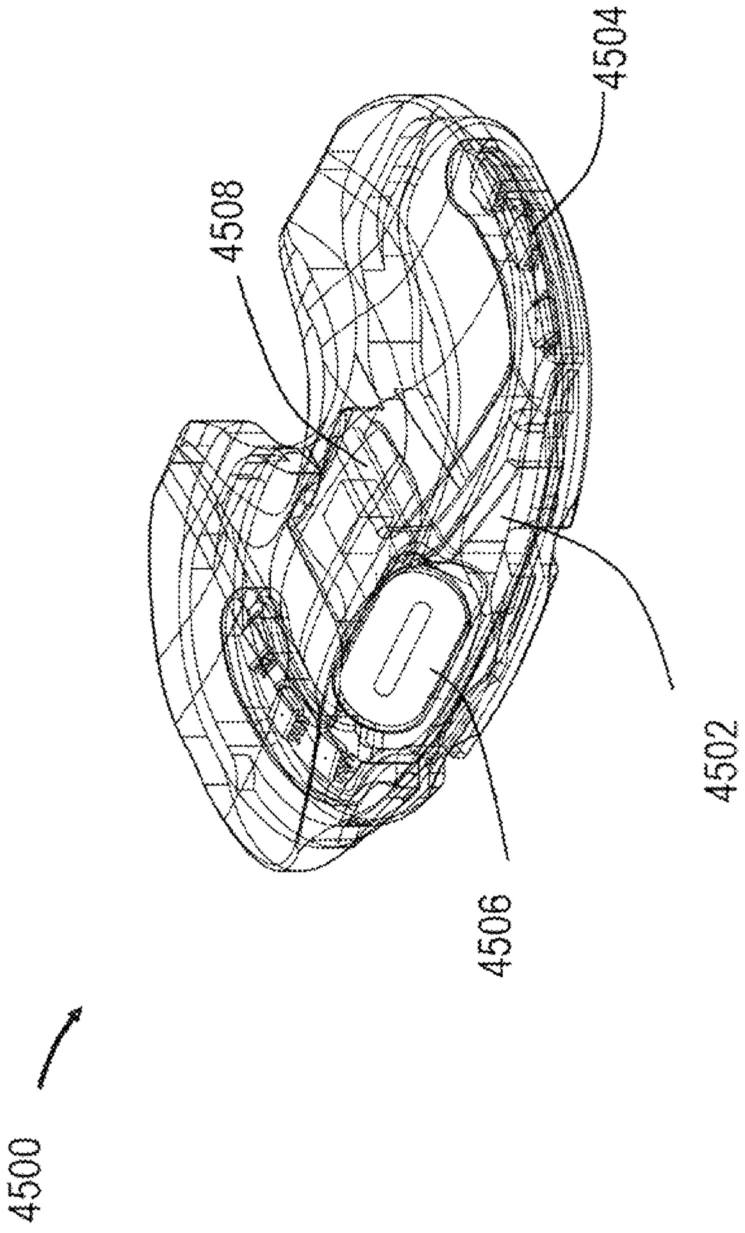
FIG. 69 is an isometric view of a tibial insert according to another embodiment of the present disclosure.

A tibial insert 4500 according to another embodiment of the present disclosure is shown in FIG. 69. Tibial insert 4500 is similar to tibial insert 4400, and therefore like elements are referred to similar numerals within the 4500-series of numbers. For example, tibial insert 4500 includes a printed circuit board assembly 4508, a battery 4502, Hall sensors 4504 and a charging coil 4506. However, battery 4502 extends along a posterior end of tibial insert and has no extensions extending from a posterior to anterior direction. A portion of the printed circuit board assembly with the Hall sensors are located along medial and lateral peripheries of tibial insert 4500 as best shown in FIG. 69. Thus, the medial and lateral centers of tibial insert 4500 are composed of entirely solid material with maximum thickness and strength to withstand high loading and impact forces experienced by the tibial insert.

Figure 70:
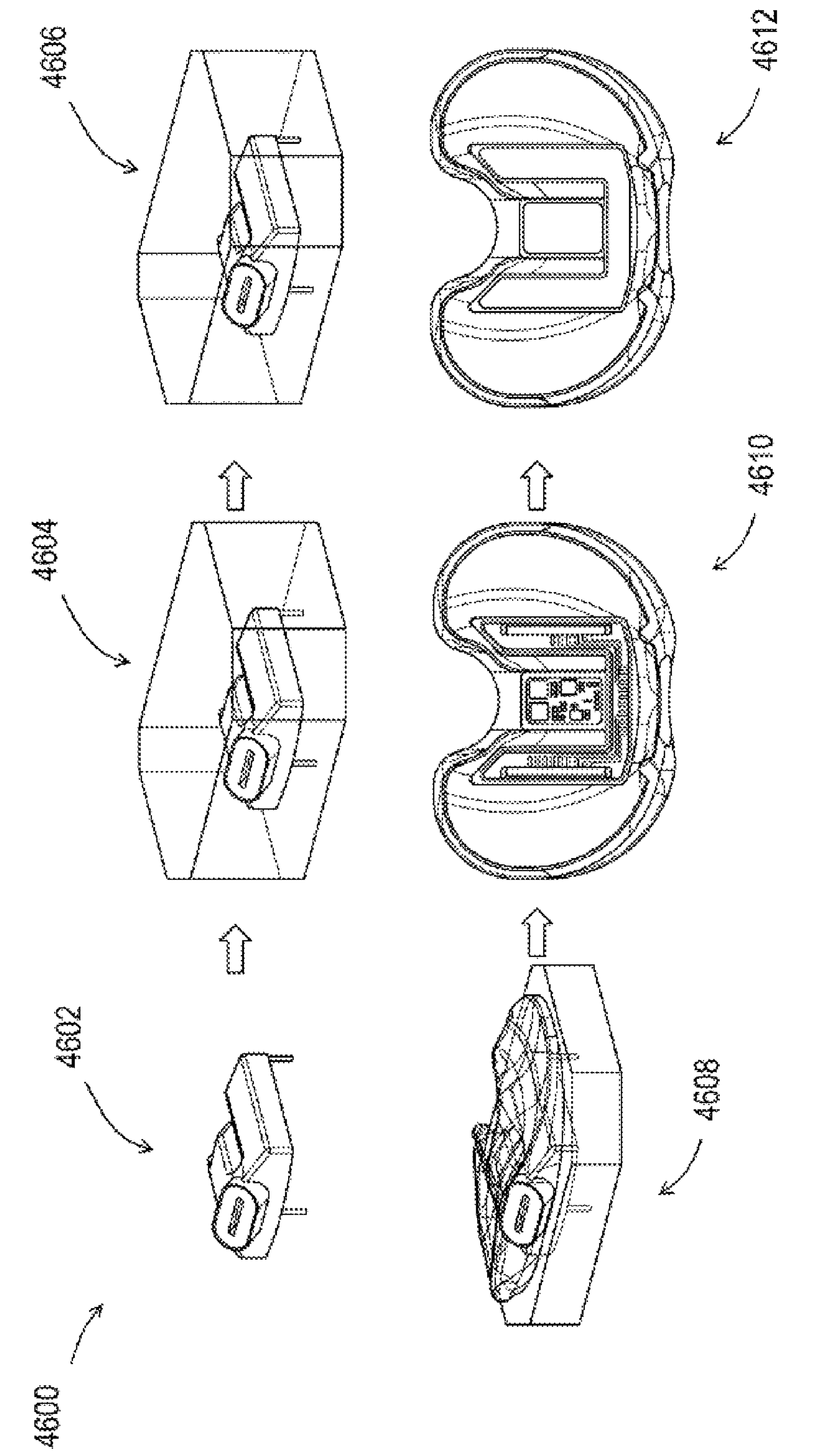
FIG. 70 is a schematic view of an implant manufacturing process according to an embodiment of the present disclosure.

Referring to FIG. 70, there is shown a method 4600 for manufacturing a tibial insert according to an embodiment of the present disclosure. In a step 4602, a metal case configured to house the electronic and non-electronic components and a charging coil is assembled. The metal case does not have a bottom surface in this step. The open bottom surface is configured to receive the electronic and non-electronic components in subsequent step as described below. A direct compression molding or other similar process can be applied in a step 4604 to cover the metal case and coil with the tibial insert material such as XLPE, etc. The assembly of step 4604 can be irradiated or annealed in a step 4606. A suitable machining process can be used in a step 4608 to form the shape of the tibial insert. Electronic and non-electronic components of the tibial insert are now inserted and assembled through the open bottom surface of the machined tibial insert of step 4608 in a step 4610. The open bottom surface of metal case is now covered and sealed by laser welding or other suitable means in a step 4612. An additional layer of XLPE can be added to the cover any portions of the bottom cover of the metal case to prevent or reduce metal on metal contact.

An implant with sensors requires power for operating these sensors throughout the lifespan of the implant. Sensors require power to detect, measure, and transmit various human body metrics to monitor implant performance and patient recovery. Accommodating a battery within an implant, particularly a battery large enough to power an implant throughout the lifespan of the implant, can be challenging. Sensors and associated electronics for the sensor require space within an implant further limit space available for a battery. Larger batteries with higher output capacity must be biocompatible for safe and long-lasting or permanent use.

Depending on the type of implant, the need for power requirements can vary considerably. For example, a pacemaker will require a continuous and steady source of power throughout its lifespan, while a joint implant may only require intermittent power to its sensors during particular activities of the patient. Utilizing rechargeable batteries in an implant may provide longer implant lifespan, however, these batteries will require periodic and regular charging from an external source. A patient's failure to timely recharge these batteries from the external source will lead to implant sensor failure and inadequate monitoring of the implant and/or patient condition. Disclosed below are implants with sensors and related methods for powering implants with sensors that address these issues.

Figure 71:
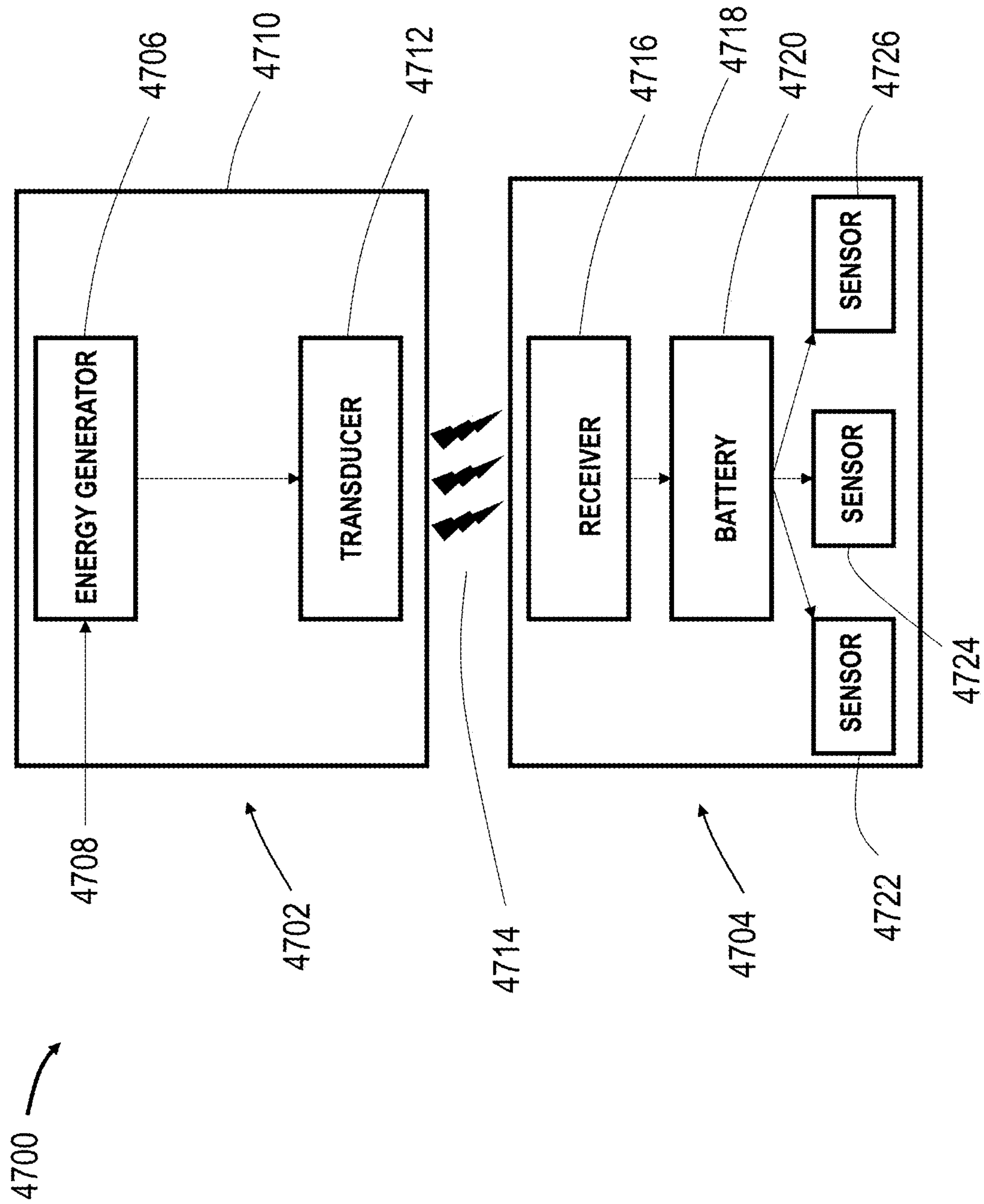
FIG. 71 is a schematic drawing of an implant with an energy generator according to an embodiment of the present disclosure.

FIG. 71 is a schematic drawing of an implant 4700 according to an embodiment of the present disclosure. Implant 4700 can be a joint implant such as a knee implant, shoulder implant, hip implant, etc. While the disclosure herein generally discusses embodiments directed to joint implants, the components and features disclosed herein are not limited to joint implants but can be used in any other implant or trial. Implant 4700 can include a first implant 4702 and a second implant 4704. First implant 4702 can include an energy generator 4706 electrically connected to a transducer 4712 within a body 4710 of the first implant as shown in FIG. 71. Energy generator 4706 can be any type of energy generating device capable of converting mechanical, chemical, heat or other forms of energy 4708 available in a human body to electrical energy. For example, energy generator 4706 can be an electromagnetic energy generator with a plurality of magnets configured to generate electricity via the relative motion of the magnets. The relative motion of the magnets can be caused by various activities of the patient including walking, standing, etc. Energy generator 4706 can be a triboelectric energy generator producing energy by motion/translation of triboelectric material. In other embodiments energy generator can include a Piezoelectric energy generator, thermocouple energy generator, etc.

Electric energy generated by energy generator 4706 is transmitted to transducer 4712. Transducer 4712 can be an electroacoustic transducer configured to convert the electrical energy received from energy generator to acoustic energy and then acoustically transfer 4714 to a receiver 4716 of second implant 4704 as shown in FIG. 71. In one embodiment, implant 4700 can include an ultrasonic transducer 4712 and an ultrasonic receiver 4716 to transfer energy from the first implant to the second implant via ultrasound. Ultrasonic receiver 4716 is configured to receive acoustic energy (ultrasound) from ultrasonic transducer 4712 and convert the acoustic energy to electrical energy. Various other types of electroacoustic transducers such as tactile transducers, Piezoelectric crystals etc., can be used in other embodiments to transfer acoustic energy between first implant 4702 and second implant 4704. The electroacoustic transducers can be selected based on the distance between the first and second implants or contact area between the first and second implants, implant thickness, implant material, etc. Other embodiments can use inductive coupling or other means to transfer electric energy from first implant 4702 to second implant 4704.

Second implant 4704 includes a battery 4720 electrically connected to receiver 4716 and one or more sensors 4722, 4724, 4726 with an implant body 4718 of the second implant. Battery 4720 is a rechargeable battery configured to be charged by the electrical energy transmitted from the receiver 4716. Battery 4720 can be any suitable biocompatible battery such as a solid state battery, lithium ion battery, lithium carbon monofluoride battery, lithium thionyl chloride battery, lithium ion polymer battery, etc. Because battery 4720 can be frequently charged during patient activity, the size and capacity of battery 4720 can be substantially minimized Thus, a smaller battery provides additional space for various sensors and associated electronics located within second implant 4704. Sensors 4722, 4724, 4725 can include a temperature sensor, pressure sensor, pH sensor, etc., depending on the type of implant and the desired measurements.

Acoustic energy transfer between first implant 4702 and second implant 4704 can be utilized with implants made of varied and/or dissimilar materials such as cobalt-chromium (CoCr), Titanium (Ti), cross-linked polyethylene (XLPE), etc., with varying implant thicknesses and separation between the implants or implants that contact each other. In contrast to RF or inductive power transfer mechanisms, acoustic energy transfer can be achieved even when one of the materials is conductive i.e., acts as a Faraday shield. Thus, conductive materials can be used in the implants disclosed herein. Acoustic energy transfer allows the various electronic components of the implants to be safely sealed within each implant while enabling highly efficient power transfer between first implant 4702 and second implant 4704. Wires or other components extending outside the implants necessary for direct coupling of the implants are not required for acoustic energy transfer thereby eliminating potential structural weakness in the implant bodies which may be susceptible to failure. The implants can be hermetically sealed to improve implant biocompatibility and patient safety. Thus, the electroacoustic transducer and receiver allow for wireless coupling and energy transfer. The size and type of electroacoustic transducer and receiver can be selected based on first and second implant material, thickness, separation, etc.

Various implant power management operations can be included in implant 4700 to extend battery life. Implant 4700 can operate in a low-power mode to conserve battery power until relevant activity is detected. Once the relevant activity is identified by one of the sensors 4722, 4724, 4726 of second implant 4704, the implant shifts to a high-power mode. Relevant activity to trigger the high-power mode can be patient and/or implant specific. For example, relevant activity for a knee implant may include knee flexion speed, gait, exposure to sudden impact loads, temperature thresholds, alkalinity levels, etc. Upon identifying the relevant activity and switching over to the high-power mode, various sensors in the knee joint implant record, store and transmit sensor measurements.

Figure 72:
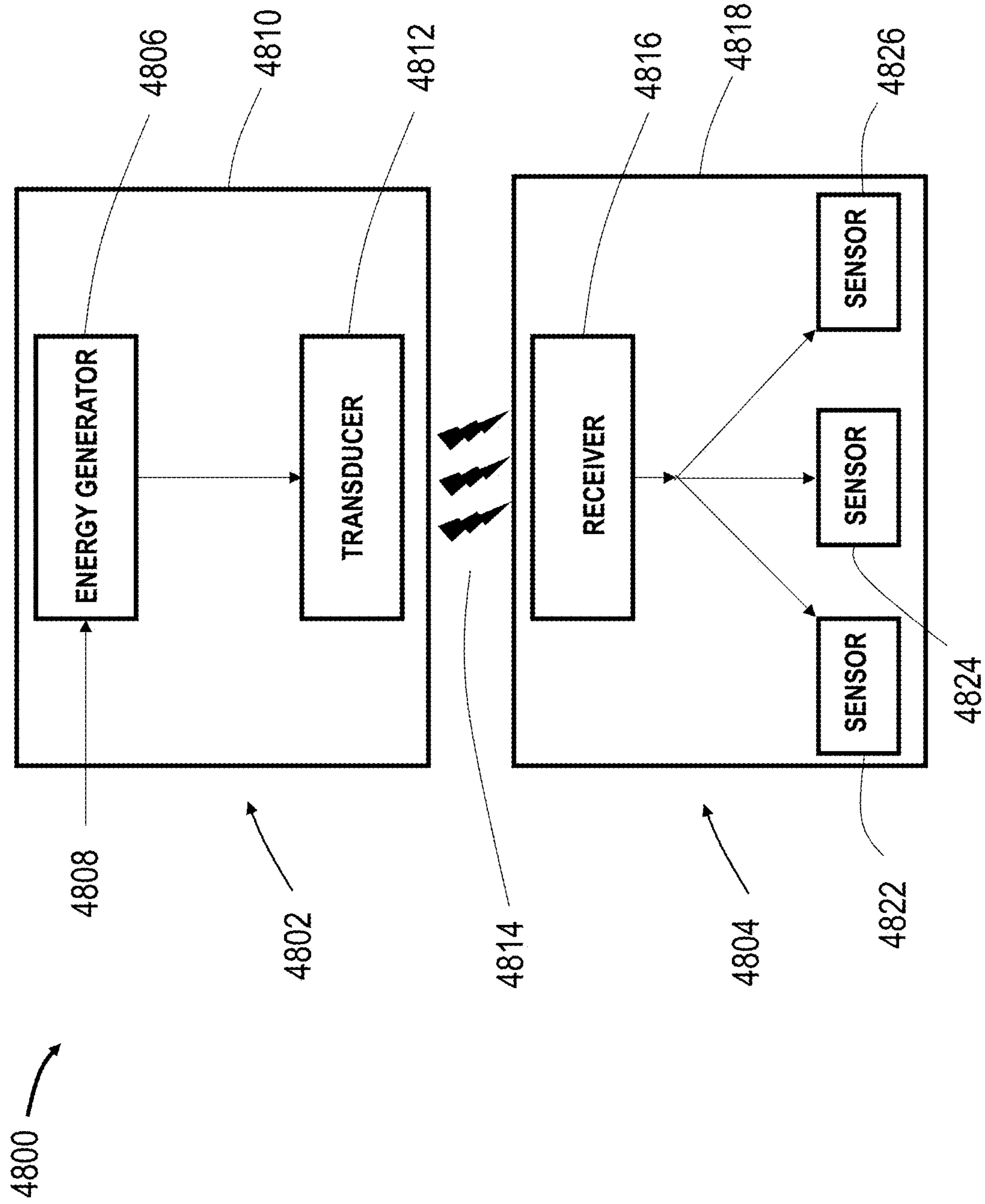
FIG. 72 is a schematic drawing of an implant with an energy generator according to another embodiment of the present disclosure.

Referring now to FIG. 72, there is shown a schematic drawing of an implant 4800 according to another embodiment of the present disclosure. Implant 4800 is similar to implant 4700, and therefore like elements are referred to with similar numerals within the 4800-series of numbers. For example, implant 4800 includes a first implant 4802 with an energy generator 4806 and a transducer 4812, and a second implant 4804 with a receiver 4816 and sensors 4822, 4824, 4826. However, second implant 4804 does not include a battery as electric energy from receiver 4816 is directly supplied to sensors 4822, 4824, 4826 as shown in FIG. 72. Thus, second implant 4804 can accommodate additional sensors within its body. Implant 4800 can be used in applications where the energy requirement of the sensors coincide with energy generation—i.e., energy generation and consumption occur simultaneously and therefore no energy storage by a battery is required. For example, a knee implant with sensors for measuring a patient's gait will require power only when the patient is walking. As energy generator 4806 creates energy while the patient walks (implant motion), the energy is directly supplied to sensors 4822, 4824, 4826 for gait measurement without the need for any storage. The sensors do not require power when the patient is at rest during which no energy is generated by energy generator 4806. In other embodiments, an energy storage device such as a super capacitor or the like can be used to store and supply energy to the sensors. A super capacitor charged to a predetermined threshold can provide energy to the sensor for sensor activity when no energy is being generated by the energy generator.

Figure 73:
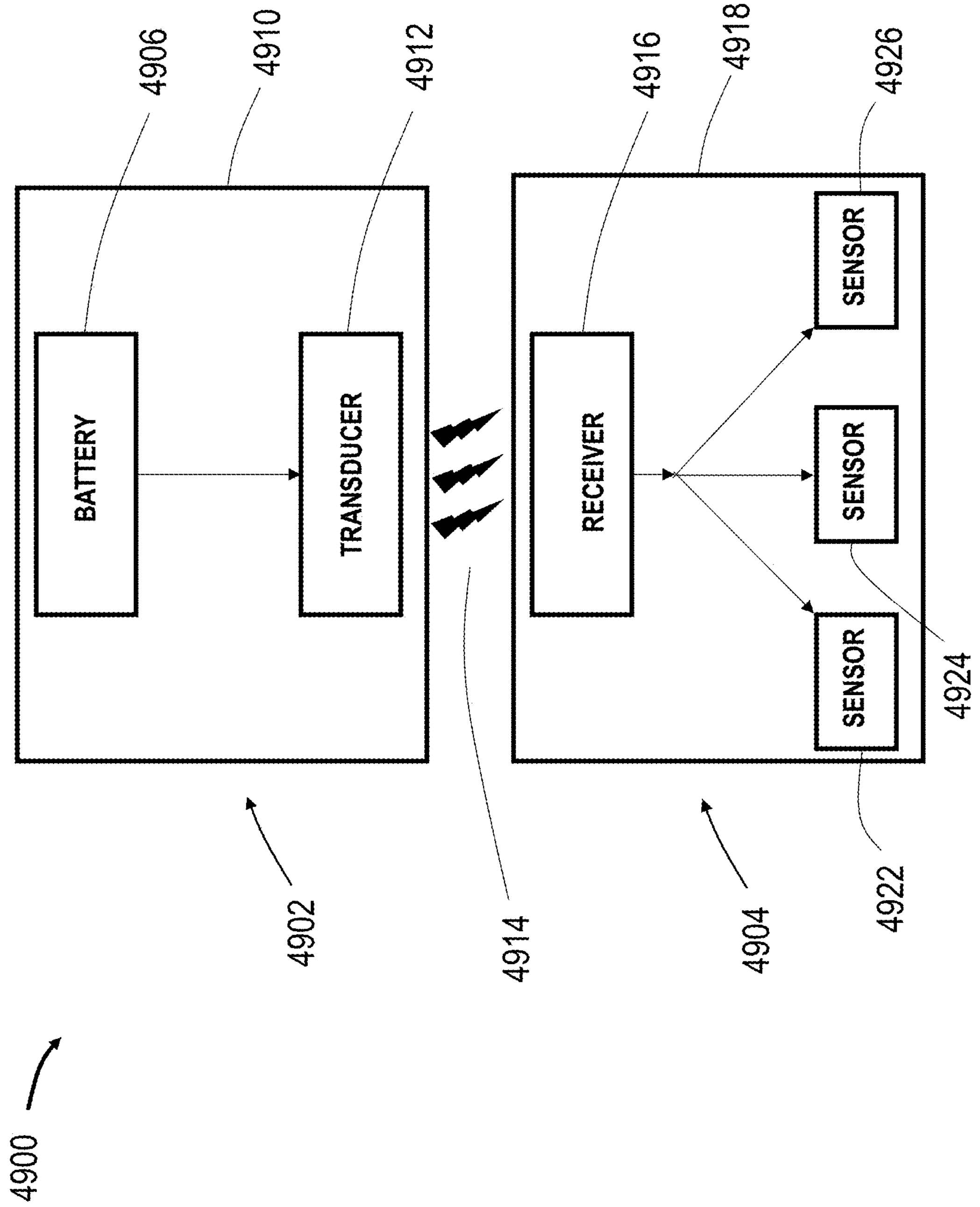
FIG. 73 is a schematic drawing of an implant with a battery according to an embodiment of the present disclosure.

FIG. 73 shows a schematic drawing of an implant 4900 according to another embodiment of the present disclosure. Implant 4900 is similar to implant 4700, and therefore like elements are referred to with similar numerals within the 4900-series of numbers. For example, implant 4900 includes a first implant 4902 with a transducer 4912, and a second implant 4904 with a receiver 4916 and sensors 4922, 4924, 4926. However, first implant 4902 has a battery 4906 instead of energy generator as shown in FIG. 73. Locating battery 4906 in first implant 4902 and acoustically transferring energy from this battery to second implant 4904 allows room for sensors and other electronics in the second implant. Implant 4900 can be used in applications where the second implant is considerably smaller than the first implant.

Figure 74:
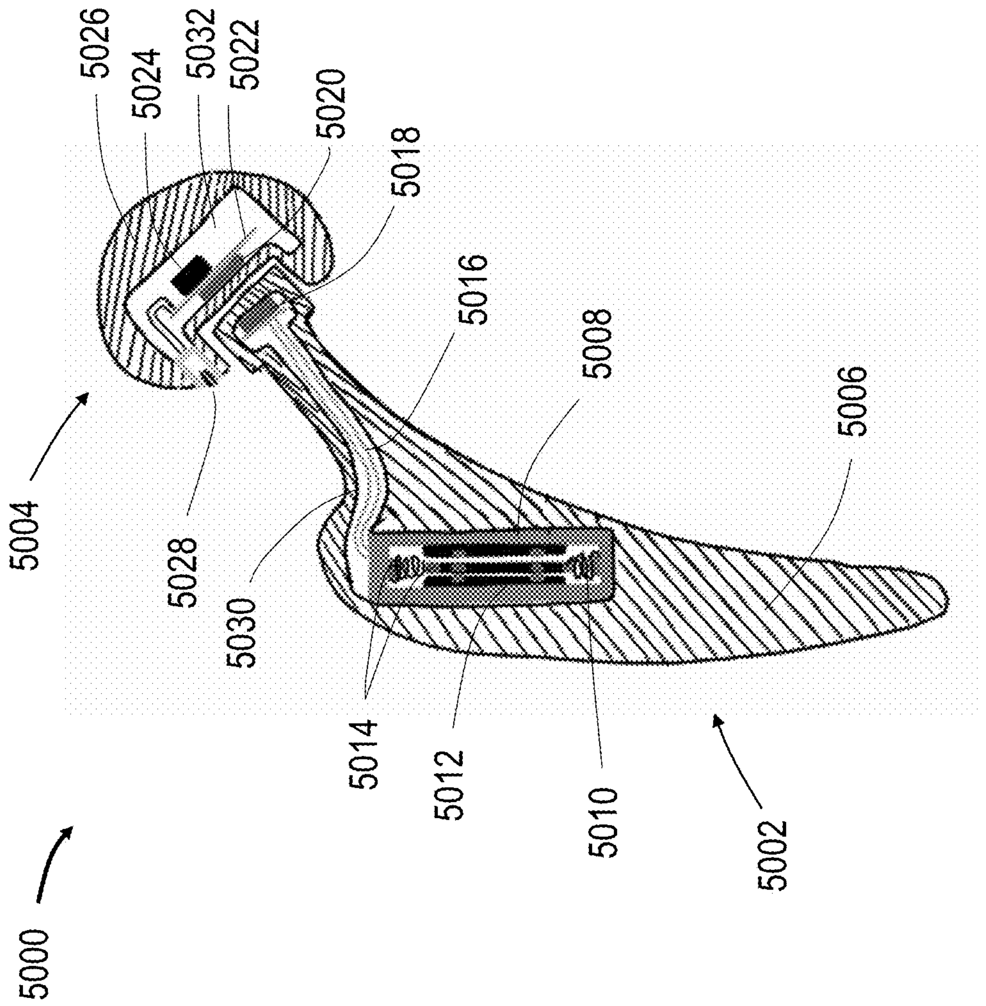
FIG. 74 is a front cross-sectional view of a hip implant according to an embodiment of the present disclosure.

FIG. 74 is a cross-section view of a hip implant 5000 according to an embodiment of the present disclosure. Hip implant 5000 includes a stem 5002 and a ball joint 5004. Stem 5002 includes an energy generator 5008 electrically connected to an ultrasonic transducer 5018 via a wire 5016. Energy generator 5008 and ultrasonic transducer 5018 are sealed within a body 5006 of stem 5002 as shown in FIG. 74. Energy generator 5008 is an electromechanical energy generator configured to convert mechanical energy to electrical energy. Energy generator 5008 includes a plurality of magnets 5014 located on fixed and moveable columns 5012 configured to generate electricity via the relative motion of the magnets. The relative motion of magnets 5014 triggered by various activities of the patient including walking, standing, etc. results in electric energy generation. Biasing members such as spring 5010 in energy generator 5008 protect magnets 5014 during hard impacts experienced by stem 5002 and aid in relative magnet motion to increase energy generation.

Electric energy generated by energy generator 5008 is transmitted to ultrasonic transducer 5018. Ultrasonic transducer 5018 converts the electrical energy received from energy generator 5008 to acoustic energy, and then acoustically transfers this energy to ultrasonic receiver 5020 of ball joint 5004 as shown in FIG. 74. Ultrasonic receiver 5020 is configured to receive acoustic energy (ultrasound) from ultrasonic transducer 5018 and convert this acoustic energy to electrical energy. Ultrasonic transducer 5018 and ultrasonic receiver 5020 can be sized and shaped based on the size and material composition of the stem and ball joint.

Ball joint 5004 includes a battery 5024 electrically connected to ultrasonic receiver 5020 and to a pH sensor 5028 via a printed circuit board (PCB) 5022 as shown in FIG. 74. pH sensor 5028 is located away from an acetabular component (not shown) to directly access synovial fluid to detect pH levels. Thus, the pH sensor does not interact with the acetabular component and is not impacted by acetabular component wear. Battery 5024 is a rechargeable battery configured to be charged by the electrical energy transmitted from ultrasonic receiver 5020. Battery 5024 can be any suitable biocompatible battery such as a solid state battery, lithium ion battery, lithium carbon monofluoride battery, lithium thionyl chloride battery, lithium ion polymer battery, etc. As battery 5024 is frequently charged during patient activity, the size and capacity of battery 5024 can be substantially minimized Thus, a smaller battery provides additional space for various sensors and associated electronics located within ball joint 5004. Ball joint 5004 can include various other sensors such as a temperature sensor, pressure sensor, etc., depending on the desired measurements.

Ultrasonic energy transfer between stem 5002 and ball joint 5004 can be utilized with implants made of dissimilar materials such as cobalt-chromium (CoCr), Titanium (Ti), cross-linked polyethylene (XLPE), etc. Ultrasonic energy transfer allows the various electronic components of stem 5002 and ball joint 5004 to be safely sealed within these implants. Wires or other components extending outside the stem and ball joint to directly couple these implants are not required for ultrasonic energy transfer thereby eliminating potential structural weakness in the implant bodies which may be susceptible to failure. Stem 5002 and ball joint 5004 can be hermetically sealed to improve implant biocompatibility and patient safety.

Figure 75:
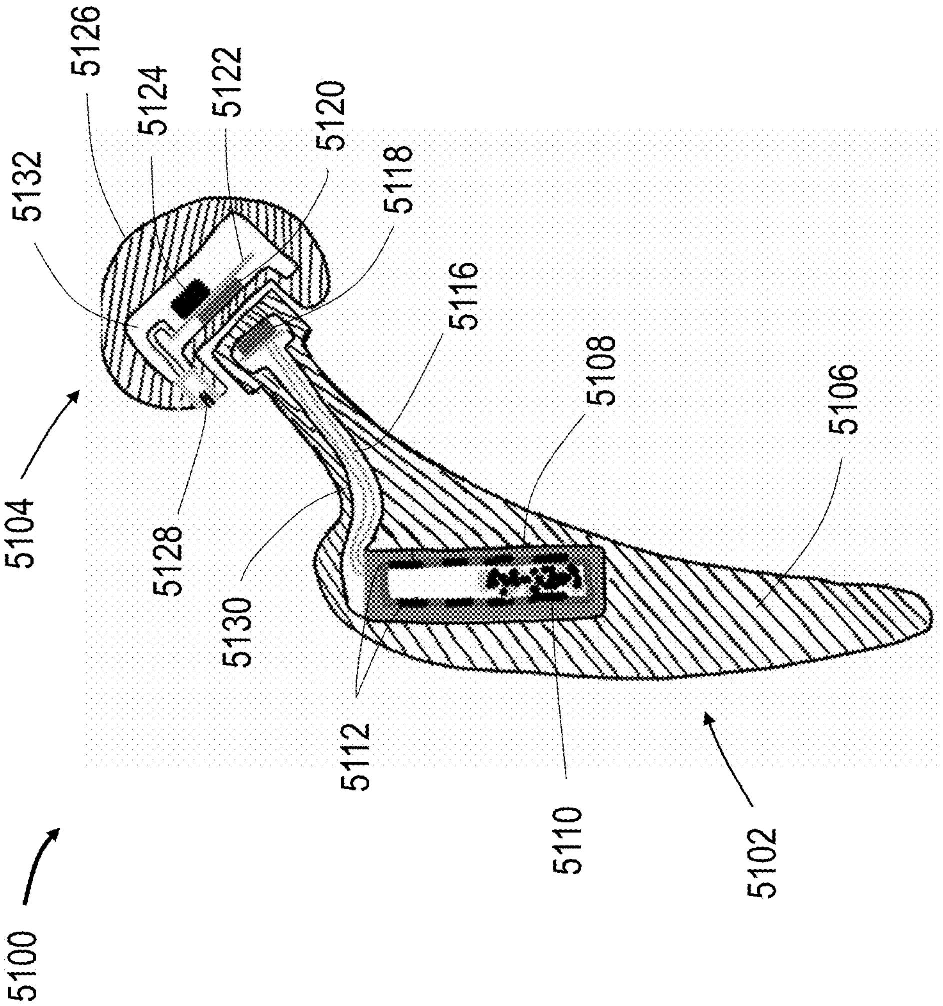
FIG. 75 is a front cross-sectional view of a hip implant according to another embodiment of the present disclosure.

A cross-sectional drawing of a hip implant 5100 according to another embodiment of the present disclosure is shown in FIG. 75. Hip implant 5100 is similar to hip implant 5000, and therefore like elements are referred to with similar numerals within the 5100-series of numbers. For example, hip implant 5100 includes a stem 5102 with an energy generator 5108, and a ball joint 5104 with an ultrasonic receiver 5120 and a battery 5124. However, energy generator 5108 of hip implant 5100 is a triboelectric energy generator. Energy generator 5108 includes triboelectric material 5110 and triboelectric receptors 5112 as shown in FIG. 75. Triboelectric material 5110 includes first and second triboelectric layers with varying electron affinity. The first and second triboelectric layer can be separated by a variable gap. A patient's movement such as walking, standing, etc., will change the gap distance between these layers to create electric charge and electric power. Alternatively, the first and second triboelectric layers can be arranged to slide against each other to create electric power during patient motion. Thus, the triboelectric energy generator can convert mechanical energy from the patient's movement to electric energy to power various sensors in hip implant 5100.

Figure 76:
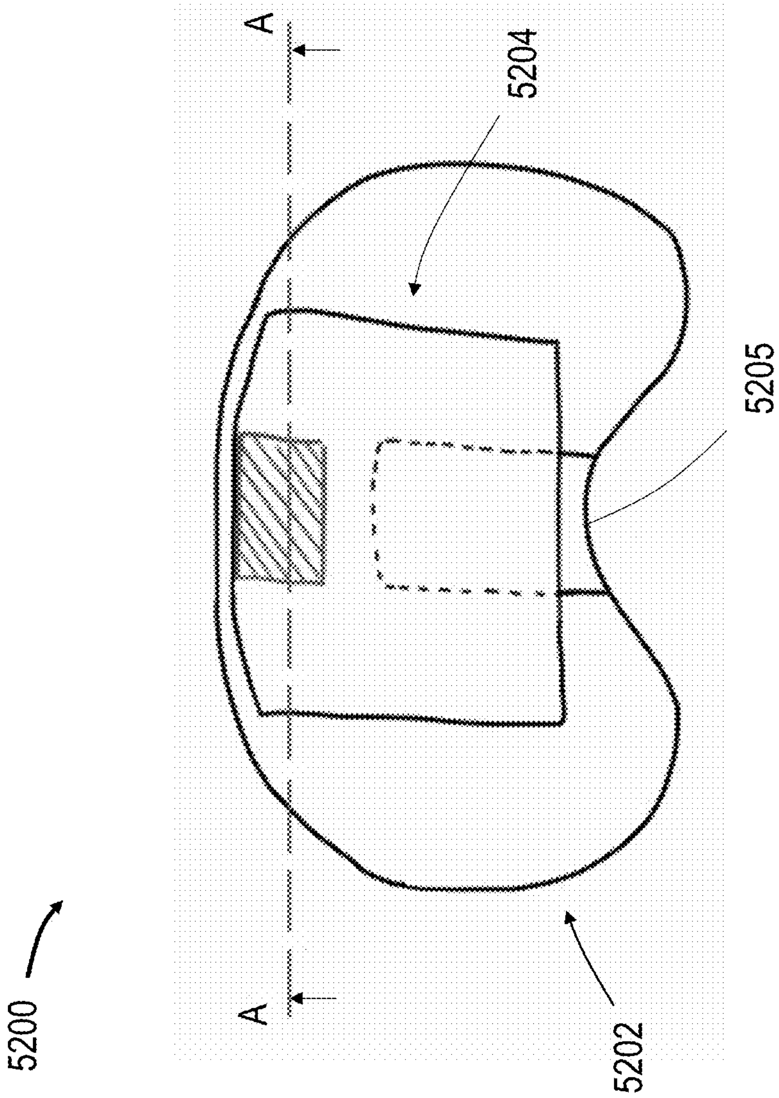
FIG. 76 is top view of a knee implant according to an embodiment of the present disclosure.
Figure 77:
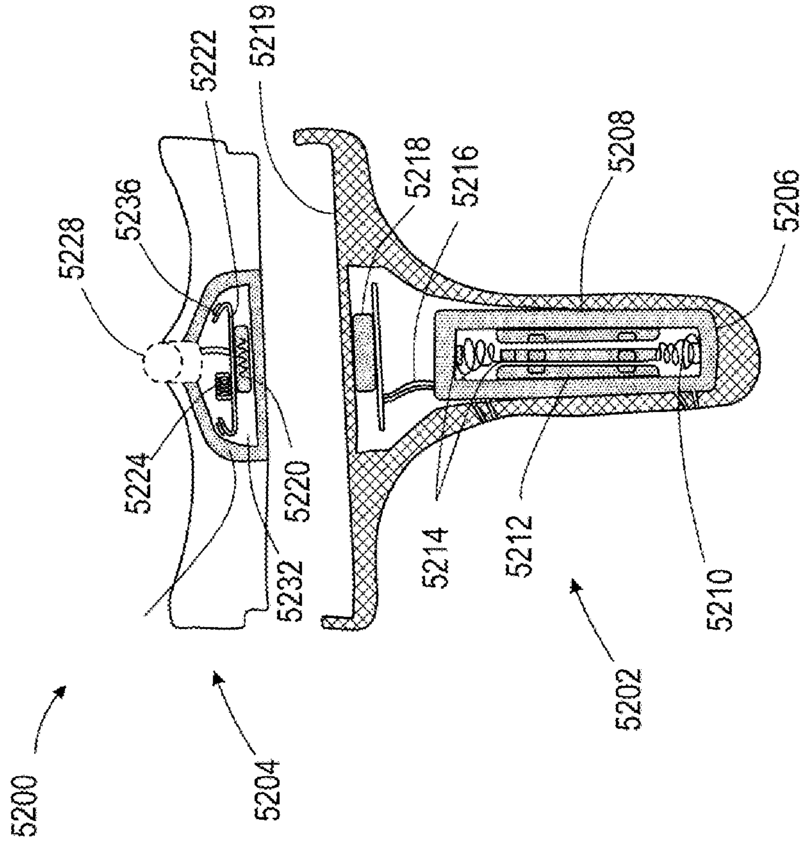
FIG. 77 is a front cross-sectional view of the knee implant of FIG. 76 taken along line A-A.

Referring now to FIGS. 76 and 77, there is shown a knee implant 5200 according to an embodiment of the present disclosure. Knee implant 5200 includes a tibial stem 5202 and a tibial insert 5204. A locking mechanism 5205 secures tibial insert 5204 to tibial stem 5202 as best shown in FIG. 76. Tibial stem 5202 includes an energy generator 5208 electrically connected to an ultrasonic transducer 5218 via a wire 5216. Energy generator 5208 and ultrasonic transducer 5218 are sealed within a body 5206 of tibial stem 5202 as best shown in FIG. 77. Energy generator 5208 is an electromechanical energy generator configured to convert mechanical energy to electrical energy. Energy generator 5208 includes a plurality of magnets 5214 located on fixed and moveable columns 5212 configured to generate electricity via the relative motion of the magnets. The relative motion of magnets 5214 triggered by various activities of the patient including walking, standing, etc. results in electric energy generation. Biasing members such as spring 5210 in energy generator 5208 protect magnets 5214 during hard impacts experienced by tibial stem 5202 and aid in relative magnet motion to increase energy generation.

Electric energy generated by energy generator 5208 is transmitted to ultrasonic transducer 5218. Ultrasonic transducer 5218 converts the electrical energy received from energy generator 5208 to acoustic energy, and then acoustically transfers this energy to ultrasonic receiver 5220 of tibial insert 5204 as shown in FIG. 77. Ultrasonic receiver 5220 is configured to receive acoustic energy (ultrasound) from ultrasonic transducer 5218 and convert this acoustic energy to electrical energy. Ultrasonic transducer 5218 and ultrasonic receiver 5220 can be sized and shaped based on the size and material composition of the tibial stem and tibial insert.

Tibial insert 5204 includes a battery 5224 electrically connected to ultrasonic receiver 5220 and a pH sensor 5228 via a printed circuit board (PCB) 5222 as shown in FIG. 77. pH sensor 5228 is located at an apex between medial and lateral condyle contact surface to directly access synovial fluid and detect pH levels. The various electronic components of tibial insert 5204 are located within a cavity 5232 surrounded by a housing 5234 as shown in FIG. 77. Housing 5234 may be metallic to hermetically seal and protect the electronic components.

Battery 5224 is a rechargeable battery configured to be charged by the electrical energy transmitted from ultrasonic receiver 5220. Battery 5224 can be any suitable biocompatible battery such as a solid state battery, lithium ion battery, lithium carbon monofluoride battery, lithium thionyl chloride battery, lithium ion polymer battery, etc. As battery 5224 is frequently charged during patient activity, the size and capacity of battery 5224 can be substantially minimized Thus, a smaller battery provides additional space for various sensors and associated electronics located within tibial insert 5204. Tibial insert 5204 can include various other sensors such as a temperature sensor, pressure sensor, etc., depending on the desired measurements.

Ultrasonic energy transfer between tibial stem 5202 and tibial insert 5204 can be utilized with implants made of varied materials such as cobalt-chromium (CoCr), Titanium (Ti), cross-linked polyethylene (XLPE), etc. Ultrasonic energy transfer allows the various electronic components of tibial stem 5202 and tibial insert 5204 to be safely sealed within these implants while allowing efficient energy transfer across these materials including a top surface of tibial stem 5222. Wires or other components extending outside the tibial stem and tibial insert to directly couple these implants are not required for ultrasonic energy transfer thereby eliminating potential structural weakness in the implant bodies which may be susceptible to failure. Tibial stem 5202 and tibial insert 5204 can be hermetically sealed to improve implant biocompatibility and patient safety.

Figure 78:
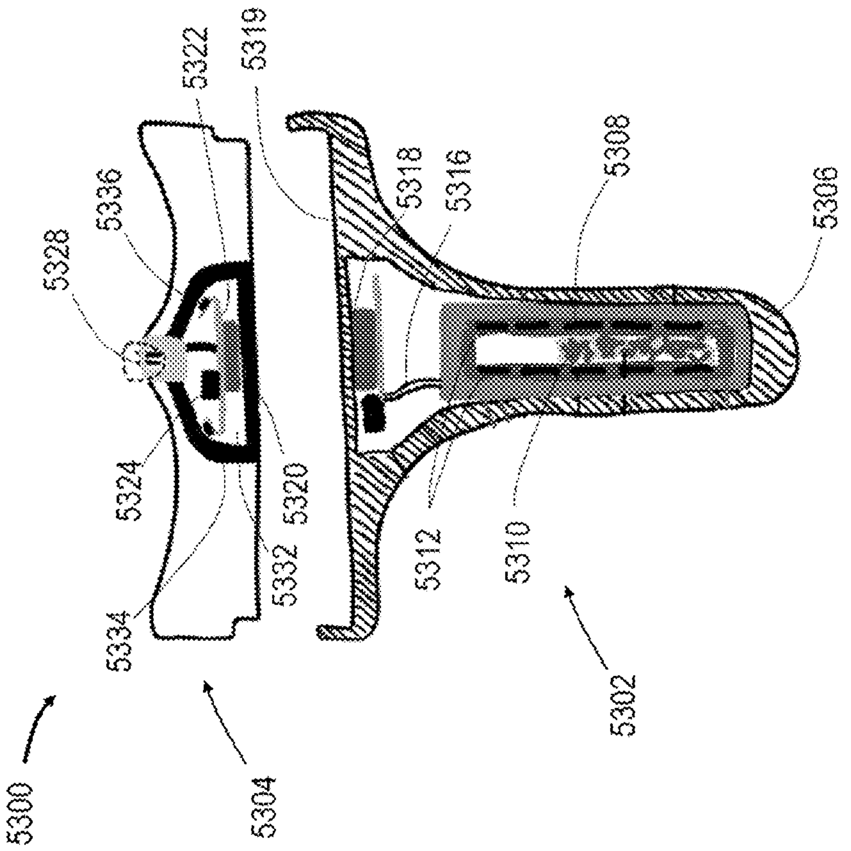
FIG. 78 is a front cross-sectional view of a knee implant according to another embodiment of the present disclosure.

FIG. 78 shows a cross-sectional drawing of a knee implant 5300 according to another embodiment of the present disclosure. Knee implant 5300 is similar to knee implant 5200, and therefore like elements are referred to with similar numerals within the 5300-series of numbers. For example, knee implant 5300 includes a tibial stem 5302 with an energy generator 5308, and a tibial insert 5304 with an ultrasonic receiver 5320 and a battery 5324. However, energy generator 5308 of knee implant 5300 is a triboelectric energy generator. Energy generator 5308 includes triboelectric material 5310 and triboelectric receptors 5312 as shown in FIG. 78. Triboelectric material 5310 includes first and second triboelectric layers with varying electron affinity. The first and second triboelectric layer can be separated by a variable gap. A patient's movement such as walking, standing, etc., will change the gap distance between these layers to create electric charge and electric power. Alternatively, the first and second triboelectric layers can be arranged to slide against each other to create electric power during patient motion. Thus, the triboelectric energy generator can convert mechanical energy from the patient's movement to electric energy to power various sensors in knee implant 5300.

Figure 79:
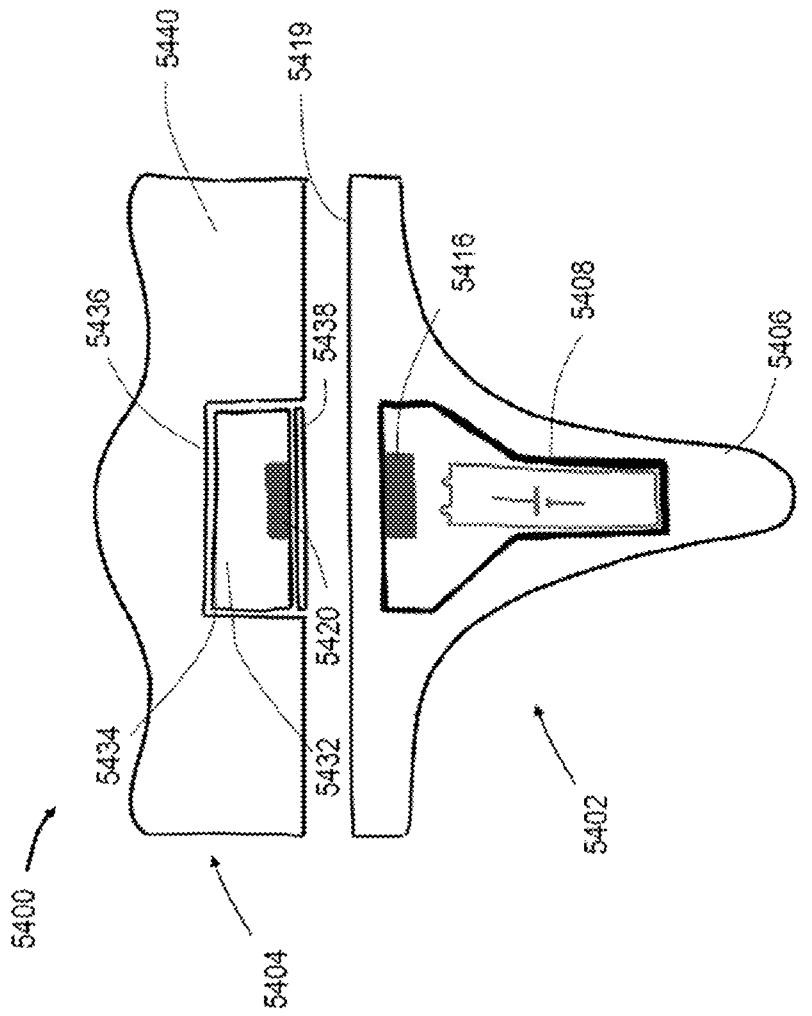
FIG. 79 is a front cross-sectional view of a knee implant according to another embodiment of the present disclosure.

FIG. 79 shows a cross-sectional drawing of a knee implant 5400 according to another embodiment of the present disclosure. Knee implant 5400 is similar to knee implant 5200, and therefore like elements are referred to with similar numerals within the 5400-series of numbers. For example, knee implant 5400 includes a tibial stem 5402 with an ultrasonic transducer 5416, and a tibial insert 5404 with an ultrasonic receiver 5420. However, tibial stem 5402 includes a battery 5408 instead of an energy generator. Locating battery 5408 in tibial stem 5402 and acoustically transferring energy from this battery to tibial insert 5404 allows room for sensors and other electronics in the tibial insert. Tibial stem 5402 being larger than tibial insert 5404 can accommodate a larger batter. Battery 5408 is a rechargeable battery that can be recharged by an external device via induction charging or other means.

Tibial insert 5404 does not include a battery as electric energy from ultrasonic receiver 5420 is directly supplied to sensors located in the tibial insert (not shown). Thus, tibial insert 5404 can accommodate additional sensors within its body. Knee implant 5400 includes a baseplate 5438 made of a XLPE.

Figure 80:
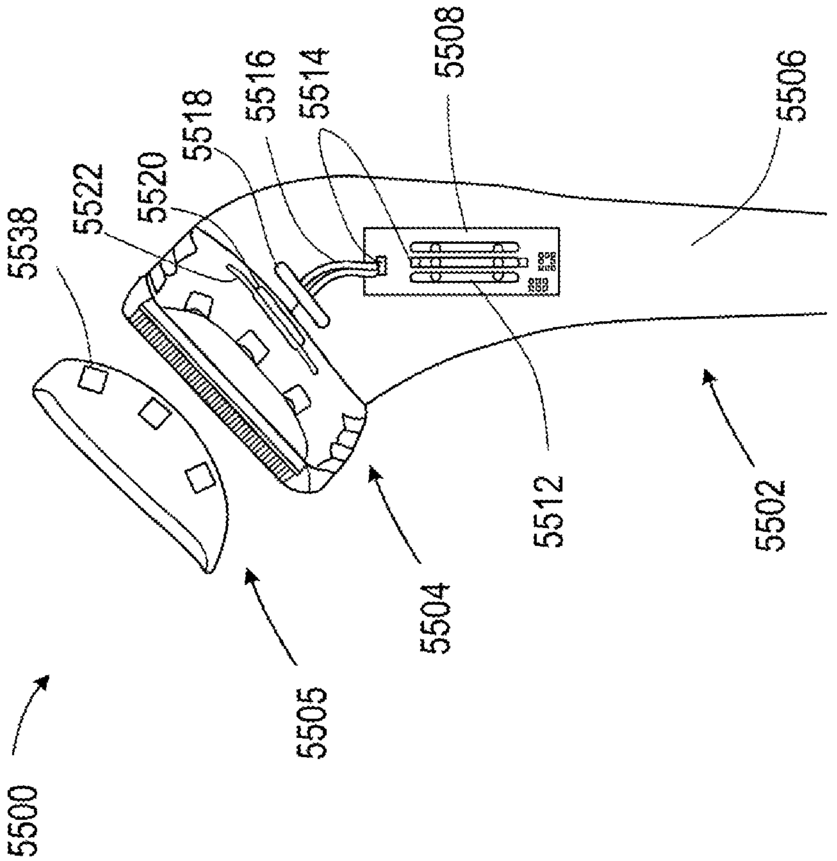
FIG. 80 is a front cross-sectional view of a shoulder implant according to an embodiment of the present disclosure.

FIG. 79 is a cross-section view of a shoulder implant 5500 according to an embodiment of the present disclosure. Shoulder implant 5500 includes a stem 5502 and a glenoid sphere 5504. Stem 5502 includes an energy generator 5508 electrically connected to an ultrasonic transducer 5518 via a wire 5516. Energy generator 5508 and ultrasonic transducer 5518 are sealed within a body 5506 of stem 5502 as shown in FIG. 80. Energy generator 5508 is an electromechanical energy generator configured to convert mechanical energy to electrical energy. Energy generator 5508 includes a plurality of magnets 5514 located on fixed and moveable columns 5512 configured to generate electricity via the relative motion of the magnets. The relative motion of magnets 5514 triggered by various activities of the patient including walking, standing, etc. results in electric energy generation. Biasing members such as a spring 5510 in energy generator 5508 protect magnets 5514 during hard impacts experienced by stem 5502 and aid in relative magnet motion to increase energy generation.

Electric energy generated by energy generator 5508 is transmitted to ultrasonic transducer 5518. Ultrasonic transducer 5518 converts the electrical energy received from energy generator 5508 to acoustic energy, and then acoustically transfers this energy to ultrasonic receiver 5520 of glenoid sphere 5504 as shown in FIG. 80. Ultrasonic receiver 5520 is configured to receive acoustic energy (ultrasound) from ultrasonic transducer 5518 and convert this acoustic energy to electrical energy. Ultrasonic transducer 5518 and ultrasonic receiver 5520 can be sized and shaped based on the size and material composition of the stem and glenoid sphere.

Glenoid sphere 5504 includes a battery (not shown) electrically connected to ultrasonic receiver 5520 and to various sensors (not shown) via a printed circuit board (PCB) 5522. The battery is a rechargeable battery configured to be charged by the electrical energy transmitted from ultrasonic receiver 5520. As the battery is frequently charged during patient activity, the size and capacity of the battery can be substantially minimized Thus, a smaller battery provides additional space for various sensors and associated electronics located within glenoid sphere 5504. Glenoid sphere 5504 can include various other sensors such as a temperature sensor, pressure sensor, etc., depending on the desired measurements.

Ultrasonic energy transfer between stem 5502 and glenoid sphere 5504 can be utilized with implants made of different materials such as cobalt-chromium (CoCr), Titanium (Ti), cross-linked polyethylene (XLPE), etc. Ultrasonic energy transfer allows the various electronic components of stem 5502 and glenoid sphere 5504 to be safely sealed within these implants. Wires or other components extending outside the stem and glenoid sphere to directly couple these implants are not required for ultrasonic energy transfer thereby eliminating potential structural weakness in the implant bodies which may be susceptible to failure. Stem 5502 and glenoid sphere 5504 can be hermetically sealed to improve implant biocompatibility and patient safety.

Figure 81:
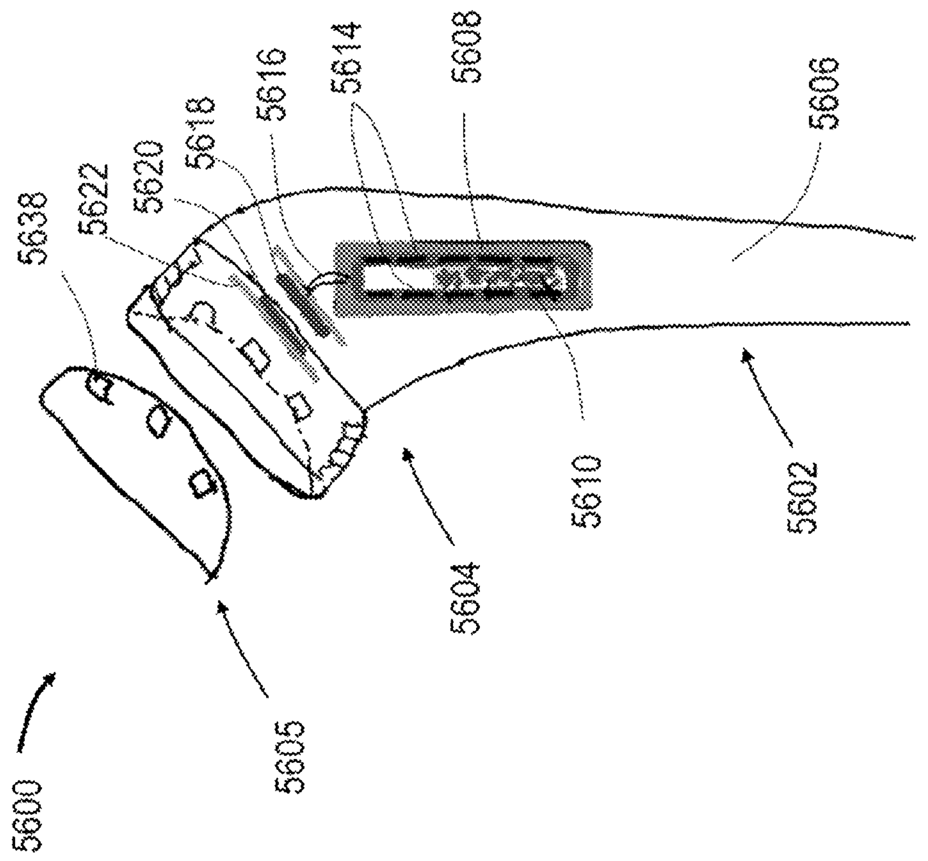
FIG. 81 is a front cross-sectional view of a shoulder implant according to another embodiment of the present disclosure.
Figure 82:
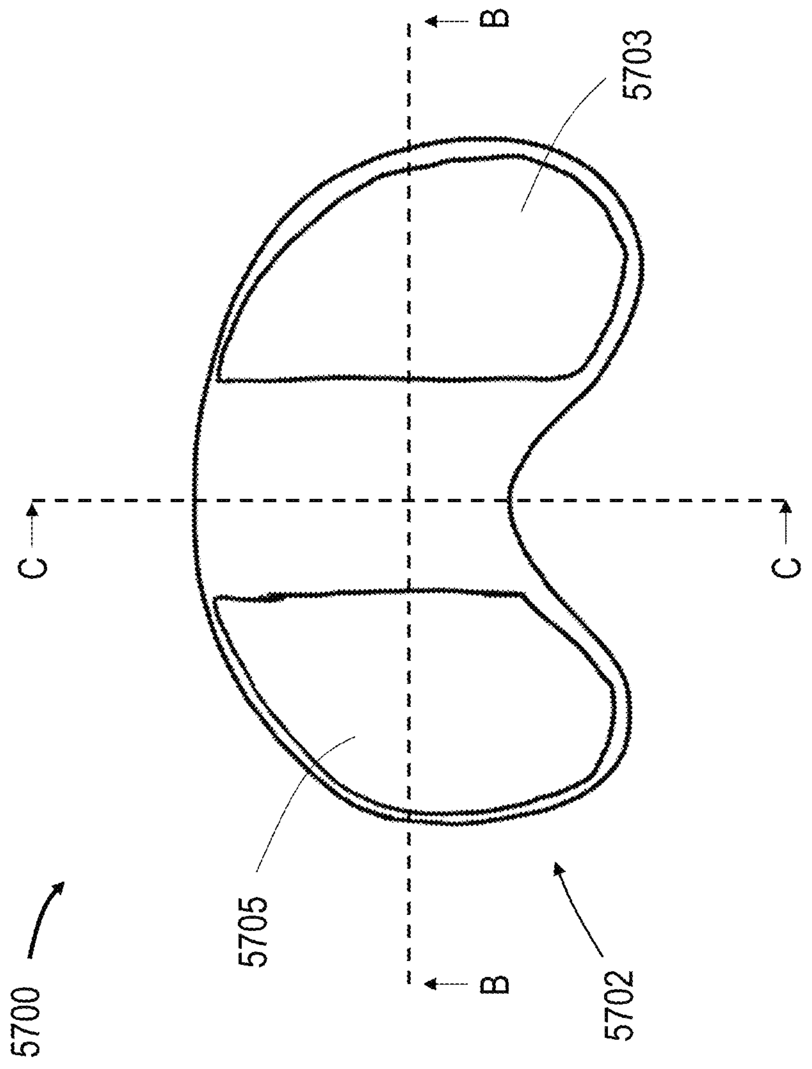
FIG. 82 is a top view of a knee implant according to another embodiment of the present disclosure.
Figure 83A:
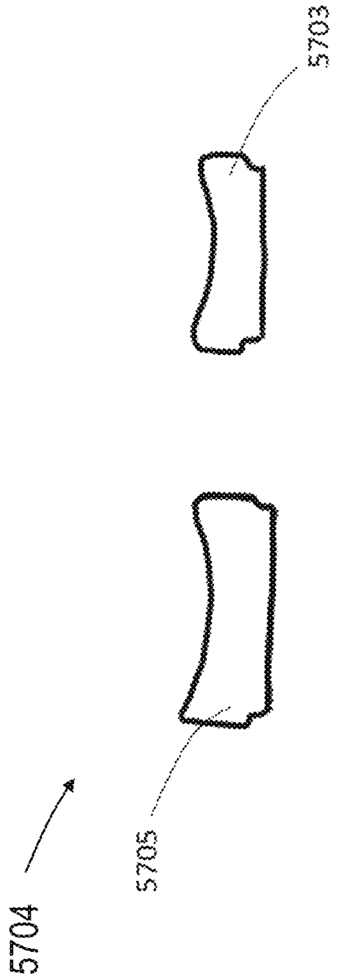
FIG. 83A is a side view of tibial inserts of the knee implant of FIG. 82.
Figure 83B:
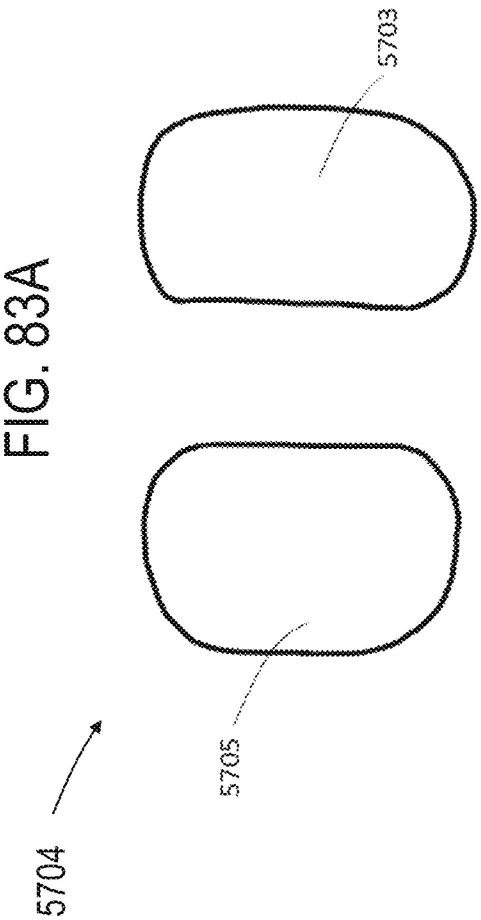
FIG. 83B is a top view of the tibial inserts of the knee implant of FIG. 82.

A cross-sectional drawing of a shoulder implant 5600 according to another embodiment of the present disclosure is shown in FIG. 81. Shoulder implant 5600 is similar to shoulder implant 5500, and therefore like elements are referred to with similar numerals within the 5600-series of numbers. For example, shoulder implant 5600 includes a stem 5602 with an energy generator 5608, and a glenoid sphere 5604 with an ultrasonic receiver 5620 and a battery (not shown). However, energy generator 5608 of shoulder implant 5600 is a triboelectric energy generator. Energy generator 5608 includes triboelectric material 5610 and triboelectric receptors 5612 as shown in FIG. 81. Triboelectric material 5610 includes first and second triboelectric layers with varying electron affinity. The first and second triboelectric layer can be separated by a variable gap. A patient's movement such as walking, standing, etc., will change the gap distance between these layers to create electric charge and electric power. Alternatively, the first and second triboelectric layers can be arranged to slide against each other to create electric power during patient motion. Thus, the triboelectric energy generator can convert mechanical energy from the patient's movement to electric energy to power various sensors in shoulder implant 5600.

Figure 84:
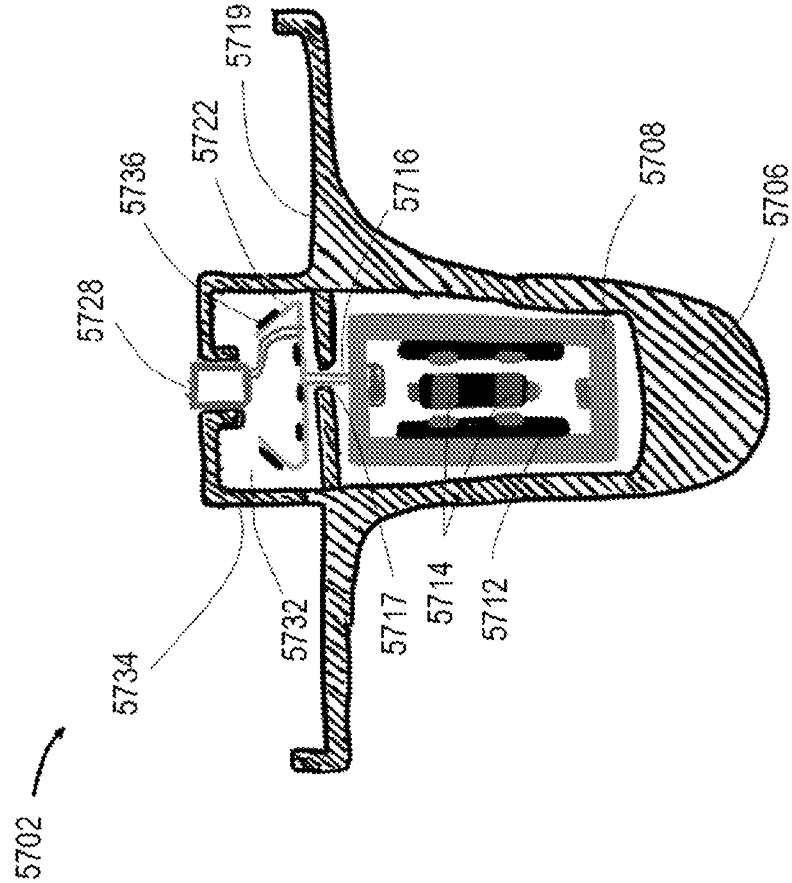
FIG. 84 is a side cross-sectional view of a tibial stem of the knee implant of FIG. 82 taken along line B-B.

FIGS. 82-85 show a knee implant 5700 according to another embodiment of the present disclosure. Knee implant 5700 is similar to knee implant 5200, and therefore like elements are referred to with similar numerals within the 5700-series of numbers. For example, knee implant 5700 includes a tibial stem 5702 with an energy generator 5708, and a tibial insert 5704 as shown in FIG. 84. However, tibial insert 5704 includes a medial tibial insert 5705 and a lateral tibial insert 5703 as best shown in FIGS. 83A and 83B. Individual tibial inserts on the medial and lateral sides allow a surgeon to use tibial inserts with asymmetric insert thicknesses to balance the knee or to vary constrains between both inserts to facilitate mobility. For example, a surgeon can select a medial tibial insert to constraint medial ligaments for a specific patient. Ligament anomalies identified during pre-op or intra-op assessments with a smart trial component for instance allow the surgeon to vary the individual tibial inserts to address the needs of a particular patient.

Figure 85:
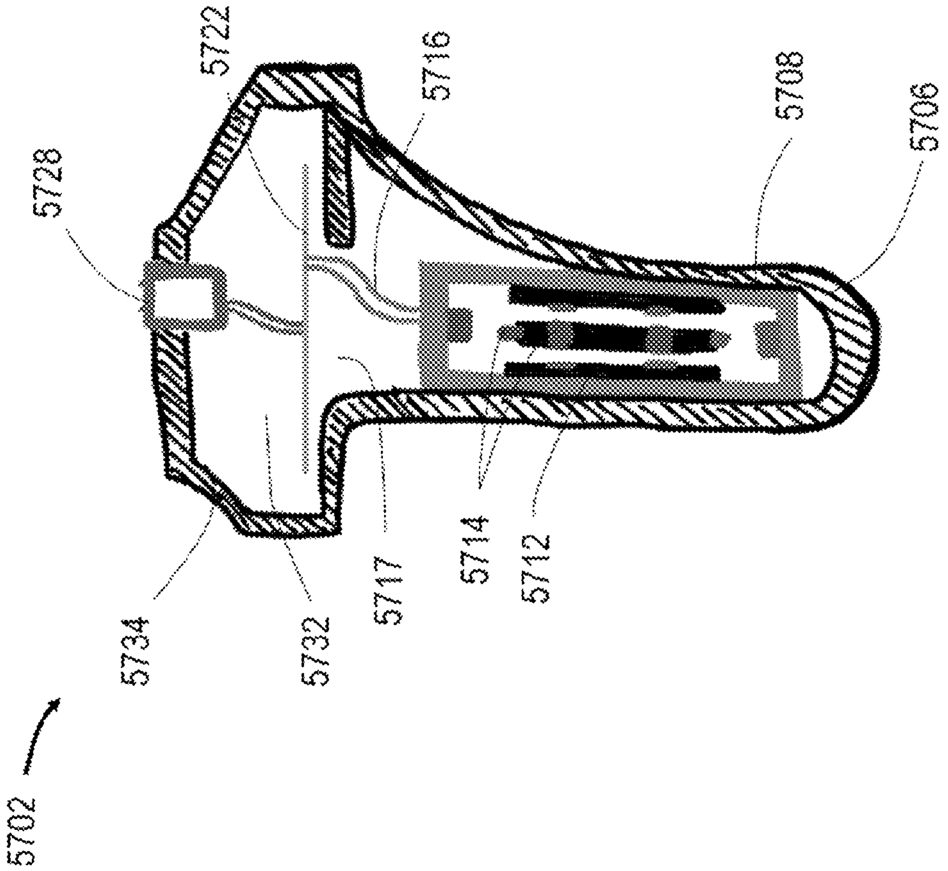
FIG. 85 is a side cross-sectional view of the tibial stem of the knee implant of FIG. 82 taken along line C-C.

Tibial stem 5702 of knee implant 5700 includes an extension with a cavity 5732 to accommodate electronic components such as PCB 5722 and sensors 5736. An opening 5717 in cavity 5732 allows energy generator 5718 to power the various electronic component located in the cavity via a wire 5716 as best shown in FIGS. 84 and 85. Thus, the energy generator and all electronic components of knee implant 5700 can be located withing a single implant (tibial stem 5702) in this embodiment. A pH sensor 5728 extends through a proximal surface of tibial stem 5702 to directly contact synovial fluid for precise and accurate measurement of synovial fluid pH levels. Cavity 5732 can be hermetically sealed to protect the electronic components.

Energy generator 5708 is an electromechanical energy generator configured to convert mechanical energy to electrical energy. Energy generator 5708 includes a plurality of magnets 5714 located on fixed and moveable columns 5712 configured to generate electricity via the relative motion of the magnets. The relative motion of magnets 5714 triggered by various activities of the patient including walking, standing, etc. results in electric energy generation. Biasing members (not shown) in energy generator 5708 protect magnets 5714 during hard impacts experienced by tibial stem 5702 and aid in relative magnet motion to increase energy generation. Electric power generated from energy generator 5708 is directly supplied (via wire 5716) to the various electronic components located in cavity 5732. In other embodiments, tibial stem 5702 can include a battery to store energy and supply same to the electronic components of tibial stem.

While a knee joint implant, hip implant, and shoulder implant are disclosed above, all or any of the aspects of the present disclosure can be used with any other implant such as an intramedullary nail, a bone plate, a spinal implant, a bone screw, an external fixation device, an interference screw, etc. For example, an energy generator disposed within a fastening element of a spinal implant such as a screw can be used to generate energy and acoustically transmit this energy to power sensors located within a spinal implant such as a spinal plate.

Although, the embodiments disclosed above generally refers to implants, the systems and method can be used with trials to provide real time information related to trial performance. While the electronic components disclosed above are generally located in the tibial implant (tibial insert and stem) of the knee joint implant, the electronic components can be located within the femoral implant in other embodiments. Battery and transducer-receiver shape, size and configuration can be customized based on the type of implant and patient-specific needs.

Figure 87:
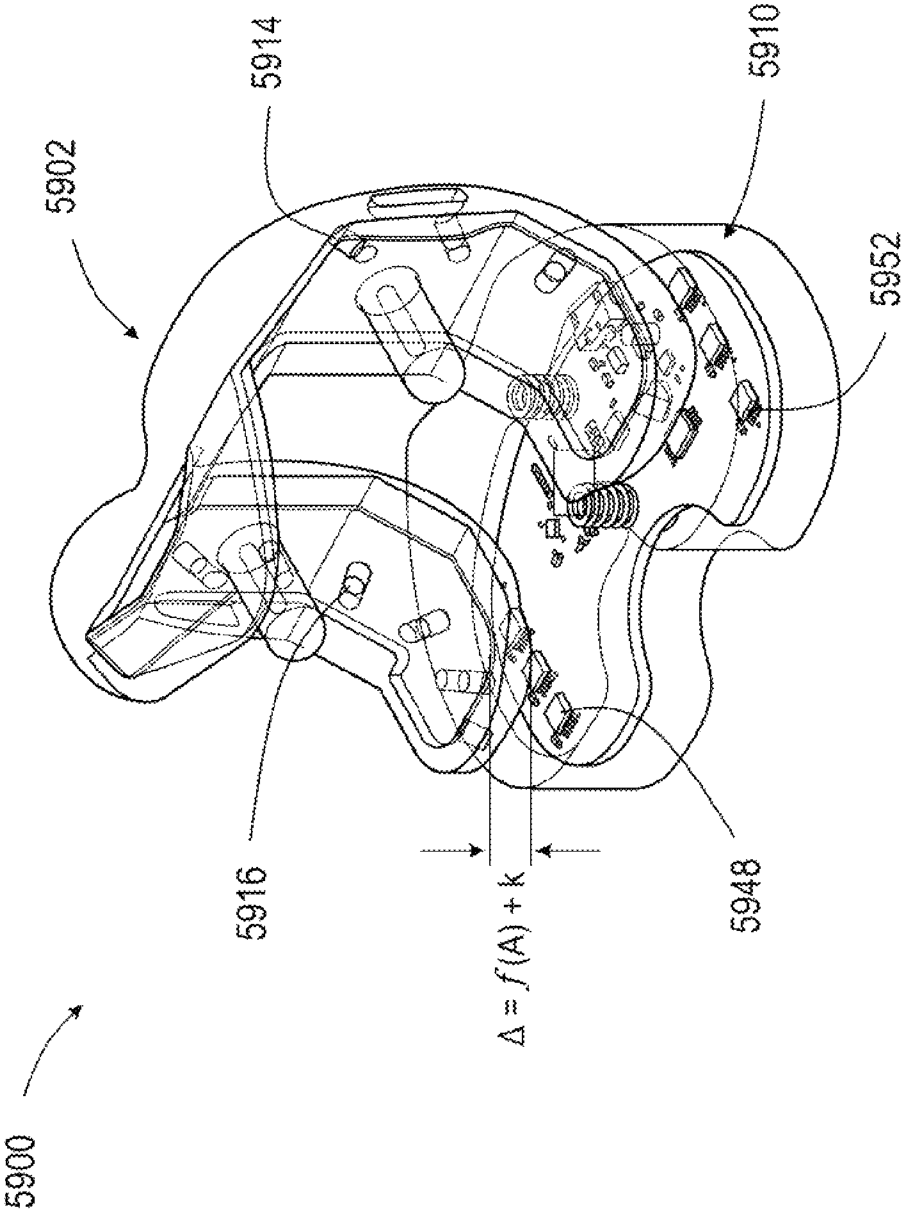
FIG. 87 is an isometric view of a knee joint implant according to another embodiment of the present disclosure.
Figure 88:
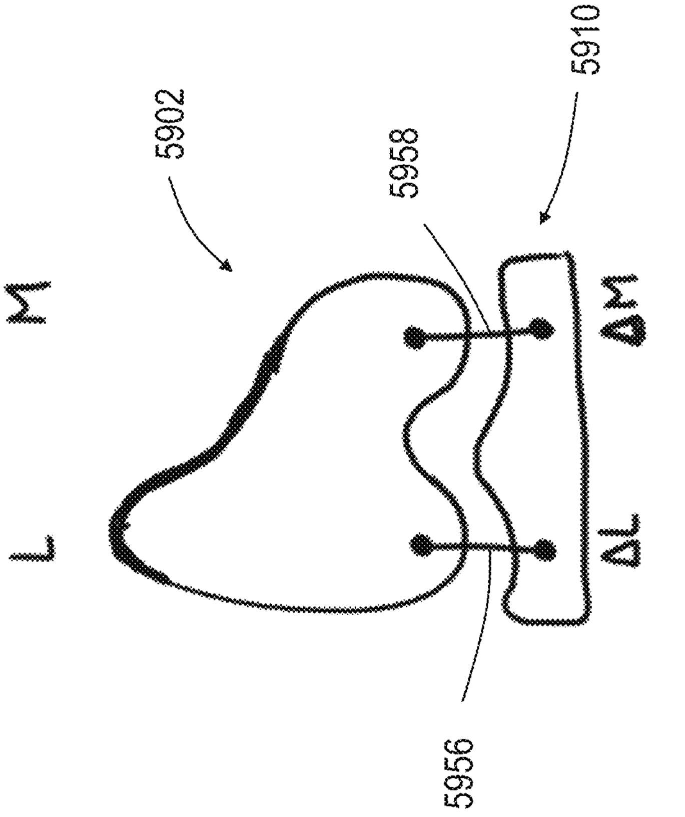
FIG. 88 is a front view the knee joint implant of FIG. 87.

FIGS. 87 and 88 show a knee joint implant 5900 according to another embodiment of the present disclosure. Knee joint implant 5900 is similar to knee joint implant 200, and therefore like elements are referred to with similar numerals within the 5900-series of numbers. For example, knee joint implant 5900 includes a femoral implant 5902 with a plurality of medial magnetic markers 5914 and lateral magnetic markers 5916, a tibial implant (not shown) and a tibial insert 5910 with medial marker readers 5952 and lateral marker readers 5948. Knee joint implant 5900 can be used to accurately measure and determine gaps between femoral implant 5902 and the tibial implant or tibial insert 5910. These measurements can be performed intra-operatively during a knee procedure such as a TKA using the magnetic markers and marker readers of knee joint implant 5900. Amplitude of the magnetic flux read by the lateral and medial markers from the respective markers can be used to precisely calculate medial and lateral gaps between the femoral implant and tibial implant using the formula below.

$$\Delta=f(A)+k$$

"Δ" represents the gap between the femoral and tibial implant, "A" is the amplitude of the magnetic flux reading and "k" is a constant dependent on the knee joint implant and marker/reader arrangement. Amplitude "A" can be derived from the magnetic flux readings and may not directly correlate to the amplitude of a single marker/reader. Intra-operative gap measurements allow a surgeon to accurately position and align the femoral and tibial implants.

A medial gap 5956 and a lateral gap 5958 can be individually calculated using the formula disclose above as best shown in FIG. 88. Thus, a surgeon can utilize knee joint implant 5900 to accurately determine medial and lateral joint gaps intra-operatively and ensure accurate positioning and alignment of the implant components. Additionally, a surgeon can determine contact points or surfaces between the knee joint implant components to ensure proper placement of same.

Referring back to FIG. 45, method 2400 in addition to showing a method to determine implant wear as more fully explained above, shows a method for intra-operative measurement and adjustment of knee joint implant gap according to another embodiment of the present disclosure. While method 2400 is described with reference to a knee joint implant below, method 2400 can be applied to any implant with sensors described in the present disclosure, including all of the implants disclosed above. In a first step 2402, a knee angle of a patient with the knee joint implant is measured. The knee is then placed in full extension in a step 2404. Hall sensor amplitudes are measured in a step 2408. This process is repeated over time to track the Hall sensor amplitude. These values are then compared with calibrated Hall sensor amplitude values obtained for known—i.e., measured, knee joint gaps. As the Hall sensor amplitudes are related (nonlinear relationship) to a distance between the markers and the marker readers—i.e., gap, a difference between the initial Hall sensor amplitudes and current Hall sensor amplitudes from step 2408 represents difference between the measure gap and the desired target gap. The correlation between two variables is not easily quantified as it is a nonlinear relationship; therefore, the gap between them can only be determined by employing the use of an algorithm or neural network. When the desired target gap on the medial and lateral sides are reached in a step 2420, the surgeon is notified that the desired knee joint implant gaps have been achieved in step 2422.

Figure 89:
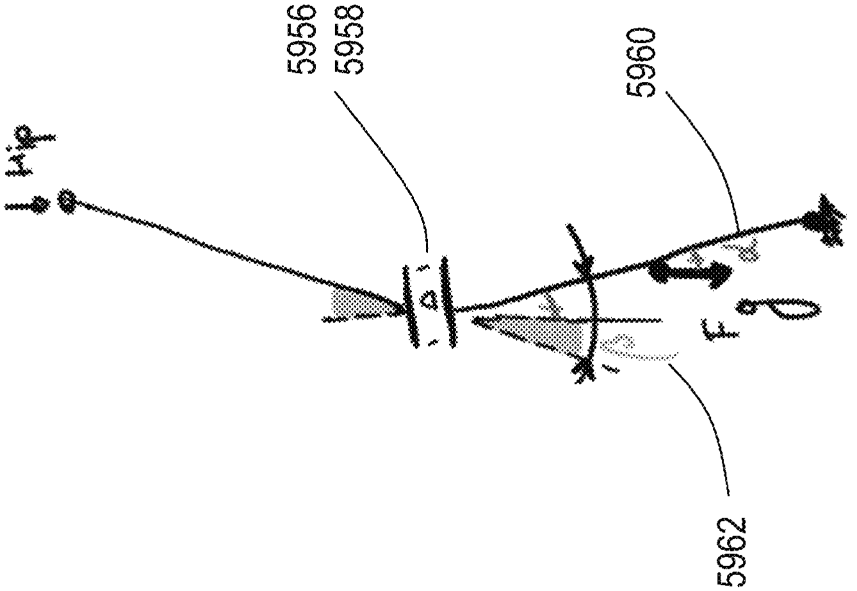
FIG. 89 is a schematic drawing of a method for gap measurement of the knee joint implant of FIG. 87.

Once the desired knee joint implant gaps are achieved, the surgeon can then apply varus-valgus movement to test for gaps in the medial and lateral sides as best shown in FIG. 89. "α" 5960 can be obtained from an IMU on knee joint implant 5900, "Δ" represent the gap distances can be determined by the markers and marker readers as described above, and "β" 5962 is an assumed constant dependent on knee joint implant 5900.

Implant lift-off (medial/latera) can be calculated during the varus-valgus movement test using the formula below:

$$\Delta_{ML\text{-}lift\ off}+V-V_{(femoral)}+V-V_{(tibial)}=\text{HKA}$$

V-V (femoral) is assumed to be a constant and "HKA" represent the hip-knee-angle. If the patient takes a standing pose and the alpha, measured by the embedded IMU in implant component 5910 (tibial insert), deviates from the initial implant reading that was taken during surgery, this indicates that the implant has shifted from its original implanted position, potentially resulting in implant migration or implant loosening.

Figure 90:
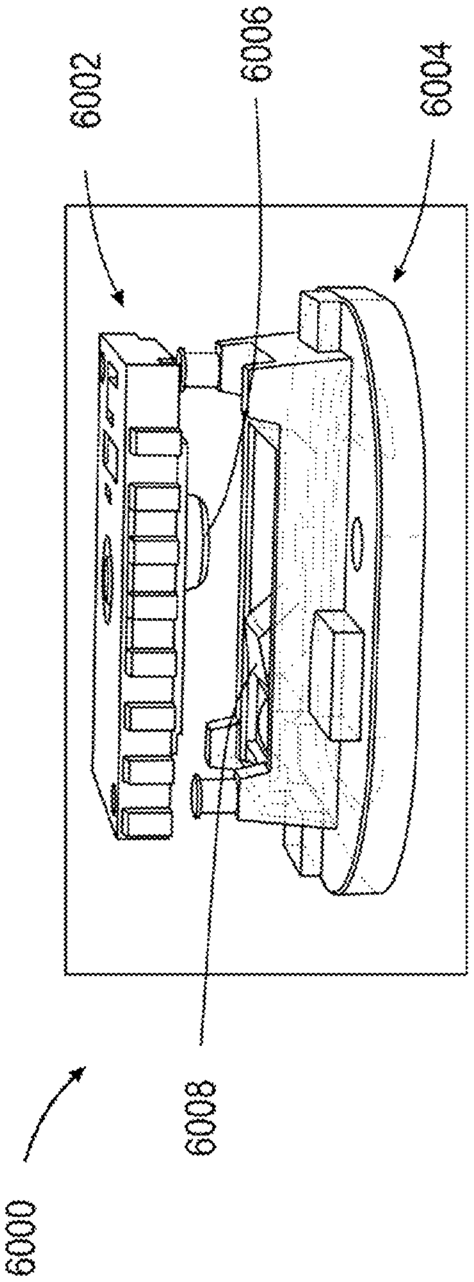
FIG. 90 is a front view of a joint implant according to another embodiment of the present disclosure.
Figure 91:
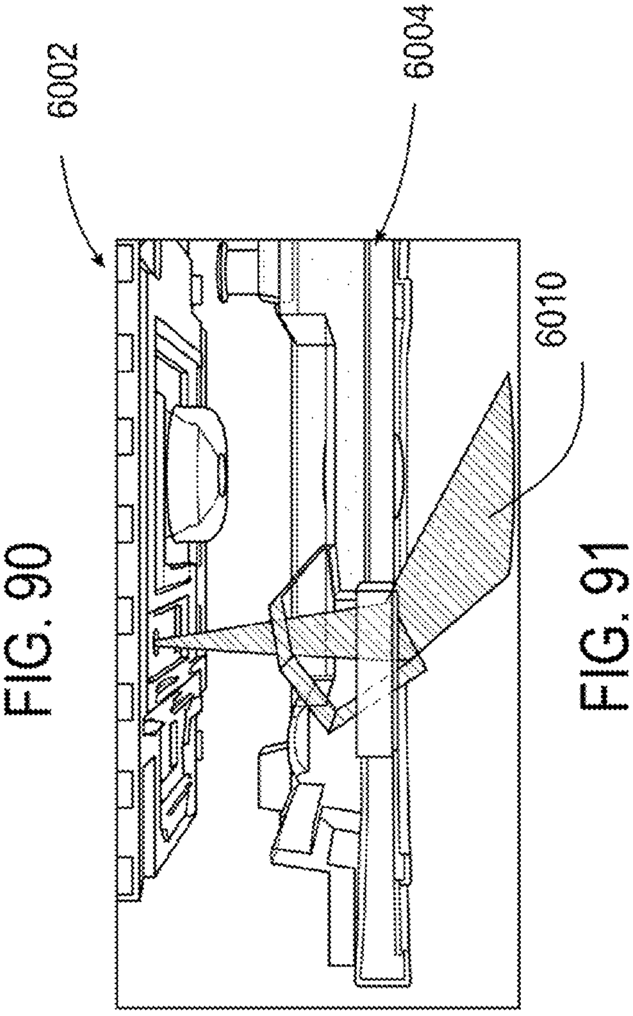
FIG. 91 is a front view of the joint implant of FIG. 90.

FIGS. 90 and 91 show a joint implant 6000 according to another embodiment of the present disclosure. Joint implant 6000 can be a knee joint implant, shoulder implant, spinal implant, hip implant, etc. Joint implant 6000 includes a first component 6002 and a second component 6004. A pattern 6008 on the second component may encode both the position based on the size and shape of the pattern and a reference point to determine a gap between the first and second components. A light source on the first component is provided at a shallow angle by means of a prism as best shown in FIG. 91. This light reflects 6010 the pattern on the second component and projects onto a retina IC 6006 of the first component. The image size is compared to a predefined value based on the position (e.g., a table with expected size as a function of position). If the size of the detected pattern is bigger than the predefined boundary, the first component is closer to the sensor (and thus the second component). The difference in detected pattern size versus the desired pattern size is directly proportionally to the difference between the actual gap versus the target gap between the first and second components. For example, if the pattern read is smaller than the predefined reference, the first component is further away from the sensor proportional to the difference in size between the read pattern and stored pattern.

Figure 93:
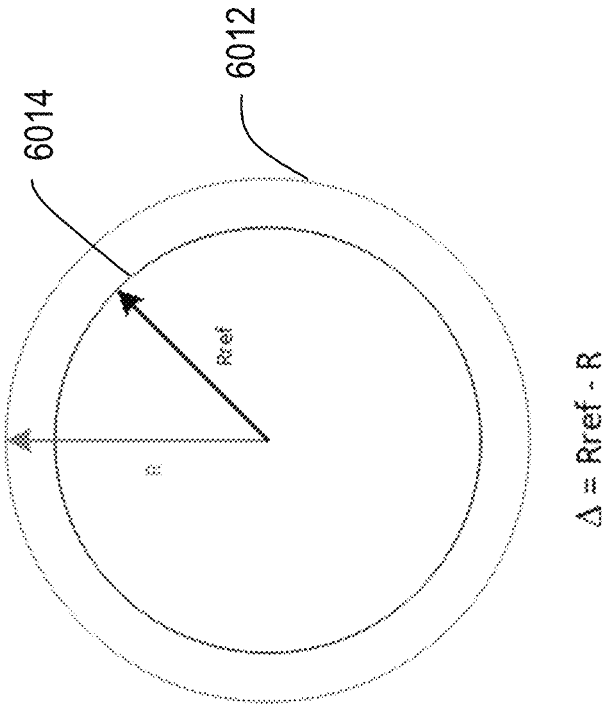
FIG. 93 is a schematic drawing of a second gap measurement of the joint implant of FIG. 90.
Figure 92:
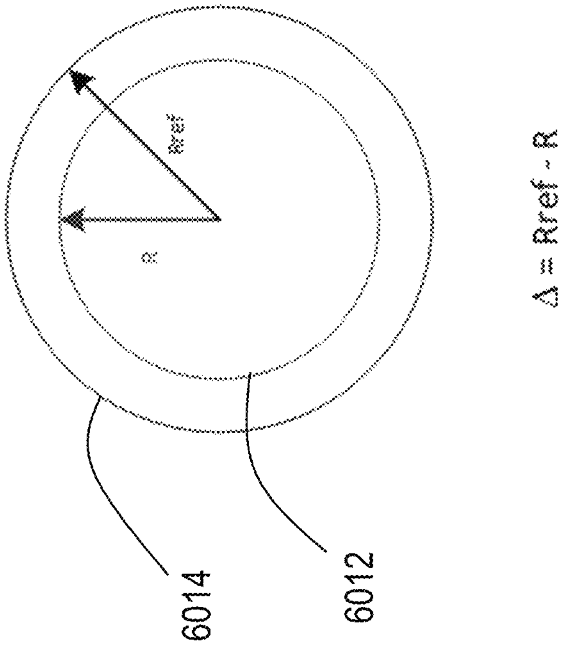
FIG. 92 is schematic drawing of a first gap measurement of the joint implant of FIG. 90.

FIGS. 92 and 93 show a circular pattern 6008 being used in joint implant 6000 to intra-operatively determine gaps between the first and second components. When a radius of the detected pattern 6012 is less than the target radius 6014 as shown in FIG. 52, the gap between the first and second components is above the target gap. Similarly, when a radius of the detected pattern 6012 is greater than the radius of the target radius 6014, the gap between the first and second is below the target gap. Thus, a surgeon can intra-operatively and in real time determine the desired gap between the first and second components of joint implant 6000. While a circle is used in this embodiment, other any other shapes such as squares, bar codes, etc. can be used in other embodiments of the present disclosure.

Figure 95:
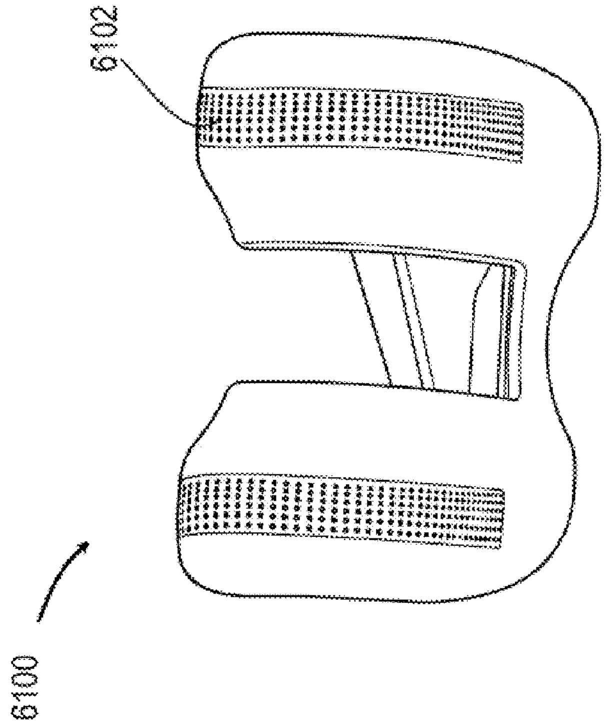
FIG. 95 is a bottom view of the femoral implant of FIG. 94.
Figure 94:
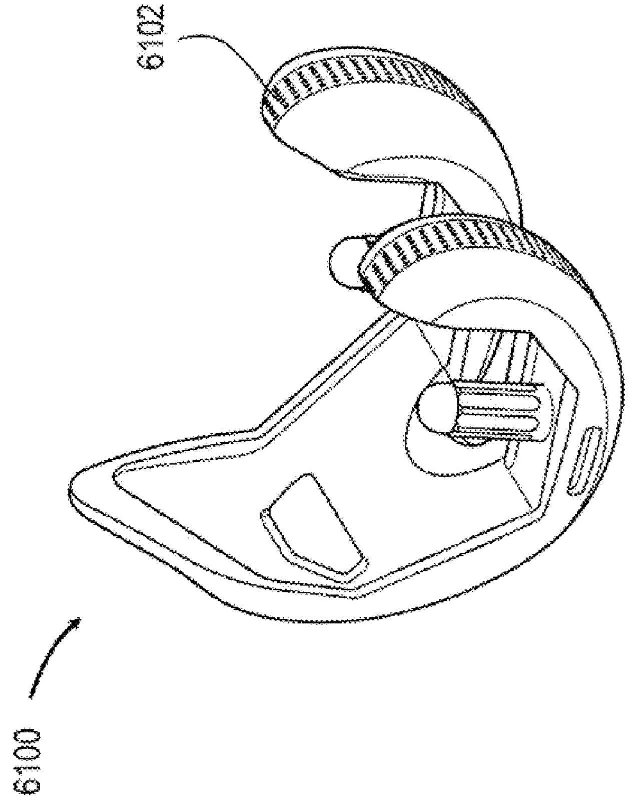
FIG. 94 is a side view of a femoral implant according to an embodiment of the present disclosure.

FIGS. 94 and 95 show a femoral implant 6100 of knee joint implant according to another embodiment of the present disclosure. A pattern 6102 can be imprinted to a surface of femoral implant 6100 by etching or other suitable techniques. An LED placed in an external device, such as a TKA gauge assembly can be used to reflect light of pattern 6102. The reflected light from the surface of the femoral implant is read on a reading device to determine the relative distance between a tibial trial or implant and the femoral implant by comparing the detected pattern to target pattern. Thus, a surgeon can intra-operatively adjust the joint gap in real time for proper positioning of the joint implants.

One issue that arises during a joint replacement surgery relates to implant component sizing. Often, a particular patient requires implant components on one side of the joint that differ in size from those on the other side of the joint. For instance, it is not uncommon for the best fit femoral component to differ from that of the best fit tibial components (e.g., a patient may require a size 4 femoral component with a size 3 tibial component during a total knee arthroplasty). This can pose issues in the case of tracking implants as disclosed herein, as like size components are typically calibrated to work with each other supported by an underlying software package for that particular implant combination. Disclosed below are implants and related methods for tracking implant performance, as well as implant components and methods that can work with each other in such tracking regardless of their respective sizes.

As noted above, different patient anatomy often results in the need for two differently sized implant components to be utilized. In accordance with the present invention, an algorithm utilized by the underlying software can be modified to properly address such a situation. This results in more accurate data to be obtained from the implant by automatically taking into account issues like the different spacing, sizing and location of markers/readers in the differently sized implant components.

Figure 97:
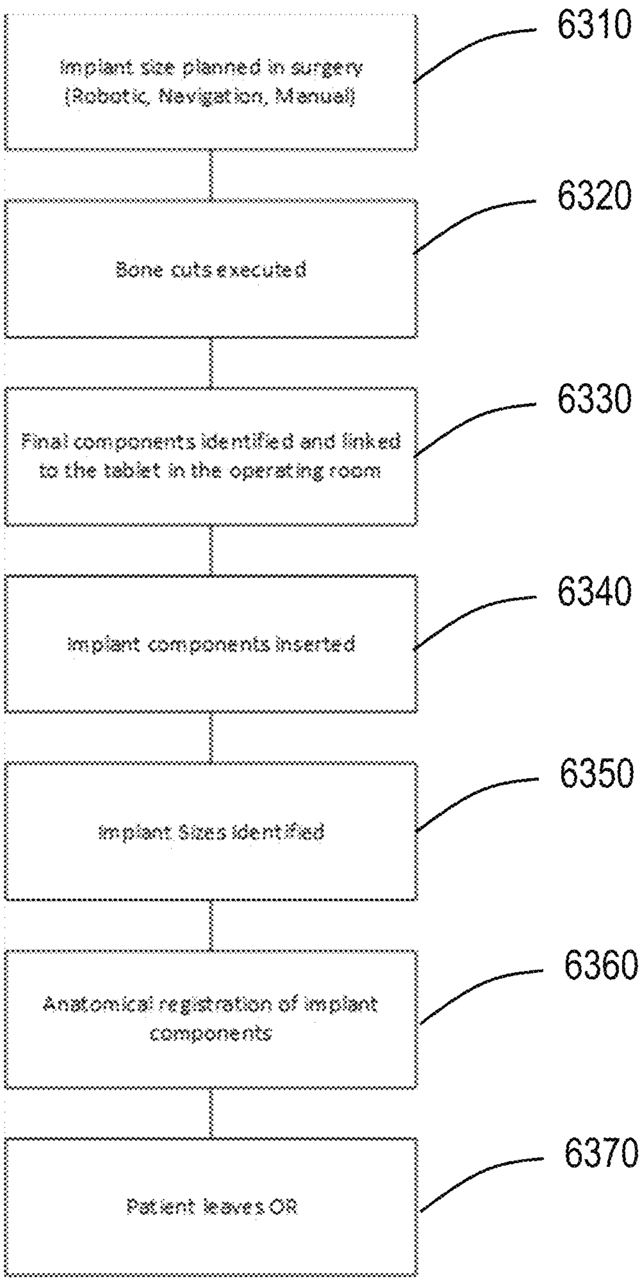
FIG. 97 is a flowchart depicting certain steps of a method of surgery utilizing differently sized components.

A methodology in connection with a first embodiment of the present invention will now be discussed, with reference to FIG. 97. The particular procedure being undertaken is a knee replacement procedure. It is to be understood that the present invention is not limited to use in knees, as the foregoing disclosure makes apparent in disclosing other joint implant designs.

The implant size is planned in a first step 6310. The surgeon typically does this iteratively during trialing steps performed during the actual surgical procedure. This often simply requires the testing of differently sized implant components on the respective bones, but can involve recutting the bone to achieve a more well-balanced surgically repaired knee. It is also possible to preoperatively select implant components based upon preoperative scans, which is what is reflected in step 6310. The preoperative implant selection can be confirmed/validated during surgery. After the initial implant sizing, which can be modified later during the surgery, the bones are resected or cut in accordance with the types of implants being implanted (step 6320). For instance, the tibia can be cut with a single flat resection, while the femur can be cut to include multiple cut facets. The cuts are ultimately dictated by the implant designs and the particular surgical procedure being undertaken.

Thereafter, a trialing procedure can be conducted (not shown) and the implant components are identified and linked to a tablet in the operating room (step 6330) by manually entering the size of the selected components or digitally scanning the selected components to identify digital markers such as QR codes, bar codes, RFID chips, etc. In step 6340, the implants are inserted and implanted on the bones through known means, such as press-fitting or cementing the implants on the bones. With the final implant components in place, step 6350 involves the algorithm adjustments in response the implant component sizes entered in step 6330. This manual entry dictates the algorithms that need to be utilized based upon the final sizes of the components. In other words, the software package knows based upon prior programming the correct algorithm to utilize based upon a size of the implant component or combination of sizes of implant components. It is contemplated that rather than manually inputting the sizes, the tablet or computer may identify such sizes after some sort of movement or kinematic task during which the magnetic readings from the Hall sensors is indicative of the implant sizes for both components. For instance, the knee joint could be taken through a typical range of motion and the software may identify the proper algorithms to utilize automatically based upon this movement.

Thereafter, in step 6360, the implant components can be registered to each other and the bones. As the implant sizes are known, the kinematics between the two implant components can be derived. The position of the implant on the bones however defines the joint kinematics and as such, a registration process is required that links both. Finally, the surgery is concluded, and the patient is discharged from the operating room (step 6370).

In a second embodiment, a manual input of the components sizes is not required. An RFID chip or the like is imbedded in one of the components (e.g., the femoral component) and contains information of the component size. The electronics (like are discussed above) in the other component (i.e., tibial component) read the information from the RFID chip which are then communicated with the underlying software. The algorithms are then changed to match the implant sizes specified in the RFID chip. In another embodiment, an external scanner can be used to read the RFID chip and transmit this information to the underlying software.

Figure 98:
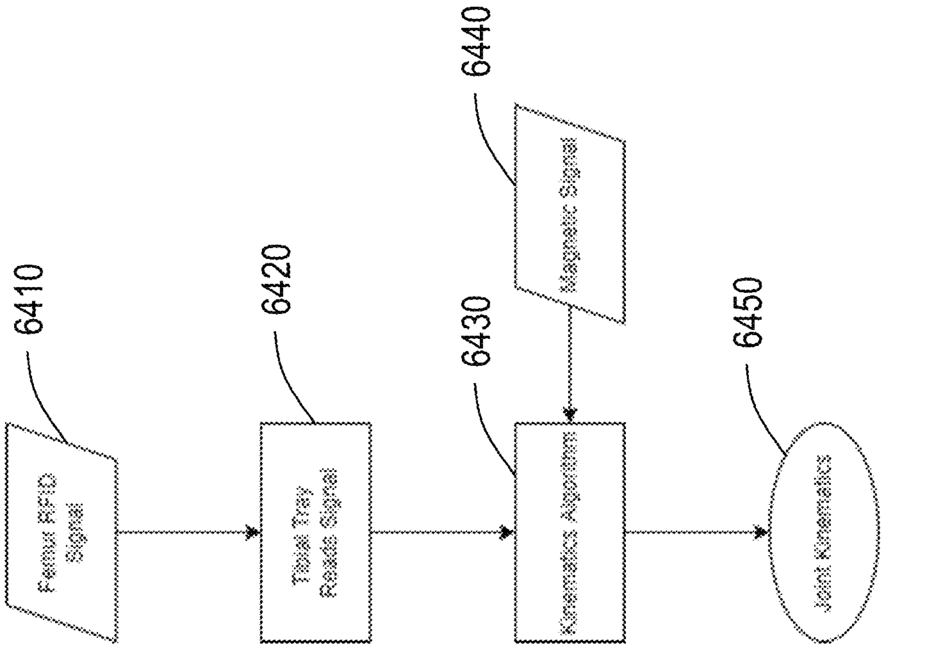
FIG. 98 is another flowchart depicting certain steps of another method of surgery utilizing differently sized components.

FIG. 98 depicts a methodology in accordance with this second embodiment. A femur RFID signal 6410 is sent and then read by the tibial tray in step 6420. Based upon this, the kinematics algorithm 6430 is changed. The calibrated kinematic algorithm then receives magnetic signal 6440 from the implant to output joint kinematics. Finally, the joint can be moved and the modified algorithm will now track the correct joint kinematics 6450.

Figure 99:
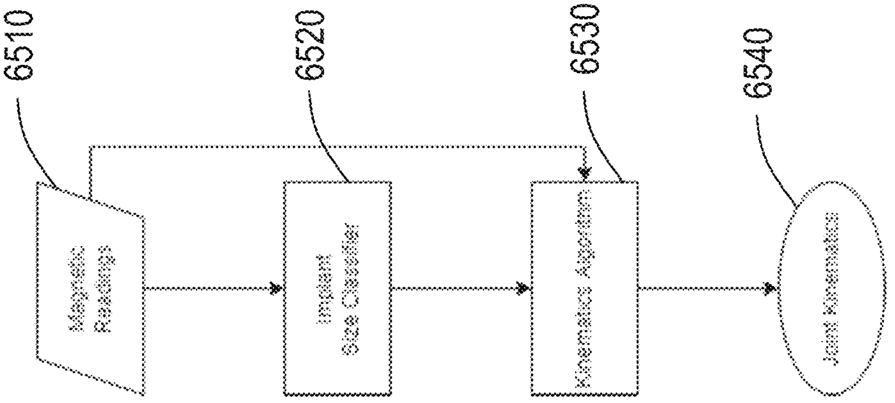
FIG. 99 is another flowchart depicting certain steps of yet another method of surgery utilizing differently sized components.

In a third embodiment, the magnets in the femoral component are placed such that each size femur has a different magnetic field signatures. Thus, instead of the RFID chip dictating which algorithm is to be utilized, the reading of the magnetic field signature does. Before or after implantation, a calibration mode is activated on the implant and the femoral component is moved relative to the tibial component in either a specified or unspecified motion. A classification algorithm takes magnetic data from this motion and determines which size implant is used. Again, the kinematic algorithm is modified to match the implant size by the classification algorithm. FIG. 99 schematically represents this third embodiment via steps 6510, 6520, 6530 and 6540. The component sizing is discussed above in connection with the modification of an algorithm utilized in the underlying software package that thereafter tracks implant performance. In most instances, the different sizing impacts kinematic readings taken by the implant, but can impact other readings as well. For instance, the different sizes of implant components can result in sensors being located at different locations, which can impact readings such as temperature or the like. Thus, modifying the algorithms utilized by the underlying software can be important for more than just getting accurate motion information for joint implants.

In another embodiment, implant sizes can be identified via imaging before, during or after surgery and provided to the algorithm. The algorithm is calibrated based on the implant sizes detected from imaging.

Any of the foregoing implants can be utilized to obtain data that can be used in estimating 6-degrees of freedom of motion for a given joint. While the following will be discussed in connection with a knee joint, it is to be understood that implants for other joints (like those discussed above in connection with the hip and shoulder) can be utilized to obtain data for determining the motion of the specific joint. In any event, a method will now be disclosed for utilizing the magnetic field strength recordings from the aforementioned Hall sensors to estimate the knee kinematics for a specific patient.

Estimating six degrees of freedom of motion from data obtained from the Hall sensors involves a difficult kinematics problem to solve. The present methodology thus employs the use of machine learning algorithms (e.g., regression or neural networks) for an accurate pose estimation. However, the advance machine learning algorithms employed herein require large quantities of training data, which can be difficult to create. The present methodology thus includes the regression algorithms as well as the creation of training data necessary for the machine learning algorithms to determine the patient kinematics, which can involve utilizing computer simulations and/or robotic assistance.

Figure 100:
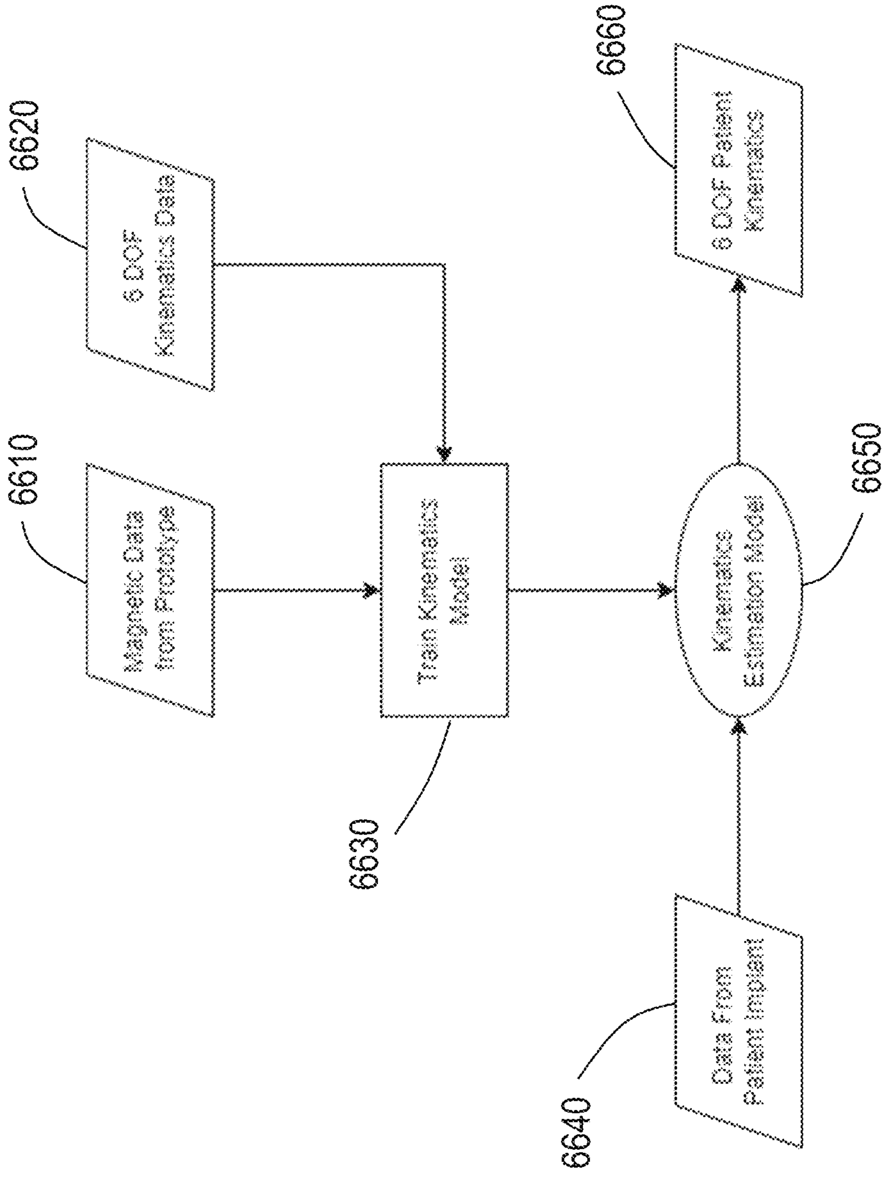
FIG. 100 is a flowchart depicting certain steps of a method of estimating motion of a joint implant.

FIG. 100 is a flowchart in accordance with a first embodiment of this methodology. In step 6610, data is collected from a physical prototype including magnets and magnetic sensors, such as the Hall effect sensors discussed above. The prototype is put into many poses representing the up to six degree-of-freedom range of motion the joint could experience after implantation barring some limiting factor such as injury. The pose of the joint can be determined using several methods. For one, video motion capture with markers attached to each piece of the component can be utilized. Alternatively, a robotic system can be used to either move the joint replacement into known poses or to measure landmarks on the components to determine poses after the implant has been moved. Data from the different poses is collected in step 6620.

Thereafter, a model (e.g., neural network) that determines the six degree-of-freedom poses from the raw magnetic sensor data or from features derived from the magnetic data is trained (step 6630). For example, tensorflow-keras in Python can be used to build and train the neural network models. A gradient-based optimizer such as Nadam for example can be used as an optimization algorithm. A portion of the raw magnetic sensor and position data can be split off and saved for validation and testing. The remaining data can be used as training data. Magnetic sensor data can be passed as a predictor variable to tensorflow-keras, while the model can be trained to predict position data. Model structures can be varied iteratively until a model is found that can be trained using only training data to predict the validation data with high accuracy. The test data can be used as a final check for accuracy. Neural network weights can be determined using the Nadam optimizer in tensorflow-keras.

This can be utilized to determine all six degrees-of-freedom simultaneously in one embodiment. In other words, separate models are not trained for each individual degree-of-freedom (DOF). Data from an actual patient implant can now be obtained (step 6640), the trained estimation model can analyze it (step 6650) and provide output on the degrees-of-freedom for the particular patient (step 6660). The output can be in many different forms, including a visual representation of the motion of the joint, such as a graph or visual representation of the motion of the joint bones. In another embodiment, each DOF can be fitted/predicted individually or collectively with other DOFs.

In one variant of this embodiment, a neural network model with 6 outputs is created to determine poses from the magnetic data. This can be one of many forms, including multi-layer perceptrons or convolutional neural networks. In another variant of this embodiment, a model is created with several linear or nonlinear equations that are solved simultaneously to get the poses. For each time frame of magnetic data, an optimization is performed to determine the pose that satisfies the magnetic field equations. Alternatively, a method where poses are routinely determined and fed back into the equations as an initial guess for the next step of the process (e.g., similar to a Newton-Raphson method) could be substituted for traditional optimization.

Figure 101:
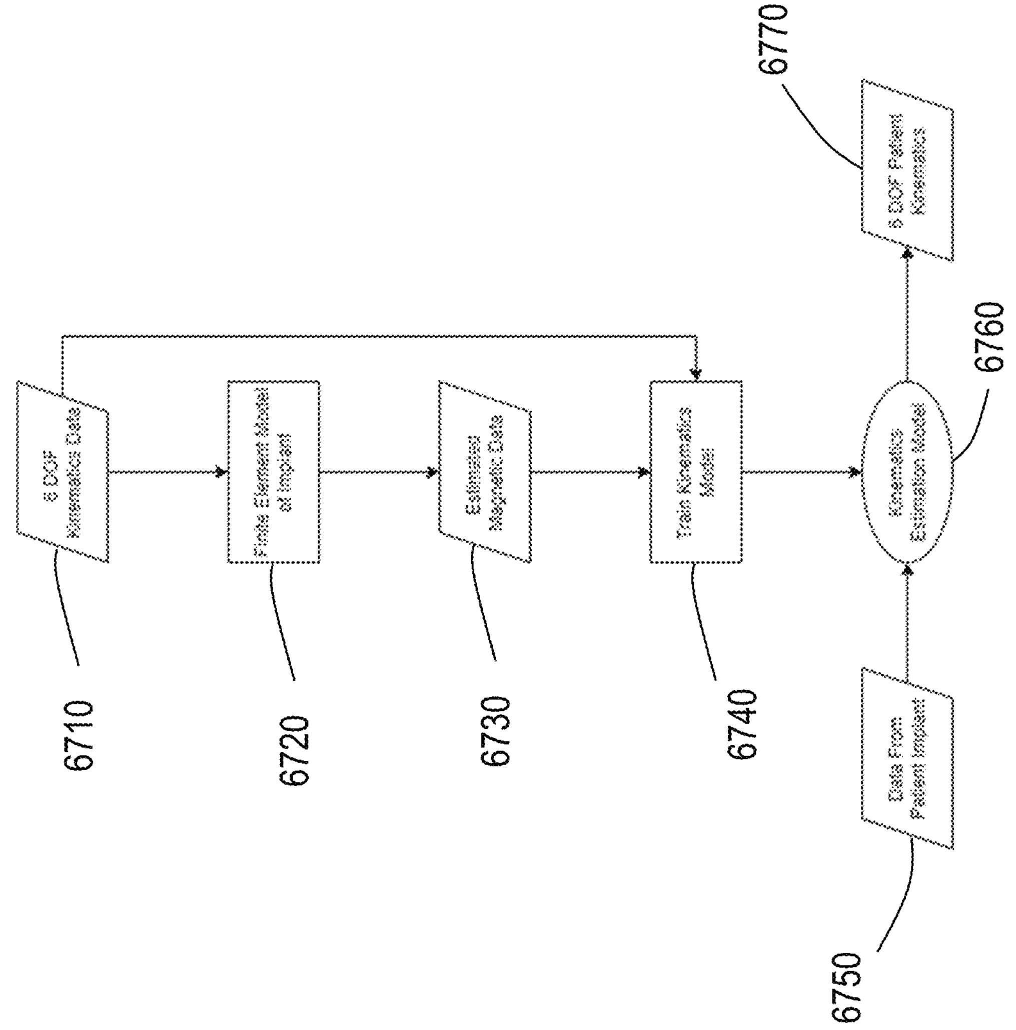
FIG. 101 is another flowchart depicting certain steps of another method of estimating motion of a joint implant.

In a second embodiment of the kinematic determination as shown in FIG. 101, instead of using physical data to train the kinematics model, the Hall sensor methods are determined using physics for the full six-DOF range of motion of the knee. Data is still collected in step 6710, but then fed into a finite-element analysis ("FEA") model of the magnetic field and sampling the field strength (step 6720). Data for step 6710 can be generated randomly. For example, a Quasi-Monte Carlo design of experiments approach can be used. Physiological bounds for knee motion can be determined and pseudo-random poses are generated within these bounds. A Sobol sequence can be used to generate poses that evenly sample the combinations of possible poses so that one region of poses is not over-sampled. This can be done at the locations of the Hall sensors while they are placed in various poses (step 6730). The kinematics model can then be trained using this information (step 6740). Thus, regression models are trained to fit the FEA model instead of the physical data. Since the data is generated from base principle, the poses are known and do not need to be measured. The methodology can thereafter follow similar steps as in the first embodiment method—data from an actual patient implant can now be obtained (step 6750), the trained estimation model can analyze it (step 6760) and information on the degrees-of-freedom for the particular patient can be outputted (step 6770).

Figure 102:
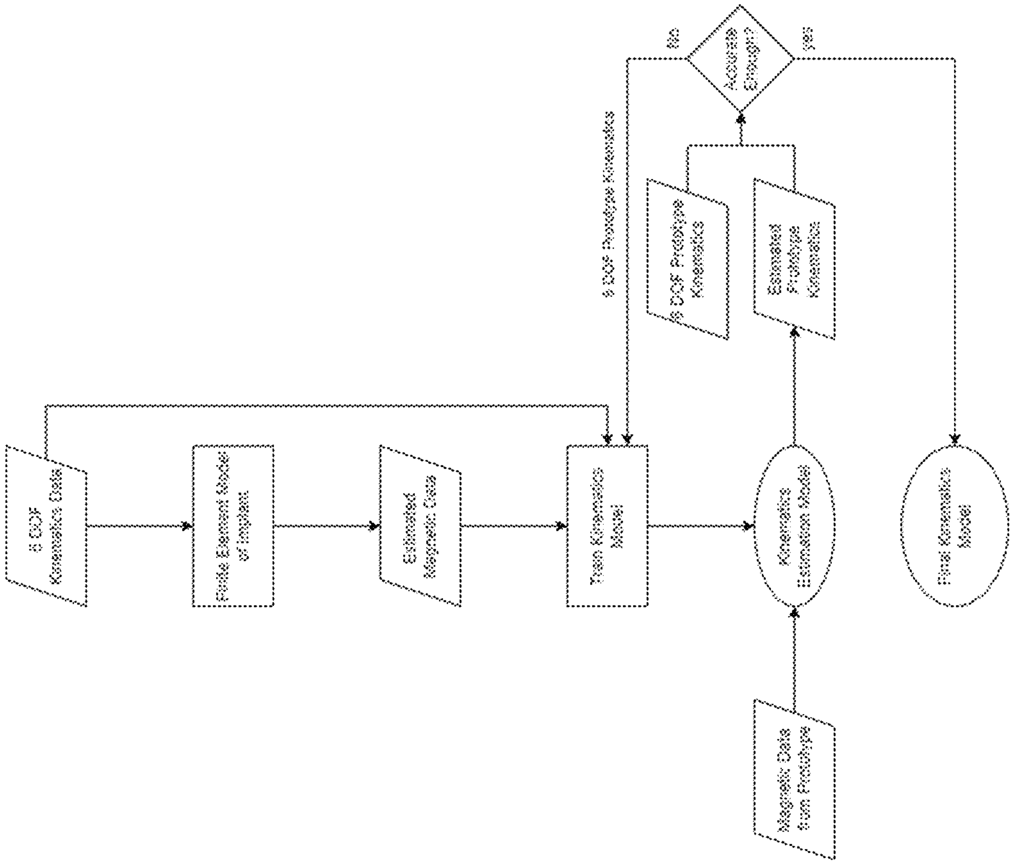
FIG. 102 is another flowchart depicting certain steps of yet another method of estimating motion of a joint implant.

A third embodiment of the methodology pertaining to the kinematic determination includes collecting physical data as in the first embodiment method and utilizing an FEA analysis as in the second embodiment. The physical and FEA data sets are combined and the regression models are trained to fit the relationship between magnetic data and pose. It is also contemplated to initially train regression models using data from the FEA analysis. Model error is then estimated by comparing poses from the model generated with physical data against the poses used to generate the data. If the error is above a threshold, the physical data is added in and the regression models are refined. A new physical dataset is then generated and the process is repeated until error are within a certain threshold. FIG. 102 is a general representation of this third embodiment.

The use of artificially generated data to train the models, as discussed above, is superior to simply obtaining data from physical prototypes. For one, a large dataset is needed to train complex regression models. Collecting this data from a physical prototype would be difficult, especially in a production environment. The error sources from a physical dataset is also greater than in the computational method. While the FEA model may have errors from the mesh noise and solution convergence, it will probably be closer to the average implant than a single physical implant prototype. Numerous prototypes can be tested to get a dataset that represents the average implantable sensor. Moreover, in the physical data, there will be errors for determining the poses of the implants. These errors can be quite large if using video motion capture. Using a coordinate measuring machine (CMM) can be more accurate but requires a great deal of human or machine effort. There will also be error introduced from manufacturing variations (e.g., misplacement of sensors or magnets within manufacturing tolerance, sensor errors, etc.). Finally, there will be magnetic and electrical noise, which all can lead to a biased model. Known potential error sources such as magnet placement error, pole alignment error, magnetic strength error, etc. can be fed into the FEA model that would not be practical in a physical model. This error modeling can be used to improve the robustness of the neural networks and predict product accuracy over the entire range of expected errors. Other error sources (sensor, noise, etc.) can also be fed into training model in both the physical and FBA workflow.

A pre-operative understanding of a patient's joint is also important in understanding the underlying defect and patient anatomy. Such understanding is often limited to pre-preoperative scans, which do not necessarily give a full picture of such issues. This holds true for fully understanding patient kinematics both before and after surgery. Disclosed below are implants and related methods for tracking implant performance, as well as apparatus and methodology for understanding pre- and post-operative kinematics of a patient's joint.

Figure 103:
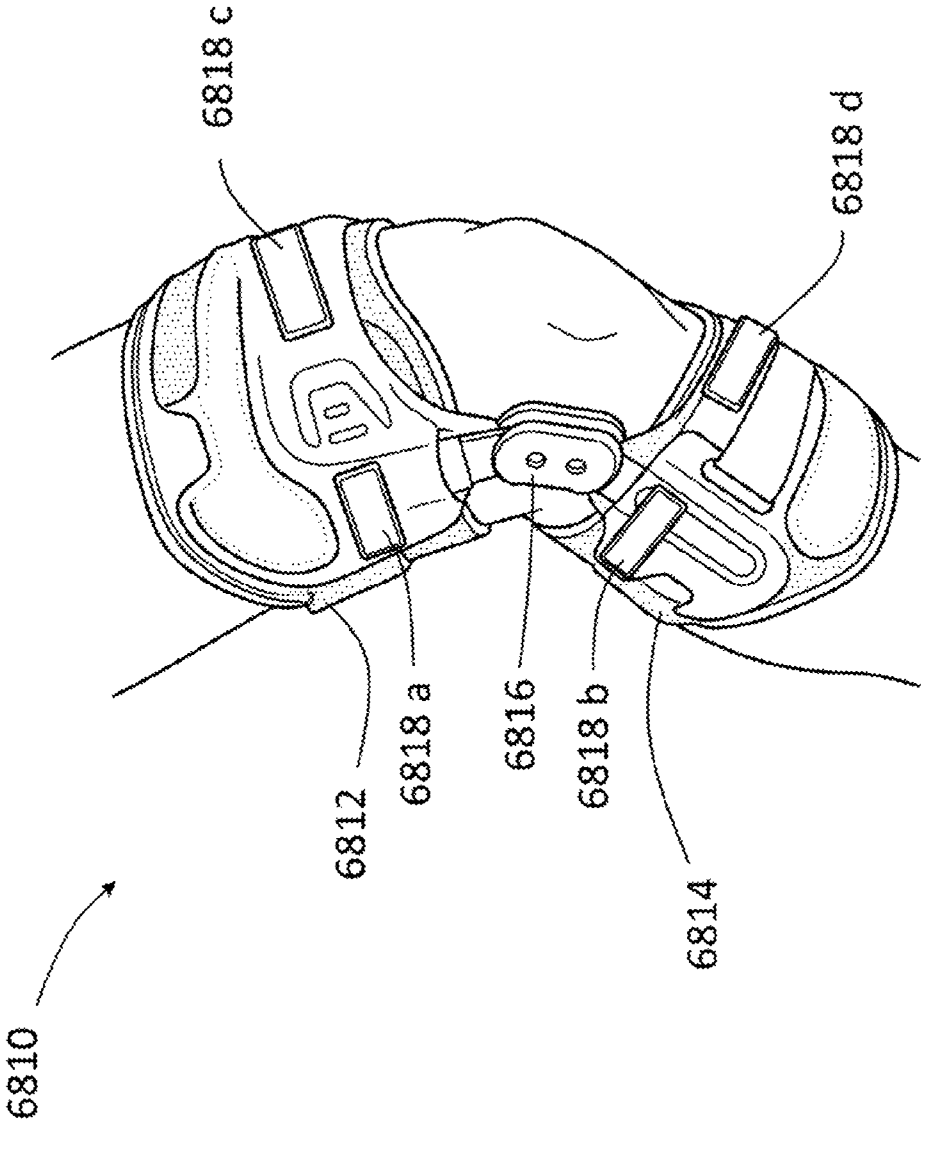
FIG. 103 is a perspective view of a knee brace in accordance with another embodiment of the present disclosure disposed on a knee joint.

FIG. 103 depicts a brace 6810 in accordance with another aspect of the present invention. Brace 6810 is shown in the form of a known knee brace, but can take the form of any known or hereafter invented brace design, including braces for use in other areas of the body (e.g., shoulder, hip, elbow). Brace 6810 includes upper leg sleeve 6812 and lower leg sleeve 6814 that are coupled together via a hinge mechanism 6816. Like known braces, brace 6810 can be useful in keeping the patient's knee in an alignment that aids in healing and/or precludes further injury. Brace 6810 is constructed of suitable materials for exterior wear by the patient, although any suitable material is contemplated.

As shown, brace 6810 includes inner spaces 6818 (their general locations are pointed to in FIG. 103). The spaces are designed to house sensors, which are discussed more fully below. As shown, brace 6810 includes six inner spaces—two medial (6818*a*, 6818*b*), two lateral (6818*c*, 6818*d*) and two frontal (6818*e*, 6818*f*—not shown in FIG. 103)) that are preferably in the form of pockets to house six different sensors. The sensors are thus fixed to the brace such that their distance with respect to each other can vary upon movement of the joint. Although not shown, brace 6810 can include an optional extended battery and/or any of the features discussed above in connection with sleeve 868.

Figure 104:
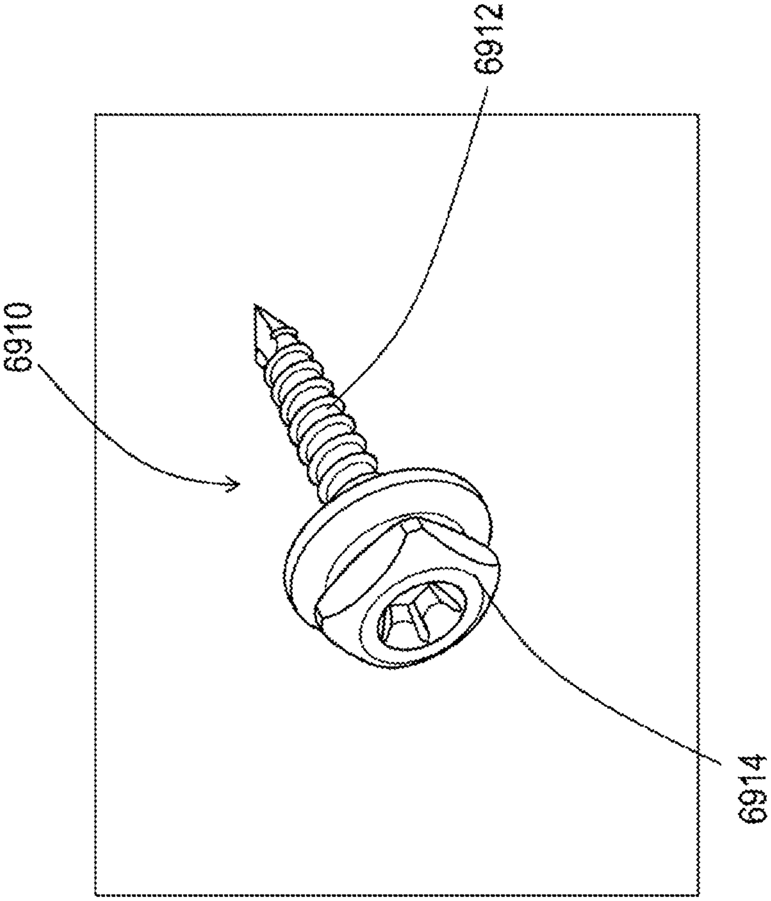
FIG. 104 is a perspective view of a tracker in accordance with another embodiment of the present disclosure.
Figure 105:
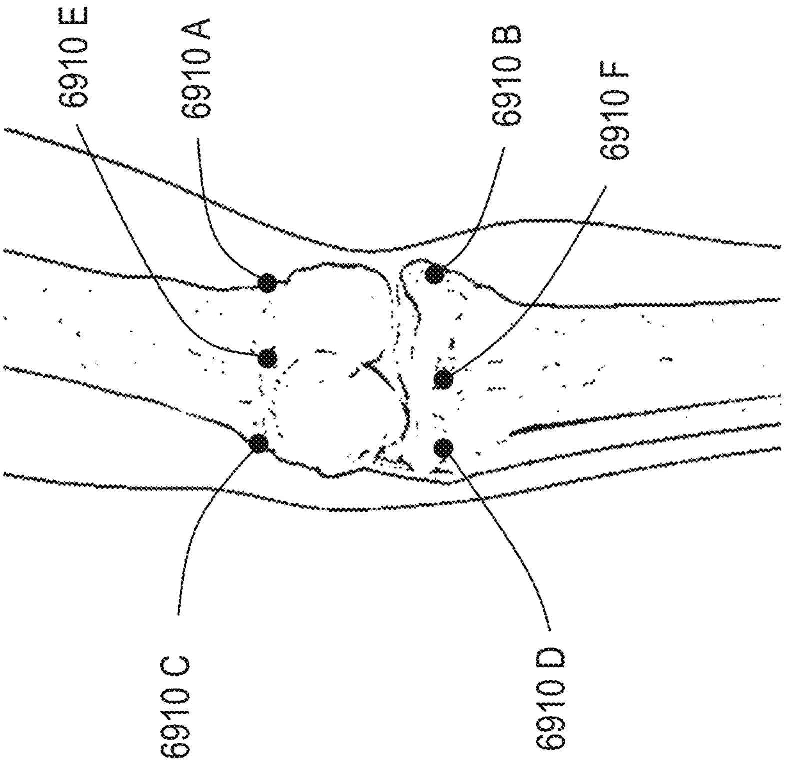
FIG. 105 is a partial view of a knee joint of a patient with several of the trackers of FIG. 49 attached to the bones of the joint.
Figure 106:
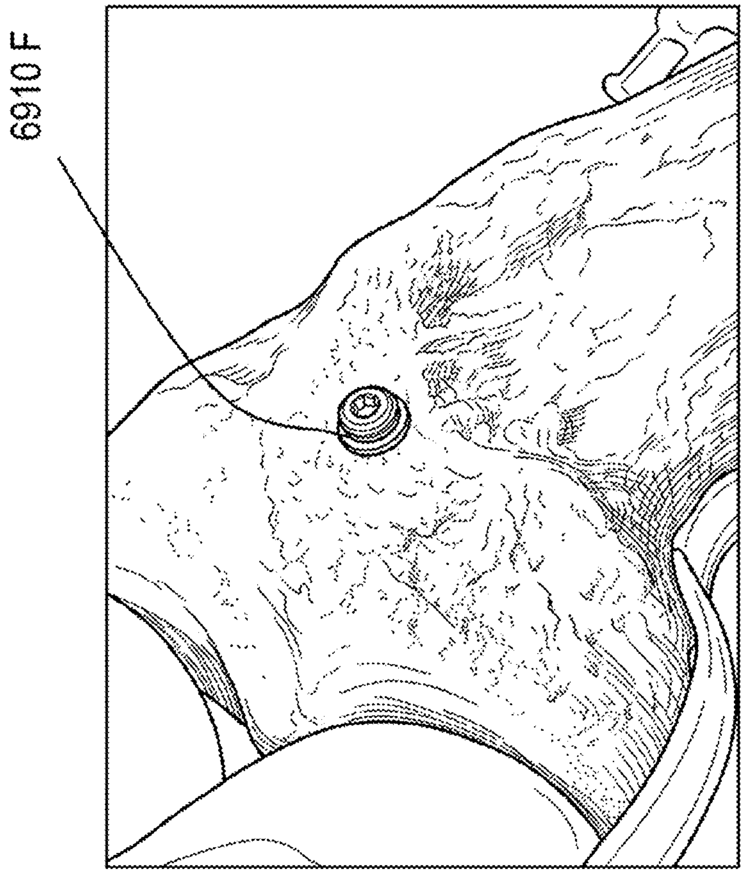

FIG. 104 depicts a tracker 6910 that can be utilized in connection with brace 6810. As shown, tracker 6910 is in the form of a bone screw having a bone attachment member in the form of a threaded shank 6912 and a head 6914. It is contemplated that the bone attachment members can take on other forms, including barbs, nails and the like. Within the tracker is a magnet or other material that generates magnetic flux density, which is then detected by one or more of the sensors of brace 6810 to provide feedback on patient kinematics or other motion information. FIG. 105 depicts trackers 6910*a-f* implanted in the knee joint. These trackers are attached to the bones in a fashion such that they correspond to the sensors housed within spaces 6818*a-f*, respectively. However, it is to be understood that while six trackers are shown attached in FIG. 105, it is to be understood that any number of trackers can be attached in a given knee joint, preferably in a manner such that each align with a different sensor of brace 6810. FIG. 106 is an enlarged view of tracker 6910*f* that is attached in the front of the tibia in FIG. 105. Pre-surgery implanted trackers can be removed at the time of the joint surgery or could be left in for post-surgical monitoring.

As is alluded to above, trackers 6910 are in association with one or more sensors of brace 6810. Brace 6810 and trackers 6910 are preferably attached prior to a knee joint replacement surgery to provide patient specific kinematic information, which can be useful to a surgeon in planning for the joint procedure. For instance, motion information pertaining to patient gait, or the like can aid the surgeon in understanding the underlying structural deformities/maladies plaguing the patient. This data can be captured for a period of time prior to the surgery in order to gather as much patient movement data as possible. It is also contemplated to use brace 6810 and trackers 6910 subsequent to a knee joint procedure to aid in understanding the success of the procedure and the patient's rehabilitation from same.

Although not shown in detail, the sensors included in brace 6810 include Hall sensors similar to those discussed above. These are matched with the magnets of trackers 6910 to record three-dimensional movement of the bones of the joint. It is also contemplated to utilize the brace and/or tracker construct in connection with existing tracking systems, such as MotionSense™ offered by Stryker. There, devices including IMUs are provided in concert with OrthoLogIQ® software to provide pre- and post-surgical information to surgeons. The present invention would complement this existing technology such that the recorded movement in the aggregate will provide a better picture as to any structural deformities that are specific to a given patient. It is contemplated to remove data pertaining to the offset movement of the brace on the skin relative to the bone.

Any data received from the use of brace 6810 can be fed into a software package (such as OrthoLogIQ®) that can model or otherwise interpret such data to provide the surgeon with a picture of the points of stress on the joint during motion and/or other motion related information. The sensors preferably communicate wirelessly (via Bluetooth or the like) with a computer, tablet, smartphone or the like, although it is possible to facilitate the downloading of data via a USB or other wired connection. In this regard, brace 6810 can include a wired array of sensors that are powered by a battery included in the brace, along with some sort of wired interface like a typical USB interface. In the case of use subsequent to a surgical procedure, the surgeon or other medical professional can be provided with information from both the above-discussed implants, as well as from the brace, in a single interface so that a complete picture of the patient's post-surgery joint operation can be easily evaluated.

Implantation of trackers 6910 can be performed either as an outpatient or inpatient procedure. Indeed, the small size of the trackers makes them particularly suited for minimally invasive placement through portal incisions. However, should the surgeon determine the need for a more invasive procedure, the trackers can be placed through larger incisions. Thereafter, the patient is simply tasked with wearing brace 6810 for a particular period of time so that data can be collected. It is contemplated that the patient can be provided with an app or similar program which can collect data via a smartphone or tablet. The patient can also receive information on their movements from such a program, or such could even be directed to perform certain movements (e.g., lunges, squats, etc.) to generate additional data. Moreover, such an interface could facilitate the remote uploading of data to a cloud or other database for subsequent viewing by the surgeon.

Figure 107:
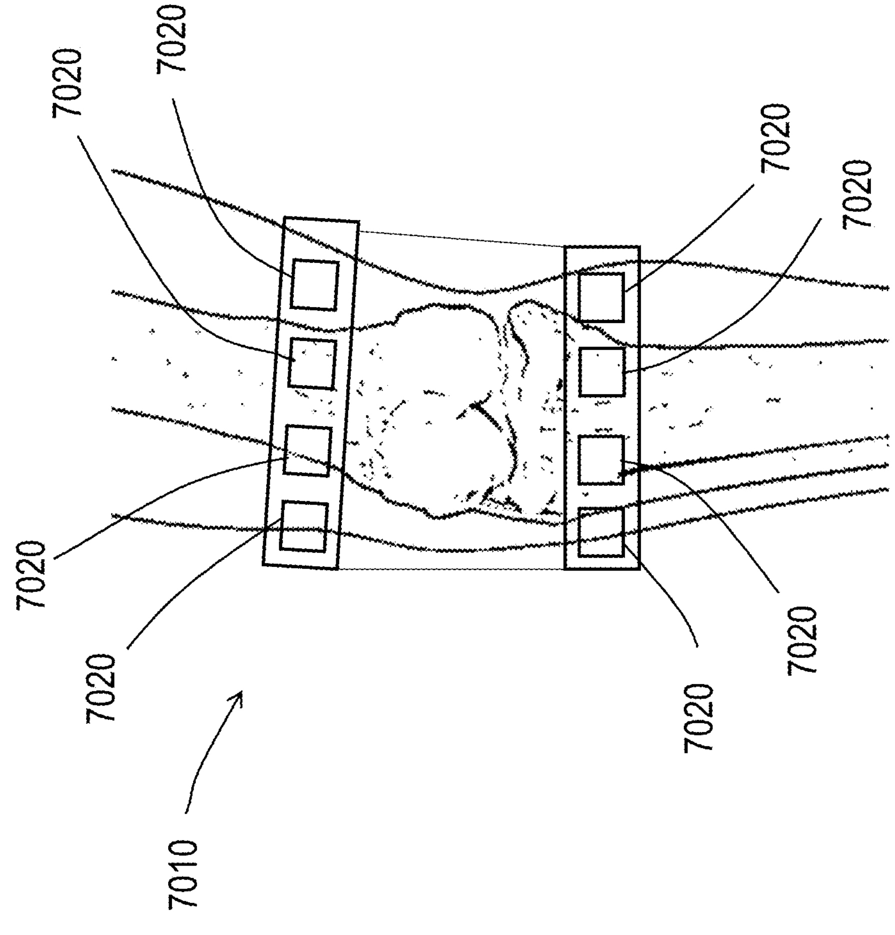

FIG. 107 schematically depicts an alternate brace 7010 that includes ultrasound sensors 7020 that are placed linearly along both upper leg and lower leg portions of the brace. Brace 7010, like brace 6810, can include a power source installed within or on it, and both braces and/or any sensors can be designed as one-time use devices. Brace 7010 precludes the need for the implantation of magnetic trackers, as ultrasound sensors 7020 do not require such devices. The use of this type of brace can therefore allow similar data collection on kinematics, without the need for a separate procedure to implant the trackers. Brace 7010 can include other sensors such as an IMU to provide bone motion classification which can be used in surgical planning or recovery/rehabilitation assessments in conjunction with bone relative movement and stress points data during joint motion obtained from ultrasound sensors 7020.

Figure 108:
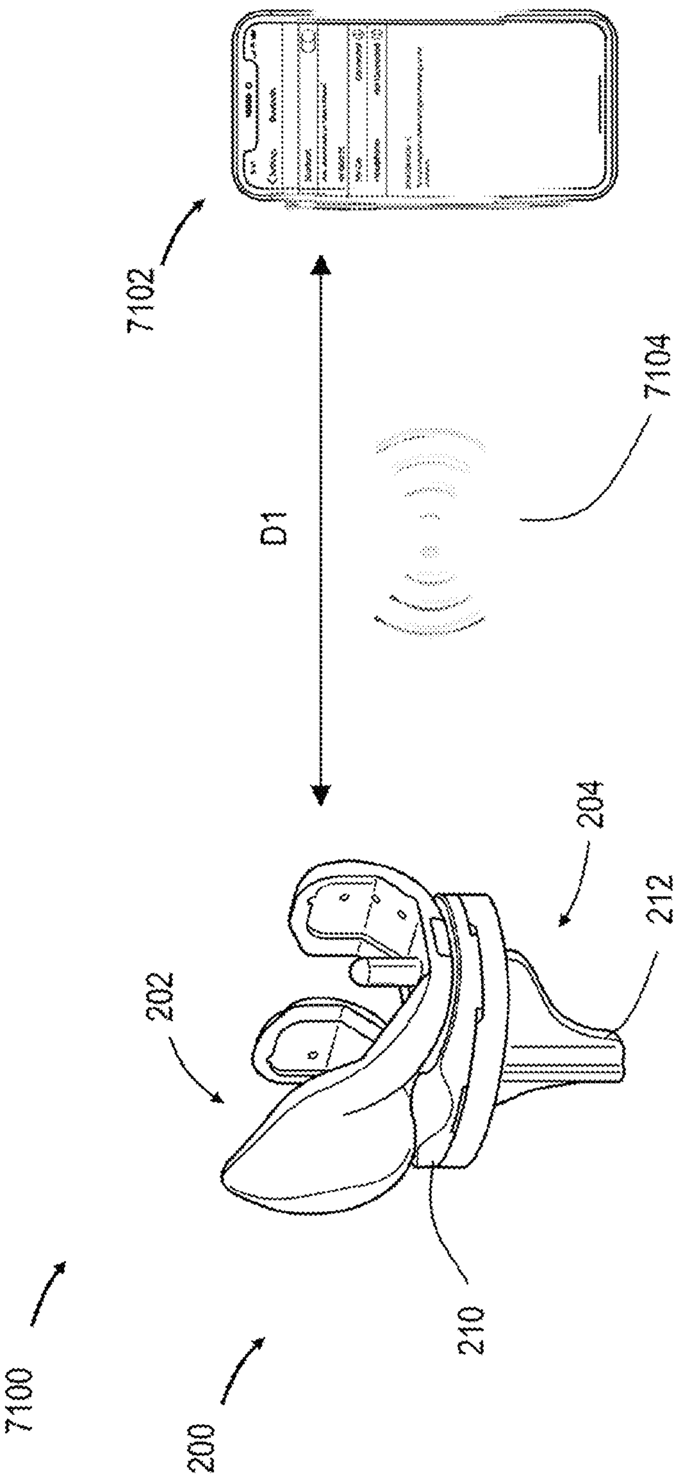
Figure 109:
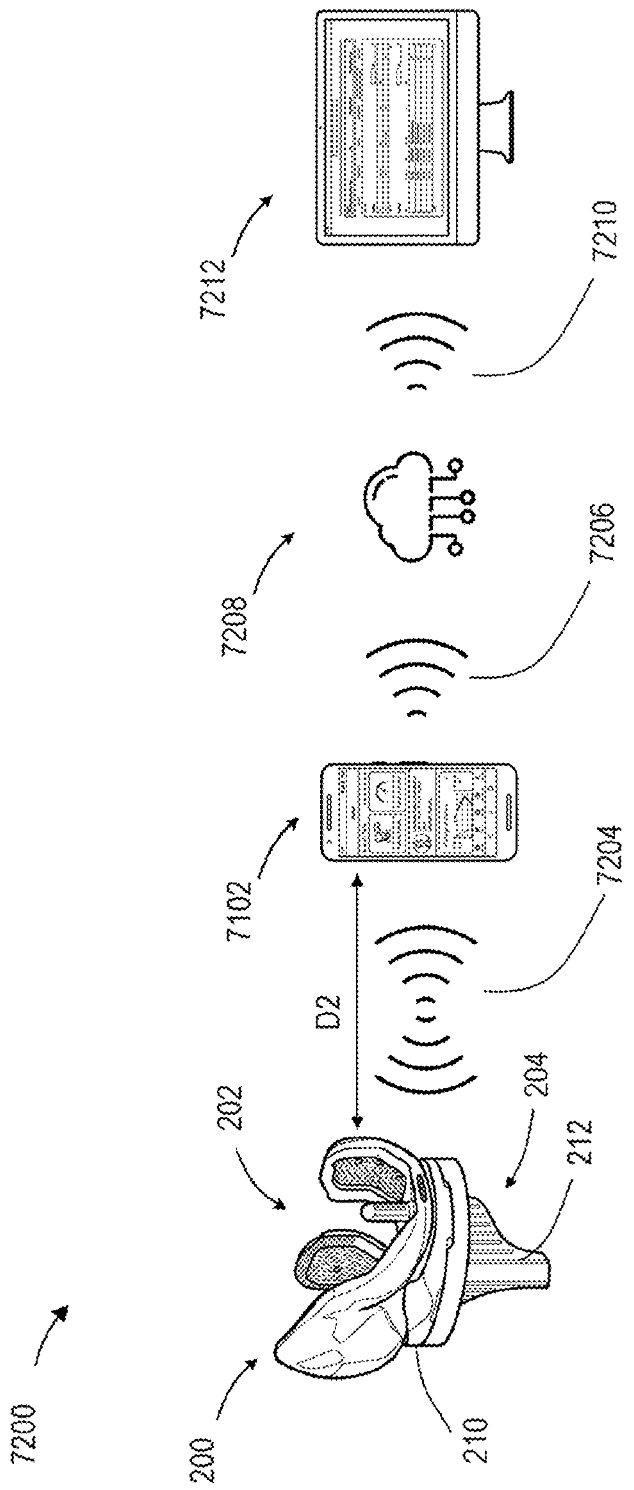

FIGS. 108 and 109 show a system for authenticating and connecting knee joint implant 200 to one or more external devices. While knee joint implant 200 is used as an exemplary example in this embodiment, any implant with sensors including any of the implants disclosed herein, can be used in other embodiments. Wirelessly connecting knee joint implant 200 to an external device allows the knee joint implant to transfer sensor data to the external device and to receive instructions from the external device to change or optimize implant performance if necessary. Ensuring regular sensor data transfer from the knee joint implant to an external source for monitoring implant performance depends, inter alia, on patient compliance and battery capacity of the implant. For example, a patient with knee joint implant 200 must regularly establish wireless connection between the implant and the external source to ensure that a surgeon or a health care professional ("HCP") can regularly monitor implant performance allowing the surgeon or HCP to quickly identify implant malfunction, abnormal patient recovery, etc., and immediately take action to correct same. The knee joint implant itself may be uncomfortable for the patient and they may not want to be reminded of it by having to regularly check it. The patient may be unfamiliar with the technology involved with monitoring the implant, and this can be daunting for some patients. For example, the patient may find it cumbersome to log on regularly to an external device using a password or other authentication credentials and wait for data transfer to be completed. The patient may have difficulty remembering to follow cumbersome monitoring schedules or passwords and may not be able or motivated to comply. Finally, the patient may not understand the importance of monitoring the implant results and may not be able to recognize the importance of following the prescribed schedule. All of these factors can make it difficult to ensure patient compliance to monitor implant performance. Further, implants with sensors require a battery that is not only small enough to fit in the implant, but also powerful enough to provide the necessary energy to all sensors and processing components located within the implant. The battery needs to be reliable and long-lasting, as well as safe to use. Knee joint implant 200 must be in advertising mode to transfer data to the external device. However, the knee joint implant will be constantly searching for wireless connections such as Bluetooth Low Energy ("BLE"), etc. in the advertising mode and thereby drain battery energy. The systems disclosed herein addresses these issues by providing a convenient and secure authentication and connectivity between knee joint implant 200 and an external device while simultaneously minimizing battery energy consumption. It should be understood that the term "implant performance" as used herein includes related patient condition such as the condition of tissue and bone around the implant, etc.

As shown in FIG. 108, knee joint implant 200 automatically establishes a bi-directional first communication 7104 with an external device such as a patient's smartphone 7102 when the smartphone is placed close to the knee joint implant. In this embodiment, first communication 7100 is a short-range wireless technology such as Near Field Communication ("NFC") 7104 that enables an NFC chip in tibial insert 210 and an NFC chip in smartphone 7102 to interact with each other when they are in close proximity with each other as shown by a distance D1 in FIG. 108. Distance D1 depends on the short-range technology being used. In the example shown in FIG. 108, a minimum distance of approximately 10-5 cm between the implant and the smartphone is necessary for the NFC chips in the tibial insert and the smartphone to interact with each other. A patient only needs to place their smartphone 7102 close to knee joint implant 200 to trigger first communication 7100. No other steps such as password entry, fingerprint authentication, etc., is required. While a smartphone is shown in this embodiment, it should be understood that other patient devices such as a watch, tablet, credential device, fob, etc. can be used in other embodiments. Once first communication 7100 is initiated, authentication data from knee joint implant 200 is transferred via NFC to smartphone 7102 and knee joint implant 200 switches from a deep sleep mode to an advertising mode. NFC-enabled knee joint implant and smartphone allow secure and convenient data transfer. NFC utilizes radio frequencies to establish a connection between the two devices, which allows for the exchange of data. NFC interaction does not require any manual configuration and is significantly faster than Bluetooth or Wi-Fi.

In the advertising mode, knee joint implant 200 establishes a bi-directional second communication 7200 between knee joint implant 200 and smartphone 7102 which then communicates with external platforms such as cloud 7208 and a remote monitoring platform 7212 as best shown in FIG. 109. Second communication 7200 between knee joint implant 200 and smartphone 7102 can be accomplished using a low energy communication protocol such as a BLE connection 7204 shown in FIG. 109. A distance D2 between knee joint implant 200 and smartphone can be considerably greater than D1—i.e., between 10 to 100 meters, to maintain BLE communication between these devices. Once a patient initiates the first communication by bringing smartphone 7102 in close proximity to knee joint implant, the smartphone no longer needs to be held close to the knee joint implant for data transfer via BLE. Thus, the patient can continue with their daily activities while the knee joint implant is transferring data to one or more external devices. Smartphone 7102 can function as an intermediary to transfer data obtained from knee joint implant 200 to cloud 7208 via a Wi-Fi connection 7206 or other suitable communication protocols. Data from cloud 7202 can be securely accessed through remote monitoring platform 7212 via a Wi-Fi connection 7210 or other suitable communication protocols. Thus, a surgeon or health care professional can conveniently and securely receive knee joint implant data to monitor implant performance and patient recovery. Thus, the authentication and connectivity between knee joint implant and one or more external devices and remote platforms can be conveniently initiated and completed by a patient momentarily bringing their smartphone in proximity with the knee joint implant. Further, as second communication 7200 provides bi-directional communication, a surgeon or healthcare professional can optimize knee joint implant performance in response to the observed data. Once data transfer is complete, knee joint implant 200 can switch off advertising mode and fall back to sleep mode to conserve battery energy. While NFC, BLE and Wi-Fi connections are disclosed in this embodiment, it should be understood that any suitable communication protocol can be used in other embodiments. For example, Zigbee, Z-Wave, etc. can be used instead of BLE in other embodiments.

Figure 110:
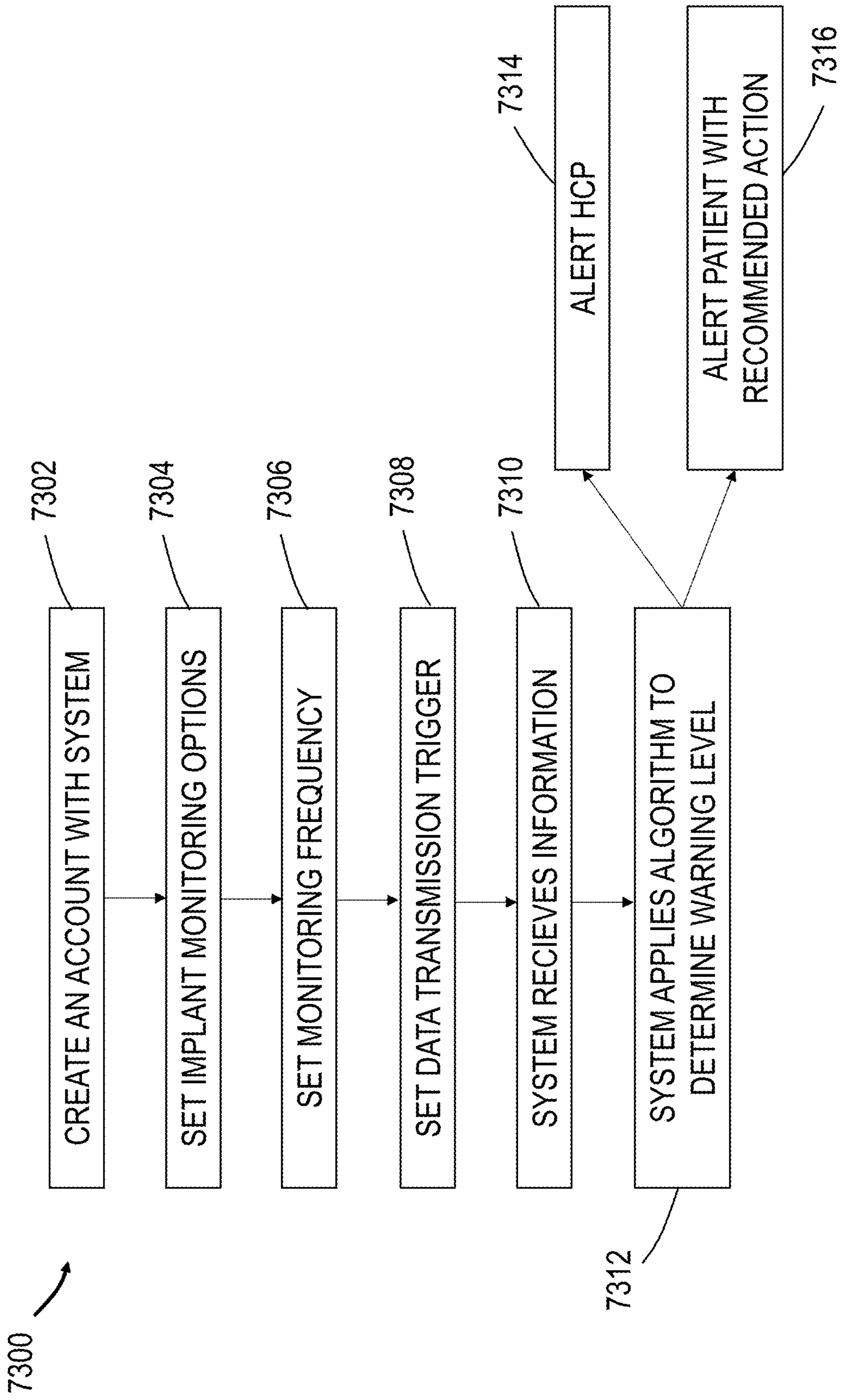

Referring now to FIG. 110, there is shown a flowchart 7300 describing steps of providing a peripheral service via a system that serves as a patient health management platform for an implant such as knee joint implant 200. While knee joint implant 200 is used as an exemplary example in this embodiment, any implant with sensors including any of the implants disclosed herein, can be used in other embodiments of the system. The system allows HCPs to provide remote medicine with no geographical boundaries. Through a mobile device such as a smart phone or remote monitoring platform 7212 shown in FIG. 109, an HCP or a patient can create a patient account with the system in a step 7302. A list of monitoring options available can then be set through the system in a step 7304. For example, an HCP can request average daily knee joint range of motion for a patient with knee joint implant 200. The HCP can request the knee joint implant 200 to provide range of motion monitoring to evaluate joint mobility and stability, implant torque monitoring to evaluate the stability of the implant, force measurements to monitor the amount of force between the femoral and tibial components, temperature of the implant and surrounding anatomy using the temperature sensors of knee joint implant 200 to monitor and detect any changes in temperature that may indicate a problem, implant displacement monitoring to detect any changes in the position or alignment of the implant, vibration monitoring to detect any abnormal vibrations in the implant, bone-implant interface monitoring to detect any changes in the attachment of the implant to the bone, etc. HCPs can also set the frequency of measurements in a step 7306. For example, the HCP can use step 7306 to set the frequency of measurements for rehabilitative monitoring to ensure that patients are receiving the best care possible. By monitoring the implant and patient performance on a regular basis, the HCP can ensure that the patient is receiving the most optimal amount of monitoring for rehabilitation. This will ensure that any changes in the patient's condition can be detected and treated quickly and effectively.

The HCP can configure the method of transferring measurement data from the implant to system in a step 7308. It should be understood that data from the knee joint implant can be transferred to the system in a variety of ways without any input from the patient. One such way is described in detail with reference to FIGS. 108 and 109. Additionally, other methods such as automatically transmitting data at preset intervals or when the patient is within range of a transmission source such as a router can be used. This allows for data to be collected without the patient having to manually initiate the transfer or provide any input. The readings that are queued by the HCP are then received by the system in a step 7310. AI algorithms are run to determine warning levels and alert the HCP of any potential issues in a step 7312. AI can be used to monitor sensor data from knee joint implant 200 to detect any problems and provide corrective steps by using a combination of machine learning algorithms and deep learning models. The AI system can be trained on a large dataset of sensor readings to learn the expected implant performance for proper rehabilitation. It can then be used to detect any anomalies in the data and provide corrective steps. For example, the AI system can detect a low battery level and recommend charging or replacing the implant. It can also detect any abnormalities in the readings and alert the patient or HCP to take corrective action in a step 7314.

The system can prompt the patient to take corrective action such as resting their joint in a specific position, or calling the HCP in a step 7316. The system may also display a predefined or real-time message from the HCP, thus initiating communication between the patient and the HCP.

Thus, the system serves as a patient health management platform for an implant such as knee joint implant 200. The system allows for sharing patient medical information between various HCPs and institutions. For example, a patient's General Practitioner may not have a complete understanding of a patient's medical history, such as a Total Knee Arthroplasty (TKA). However, the General Practitioner can now quickly and easily obtain this information via the system. Despite the convenience of the system, it is important to note that the system is configured to address privacy concerns before the General Practitioner is granted access to the information. This ensures that the patient's privacy is being respected and protected. Currently, medical history sharing is a manually initiated process subjected to delays. The system disclosed herein allows for data to be available readily including in an emergency. It provides continuity of support and assurance regardless of the location and distance to an HCP.

In accordance with another embodiment of the present disclosure, the system can be utilized to effectively track and display implant performance for both patient and HCP. The system is designed to provide an alternative solution to the current issue of patients over- or under-utilizing their joint post-op, with limited feedback and subjectivity as to their return to activity. Instead of relying on surgeon guidance based on what is known about a patient's expected use, the system disclosed herein collects and displays patient data, including mobility and sensor data, as well as activity and goal achievements, physical therapy, etc. The patient is given the ability to enter their own pain levels and joint restrictions such as limited range of motion, etc., as well as other personal factors which can then be evaluated using the AI algorithm and passed on to the HCP for recommendations of corrective action. Through this close monitoring of the patient's recovery, any deviations from the normal course can be identified and addressed swiftly, avoiding the need for more drastic interventions such as a revision surgery.

In another embodiment of the system of the present disclosure, HCPs can interact with patients in real time, either through voice or video connection. For example, an HCP can instruct a patient to position the joint in a specific pose, direct specific actions for additional evaluation, and command actions on the implanted sensor technology. The patient's movements can be monitored in real time and the data collected is streamed directly to the HCP. In addition, the HCP can instruct patients to move their joint in any desired direction and the measurements taken can be queued and transmitted to the HCP as soon as they are completed. This provides the HCP with an effective method of monitoring the patient's progress and accurately evaluating their condition.

Figure 111:
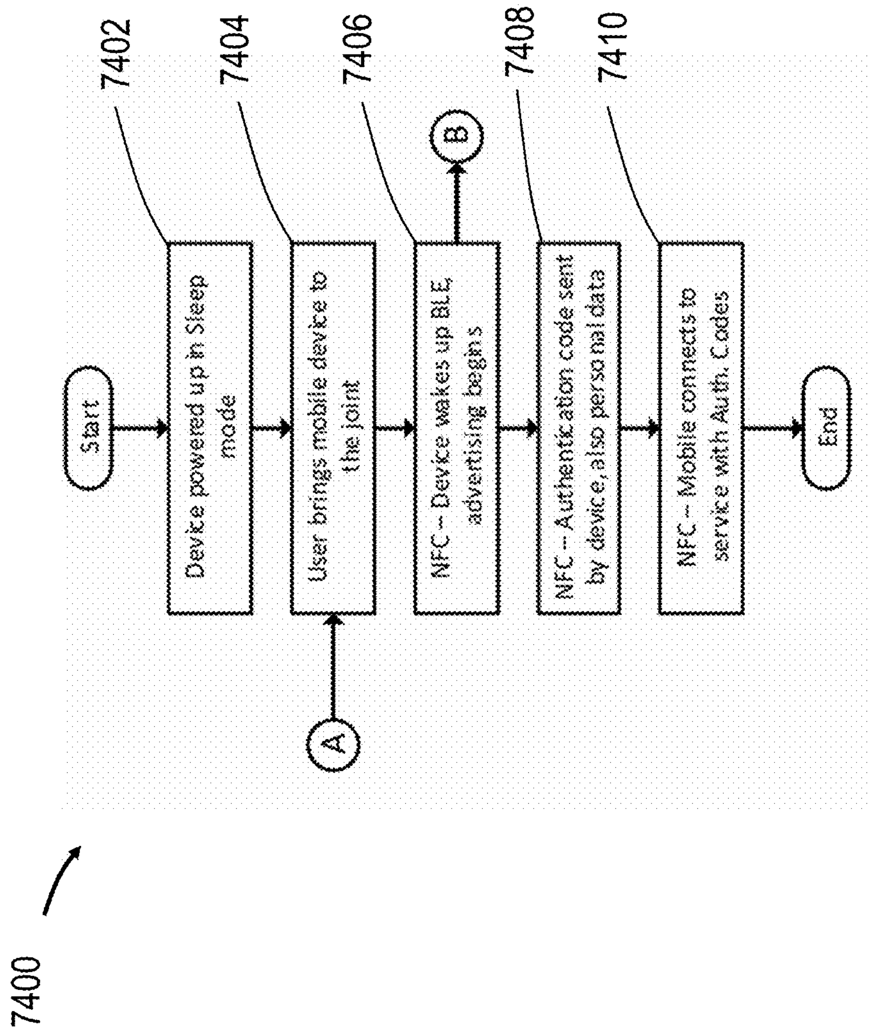

Referring now to FIG. 111, there is shown a flowchart 7400 describing steps of a first communication between an implant with sensors such as knee joint implant 200 and an external device such as a patient's smartphone 7102. Prior to initiating a first communication such as an NFC connection between knee joint implant 200 and smartphone 7102, knee joint implant 200 can be in a deep sleep mode in a step 7402. A deep sleep mode ensures that knee joint implant's battery is not consuming any energy for data transfer. A patient then places a mobile device or an external device such as smartphone 7102 adjacent knee joint implant 200 in a step 7404. NFC chips in each of the knee joint implant 200 and smartphone 7102 interact with each other when a distance between the two devices is equal to or less than D1 in a step 7406. The NFC interaction results in switching on knee joint implant 200 to an advertising mode. Authentication credentials such as implant serial number, health care professional ID, location of implant, type of implant, patient details, etc. stored on knee joint implant 200, smartphone 7102, or a cloud-service platform 2808, is exchanged via NFC in a step 7408 to complete authentication. Upon successful authentication, a communication link between knee joint implant 200 and smartphone 7102 is established in a step 7410.

Figure 112:
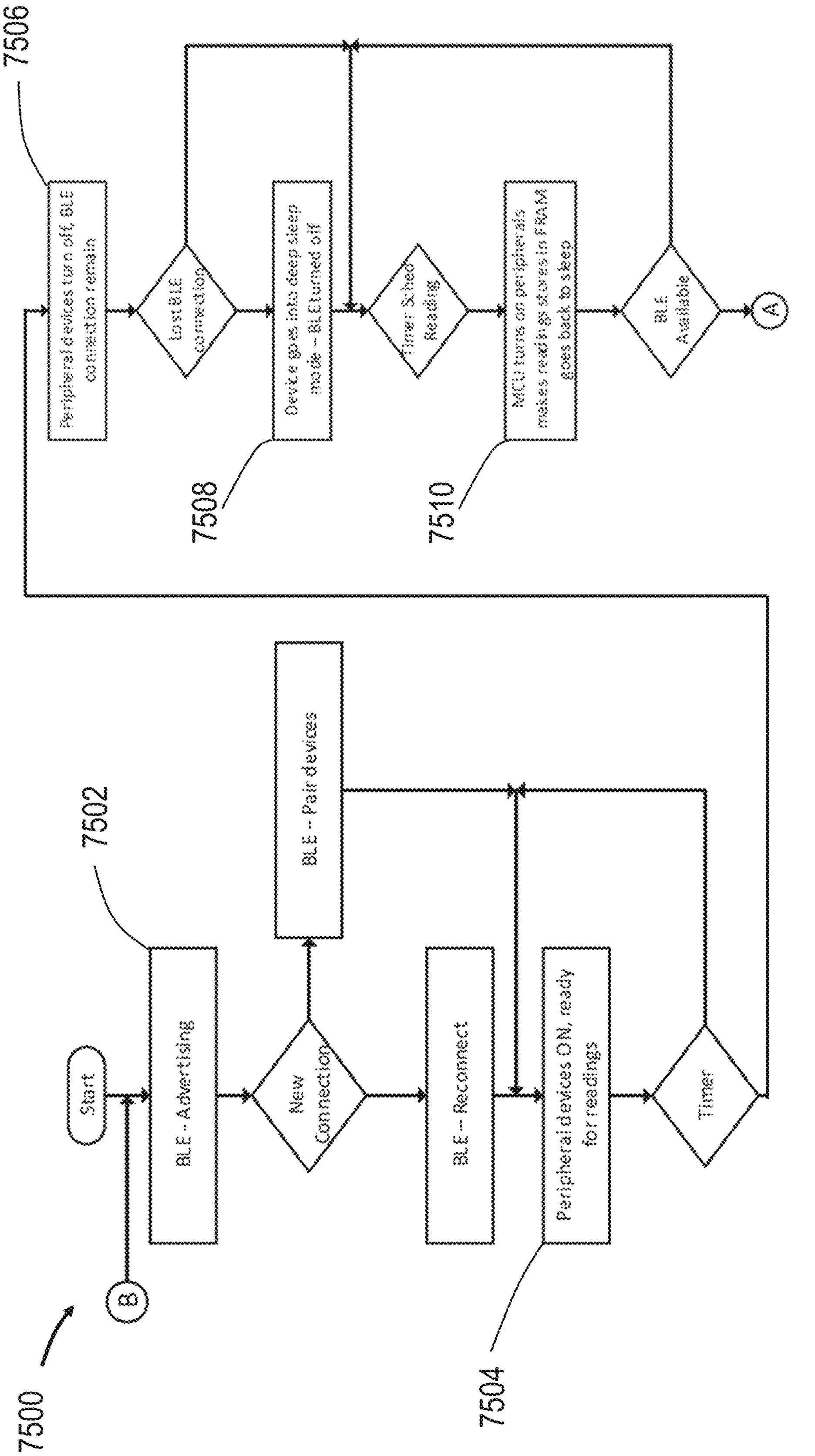

FIG. 112 shows a flowchart 7500 describing various steps of a second communication such as a BLE connection between knee joint implant 200 and smartphone 7102. As more fully described above, the second communication between knee joint implant 200 and smartphone follows the first communication. Once the knee joint implant turns on the advertising mode in a step 7502, knee joint implant broadcasts a wireless radio signal which is picked up by a previously paired BLE device such as smartphone 7102 or another device to establish a connection between the knee joint implant and the smartphone or other device. Peripheral devices are now activated to receive data in step 7504. A timer or signal to indicate completion of data transfer can be used to turn off the peripheral devices in a step 7506. Upon realizing that the peripheral devices are turned off, knee joint implant once again returns to a deep sleep mode in a step 7508 to conserve battery energy. Alternately, knee joint implant can include a timer to attempt to reconnect to the peripheral devices if, for example, connection is lost before completion of data transfer. Once connection is restored, data transfer can be completed as shown in a step 7510.

Figure 113:
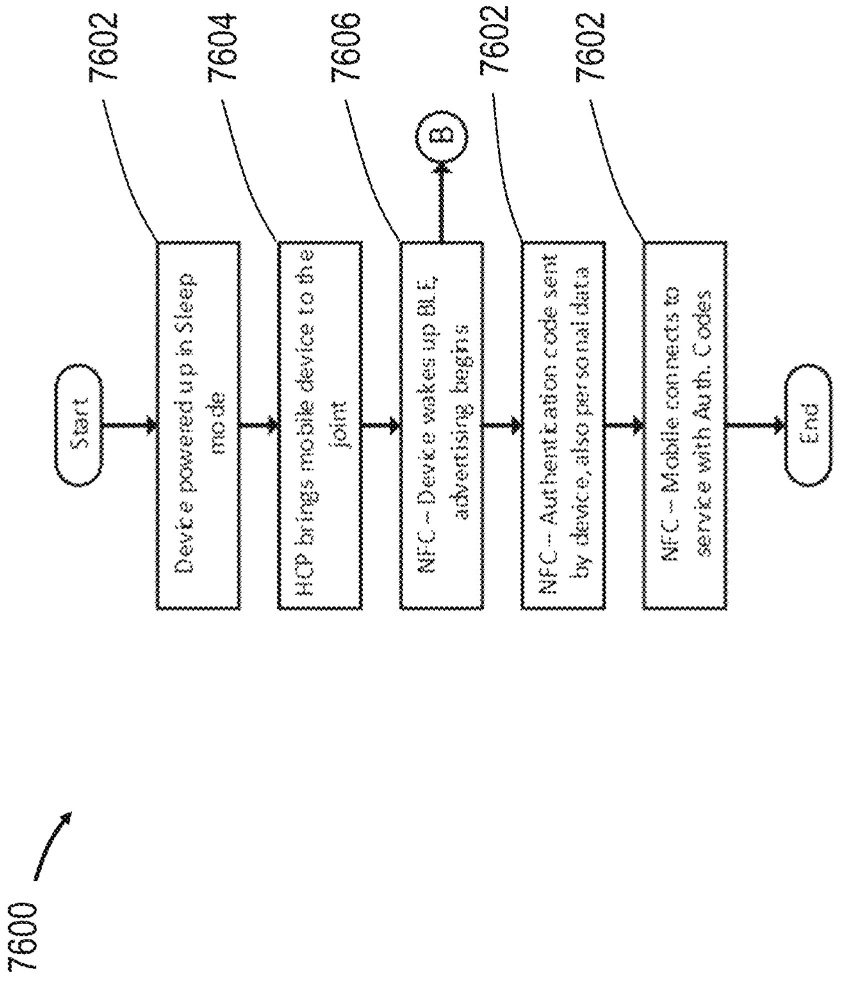
Figure 114:
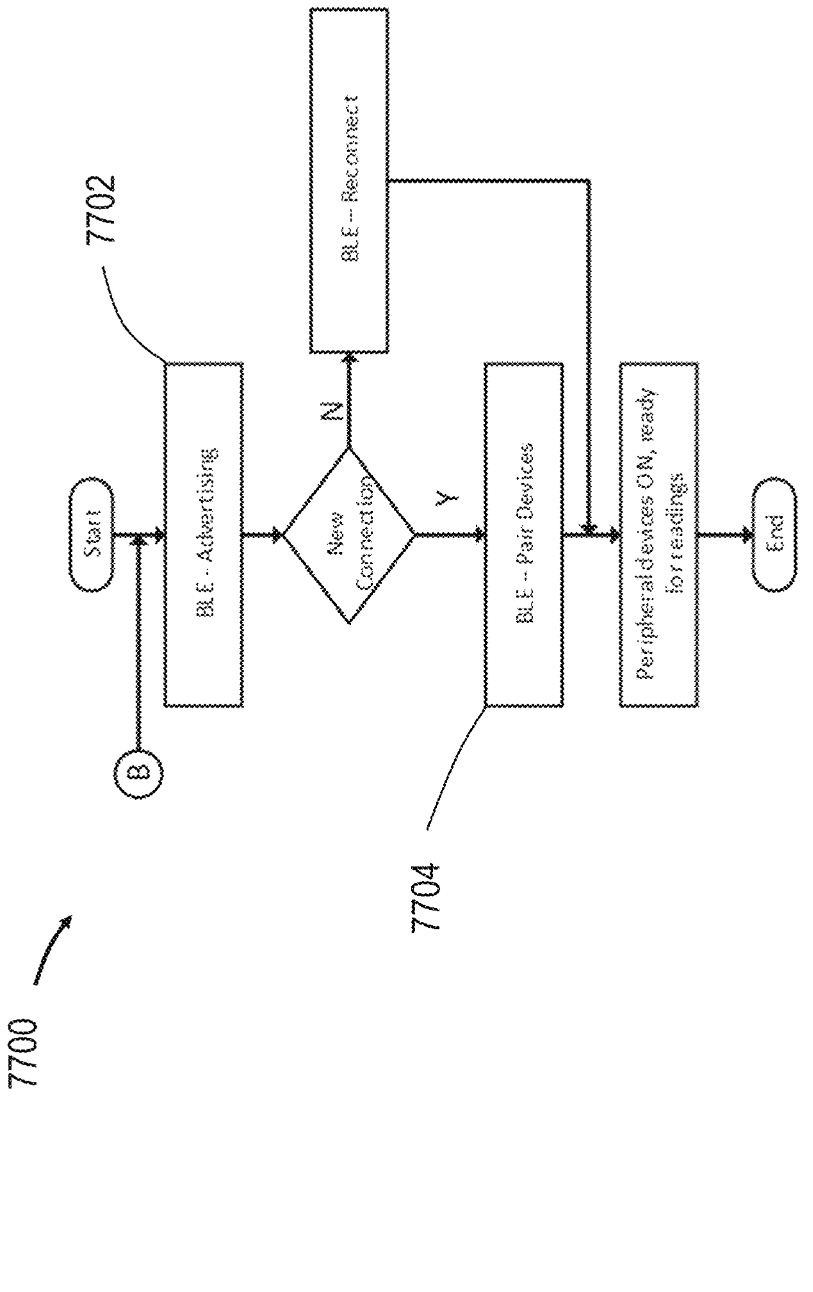

FIG. 113 is a flowchart 7600 describing steps of a first communication between an implant with sensors such as knee joint implant 200 and an external device such as a HCP's smartphone 7102. Flowchart 7600 is similar to flowchart 7400, and therefore like steps are referred to with similar numerals within the 7600-series. However, an HCP uses an external device to initiate the first communication via NFC in step 7606. Thus, no patient action is required to establish first communication in this embodiment. FIG. 114 shows a flowchart 7700 showing steps of a second communication following the first communication described in flowchart 7600. Flowchart 7700 is similar to flowchart 7400, and therefore like steps are referred to with similar numeral within the 7700-series.

Figure 115:
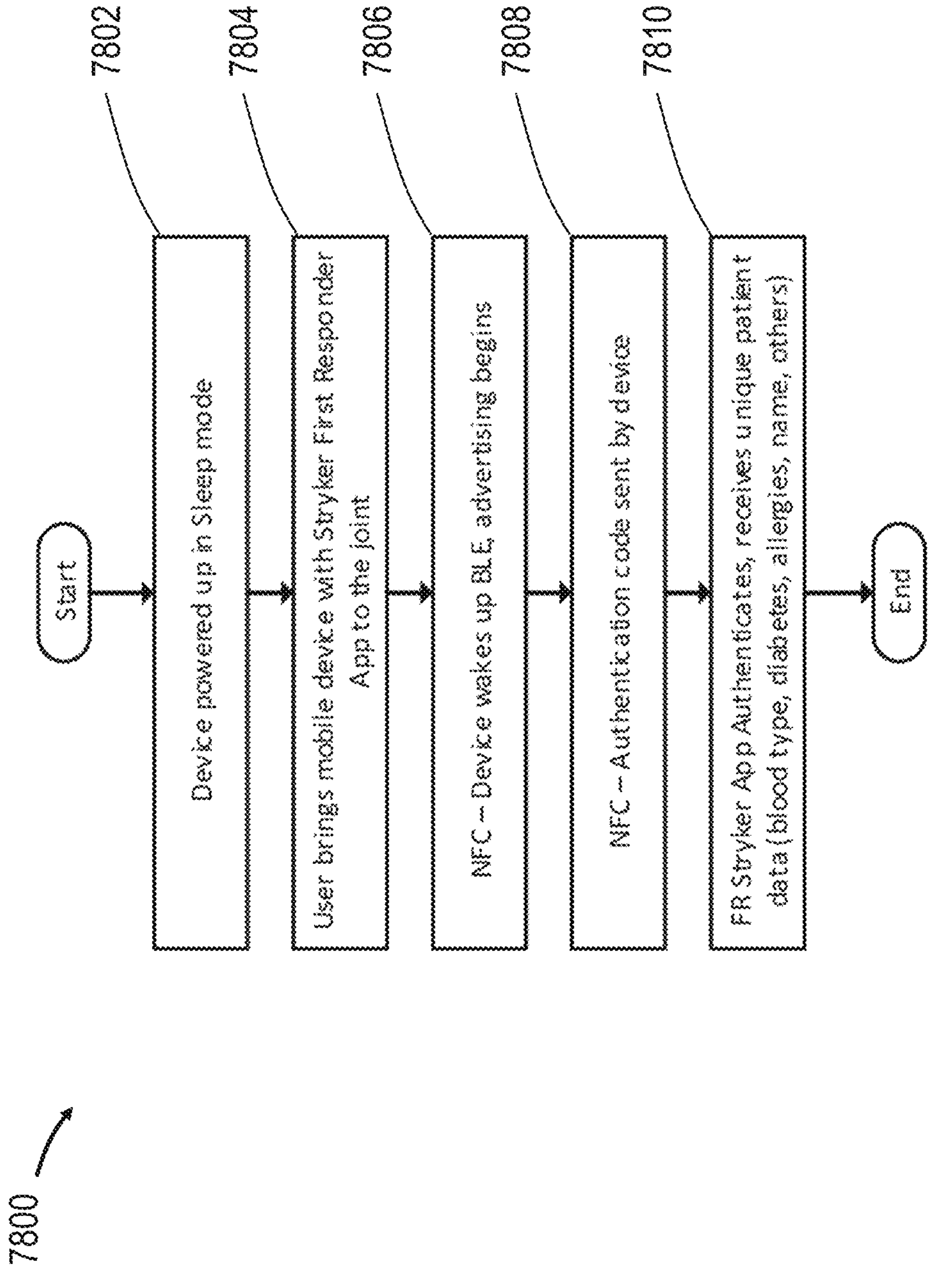

Referring now to FIG. 115, there is shown a flowchart 7800 describing steps for a first responder such as an EMT, paramedic, firefighter, emergency service personnel, etc. to establish communication with a disabled patient using a patient implant such as knee joint implant 200. Prior to initiating a first communication such as an NFC connection between knee joint implant 200 and a first responder device such as smartphone, watch, fob, etc., knee joint implant 200 can be in a deep sleep mode 7802. The first responder then places the first responder device adjacent knee joint implant 200 in a step 7804. NFC chips in each of the knee joint implant 200 and the first responder device interact with each other when a distance between the two devices is less than D1 in a step 7806. The NFC interaction results in switching on knee joint implant 200 to an advertising mode. Authentication credentials such as implant serial number, health care professional ID, location of implant, type of implant, etc., stored on knee joint implant 200 is transmitted to the first responder device via NFC in a step 7808 to complete authentication. Upon successful authentication, a communication link between knee joint implant 200 and the first responder device is established in a step 7810. Upon establishing this secure communication, unique patient information stored on knee joint implant such as patient blood type, allergies, diabetes, etc. is transmitted via NFC to a secure app on the first responder device in a step 7810. Thus, a first responder can retrieve vital patient information from a disabled, unresponsive, or unconscious patient by simply placing the first responder device in proximity with the knee joint implant. While a knee joint implant is described in this embodiment, any implant with sensors such as the examples disclosed herein, or an implant without sensors but with a memory storing patient data can be used in other embodiments.

FIG. 116 is a front view of a knee joint implant 7900 according to an embodiment of the present disclosure. Knee joint implant 7900 includes a femoral implant 7902 located on a femur 7906 and a tibial implant 7904 located on a tibia 7908. Tibial implant 7904 has a tibial insert 7910 configured to contact femoral implant 7902, and a tibial baseplate or tibial stem 7912 extending distally into tibia 7908. Tibial insert 7910 includes at least one transducer, e.g., a medial transducer 7914 and a lateral transducer 7916, each configured to read analog knee implant parameters, such as vibration, magnetic flux density, etc. An analog to digital converter 7918 is configured to convert the analog knee implant parameter data to digital data (FIG. 118). A processor 7920 analyzes and stores the digital data, which a data transmitter, such as an antenna 7936 located on tibial insert 7910, transmits to an external source 7926 like a smart phone, tablet, monitor, network, etc. to allow for real time review of the knee joint implant performance.

Figure 117:
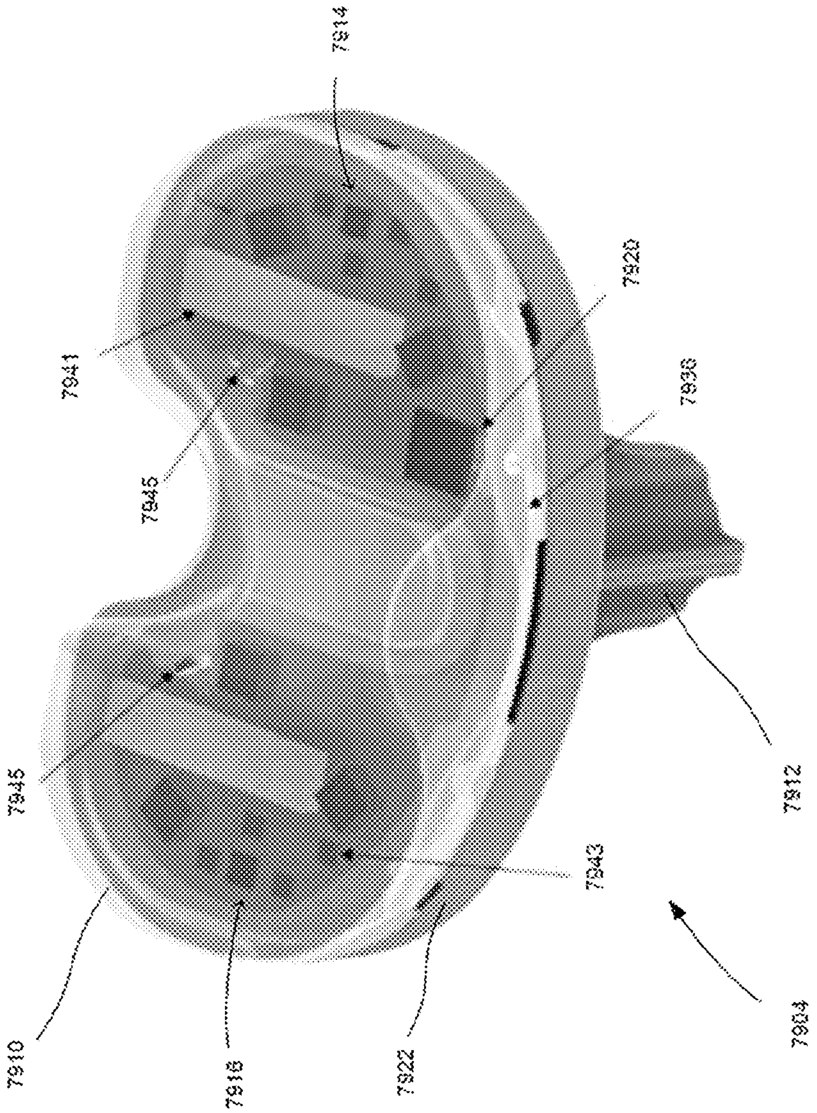

FIG. 117 illustrates additional details of tibial implant 7904 and tibial insert 7910. Tibial insert 7910 includes a tibial stem 7912 and tibial tray 7922 to receive tibial insert 7910. Tibial insert 7910 extends in a tray-like fashion in a superior direction away from the tibia and toward the femur. Tibial insert 7910 is preferably enclosed on all sides to protect the components within the insert, but may be accessed through an opening (not shown) or hinged region (not shown) to analyze, remove, or replace components within tibial insert 7910.

Continuing with FIG. 117, tibial insert 7910 includes a pair of transducers, e.g., a medial transducer 7914 and a lateral transducer 7916. Each transducer 7914, 7916 is positioned adjacent a respective condyle 7928, 7930 such that each transducer determines knee implant parameters based on a reading from separate condyles. Each transducer 7914, 7916 may be a standard type of transducer known in the art that can detect a vibration signal. For example, the transducers may be a strain gauge, accelerometer, microphone sensor, eddy-current sensor, or other sensor type known in the art. Transducers 7914, 7916 are configured to determine a vibration parameter of each respective condyle when an acoustic exciter 7932 emits a signal through a patient's knee. Thus, a transducer may be selected that is compatible with the type of acoustic exciter 7932 used in a particular implantation. For example, in an embodiment where the acoustic exciter 7932 is an ultrasound machine, the transducers 7914, 7916 may be microphone sensors. It is envisioned that other transducer types may be implemented with other acoustic exciters. Transducers 7914, 7916 may be secured to tibial insert 7910 using conventional securement means known in the art, such as fasteners or friction fits. In an alternative embodiment, transducers 7914, 7916 may be positioned in a medial encoder track (not shown) extending around a medial side of insert 7910 and/or a lateral encoder track (not shown) extending around a lateral side of the insert 7910. Tibial insert 7910 may further include additional transducers, such as Hall sensors 7943 and infection or injury detection sensors 7945.

Acoustic exciter 7932 may be a unique ultrasound machine or other exciter configured to send a readable signal. In other embodiments, acoustic exciter 7932 may be a commonly available ultrasound machine that analyzes the harmonics of bone resonance. Acoustic exciter 7932 may be placed at various locations relative to the patient to achieve a desired result. Typically, placing exciter 7932 close to bone will yield the clearest signal that is less affected by soft tissue artefact. Often, it is desirable to place exciter close to a portion of bone in which the bone is close to the surface of the overlying skin. Examples of such places include the anterior portion of the tibia and the medial and lateral sides of the knee epicondyles.

Each of transducers 7914, 7916 is configured to detect and output a vibration signal 7950, shown in FIG. 116, when an acoustic exciter 7932 emits a pulse through a patient's knee. Due to the transducers' location in tibial insert 7910, the transducers can detect the vibration signal 7950 for both the medial and lateral sides of the entire knee implant 7900 and any bone cement used to secure the implant. The vibration signal 7950 can then be remeasured at various time intervals after the initial implantation to detect a change in vibration signal that could indicate implant loosening, subsidence, implant damage, or other signs of implant detachment. This method is advantageous over other detachment detection methods as the patient's leg does not require excessive manipulation in ways that could further harm a patient or provide false readings due to human error.

FIGS. 118-119 illustrate a processor system 7920 for processing the vibration signal experienced in the knee implant 7900. An onboard processor 7920 is also positioned within tibial insert 7910. Processor 7920 may be any processor known in the art, and preferably includes an arithmetic and logical unit (ALU) (not shown), a control unit such as a microcontroller 8002, and a memory unit (not shown). In order for processor 7920 to receive analog data from transducers 7914, 7916, the vibration signal 7950 is converted from analog to digital form by an analog to digital converter 7918. Such a converter may be any converter known in the art and may have any architecture type known in the art. After conversion, the vibration signal 7950 may be referred to as a vibration signature 7960.

FIG. 119 illustrates a series of operations in flowchart form the processor 7920 may make to determine whether the implant has detached from its original, implanted position, implant subsidence, or implant damage. Processor 7920 may receive multiple streams of data. A first data stream 8006 may be initiated with input data samples from transducers 7914, 7916 being stored in a buffer 8010. The first data stream 8006 may then be transformed using fast Fourier transformations 8012 or other transformation types known in the art. A second buffer 8014 may then store the transformed data. A peak detector 8016 may then determine the maximum vibration value for the first data stream 8006. A second data stream 8008 may include a set of threshold vibration values 8026 that were stored in memory just after initial implantation. The microcontroller 8002 may then compare the measured data from the first data stream 8006 to the threshold stored data in the second data stream 8008. Result data 8018 may then be released from processor 7920 and emitted to an external source 7926. The result data 8018 may be emitted by a transmitter, such as a Bluetooth transmitter 7940 or other wireless communication types known in the art. An antenna 7936 may be positioned in or on tibial insert 7910 to aid in the data transmission process. Antenna 7936 includes may include screw threads configured to be attached to tibial insert 7910. Antenna 7936 can include a coax interface to shield knee joint and improve transmission between knee joint implant 7900 and the external source. A battery 7941 may be located adjacent antenna 7936 to power the various components of knee joint implant 7900. Antenna 7936 can serve as a charging port via radio frequency (RF) or inductive coupling if a rechargeable battery is used. The location of battery 7941 and antenna 7936 in tibial insert 7910 allow for convenient access to remove and replace these components if necessary.

FIGS. 120-121 illustrate graph outputs from the data computed by microcontroller 8002 as it compares the values from data streams 8006, 8008. The output data ideally includes response, peak, and magnitude data of the signal under various frequencies. From this data, a peak amplitude 8020 may correspond to a given frequency and thus create a signature of the implant, bone, cement, or the system of the implant, bone, and cement. The graphs may chart the amplitude in decibels along the y-axis and the frequency in kHz along the x-axis. The peak amplitudes 8020 at various frequencies may then be recorded and compared to previous values. The peak amplitude 8020 as a function of the frequency is the signature of the implant and the patient's bone density at the time of implantation. Thus, a change in amplitude over time may indicate a loss of connection between the implant and the bone. An operator or external computer program may then analyze the data and graphs over a given time period to determine if the implant has shifted from its original position. For example, FIG. 120 depicts a graph with a nearly constant amplitude of around −60 dB for various frequencies. Alternatively, FIG. 121 depicts a graph with a peak amplitude that varies at different frequencies. If the nature—i.e., pattern of the signal, varies over time, it may be indicative of implant loosening, detachment, or subsidence.

A method of using the system described in FIGS. 116-120 is provided herein. First a patient undergoes a total knee arthroscopy and a knee implant including a femoral implant 7902, a tibial implant 7904, and a tibial insert 7910 are implanted in the patient's knee. The tibial insert 7910 includes a pair of transducers 7914, 7916, one transducer positioned within insert 7910 and corresponding to a medial condyle 7928 and one positioned within insert 7910 and corresponding to a lateral condyle 7930, as is depicted in FIG. 117. After the operation and once any bone cement has hardened, an operator may activate an acoustic exciter 7932 located external to the patient's body such that the acoustic exciter 7932 sends a pulse through the patient's knee at various frequencies. For example, the exciter 7932 may provide a fixed input of 0 dB for each 1 kHz, 3 kHz, and 5 kHz signal to the transducer. The initial vibration readings post-operation (or after the patient has had the time to properly heal), provide a threshold value that act as a baseline for determine the implant's position, as the implant likely experienced minimal shift post-operation. Subsequent readings may be taken at time intervals after the threshold readings are taken. For example, a patient may be tested annually. After the threshold readings have been collected, they may be stored in the processor's memory system as vibration signatures 7960 such that they can later be compared with measured values.

As the acoustic exciter 7932 emits a pulse through the patient's knee, the pulse transfers a vibration energy through the bone and through the implant structure. Thus, transducers 7914, 7916 located in tibial insert 7910 are configured to detect the vibration energy being transferred from the femur 7906 and tibia 7908 to the knee implant 7900. Further, because each transducer 7914, 7916 is positioned adjacent a condyle 7928, 7930, each transducer 7914, 7916 can provide specific data relating to a medial and lateral side of the patient's knee.

The transducers 7914, 7916, are preferably vibration-detecting transducers such as strain gauges, accelerometers, microphone sensors, or the like. Each transducer 7914, 7916 is configured to read a vibration signal being transmitted between bone, bone cement, and the knee implant 7900. Transducers 7914, 7916 record the vibration signal as an analog signal, which is then passed through an analog to digital converter 7918 to a microcontroller 8002. The vibration signal is passed through a series of buffers 8010, 8014 and is then transformed using fast Fourier transformations 8012 or other transformation types known in the art. The data then moves through a peak detector 8016 to determine peak amplitudes of the vibration signatures 7960. Finally, the data is compared to the stored threshold data to determine if a delta occurs over time. This delta is subsequently stored as a DC offset in non-volatile RAM in the processor's memory system. Alternatively, the measured data may be compared against a previously measured data. Incoming data into the processor 7920 may be compensated by the offset to read 0 dB by the transducer at each frequency. Thus, various noises can be filtered from the system when the acoustic exciter 7932 is oriented at different positions relative to the patient.

Several methods may be implemented to filter noise throughout the system. First, positioning acoustic exciter 7932 in a clearly defined position relative to the patient can limit noise based at least on the tissue thickness and distance between the bone and the tissue. Various instrumentation, such as inertial measurement units (including inertial measurement units in the implant), may be used to ensure the exciter 7932 is in the same location for repeated tests. The same instrumentation may also be used to ensure that the patient and the patient's extremities are in the same position for repeated tests. Second, multiple vibration profiles may be taken at various poses and average profiles may be created to ensure the algorithm is resistant to bias from a single measurement. Finally, false positives or other abnormal changes in signal readings can be remeasured to confirm accuracy.

Once the processor 7920 has finished comparing the measured data to the threshold data or to previously measured data, the processor 7920 outputs the data using wireless communication technology, such as Bluetooth, to an external source 7926 (FIG. 116). The external source 7926 may be a computer program configured to further analyze and present the data. For example, the data may be prepared as graphs as illustrated in FIGS. 120-122. The graphs may chart the amplitude in decibels along the y-axis and the frequency in kHz along the x-axis. The peak amplitudes 8020 at various frequencies may then be recorded and compared to previous values. The peak amplitude 8020 as a function of the frequency is the signature of the implant 7900 and the patient's bone density at the time of implantation. Thus, a change in amplitude over time may indicate a loss of connection between the implant and the bone, implant subsidence or other implant defect. As illustrated in FIG. 122, because each transducer 7914, 7916 measures data corresponding to a condyle, it is foreseeable that each condyle may have a different vibration signature. The difference between the medial and lateral condyle vibration signals may also be used to determine the amount of variation and the direction the implant is shifting. Thus, a graph may be created that shows the difference between each condyle's vibration signature.

Once the processor 7920 has compared and analyzed the input data, it determines result data 8018 corresponding to overall implant detachment. This result data 8018 may include a change in amplitude over time and a direction of change, the direction corresponding to at least one of the medial and lateral directions. The processor 7920 then sends the result data 8018 to a transmitter which transmits the data to an external source 7926. The external source may be a computer, smartphone app, or other electronic source configured to show data. The external source 7926 ideally may provide recommendations for patients experiencing implant detachment. Machine learning may be implemented to provide said recommendations or create alerts if the implant becomes detached.

FIG. 123 illustrates another embodiment of detecting implant detaching. In this embodiment, knee joint implant 8100 is similar to knee joint implant 7900, and therefore like elements are referred to with similar numerals within the 8100-series of numbers. Knee joint implant 8100 includes a femoral implant 8102 located on a femur 8106 and a tibial implant 8104 located on a tibia 8108. Tibial implant 8104 has a tibial insert 8110 configured to contact femoral implant 8102, and a tibial baseplate or tibial stem 8112 extending distally into tibia 8108 (not shown). Tibial insert 8110 includes at least one transducer, e.g., a medial transducer 8114 and a lateral transducer 8116, each configured to read analog knee implant parameters, such as vibration or magnetic flux density. An analog to digital converter 8118 (not shown) is configured to convert the analog knee implant parameter data to digital data. A processor 8120 analyzes and stores the digital data, which a data transmitter, such as an antenna 8136 located on tibial insert 8110, transmits to an external source 8126 like a smart phone, tablet, monitor, network, etc. to allow for real time review of the knee joint implant performance.

FIG. 124 illustrates a flowchart of the method steps for using implant 8100. Unlike the previous embodiment, the method of detecting implant detachment does not involve the use of an acoustic exciter. Rather, the method includes the steps of performing a TKA in a patient and implanting a knee implant 8100 including the above-mentioned components. After implantation, the patient undergoes a range of movement test to determine baseline movement data 8140 that can later be compared to other movement data. For example, the patient may perform an anterior-posterior drawer test to determine a range of motion. Alternatively, patients may perform other tests or potentially random range of motion tests as long as patient has a large range of motion. The transducers 8114, 8116 may be the same types of transducers mentioned above to detect vibration. Unlike the method where the patient remains stationary and a vibration signature is created from an acoustic exciter, this method requires a patient to move and create the patient's own vibration signature 7960. Accordingly, transducers 8114, 8116 may detect a vibration signature 7960 as the patient's knee is manipulated, and that data may be processed similarly to the data in the method.

After the baseline movement data 8140 is determine post-operation, a patient may perform identical range of motion tests at given time intervals to determine a new data point 8142 after potential loosening has occurred. For example, a patient may undergo a range of motion test annually, and the tenth annual test may indicate implant detachment compared to the reference movement data 8140. Accordingly, it is imperative that each resulting data gained from each range of motion test is properly stored in a memory system to ensure that results can be compared over a long time period.

Machine learning may be implemented to compare the data over time and provide recommendations for patients. As such, manual comparison may not be required to detect implant detachment. A database (not shown) of movements and average vibration responses for various patients may first be created. This database ideally includes information from patients of all ages, all body types, all knee operations performed, all range of movement tests performed, and the like. The machine learning algorithm may then extract feature data 8146 from the database and compare that feature data to similar feature data 8144 measured in a particular patient's range of movement test. An example of feature data 8146 is a reference vibration amplitude recorded when a patient undergoes an anterior drawer test under a maximum range of motion. This feature data 8146 may then be compared to the patient's measured vibration amplitude 8144 recorded from an anterior drawer test to determine if implant detachment is present. The machine learning algorithms may use classifier algorithms such as random forest or support vector algorithms to compare and contrast the data 8148. Alternatively, other algorithm types capable of comparing and contrasting data may be utilized to determine if implant loosening 8150 has taken place.

Similar graphs to those shown in FIGS. 120-122 may also be created using the previous method. Thus, an external source 8126 such as a computer or smartphone app may show the graphs and allow a clinician to interpret the data to the patient. The external source 8126 may also create alerts such as an audio alert or a visual alert when implant detachment is detected.

FIGS. 125-126 illustrates another embodiment of detecting implant detachment. In this embodiment, knee joint implant 8200 is similar to knee joint implant 7900, and therefore like elements are referred to with similar numerals within the 8200-series of numbers. Knee joint implant 8200 includes a femoral implant 8202 located on a femur 8206 and a tibial implant 8204 located on a tibia 8208. Tibial implant 8204 has a tibial insert 8210 configured to contact femoral implant 8202, a tibial baseplate and a tibial stem 8212 extending distally into tibia 8208. Tibial insert 8210 includes at least one Hall sensor, e.g., a medial Hall sensor 8214 and a lateral Hall sensor 8216, each configured to read knee implant parameters, such as magnetic flux density. An analog to digital converter 8218 may be configured to convert the analog knee implant parameter data to digital data. A processor 8220 analyzes and stores the digital data, which a data transmitter, such as an antenna located on tibial insert 8210, transmits to an external source 8226 like a smart phone, tablet, monitor, network, etc. to allow for real time review of the knee joint implant performance.

Continuing with FIG. 125, at least one magnet 8228 and at least one magnet 8230 are placed in the femur 8206 and tibia 8208, respectively. In such a configuration, the magnets 8228, 8230 may be detected by Hall sensors 8214, 8216 to provide a knee implant parameter correlating to the distance and strength of a magnetic field between the magnets 8228, 8230 and Hall sensors 8214, 8216. Additionally, other magnets 8232 may be placed within femoral implant 8202 to allow the Hall sensors in the tibial implant to track the position of the femoral implant. Magnets 8228, 8230 may be placed in predrilled holes in bone and may be oriented perpendicular to magnets in the knee implant 8200, such that the magnetic field generated by magnets 8228, 8230 is different from magnets 8232 in the femoral implant. Magnet 8228 in femur 8206 may be placed in a position that is not along the flexion-extension axis of the knee. Thus, the orientation of the magnets 8228, 8230—being different from magnets 8232—provide magnetic field readings and vibration signatures that are different from magnets 8232.

FIG. 126 depicts a flowchart method 8238 for determine implant detachment, loosening, or subsidence. First, a patient undergoes a TKA procedure. During the TKA procedure, a clinician may drill holes into femur 8206 and tibia 8208 to place magnets 8228, 8230 in an optimal location to be recognized by Hall sensors 8214, 8216 in tibial insert 8210. Kinematic motion of the knee with magnets 8228, 8230 is recorded in a step 8242, and inputted into a computer program that utilizes finite element analysis (FEA) to generate magnetic data in many knee poses for various training kinematics models. This computer program may further utilize machine learning, similar to the machine learning in the previous method, and thus will not be described again for sake of brevity. A clinician may also manipulate the patient's leg during surgery and collect and record the corresponding movement data during said movements. This movement data may provide a reference point for future movement tests.

First, the tibia 8208 may be tested to determine if the tibial implant 8204 is loose. In one configuration, the tibia 8208 may be manipulated in positions where the femoral bone magnet 8228 is arranged at a point furthest from Hall sensors 8214, 8216 such that it will not interfere with the magnetic field of the tibia 8208. However, in other configurations, the magnets within the femur 8206 and tibia 8208 may be placed at different distances from Hall sensors 8214, 8216, and the operating algorithm may account for any resulting magnetic field overlap or interaction. The tibia 8208 may be manipulated with anterior/posterior motions or other motions generated by the FEA modules that pass the embedded magnet 8232 by the corresponding Hall sensor 8214, 8216. This movement will generate a magnetic flux density, which can be recorded by Hall sensor 8214, 8216 and processed by processor 8220 using methods 8244 similar to those described herein. If the magnitude of the magnetic signal from the embedded tibial magnet 8230 changes through the same motion over time, for example, five years after surgery, the change could be indicative of tibial implant loosening 8248, but could also be indicative of the tibial insert 8210 moving relative to the implanted magnet. Thus, the femoral implant 8202 may also be tested to determine if loosening has occurred.

To test the femoral implant 8202 for implant loosening 8250, a clinician may manipulate femur 8206 through a predetermined set of movements, such as flexion and extension. The movements may ideally allow the implanted magnet 8228 in femur 8206 to pass by Hall sensors 8214, 8216. This movement may be repeated multiple times and a vibration signature 7960 from each movement may be recorded and stored using similar methods 8246 to those described herein. Likewise, a clinician may prescribe poses that generate maximum magnetic fields from the femoral magnet 8228, such that the magnetic field may be recorded and stored in the processor's memory system. In one embodiment, changes in the vibration signature or the magnetic field over time may indicate implant detachment. In another embodiment, regression models may be used for pose estimation. The regression models may manifest knee implant 8200 positions relative to magnets 8228, 8230 as noise artifacts as the Hall sensors 8214, 8216 pass near magnets 8228, 8230. In yet another embodiment, an acoustic exciter may provide vibration pulses through a patient's leg such that the vibration may cause the magnetic fields between the implanted magnets 8228, 8230 to change. If the change in magnetic field changes over time for similar vibration frequencies, implant loosening may have occurred.

FIG. 127 shows a knee joint implant 8300 according to another embodiment of the present disclosure. Knee joint implant 8300 is similar to knee joint implant 200, and therefore like elements are referred to with similar numerals within the 8300-series of numbers. For example, knee joint implant 8300 includes a femoral implant 8302, a tibial implant 8304, and a tibial insert 8310. However, knee joint implant 8300 includes a magnetic switch 8320 disposed in tibial insert 8310 to activate—i.e., turn on and off, the various electronic components 8313 (such as sensors, processors, etc.) housed in the knee joint implant. Magnetic switch 8320 is configured to detect a magnetic field strength and turn on the various electronic components. For example, when femoral implant 8302 with magnetic markers 8314 is placed near tibial insert 8310, separated by a distance D, magnetic switch 8320 detects the magnetic field from magnetic marker and allows power from the battery of the knee joint implant to flow to the various electronic components. The distance D indicates the maximum distance between tibial insert 8310 and femoral implant 8302 necessary for magnetic switch 8320 to activate the electronic components. In other words, magnetic switch 8320 requires a threshold magnetic field strength to activate the electronic components. The threshold magnetic field strength can be varied depending on the desired distance D required to allow magnetic switch 8320 to activate the electronic components. Conversely, when tibial insert 8310 and femoral implant are separated by a distance greater than D—i.e., the magnetic field strength is less than the threshold magnetic field strength, magnetic switch 8320 cuts off power from the battery to the electronic component and thereby deactivates sensors and processors of knee joint implant 8300. Thus, magnetic switch 8320 acts as a gate to control power supply to the various electronic components of knee joint implant.

Knee joint implant 8300 can be manufactured and shipped in an ultra low-power mode or completely turned off to minimize or eliminate battery consumption prior to use. Holding a magnet adjacent the magnetic switch allows the microprocessor of knee joint implant 8300 to boot. Using magnets such as magnetic markers 8314 embedded in femoral implant 8302 allows for automatic activation of the knee joint implant during surgery. Thus, there is no need for the surgeon to perform a separate and additional step during surgery to turn on the knee joint implant.

FIG. 128 shows a partial knee joint implant 8400 according to another embodiment of the present disclosure. Knee joint implant 8400 is similar to knee joint implant 8300, and therefore like elements are referred to with similar numerals within the 8400-series of numbers. For example, knee joint implant 8400 includes a femoral implant 8402, a tibial insert 8410, and a magnetic switch 8420. FIG. 128 illustrates the magnetic field generated by placing femoral implant 8402 on tibial insert 8410. Magnetic switch 8420 detects a magnetic field strength generated by magnets 8414 that is greater than a threshold magnetic field strength to activate the electronic components. Thus, even if the knee joint implant needs to be shut down or rebooted or is automatically shut down due to a software or hardware fault condition, etc., the magnetic switch will automatically power and reboot the joint implant after this condition passes.

Referring now to FIG. 129, there is shown a circuit diagram 8500 of a magnetic switch 8504 according to an embodiment of the present disclosure. Passive components associated with magnetic switch 8504 are omitted from FIG. 129 for brevity. Magnetic switch 8504 gates power from a battery 8502 via PFET and NFET switches to various electronic components including sensors (not shown) and the microprocessor as shown in FIG. 129. Magnetic switch 8504 includes a magnetic sensor to detect magnetic field strength as described with reference to knee joint implants 8300 and 8400. It should be noted that magnetic switch 8504 can be used with any of the implants of the present disclosure.

While knee joint implants 8300 and 8400 show a magnetic switch disposed in the tibial insert, the magnetic switch can be located within the tibial baseplate/stem or the femoral implant in other embodiments. In other embodiments, a magnet separate from the magnetic markers of the femoral implant can be used to activate the knee joint implant. For example, a surgeon can activate the electronic components of tibial insert prior to implantation using a separate magnetic source to ensure that the electronic components are functioning satisfactorily prior to surgery. In other embodiments, the magnetic switch may only activate and boot the electronic components—i.e., the electronic components continue working even when no magnetic field is detected by the magnetic switch. In other embodiments, a knee joint implant may include two or more batteries with the magnetic switch configured to activate only one or some of the batteries. For example, a battery supplying power to an IMU within a tibial insert may not be connected to the magnetic switch to ensure operation of the IMU prior to placing the femoral component adjacent to the tibial insert. Other sensors, such as the load sensors can be powered from a second battery controlled by the magnetic switch. The magnetic switch disclosed here can be used with any of the implants of the present disclosure.

FIG. 130 is a front view of a knee joint implant 8600 according to an embodiment of the present disclosure. Knee joint implant 8600 includes a femoral implant 8602 located on a femur 8608 and a tibial implant 8604 located on a tibia 8610. A tibial insert 8609 is located between tibial implant 8604 and femoral implant 8602. A patellar implant 8606 (not shown) is coupled to the posterior side of patella 8612 and contacts femoral implant 8602. Femoral implant 8602 includes at least one magnet 8636. Patellar implant 8606 includes at least one Hall sensor 8646 configured to sense a magnetic field from magnet 8636. Patellar implant 8606 further includes a power source, such as a battery 8648 and a microcontroller 8650 for storing, processing, and transmitting sensor data 8652 from Hall sensor 8646.

FIG. 131 illustrates additional details of femoral implant 8602. Femoral implant 8602 extends in a general arc-shape and defines a central opening 8614. Central opening 8614 defines medial and lateral condyles 8616, 8618 extending in arc-shapes adjacent to central opening 8614. A first axis 8632 extends from an anterior portion 8628 of femoral implant 8602 to a posterior portion 8630 of femoral implant 8602. Similarly, a second axis 8634 extends from an anterior portion 8628 to a posterior portion of femoral implant 8602. Various structures, including magnetic tape of varying lengths and magnetic markers can be positioned at discrete locations along or around first axis 8632 and second axis 8634 as shown in FIG. 131. The shape, size, and location of the magnets can vary depending on the implant.

Magnets 8636 may be any type of magnet capable of producing a magnetic field detectable by a Hall sensor. Examples of such magnet types include neodymium, samarium-cobalt (SmCo), aluminum-nickel-cobalt (AlNiCo), and ferrite. Such magnets may be in the form of magnetic tape or individual structures as shown in FIG. 131.

FIGS. 8632 and 8633 depict a patellar implant 8606 according to one embodiment of the present disclosure. Patellar implant 8606 includes an outer shell 8638 that surrounds various internal components and circuitry. Outer shell 8638 is generally disc-shaped with a bulbous outer face 8640. Outer face 8640 is configured to contact and articulate against femoral implant 8602 during knee flexion and extension. As such, patellar implant 8606 may have a coating to lubricate the articulating surfaces of outer face 8640 and femoral implant 8602 to minimize wear on the implant. Patellar implant 8606 further includes at least one leg 8642 configured to extend into and engage with patella 8612. As depicted, patellar implant 8606 includes two legs 8642, although other leg configurations are envisioned. Legs 8642 may have attachment structures such as barbs or arcs that facilitate attachment with patella 8612. Bone cement may also be used to secure patellar implant 8606 to patella 8612.

A printed circuit board 8644 is housed within shell 8638. Printed circuit board 8644 may be any board known in the art, such as a single sided, double sided, multilayered, or the like. Various electrical components attach to printed circuit board 8644. Such components include at least one Hall sensor 8646, at least one battery 8648, and at least one microcontroller 8650. Each of these components is described in detail below.

Hall sensor 8646 includes three Hall effect sensors placed on medial, superior, and lateral locations of the printed circuit board 8644. Such Hall sensors 8646 may be oriented in Cartesian coordinates or arranged in other configurations. For example, four Hall effect sensors may be implemented, with the fourth sensor being located at an inferior location on printed circuit board 8644. Hall sensor 8646 is configured to sense a magnetic flux density created by magnets 8636 and output a signal proportional to the strength of the sensed magnetic field. Such an output may be readable via serial communication. The location of Hall sensor 8646 may be optimized to indicate patella shift, patella rotation or any deviation of patellar position, which may ultimately lead to patellar tendonitis.

Microcontroller 8650 includes at least one microcontroller chip. As depicted, microcontroller 8650 includes two microcontroller chips. At least one processor (CPU), memory system 8658, and a communication interface are integrated within microcontroller 8650. The CPU is configured to execute a computer program tailored to the operation of Hall sensor 8646. As such, the CPU may be configured to gather, analyze, and output sensor data 8652. Such a program and its corresponding settings may be adjusted by an operator before, during, or after implantation. The program memory may be any type configured to store sensor data, such as RAM, ROM, flash, or the like. The communication interface, otherwise known as input/output (I/O) peripherals, is configured to receive sensor data from Hall sensor 8646 and communicate the sensor data 8652 to the processor. The data is then transmitted to an external source such as a computer or a smartphone via near-field communication (NFC), Bluetooth or other wireless communication such that an operator can analyze the data. An antenna 8656 may facilitate transmission of sensor data 8652 to the external device. Microcontroller 8650 may further include an inertial measurement unit to measure acceleration changes in and around microcontroller 8650. In alternative embodiments, microcontroller 8650 may include a first microcontroller chip including an advanced RISC machine (ARM) core and a communication system. Such a communication system may be compatible with at least one of Bluetooth and near-field communications. A second microcontroller may further be utilized. Such a second microcontroller may include any combination of cores, communication systems, and memory systems.

Battery 8648 is configured to power printed circuit board 8644 and may be any battery type known in the art. For example, battery 8648 can be solid state batteries, lithium-ion batteries, lithium carbon monofluoride batteries, lithium thionyl chloride batteries, lithium ion polymer batteries, etc.

FIGS. 134-135 illustrate another embodiment of a patellar implant. In this embodiment, patellar implant 8706 is similar to patellar implant 8606, and therefore like elements are referred to with similar numerals within the 8700-series of numbers. Patellar implant 8706 includes an outer shell 8738 surrounding internal circuitry and components. Outer shell 8738 is generally disc-shaped and has a bulbous outer face 8740. Outer shell 8738 may have a coating that decreases friction between outer shell 8738 and femoral implant 8602 to allow outer shell 8738 to articulate against femoral implant 8602 without causing excess wear. Patellar implant 8706 may further include at least one leg 8742 configured to extend within and engage patella 8612. As depicted, patellar implant 8706 includes three legs spaced approximately 120° from each other; however, it is envisioned that other leg configurations may be implemented. Leg 8742 may have arcs, barbs, or other attachment features to secure leg 8742 within patella 8612. Bone cement may additionally be used to secure legs 8742 within patella 8612.

A printed circuit board 8744 is housed within shell 8738. Printed circuit board 8744 may be similar to printed circuit board 8644, and as such may be single sided, double sided, multilayered, or the like. At least one Hall sensor 8746 and at least one microcontroller 8750 are attached to printed circuit board 8744. Unlike printed circuit board 8644, printed circuit board 8744 includes a coil 8748 that provides inductive power to the printed circuit board 8744 and its components. Such a coil 8748 may be advantageous over a battery 8648 as the coil may prolong the utility of patellar implant 8706 as a battery would otherwise deteriorate over time and lose battery-life. In this way, printed circuit board 8744 may be powered solely by an external device or in a combination of an external device and a batter. Coil 8748 may be activated using near-field communication (NFC). Accordingly, to power printed circuit board 8744, a mobile device with NFC capability is moved into range of coil 8748. Once in place, the mobile device can activate to power coil 8748, which in turn powers printed circuit board 8744. NFC technology also allows microcontroller 8750 to communicate with an external mobile device, such that the mobile device can obtain the measured sensor data 8652.

Hall sensor 8746 and microcontroller 8750 operate similarly to Hall sensor 8646 and microcontroller 8650, and thus will not be fully described for sake of brevity. Unlike microcontroller 8650, microcontroller 8750 transmits data via NFC, which requires an external mobile device with NFC capability to be within a close proximity to microcontroller 8750 such that data can be transmitted between the two devices.

Machine learning may be implemented within a mobile device to analyze the sensor data from Hall sensors 8646, 8746. As such, manual comparison of sensor data points may not be required to determine when a patient is developing patellar tendonitis. A database (not shown) of average magnetic flux densities for various leg movements may be created and stored within the mobile device. This database ideally includes information from patients of all ages, body types, and various parameters regarding the surgery that took place. The machine learning algorithm may extract data from the database and compare it to measured data from Hall sensors 8646, 8746. Based on the difference between the two data sets, the machine learning algorithm may indicate to the patient and/or an operator that knee implant 8600 is imparting improper forces on patella 8612, which may lead to patellar tendonitis. The machine learning algorithms may use classifier algorithms such as random forest or support vector algorithms to compare and contrast the data. Alternatively, other algorithm types capable of comparing and contrasting data may be utilized to determine if forces are being imparted on patella 8612.

FIG. 136 illustrates a perspective view of femoral implant 8602 and patellar implant 8706. As illustrated, patellar implant 8606 is positioned at an anterior portion of femoral implant 8602 such that outer face 8740 of patellar implant 8706 contacts and articulates against femoral implant 8602. Magnets 8636 within first and second axis 8632, 8624 may pass by Hall sensors (not shown) as articulation of the knee joint takes place. Accordingly, different magnetic flux densities are created based on the position of the femoral implant 8602 relative to patellar implant 8706. Based on these different magnetic fluxes, one may determine whether improper forces are being imparted to patella 8612 to cause the patellar component to deviate from the expected path such that patellar tendonitis is more likely to occur. Although FIG. 136 illustrates patellar implant 8706, patellar implant 8606 operates in a similar manner.

FIG. 137 illustrates a data flow block diagram implemented by the systems described herein. Such a method begins with sensor data 8652 collection from Hall sensors 8646. Sensor data 8652 then flows into microcontroller 8650, where it is processed and analyzed. From microcontroller 8650, processed data 8654 flows into a memory system 8658 configured to store processed data. To transmit data to an external source, such as a mobile device, two separate methods are possible using the methods described herein. The first method involves the use of patellar implant 8606. After processed data 8654 flows from memory 8658 and microcontroller 8650 to a data transmitter, such as antenna 8656, wireless communication such as Bluetooth low energy (BLE) can be used to transmit data to an external source. Alternatively, the second method involve the use of patellar implant 8706 and NFC technology. After processed data 8654 flows from memory 8658 to a data transmitter, such as antenna 8656 within microcontroller chip 8650, wireless NFC communication types can be implemented to communicate with an external mobile device.

In addition to detecting patellar tendonitis by detecting movement of patella 8612 relative to femoral component 8602, the system described herein may also be used to detect other knee abnormalities. Anterior knee pain is a common symptom after a TKA. The system described herein can be utilized to determine if the patella 8612 is tracking medially, centrally, or anteriorly within the femoral groove. If such a determination is made, a physiotherapist may direct the patient to strengthen certain muscle groups of the patient's quadriceps to balance the loads acting on the knee. This same method may ultimately determine whether a patient's quadriceps are properly activated in relation to certain knee movements. Further, the system described herein may communicate with other sensor systems or smart implants to determine various other abnormalities throughout a patient's body.

A method of using patellar implant 8606 of FIGS. 130-133 is provided herein. First, a patient undergoes a total knee arthroscopy and a knee implant including a femoral implant 8602, a patellar implant 8606, and a tibial implant 8604 is implanted in the patient's knee. An operator may select a unique patellar implant 8606 containing a specific microcontroller 8650 desirable for a specific patient. Once the implant is secured in place, magnets 8636 of first axis 8632 correspond to a medial portion of femoral implant 8602 and magnets 8636 of second axis 8634 correspond to a lateral portion of femoral implant 8602. Outer face 8640 of patellar implant 8606 can then articulate relative to femoral implant 8602, thus causing Hall sensors 8646 to pass through various magnetic fields depending on the specific movement the patient's leg is undergoing.

Once the knee implant is implanted, sensor data 8652 can be collected to determine baseline position data. An operator may manipulate a patient's leg through various movements to ensure a variety of data points are captured and that Hall sensors 8646 sense magnetic flux from a plurality of magnets 8636. Over time, a patient may repeat the same movements under similar conditions. For example, a patient may repeat the same movements annually. At each iteration, sensor data 8652 is taken, compared to previous sensor data, and stored in memory system 8658. If microcontroller 8650 detects a change in sensor data 8652 over a period time, it may transmit sensor data 8652 to an external source via Bluetooth or other wireless communication methods to create an alert that forces may be acting on patella 8612 that could indicate patellar tendonitis is developing. Sensor data 8652 may also be used to detect a change in kinematic pathways. Rather than measuring direct forces applied to the patella 8612, sensors 8646 may be used to measure and track the kinematic position of the patella 8612 relative to the femoral implant 8602. A change in the kinematic pathways may indicate patellar tendonitis or other worsening knee conditions. Alternatively, microcontroller 8650 may transmit sensor data 8652 to an external source each time sensor data 8652 is measured, and the external source may analyze sensor data 8652 using machine learning or other algorithms to determine if the magnetic fields have shifted between femoral implant 8602 and patellar implant 8606, which could indicate patellar tendonitis.

A method of using patellar implant 8706 of FIGS. 134-135 is provided herein. First, a patient undergoes a total knee arthroscopy and a knee implant including a femoral implant 8602, a patellar implant 8706, and a tibial implant 8604 is implanted in the patient's knee. An operator may select a unique patellar implant 8706 containing a specific microcontroller 8750 desirable for a specific patient. Once the implant is secured in place, magnets 8636 of first patellar track 8620 correspond to a medial portion of femoral implant 8602 and magnets 8636 of second patellar track 8622 correspond to a lateral portion of femoral implant 8602. Outer face 8740 of patellar implant 8706 can then articulate relative to femoral implant 8602, thus causing Hall sensors 8746 to pass through various magnetic fields depending on the specific movement the patient's leg is undergoing.

Once the knee implant is implanted, sensor data 8652 can be collected to determine baseline position data. An operator may manipulate a patient's leg through various movements to ensure a variety of data points are captured and that Hall sensors 8746 sense magnetic flux from a plurality of magnets 8636. Over time, a patient may repeat the same movements under similar conditions. For example, a patient may repeat the same leg movements annually. At each iteration, sensor data 8652 is taken, compared to previous sensor data, and stored in memory system 8658. If microcontroller 8750 detects a change in sensor data 8652 over a period of time, it may transmit sensor data 8652 to an external source via NFC communication methods to create an alert that forces may be acting on patella 8612 that could indicate patellar tendonitis is developing. Alternatively, microcontroller 8750 may transmit sensor data 8652 to an external source each time sensor data 8652 is measured, and the external source may analyze sensor data 8652 using machine learning or other algorithms to determine if the magnetic fields have shifted between femoral implant 8602 and patellar implant 8606, which could indicate patellar tendonitis.

Each component described herein may be provided in a kit. Such a kit (not shown) may include different size implant components that correspond to different patients and different TKA scenarios. For instance, an operator may select implant components from a kit that correspond to the patient's unique knee geometry. Further, additional software programs may be programmed into microcontroller 8650 such that other knee parameters, such as implant loosening or subsidence, may also be measured from various Hall sensors through the implant. Accordingly, providing a kit allows an operator flexibility to determine the best treatment option for individual patients.

FIGS. 138 and 139 show exploded views of a tibial implant 8800 according to another embodiment of the present disclosure. Tibial implant 8800 includes a tibial insert 8802, a case 8804, a tibial baseplate 8806 and a tibial stem 8808. Case 8804 is a modular case that is designed specifically to securely fit tibial insert 8802 via a slot 8817 with an opening 8819 as shown in FIG. 138. Case 8804 can be inserted posteriorly into the opening of tibial insert 8802 as more fully described below. The posterior assembly ensures a soft tissue friendly assembly while simultaneously providing a secure fit and reducing the amount of pressure placed on the soft tissue surrounding the implant. The posterior assembly is intended to enhance the performance of the posterior cruciate ligament by allowing a surgeon to place the case and tibial insert 8802 securely where the posterior cruciate ligament articulates. This secure placement ensures that the posterior cruciate ligament is able to move freely and perform its intended function without any obstructions. The posterior assembly helps to reduce the risk of post-operative complications, such as fretting wear or other forms of wear, which may arise from metal-to-metal contact between the tibial baseplate and the sealed container, both of which can be made of Titanium, Cobalt-Chromium, etc., to ensure optimal results from the procedure.

Once case 8804 is secured to tibial insert 8802 as shown in FIG. 143, the tibial insert can be attached to baseplate 8806 as more fully explained below. It should be understood that while case 8804 is described with reference to tibial implant 8800 in this embodiment, a modular case can be provided with any of the tibial implants or other joint implants disclosed herein as well, working in the same manner, and accomplishing the same functions.

A top view of tibial insert 8802 is shown in FIG. 140. Tibial insert 8802 includes an anterior relief 8810 and a central ridge 8812 separating a medial articular surface 8814 and a lateral articular surface 8816. Opening 8819 to slot 8817 (FIG. 139) at a posterior end 8822 of central ridge 8812 allows for the insertion of sensors, batteries, and various other components disclosed herein into tibial insert 8802. The electronic components can be conveniently disposed within tibial insert 8802 prior to inserting case 8804 to seal and lock these components with the tibial insert.

FIG. 141 is a cross-sectional view of tibial insert 8802, featuring opening 8819 configured to receive case 8804. An outline 8820 is present, indicating the position of case 8804 once it is seated within tibial insert 8802. Additionally, the electronic components (not shown) are arranged around outline 8820 within hollow volumes of tibial insert 8802. This is to ensure that the sensor and other electronic components are in areas subjected to less loading, unlike the medial articular surface 8814 and lateral articular surface 8816, which experience high loading allowing the medial and lateral articular surfaces to be composed of solid regions. Thus, the tibial inserts disclosed below are specifically configured to maximize strength, wear, and fatigue resistance of these high loading areas by locating electronic and non-electronic component outside the high loading areas.

Referring now to FIG. 142, there is shown a perspective view of case 8804. Case 8804 includes two projections 8826 on the lateral and medial sides which are configured to engage with notches 8824 of tibial insert 8802. The projections can be any of tabs, barbs, clips, or other features configured to engage and lock with corresponding features on tibial insert to ensure that the two components are secured connected within tibial insert 8802. Projections 8826 shown in this embodiments are living hinges which can be made of thin portions of the same material as case 8804. This allows projections 8826 to flex and bend without breaking. The living hinges provide a durable, low-cost hinge that is easy to manufacture. It does not require any additional hardware, like a traditional hinge, and is designed to allow the material to flex and move freely.

A posterior cruciate relief opening 8830 in case 8804 allows the PCL to move freely and without obstruction. The angular tapered shape of a posterior end 8828 of case 8804 enables the surgeon to easily grip the case and insert it into opening 8819 of the tibial insert 8802 flexing projections 8826, until the projections 8826 snap fit into the notches 8824, thus ensuring that the case 8804 is securely attached to the tibial insert, as illustrated in FIG. 143. Case 8804 can include a coating such as cross-linked polyethylene material silicone, polyurethane, parylene, etc. to enhance its sealing properties to hermetically seal and protect the sensor module comprising any combination of sensors, batteries, processing components, transmission components, etc. The tibial insert and its accompanying packaging can be exposed to sterilization treatments such as the ethylene oxide sterilization process, without the need for a modular case to be present, in order to optimize the manufacturing process and ensure more cost-effective production.

The modularity of tibial implant 8800 offers several distinct advantages. It allows for convenient manufacturing and shipping of the knee joint implant components, as each component can be packaged and shipped separately without assembly. A surgeon can first select the required tibial insert size for a patient and then determine the type of sensor module, such as sensors, to be inserted into the selected tibial insert. The tibial insert is hermetically sealed intra-operatively prior to coupling the tibial implant to the patient. This versatility means that the electronic components can be manufactured and shipped in various sensor module configurations, allowing the surgeon to select the sensor module best suited for the patient's needs.

FIGS. 144 and 145 show top and bottom views, respectively, of tibial baseplate 8806. As shown in FIG. 144, an upper or proximal surface of tibial baseplate 8806 includes various features to allow securement to tibial insert 8802. Tibial baseplate 8806 includes a center island 8838 to fit and be secured within a corresponding opening in tibial insert 8802. An anterior wall 8834 with multiple anterior tabs 8832 along the outside edge and facing the rear, as well as a posterior wall 8836 with an intracondylar recess. An anterior locking wire (not shown) is used to attach tibial insert 8802 to tibial baseplate 8806 as best shown in FIG. 146.

FIG. 147 shows a tibial insert 8900 with a sensor module 8902 according to another embodiment of the present disclosure. Sensor module 8902 can include various sensors such as Hall sensors, load sensors, IMUs, pH sensors, temperature sensors, etc., along with the various other electronic components such as batteries, MCUs, data storage and transfer components, etc. Sensor module 8902 can be provided in various configurations—i.e., sensor types, arrangement of sensors, battery size, etc., for patient-specific needs. Sensor module 8902 can be inserted into a corresponding aperture 8904 of tibial insert 8900 as shown in FIG. 147.

Aperture 8904 is shaped and sized to match the profile of sensor module 8902 to receive the sensor module through an opening 8906. Aperture 8904 is configured to allow the sensor module to freely fit into opening 8906 and travel freely to a specified depth when the sensor module is engaged with tibial insert. Sensor module 8902 is configured to be a secured with a press-fit on both the anterior and posterior sides of the sensor module via tabs 8908 or other engagement features which interact with aperture 8904 to create a press-fit assembly. Thus, sensor module 8902 can be securely attached to tibial insert 8900 to prevent any micro-motion between the sensor module and the tibial during regular articulation and loading of the femoral implant and the tibial insert. Final assembly and press-fit can be achieved through user impact or the use of a clamp.

FIG. 148 shows a tibial insert 9000 with a sensor module 9002 according to another embodiment of the present disclosure. Tibial insert 9000 is similar to tibial insert 8900, and therefore like elements are referred to with similar numerals within the 9000-series of numbers. For example, tibial insert 9000 includes a sensor module 9002 and an aperture 9004 with an opening 9006 to receive the sensor module. However, sensor module 9002 includes barbs 9008 to engage with aperture 9004 of tibial insert 9000 to secure the sensor module to the tibial insert.

Referring now to FIG. 149, there is shown a tibial insert 9100 with a sensor module 9102 according to another embodiment of the present disclosure. Tibial insert 9100 is similar to tibial insert 8900, and therefore like elements are referred to with similar numerals within the 9100-series of numbers. For example, tibial insert 9100 includes a sensor module 9102 with tabs 9108 for securing the sensor module to the tibial insert. However, tibial insert 9100 includes a recess 9104 to receive and secure the sensor module as shown in FIG. 149. Thus, when sensor module 9102 is secured to tibial insert 9100, at least one surface of this assembly is defined by the sensor module and the tibial insert. Thus, two surfaces of sensor module 9102 define exterior surfaces of the tibial insert assembly.

As disclosed above, a tibial insert with a modular case and a sensor module is designed to address the complexities of medical device systems through a variety of enhancements to the surgical process. These include a simpler implantation process, customizing the sensor module to fit a patient's specific needs, reducing distractions in the operating room, streamlining the manufacturing process, improving cleaning and sterility, and providing a clinically proven insert to baseplate assembly locking mechanism. Furthermore, it provides better inventory management of the modular cases, thus making it easier to keep track of.

Referring now to FIGS. 150-153, there is shown a reverse shoulder implant 9200 according to an embodiment of the present disclosure. The shoulder implant 9200 comprises a stem 9202, a cup 9204 which can be integrated with stem 9202, an insert 9206 and a glenoid sphere 9208 as best shown in FIG. 150. Magnetic flux density sensors, such as Hall sensor assemblies 9216, are located on a printed circuit board (PCB) 9223 of insert 9206 as shown in FIG. 152. Magnetic markers 9210 are located on glenoid sphere 9208 as best shown in FIG. 151. The Hall sensor assemblies 9216 measure the change in magnetic flux density when the glenoid sphere 9208 moves relative to the Hall sensors, thereby functioning as an absolute or incremental encoder to detect shoulder movement of a patient during daily activities. The shoulder implant 9200 includes a battery 9214 which can be located in cup 9204, insert 9206 or stem 9202. An electronic assembly including various support electronic components such as nonvolatile storage, data transmission components, etc. can be located within the insert 9206 or cup 9204. Nonvolatile storage allows the shoulder implant to store data that has been captured and processed by the sensors and MCU, respectively. This data is stored reliably, even when the power is turned off. The data stored in the nonvolatile storage is easily accessible and can be used to further enhance the operation of the implant.

PCB 9223 can include various other sensors such as IMUs 9222 as shown in FIG. 152. IMUs 9222 provides motion classification of the shoulder implant in order to focus the kinematic data associated with the positional data provided by the magnetic markers 9210 and Hall sensor assemblies 9216. By combining these two sources of data, shoulder implant 9200 is able to provide accurate and reliable motion classification of the shoulder. This motion classification helps to accurately assess the functionality of the shoulder implant, as well as provide valuable insight into the patient's condition. The readings obtained from IMUs 9222 can be used in combination with readings from an external IMU sensor worn by the patient. For example, FIG. 159 shows a patient with reverse shoulder implant 9200 and an external IMU 9230 worn on the sternum or other body parts such as the hand, wrist, legs, etc. External IMU 9240 provides a comprehensive understanding of the movement of the arm relative to the torso. Furthermore, IMUs 9222 of shoulder implant 9200 enables the detection of the movement of the humerus in relation to the scapula.

A pH sensor can be located on cup 9204, insert 9206 or stem 9202 to measure alkalinity and provide early detection notice of implant related infection. An antenna located on the insert 9206 allows for the transmission of sensor data to an external source, enabling monitoring and transmission of the shoulder implant 9200's performance during patient rehabilitation and recovery.

FIG. 154 shows a schematic view of magnetic flux density 9211 between magnetic markers 9210 of glenoid sphere 9208 and Hall sensor assemblies 9216 of insert 9206. The flux of the magnetic field over the Hall sensors will be used to capture kinematic and position data based on the intensity read by each Hall sensor assembly 9216. The magnetic field intensity will be read by each sensor assembly, allowing for accurate data capture and analysis. This will help to ensure that the readings are precise and reliable. The data collected will provide useful information on the behavior of the system.

Inertial data from IMUs 9222, a type of kinematic data, can be used to track shoulder movement. In the case of shoulder implant 9200, inertial data can be used to classify movement and further focus on the kinematic data of the shoulder implant. This can help to provide more accurate and precise readings of the implant's performance and can be used to develop treatments and improve the implant's functionality. Inertial data can be used to track a patient's recovery after a surgery without the need for them to visit a Healthcare Professional ("HCP") or having traditional imaging, such as X-rays or MRIs, done to assess the implant and patient's recovery progress.

FIGS. 155-157 illustrate the measured magnetic flux density 9300, 9400, 9500 in relation to shoulder constrained flexion angles for the three separate Hall sensor assemblies shown in FIG. 152, each in the x, y, and z axis, respectively. Using a Neural Network, data will be processed to determine the x, y, and z position value, as well as the rotations along these respective axes. The flux strength of the Hall sensors can be read to calculate the distance between the glenoid sphere and the Hall sensors, thus calculating the amount of lift off and other performance metrics of the shoulder implant. With the Neural Network, this data can be quickly and accurately processed to provide a reliable and accurate result.

FIG. 158 shows a graphic user interface 9600 to monitor and evaluate shoulder implant 9200 performance according to an embodiment of the present disclosure. Shoulder implant 9200 and the patient's associated recover can be conveniently monitored and evaluated by an HCP intra-operatively and post-operatively via graphic user interface 9600. For example, dislocation and impingement can be accurately calculated and predicted by assessing the lift-off in one direction, and comparing it to a pre-defined threshold. Measurements such as flexion-extension, abduction-adduction, internal-external rotation, lift-off, the direction vector of the lift-off, etc., can be readily monitored and evaluated in order to determine whether an excursion of the position has passed a predetermined threshold. If this is detected, warnings can be transmitted to alert the user or the HCP of the possibility of dislocation or impingement.

FIG. 160 shows a flowchart 9700 for monitoring a patient's shoulder joint condition using shoulder implant 9200. In order to provide effective feedback to the patient in a clinical setting, special attention must be paid to the detection of lift-off. The glenohumeral kinematics is carefully monitored by a clinician or physiotherapist while the patient explores the limits of motion. When the glenoid lift off from the humeral insertion point, a warning is displayed to alert the patient and provide them with guidance to avoid these positions. To further support patient safety, real-time feedback can be provided using the IMU sensor to accurately detect when such critical positions are reached. This will allow for a better understanding of the patient's position and enable a more personalized and individualized treatment plan. IMUs can be used in this application due to their low power consumption. This allows the sensors to run in the background for extended periods of time without draining the battery.

Thus, shoulder implant 9200 has the capability to detect, alert, estimate, and measure lift off, dislocation, and impingement of the shoulder joint. Additionally, it can provide actual rotation, elevation, and other kinematic data intra-operatively and post operatively as best shown in FIG. 158. This information is not currently accessible to evaluate the progress of shoulder implant technology and measure the success of the design, dynamic loads, and mechanical structures to prevent misalignment and dislocation. This implant can also provide guidance and progress tracking to aid in recovery and determine the effectiveness of such efforts by quantifying shoulder implant metrics. Moreover, it can offer a real-time method of determining and warning about implant loose-fitting (like tendon relaxation) and other similar conditions.

While a knee joint implant, hip implant, shoulder implant and a spinal implant are disclosed above, all or any of the aspects of the present disclosure can be used with any other implant such as an intramedullary nail, a bone plate, a bone screw, an external fixation device, an interference screw, etc. Although, the present disclosure generally refers to implants, the systems and method disclosed above can be used with trials to provide real time information related to trial performance. While sensors disclosed above are generally located in the tibial implant (tibial insert) of the knee joint implant, the sensors can be located within the femoral implant in other embodiments. Sensor shape, size and configuration can be customized based on the type of implant and patient-specific needs.

Furthermore, although the invention disclosed herein has been described with reference to particular features, it is to be understood that these features are merely illustrative of the principles and applications of the present invention. It is therefore to be understood that numerous modifications, including changes in the sizes of the various features described herein, may be made to the illustrative embodiments and that other arrangements may be devised without departing from the spirit and scope of the present invention. In this regard, the present invention encompasses numerous additional features in addition to those specific features set forth in the paragraphs below. Moreover, the foregoing disclosure should be taken by way of illustration rather than by way of limitation as the present invention is defined in the examples of the numbered paragraphs, which describe features in accordance with various embodiments of the invention, set forth in the paragraphs below.

The invention claimed is:

1. A joint implant comprising:

a first implant configured to be coupled to a first bone of a joint, the first implant including at least one marker;

a second implant configured to be coupled to a second bone of the joint and contacting the first implant, the second implant including:

at least one marker reader to detect a position of the marker to identify positional data of the first implant with respect to the second implant, and at least one load sensor to measure load data between the first and second implants; and a processor operatively coupled to the marker reader and the load sensor, wherein the processor outputs the positional data and the load data to an external source, wherein the marker is a magnetic track disposed along a surface of the first implant and the marker reader includes a Hall sensor assembly with at least one Hall sensor.

2. The joint implant of claim 1, wherein the first implant includes a first magnetic track extending along a medial side of the first implant and a second magnetic track extending along a lateral side of the first implant.

3. The joint implant of claim 2, wherein the second implant includes a first Hall sensor assembly on a medial side of the second implant and a second Hall sensor assembly on a lateral side of the second implant, the first Hall sensor assembly configured to read a magnetic flux density of the first magnetic track and the second Hall sensor assembly configured to read a magnetic flux density of the second magnetic track.

4. The joint implant of claim 3, wherein a central portion of the first magnetic track is narrower than an anterior end and a posterior end of the first magnetic track.

5. The joint implant of claim 4, wherein the first magnetic track includes curved magnetic lines extending across the first magnetic track.

6. The joint implant of claim 1, wherein the Hall sensor assembly is coupled to the load sensor by a connecting element.

7. The joint implant of claim 6, wherein the connecting element is a rod configured to transmit loads from the magnetic track to the load sensor.

8. The joint implant of claim 1, wherein the joint is a knee joint, the first implant is a femoral implant configured to be coupled to a femur and the second implant is a tibial implant configured to be coupled to a tibia.

9. The joint implant of claim 8, wherein the tibial implant includes a tibial insert and a tibial stem, the marker reader and the processor being disposed within the tibial insert.

10. The joint implant of claim 9, wherein the positional data includes any of a knee flexion angle, knee varus-valgus rotation, knee internal-external rotation, knee medial-lateral translation, superior-inferior translation, anterior-posterior translation, and time derivatives thereof.

11. The joint implant of claim 9, wherein the tibial insert includes any of a pH sensor, a temperature sensor and a pressure sensor operatively coupled to the processor.

12. A joint implant comprising:

a first implant configured to be coupled to a first bone of a joint, the first implant including:

a plurality of medial markers located on a medial side of the first implant, and a plurality of lateral markers located on a lateral side of the first implant;

a second implant configured to be coupled to a second bone of the joint and contacting the first implant, the second implant including:

at least one medial marker reader to identify a position of the medial markers and at least one lateral marker reader to identify a position of the lateral markers, the position of the medial markers and the position of the lateral markers providing a positional data of the first implant with respect to the second implant, a medial load sensor to measure medial load data between the first and second implants on a medial side of the joint implant, a lateral load sensor to measure lateral load data between the first and second implants on a lateral side of the joint implant, and a processor operatively coupled to the medial marker reader, the lateral marker reader, the medial load sensor and the lateral load sensor, wherein the processor simultaneously outputs the positional data, the medial load data and the lateral load data to an external source, wherein a number of medial markers is different from a number of lateral markers.

13. The joint implant of claim 12, wherein the medial markers and the lateral markers include magnets located at discrete locations on the first implant.

14. The joint implant of claim 13, wherein the medial marker reader and the lateral marker reader include Hall sensor assemblies with at least one Hall sensor.

15. A joint implant comprising:

a first implant configured to be coupled to a first bone of a joint, the first implant including at least one marker, the marker being a magnetic track disposed along a surface of the first implant;

a second implant configured to be coupled to a second bone of the joint and configured to contact the first implant, the second implant including:

at least one marker reader to detect a position of the marker to identify a positional data of the first implant with respect to the second implant, the marker reader being a Hall sensor assembly including at least one Hall sensor, and at least one inertial measurement unit to measure a motion data of the second implant, and a processor operatively coupled to the marker reader and the inertial measurement unit, wherein the processor outputs the positional data and the motion data to an external source.

* * * * *